United States Patent
Caroff et al.

(10) Patent No.: US 9,266,876 B2
(45) Date of Patent: Feb. 23, 2016

(54) 4-(BENZOIMIDAZOL-2-YL)-THIAZOLE COMPOUNDS AND RELATED AZA DERIVATIVES

(71) Applicant: Actelion Pharmaceuticals Ltd., Allschwil (CH)

(72) Inventors: Eva Caroff, Allschwil (CH); Marcel Keller, Allschwil (CH); Thierry Kimmerlin, Allschwil (CH); Emmanuel Meyer, Allschwil (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 0 days.

(21) Appl. No.: 14/376,307

(22) PCT Filed: Feb. 1, 2013

(86) PCT No.: PCT/IB2013/050870
§ 371 (c)(1),
(2) Date: Aug. 1, 2014

(87) PCT Pub. No.: WO2013/114332
PCT Pub. Date: Aug. 8, 2013

(65) Prior Publication Data
US 2014/0371204 A1   Dec. 18, 2014

(30) Foreign Application Priority Data

Feb. 2, 2012  (WO) .................. PCT/IB2012/050489

(51) Int. Cl.
| C07D 277/28 | (2006.01) |
| C07D 417/04 | (2006.01) |
| C07D 417/14 | (2006.01) |
| C07D 471/04 | (2006.01) |
| C07D 487/04 | (2006.01) |
| C07D 519/00 | (2006.01) |

(52) U.S. Cl.
CPC ............ *C07D 417/14* (2013.01); *C07D 471/04* (2013.01); *C07D 487/04* (2013.01); *C07D 519/00* (2013.01)

(58) Field of Classification Search
CPC ........................... C07D 277/28; C07D 417/04
See application file for complete search history.

(56) References Cited

U.S. PATENT DOCUMENTS

| 2006/0276465 A1 | 12/2006 | Kawahara et al. |
| 2010/0094006 A1 | 4/2010 | Nam et al. |
| 2010/0280028 A1 | 11/2010 | Kowalski et al. |
| 2011/0136823 A1 | 6/2011 | Deprez et al. |
| 2013/0072497 A1 | 3/2013 | Lorsbach et al. |

FOREIGN PATENT DOCUMENTS

| EP | 1 698 620      | 9/2006 |
| WO | WO 02/059108   | 8/2002 |
| WO | WO 02/070511   | 9/2002 |
| WO | WO 2005/003127 | 1/2005 |
| WO | WO 2005/035534 | 4/2005 |
| WO | WO 2005/040136 | 5/2005 |
| WO | WO 2005/042516 | 5/2005 |
| WO | WO 2005/044797 | 5/2005 |
| WO | WO 2005/051304 | 6/2005 |
| WO | WO 2006/088836 | 8/2006 |
| WO | WO 2006/088837 | 8/2006 |
| WO | WO 2006/088840 | 8/2006 |
| WO | WO 2006/088919 | 8/2006 |
| WO | WO 2006/088920 | 8/2006 |
| WO | WO 2006/088921 | 8/2006 |
| WO | WO 2006/091428 | 8/2006 |
| WO | WO 2007/002742 | 1/2007 |
| WO | WO 2007/014290 | 2/2007 |
| WO | WO 2007/047202 | 4/2007 |

(Continued)

OTHER PUBLICATIONS

Gould, Philip, "Salt selection for basic drugs," International Journal of Pharmaceutics (1986), vol. 33, pp. 201-217.

Greene, T. W. et al., "Protecting Groups in Organic Synthesis," (3rd Edition, 1999), (TOC Only).

Groom, J. et al., "CXCR3 in T Cell Function," Exp. Cell Res. (2011), vol. 317, pp. 620-631.

Groom, J. et al., "CXCR3 Ligands: Redundant, Collaborative and Antagonistic Functions," Immunol. & Cell Biol. (2011), vol. 89, pp. 1-9.

Hancock, W. et al., "Requirement of the Chemokine Receptor CXCR3 for Acute Allograft Rejection," J. Exp. Med. (2000), vol. 192, No. 10, pp. 1515-1519.

(Continued)

*Primary Examiner* — Michael Barker
*Assistant Examiner* — Karen Cheng
(74) *Attorney, Agent, or Firm* — Arent Fox LLP

(57) ABSTRACT

The invention relates to compounds of Formula (I),

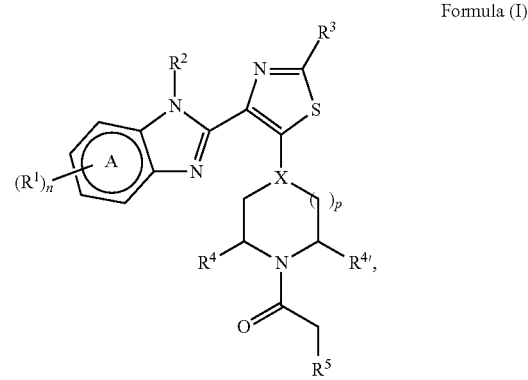

Formula (I)

wherein ring A, X, $(R^1)_n$, $R^2$, $R^3$, $R^4$, $R^{4'}$, $R^5$, n, and p are as described in the description; to pharmaceutically acceptable salts thereof, and to the use of such compounds as medicaments, especially as modulators of the CXCR3 receptor.

41 Claims, No Drawings

(56) References Cited

FOREIGN PATENT DOCUMENTS

| WO | WO 2007/064553 | 6/2007 |
| --- | --- | --- |
| WO | WO 2007/070433 | 6/2007 |
| WO | WO 2007/076318 | 7/2007 |
| WO | WO 2007/100610 | 9/2007 |
| WO | WO 2007/109238 | 9/2007 |
| WO | WO 2008/003861 | 1/2008 |
| WO | WO 2008/008453 | 1/2008 |
| WO | WO 2008/013622 | 1/2008 |
| WO | WO 2008/013925 | 1/2008 |
| WO | WO 2008/079279 | 7/2008 |
| WO | WO 2008/091580 | 7/2008 |
| WO | WO 2008/091954 | 7/2008 |
| WO | WO 2009/020534 | 2/2009 |
| WO | WO 2009/055514 | 4/2009 |
| WO | WO 2009/079490 | 6/2009 |
| WO | WO 2009/094407 | 7/2009 |
| WO | WO 2009/094445 | 7/2009 |
| WO | WO 2009/105435 | 8/2009 |
| WO | WO 2009/132785 | 11/2009 |
| WO | WO 2010/037479 | 4/2010 |
| WO | WO 2010/065579 | 6/2010 |
| WO | WO 2010/066353 | 6/2010 |
| WO | WO 2010/126811 | 11/2010 |
| WO | WO 2010/126851 | 11/2010 |
| WO | WO 2010/149275 | 12/2010 |
| WO | WO 2011/018401 | 2/2011 |
| WO | WO 2011/018415 | 2/2011 |
| WO | WO 2011/051243 | 5/2011 |
| WO | WO 2011/051244 | 5/2011 |
| WO | WO 2011/076699 | 6/2011 |
| WO | WO 2011/084985 | 7/2011 |
| WO | WO 2011/134969 | 11/2011 |
| WO | WO 2011/144586 | 11/2011 |
| WO | WO 2011/146182 | 11/2011 |
| WO | WO 2011/147765 | 12/2011 |
| WO | WO 2012/020060 | 2/2012 |
| WO | WO 2012/025557 | 3/2012 |
| WO | WO 2012/055837 | 5/2012 |
| WO | WO 2012/069633 | 5/2012 |
| WO | WO 2012/082580 | 6/2012 |
| WO | WO 2012/104273 | 8/2012 |
| WO | WO 2012/107475 | 8/2012 |
| WO | WO 2012/107477 | 8/2012 |
| WO | WO 2012/171337 | 12/2012 |
| WO | WO 2013/037768 | 3/2013 |
| WO | WO 2013/056911 | 4/2013 |
| WO | WO 2013/056915 | 4/2013 |
| WO | WO 2013/083741 | 6/2013 |
| WO | WO 2013/127784 | 9/2013 |
| WO | WO 2013/127808 | 9/2013 |
| WO | WO 2014/062938 | 4/2014 |
| WO | WO 2014/075873 | 5/2014 |
| WO | WO 2014/075874 | 5/2014 |

OTHER PUBLICATIONS

Jenh, C. et al., "A Selective and Potent CXCR3 Antagonist SCH 546738 Attenuates the Development of Autoimmune Diseases and Delays Graft Rejection," BMC Immunology (2012), vol. 13, No. 2, pp. 1-14.

Lacotte, S. et al., "CXCR3, Inflammation, and Autoimmune Diseases," Ann. N.Y. Academy of Science (2009), vol. 1173, pp. 310-317.

Lammers, K et al., "Gliadin Induces an Increase in Intestinal Permeability and Zonulin Release by Binding to the Cheomokine Receptor CXCR3," Gastroenterology (2008), vol. 135, pp. 194-204.

Mach, F. et al., "Differential Expression of Three T Lymphocyte-activating CXC Chemokines by Human Atheroma-Associated Cells," The Journal of Clinical Investigation (1999), vol. 104, No. 8, pp. 1041-1050.

McGuinness, B. et al., "Novel CXCR3 Antagonist with a Piperazinyl-Piperidine Core," Bioorganic & Medicinal Chemistry Letters (2009) (doi:10.1016/j.bmcl.2009.07.020).

Menke J. et al., "CXCL9, but not CXCL10, Promotes CXCR3-Dependent Immune-Mediated Kidney Disease," J. Am. Soc. Nephrol (2008), vol. 19, pp. 1177-1189.

Mohan, K. et al., "Blockade of Chemokine Receptor CXCR3 Inhibits T Cell Recruitment to Inflamed Joints and Decreases the Severity of Adjuvant Arthritis," The Journal of Immunol (2007), vol. 179, pp. 8463-8469.

Nie, L. et al., "Attenuation of Acute Lung Inflammation Induced by Cigarette Smoke in CXCR3 Knockout Mice," Respiratory Research (2008), vol. 9, No. 82 (10 pages).

Pradelli, E. et al., "Antagonism of Chemokine Receptor CXCR3 Inhibits Osteosarcoma Metastasis to Lungs," Int. J. Cancer (2009), vol. 125, No. 11, 2586-2594.

Prokopowicz, A. et al., "Optimization of a Biaryl Series of CXCR3 Antagonists," $244^{th}$ ACS National Meeting, Philadelphia, U.S. (2012).

Reinhart, P. et al., "Identification of Anti-Inflammatory Targets for Huntington's Disease Using a Brain Slice-Based Screening Assay," Neurobiology of Disease (2011), vol. 43, pp. 248-256.

Remington: The Science and Practice of Pharmacy (21st Edition, 2005) (5 pages, TOC).

Saetta, M. et al., "Increased Expression of the Chemokine Receptor CXCR3 and Its Ligand CXCL10 in Peripheral Airways of Smokers with Chronic Obstructive Pulmonary Disease," Am. J. Respir. Crit. Care Med (2002), vol. 165, pp. 1404-1409.

Sakthivel, S. et al., "CXCL10 Blockade Protects Mice from Cyclophosphamide-Induced Cystitis," Journal of Immune Based Therapies and Vaccines (2008), vol. 6, No. 6 (38 pages).

Singh, U. et al., "CXCL10-Producing Mucosal CD4+ T Cells, NK Cells, and NKT Cells Are Associated with Chronic Colitis in IL-10-/- Mice, Which Can Be Abrogated by Anti-CXCL10 Antibody Inhibition," J Interferon Cytokine Res (2008), vol. 28, No. 1, pp. 31-43.

Tacke, F. et al., "Serum Chemokine Receptor CXCR3 Ligands are Associated with Progression, Organ Dysfunction and Complications of Chronic Liver Diseases," Liver Int (2011), vol. 31, pp. 840-849.

Trentin, L. et al., "The Chemokine Receptor CXCR3 is expressed on Malignant B. Cells and Mediates Chemotaxis," The Journal of Clinical Investigation (1999), vol. 104, No. 1, pp. 115-121.

Van Weering, H. et al., "CXCL10/CXCR3 Signaling in Glia Cells Differentially Affects NMDA-Induced Cell Death in CA and DG Neurons of the Mouse Hippocampus," Hippocampus (2011), vol. 21, pp. 220-232.

Veillard, N. et al., "Differential Influence of Chemokine Receptors CCR2 and CXCR3 in Development of Atheroscloerosis In Vivo," Circulation (2005), vol. 112, pp. 870-878.

Wang, Y. et al., "Camphor Sulfonamide Derivatives as Novel, Potent and Selective CXCR3 Antagonists," Bioorganic & Medicinal Chemistry Letters (2009), vol. 19, pp. 114-118.

Watson, R. et al., "Development of CXCR3 Antagonists. Part 2: Identification of 2-amino(4-piperidinyl)azoles as Potent CXCR3 Antagonists," Bioorganic & Medicinal Chemistry Letters (2007), vol. 17, pp. 6806-6810.

Wijtmans, M. et al., "Towards Small-Molecule CXCR3 Ligands with Clinical Potential," Chem Med Chem (2008), vol. 3, pp. 861-872.

Xia, Meng Qi et al., "Expression of the chemokine receptor CXCR3 on neurons and the elevated expression of its ligand IP-10 in reactive astrocytes: in vitro ERK1/2 activation and role in Alzheimer's disease," Journal of Neuroimmunology (2000), vol. 108, pp. 227-235.

Press, R. et al., "Aberrated Levels of Cerebrospinal Fluid Shemokines in Guillain-Barré Syndrome and Chronic Inflammatory Demyelinating Polyradiculoneuropathy," Journal of Clinical Immunology (2003), vol. 23, pp. 259-267.

Ruschpler, Peter et al., "High CXCR3 expression in synovial mast cells associated with CXCL9 and CXCL10 expression in inflammatory synovial tissues of patients with rheumatoid arthritis," Arthritis Research & Therapy (2003), vol. 5, pp. R241-R252.

Howard, O.M. Zack et al., "Autoantigens signal through chemokine receptors: uveitis antigens induce CXCR3- and CXCR5-expressing lymphocytes and immature dendritic cells to migrate," Blood (2005), vol. 105, pp. 4207-4215.

Loos, Tamara et al., "TLR ligands and cytokines induce CXCR3 ligands in endothelial cells: enhanced CXCL9 in autoimmune arthritis," Laboratory Investigation (2006), vol. 86, pp. 902-916.

(56) References Cited

OTHER PUBLICATIONS

Vergote, David et al., "Proteolytic processing of SDF-1α reveals a change in receptor specificity mediating HIV-associated neurodegeneration," *PNAS* (2006), vol. 103, pp. 19182-19187.
Walser, Tonya et al., "Antagonism of CXCR3 Inhibits Lung Metastasis in a Murine Model of Metastatic Breast Cancer," *Cancer Research* (2006), vol. 66, pp. 7701-7707.
Antonelli, A. et al., "CXCL10 (α) and CCL (β) chemokines in systemic sclerosis—a longitudinal study," *Rheumatology* (2008), vol. 47, pp. 45-49.
Cameron, Cheryl M. et al., "Gene Expression Analysis of Host Innate Immune Responses during Lethal H5N1 Infection in Ferrets," *Journal of Virology* (2008), vol. 82, pp. 11308-11317.
Campanella, Gabriele S.V. et al., "Chemokine receptor CXCR3 and its ligands CXCL9 and CXCL10 are required for the development of murine cerebral malaria," *PNAS*, vol. 105, pp. 4814-4819.
Costa, Claudia et al., "CXCR3 and CCR5 Chemokines in Induced Sputum From Patients With COPD," *Chest* (2008), vol. 133, pp. 26-33.
He, Shan et al., "A New Approach to the Blocking of Alloreactive T Cell-Mediated Grat-versus-Host Disease by In Vivo Administration of Anti-CXCR3 Neutralizing Antibody," *The Journal of Immunology* (2008), vol. 181, pp. 7581-7592.
Maru, Seema V. et al., "Chemokine production and chemokine receptor expression by human glioma cells: Role of CXCL10 in tumour cell proliferation," *Journal of Neuroimmunology* (2008), doi:10.1016/j.jneuroim.2008.04.029.
Suzaki, Y. et al., "A small-molecule compound targeting CCR5 and CXCR3 prevents airway hyperresponsiveness and inflammation," *Eur. Respir. J.* (2008), vol. 31, pp. 783-789.
van Wanrooij, Eva J.A. et al., "CXCR Antagonist NBI-74330 Attenuates Atherosclerotic Plaque Formation in LDL Receptor-Deficient Mice," *Arterioscler. Thromb. Vasc. Biol.* (2008), vol. 28, pp. 251-257.
Busuttil, A. et al., "CXCR3 ligands are augmented during the pathogenesis of pulmonary sarcoidosis," *Eur. Respir. J.* (2009), vol. 34, pp. 676-686.
Cho, J. et al., "Chronic CXCL10 alters neuronal properties in rat hippocampal culture," *Journal of Neuroimmunology* (2009), doi: 10:1016/j.jneuroim.2008.12.007.
Enghard, P. et al., "CXCR3+CD4+T Cells Are Enriched in Inflamed Kidneys and Urine and Provide a New Biomarker for Acute Nephritis Flares in Systemic Lupus Erythematosus Patients," *Arthritis & Rheumatism* (2009), vol. 60, pp. 199-206.
Feferman, T. et al., "Suppression of experimental autoimmune myasthenia gravis by inhibiting the signaling between IFN-γ inducible protein 10 (IP-10) and its receptor CXCR3," *Journal of Neuroimmunology* (2009), doi: 10:1016/j.jneuroim.2009.01.021.
Fulton, A., "The Chemokine Receptors CXCR4 and CXCR3 in Cancer," *Current Oncology Reports* (2009), vol. 11, pp. 125-131.
Steinmetz, Oliver M. et al., "CXCR3 Mediates Renal Th1 and Th17 Immune Response in Murine Lupus Nephritis," *The Journal of Immunology* (2009), doi:10.4049/jimmunol.0802626.
Chen, Shu-Cheng et al., "Expression of chemokine receptor CXCR3 by lymphocytes and plasmacytoid dendritic cells in human psoriatic lesions," *Arch. Dermatol. Res.* (2010), doi:10.1007/s00403-009-0966-2.
Matl, Ivo et al., "Potential Predictive Markers in Protocol Biopsies for Premature Renal Graft Loss," *Kidney Blood Press Res.* (2010), vol. 33, pp. 7-14.
Ogawa, Teruyuki et al., "CXCR3 Binding Chemokine and TNFSF14 Over Expression in Bladder Urothelium of Patients With Ulcerative Interstitial Cystitis," *The Journal of Urology* (2010), vol. 183, pp. 1206-1212.
Schroepf, Sebastian et al., "Strong Overexpression of CXCR3 Axis Components in Childhood Inflammatory Bowel Disease," *Inflamm. Bowel Dis.* (2010, doi:10.1002/ibd.21312.
Sporici, Romeo et al. "CXCR3 blockade inhibits T-cell migration nto the CNS during EAE and prevents development of adoptively transferred, but not actively induced, disease," *Eur. J. Immunol.* (2010), vol. 40, pp. 2751-2761.
Uzawa, Akiyuki et al., "Expression of chemokine receptors on peripheral blood lymphocytes in multiple sclerosis and neuromyelitis optica," *BMC Neurology* (2010), 10:113, http://www.biomedcentral.com/1471-2377/10/113.
Uno, Sae et al., "Expression of chemokines, CXC chemokine ligand 10 (CXCL10) and CXCR3 in the inflamed islets of patients with recent-onset autoimmune type 1 diabetes," *Endocrine Journal* (2010), doi:10.1507/endocrj.K10E-076.
Yoon, Kyung-Chul et al., "Expression of CXCL9, -10, -11, and CXCR3 in the Tear Film and Ocular Surface of Patients with Dry Eye Syndrome," *Investigative Ophthalmology & Visual Science* (2010), vol. 51, pp. 643-650.
Comini-Frota, Elizabeth R. et al., "Evaluation of Serum Levels of Chemokines during Interferon-β Treatment in Multiple Sclerosis Patients," *CNS Drugs* (2011), vol. 25, pp. 971-981.
Lin, Yi et al., "Attenuation of antigen-induced airway hyper-responsiveness and inflammation in CXCR3 knockout mice," *Respiratory Research* (2011), 12:123, http://respiratory-research.com/content/12/1/123.
Liu, Che et al., "Chemokine receptor CXCR3 promotes growth of glioma," *Carcinogenesis* (2010), vol. 32, pp. 129-137.
Seung, Edward et al., "Inhibiting CXCR3-Dependent CD8+ T Cell Trafficking Enhances Tolerance Induction in a Mouse Model of Lung Rejection," *J. Immunol.* (2011), vol. 186, pp. 6830-6838.
Tacke, Frank et al., "Serum chemokine receptor CXCR3 ligands are associated with progression, organ dysfunction and complications of chronic liver diseases," *Liver International* (2011), vol. 31, pp. 840-849.
Crescioli, Clara et al., "Inflammatory response in human skeletal muscle cells: CXCL10 as a potential therapeutic target," *European Journal of Cell Biology* (2011), doi:10.1016/j.ejcb.2011.09.011.
Romagnani, Paola et al., "CXCL10: A candidate biomarker in transplantation," *Clinica Chimica Acta* (2012), doi:10.1016/j.cca.2012.02.009.
Ross, David J. et al., "Type I immune response cytokine-chemokine cascade is associated with pulmonary arterial hypertension," *The Journal of Heart and Lung Transplantation* (2012), doi:10.1016/j.healun.2012.04.008.

4-(BENZOIMIDAZOL-2-YL)-THIAZOLE COMPOUNDS AND RELATED AZA DERIVATIVES

CROSS-REFERENCE TO RELATED APPLICATIONS

This application is the U.S. National Phase of International Patent Application No. PCT/IB2013/050870, filed Feb. 1, 2013, which claims the benefit of priority to International Patent Application No. PCT/IB2012/050489, filed Feb. 2, 2012.

The present invention relates to novel 4-(benzoimidazol-2-yl)-thiazole compounds and related aza-derivatives of Formula (I), and their use as pharmaceuticals. The invention also concerns related aspects including processes for the preparation of the compounds, pharmaceutical compositions containing one or more compounds of Formula (I), and especially their use as CXCR3 receptor modulators.

Chemokine receptors are a group of G-protein coupled receptors (GPCRs) that bind peptidic chemokine ligands with high affinity. The predominant function of chemokine receptors is to guide leukocyte trafficking to lymphoid organs and tissues under resting conditions as well as during inflammation, but a role for certain chemokine receptors on non-hematopoietic cells and their progenitors has also been recognized.

The chemokine receptor CXCR3 is a G-protein coupled receptor binding to the inflammatory chemokines CXCL9 (initially called MIG, monokine induced by interferon-γ [INF-γ]) CXCL10 (IP-10, INF-γ-inducible protein 10), and CXCL11 (I-TAC, INF-γ-inducible T cell α chemo-attractant). CXCR3 is mainly expressed on activated T helper type 1 (Th1) lymphocytes, but is also present on natural killer cells, macrophages, dendritic cells and a subset of B lymphocytes. The three CXCR3 ligands are expressed mainly under inflammatory conditions, expression in healthy tissue is very low. Cells that can express CXCR3 ligands, for instance after exposure to inflammatory cytokines such as interferon-γ or TNF-α, include diverse stromal cells such as endothelial cells, fibroblasts, epithelial cells, keratinocytes but also includes hematopoietic cells such as macrophages and monocytes. The interaction of CXCR3 and its ligands (henceforth referred to as the CXCR3 axis) is involved in guiding receptor bearing cells to specific locations in the body, particularly to sites of inflammation, immune injury and immune dysfunction and is also associated with tissue damage, the induction of apoptosis, cell growth, and angiostasis. CXCR3 and its ligands are upregulated and highly expressed in diverse pathological situations including autoimmune disorders, inflammation, infection, transplant rejection, fibrosis, neurodegeneration and cancer.

A role of the CXCR3 axis in autoimmune disorders is corroborated by several preclinical and clinical observations. Autoimmune disorders in which histological analysis of inflammatory lesions or serum levels of patients revealed elevated levels of CXCR3 ligands or increased numbers of CXCR3 positive cells include rheumatoid arthritis (RA), systemic lupus erythematosus (SLE), lupus nephritis, multiple sclerosis (MS), inflammatory bowel disease (IBD; comprising Crohn's disease and ulcerative colitis), and type I diabetes mellitus (Groom, J. R. & Luster, A. D. Immunol Cell Biol 2011, 89, 207; Groom, J. R. & Luster, A. D. Exp Cell Res 2011, 317, 620; Lacotte, S., Brun, S., Muller, S. & Dumortier, H. Ann N Y Aced Sci 2009, 1173, 310.). As expression of CXCR3 ligands is very low in healthy tissue, the above cited correlative evidence strongly suggest a role for CXCR3 in human autoimmune diseases.

Preclinical disease models performed with CXCR3 deficient mice, mice deficient for one of the CXCR3 ligands or the use of antibodies blocking the function of either CXCR3 or one if its ligands further corroborate a role for the CXCR3 axis in immune pathology. For instance, it has been shown that mice deficient for either CXCR3 or the CXCR3 ligand CXCL9 show reduced pathology in a model for lupus nephritis (Menke, J. et al. J Am Soc Nephrol 2008, 19, 1177). In an animal model for another form of kidney inflammation, interstitial cystitis, administration of an antibody blocking CXCL10 function was shown to reduce pathology in cyclophosphamide-induced cystitis (Sakthivel, S. K. et al. J Immune Based Ther Vaccines 2008, 6, 6.). Similarly, blocking CXCL10 with an antibody reduced pathology in a rat model of rheumatoid arthritis (Mohan, K. & Issekutz, T. B. J Immunol 2007, 179, 8463.). Similarly, in a murine model of inflammatory bowel disease, a blocking antibody against CXCL10 could prevent pathology in a therapeutic setting (Singh, U. P. et al. J Interferon Cytokine Res 2008, 28, 31.) Further, experiments performed with tissue from CXCR3 deficient mice suggests a role for CXCR3 in celiac disease, another autoimmune type disorder (Lammers, K. M. et al. Gastroenterology 2008, 135, 194.)

Inflammatory diseases that are associated with an elevated expression of the CXCR3 axis include chronic obstructive pulmonary disorder (COPD), asthma, sarcoidosis, atherosclerosis and myocarditis (Groom, J. R. & Luster, A. D. Immunol Cell Biol 2011, 89, 207; Groom, J. R. & Luster, A. D. Exp Cell Res 2011, 317, 620).

One study has shown that CXCR3 positive cells are increased in the lungs of smokers with COPD compared to healthy subjects and immunoreactivity for the CXCR3-ligand CXCL10 was present in the bronchiolar epithelium of smokers with COPD but not in the bronchiolar epithelium of smoking and nonsmoking control subjects (Saetta, M. et al. Am J Respir Crit Care Med 2002, 165, 1404.). These findings suggest that the CXCR3 axis may be involved in the immune cell recruitment that occurs in peripheral airways of smokers with COPD. In agreement with these observations, a preclinical study of COPD revealed an attenuation of acute lung inflammation induced by cigarette smoke in CXCR3 deficient mice (Nie, L. et al. Respir Res 2008, 9, 82.).

In one investigation of atherosclerosis, CXCR3 expression was found on all T cells within human atherosclerotic lesions. CXCR3 ligands CXCL9, CXCL10 and CXCL11 were all found in endothelial and smooth muscle cells associated with those lesions, suggesting that they are involved in the recruitment and retention of CXCR3 positive cells, particularly activated T lymphocytes, observed within vascular wall lesions during atherogenesis (Mach, F. et al. J Clin Invest 1999, 104, 1041.).

Preclinical studies further support a role of CXCR3 in the development of atherosclerosis. CXCR3 genetic deletion in mice lacking ApoE results in a significantly reduced atherosclerotic lesion development within abdominal aortas (Veillard, N. R. et al. Circulation 2005, 112, 870.).

A pivotal role for the CXCR3 axis has also been suggested in rejection reactions after organ transplantation and bone marrow transplantation related toxicity (Groom, J. R. & Luster, A. D. Exp Cell Res 2011, 317, 620.). Preclinically, CXCR3 deficient mice show a significant resistance to allograft rejection (Hancock, W. W. et al. J Exp Med 2000, 192, 1515.).

CXCR3 ligand plasma concentrations also positively correlate with diverse liver pathologies, including liver cirrhosis and fibrosis in humans (Tacke, F., et al. Liver Int 2011, 31, 840.) In the field of oncology, blocking the CXCR3 axis has been proposed to help limit the metastatic spread of cancer cells. For instance, administration of the small molecule CXCR3 receptor antagonist AMG487 could limit the metastasis of tumor cells to the lungs (Pradelli, E. et al. Int J Cancer 2009, 125, 2586). Functional evidence for a role of CXCR3 in regulating B-cell chronic lymphocytic leukemia (CLL) was reported by Trentin and coworkers (Trentin, L. et al. J Clin Invest 1999, 104, 115.).

In the central nervous system, blocking the CXCR3 axis may have beneficial effects and prevent neurodegeneration. Increased expression of CXCL10 in the CNS has been demonstrated in ischemia, Alzheimer's disease, multiple sclerosis (MS), and human immunodeficiency virus (HIV)-encephalitis. For example, ex vivo experiments have shown that tissue derived from either CXCR3 or CXCL10 deficient mice, neuronal cell death was diminished after neurotoxic NMDA-treatment when compared to tissue derived from wild type mice (van Weering, H. R. et al. Hippocampus 2011, 21, 220). In a study looking to indentify drug-like molecules that provide neuroprotection against HTT fragment-induced neurodegeneration in a model for Huntington's disease, two CXCR3 receptor antagonists were identified (Reinhart, P. H. et al. Neurobiol Dis 2011, 43, 248.)

It has now surprisingly been found that particular thiazole derivatives substituted in position 4 with a benzoimidazol-2-yl-group are potent CXCR3 modulators which may be useful for the treatment of diseases that are mediated or sustained through the CXCR3 axis, including autoimmune disorders (e.g. rheumatoid arthritis, multiple sclerosis, inflammatory bowel disease, systemic lupus erythematosus, lupus nephritis, interstitial cystitis, celiac disease), inflammatory disorders (e.g. asthma, COPD, atherosclerosis, myocarditis, sarcoidosis), transplantation rejection, fibrosis (e.g. liver cirrhosis), neurodegeneration and conditions involving neuronal death (e.g. Alzheimer's disease, Huntington's disease), and cancer.

1) In a first embodiment, the present invention relates to compounds of Formula (I)

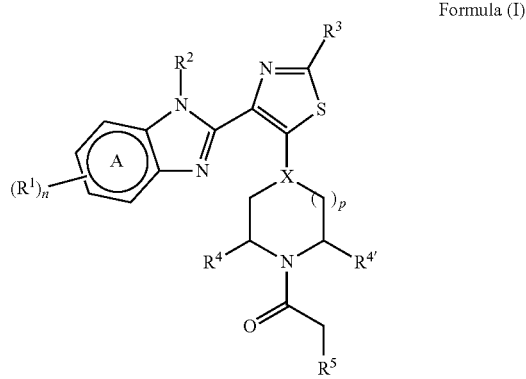

Formula (I)

wherein
X represents CH, or (especially) N;
ring A represents a benzene, pyridine, or pyrimidine ring;
$(R^1)_n$ represents one or two optional substituents each independently selected from the group consisting of $(C_{1-4})$alkyl; $(C_{1-4})$alkoxy; $(C_{1-3})$fluoroalkyl; $(C_{1-3})$fluoroalkoxy; halogen; cyano; $(C_{3-6})$cycloalkyl optionally mono-substituted with hydroxy; $(C_{1-3})$alkoxy-$(C_{1-4})$alkyl; $(C_{1-3})$alkoxy-$(C_{2-4})$alkoxy; hydroxy-$(C_{1-4})$alkyl; hydroxy-$(C_{2-4})$alkoxy; hydroxy; $(C_{1-4})$alkyl-sulfonyl; phenyl; 5-membered heteroaryl optionally substituted with $(C_{1-4})$alkyl; —CO—$(C_{1-4})$alkyl; —CO—$(C_{1-4})$alkoxy; —$(CH_2)_q$—$NR^6R^7$, wherein $R^6$ and $R^7$ independently represent hydrogen or $(C_{1-4})$alkyl, and q represents the integer 0, 1, or 2; and -L-heterocyclyl, wherein -L- represents —O— or —$(CH_2)_r$— wherein r represents the integer 0, 1, or 2, and the heterocyclyl independently is a 4- to 7-membered mono-cyclic saturated ring containing one or two heteroatoms independently selected from nitrogen and oxygen, wherein said heterocyclyl is optionally substituted with one substituent independently selected from $(C_{1-4})$alkyl, $(C_{1-4})$alkoxy, and oxo;

$R^2$ represents hydrogen, $(C_{1-4})$alkyl, $(C_{1-3})$fluoroalkyl; $(C_{1-3})$alkoxy-$(C_{2-4})$alkyl; or hydroxy-$(C_{2-4})$alkyl;

$R^3$ represents hydrogen, $(C_{1-4})$alkyl, $(C_{1-4})$alkoxy; $(C_{1-3})$fluoroalkyl; halogen; $(C_{3-6})$cycloalkyl, wherein optionally one ring carbon atom may be replaced by oxygen; $(C_{1-3})$alkoxy-$(C_{1-4})$alkyl; hydroxy-$(C_{1-4})$alkyl; —$(C_{1-3})$alkylene-COOH; —$(C_{1-3})$alkylene-$NR^8R^9$ wherein $R^8$ and $R^9$ independently represent $(C_{1-3})$alkyl; or 5- or 6-membered monocyclic heteroaryl or phenyl, wherein said 5- or 6-membered monocyclic heteroaryl or phenyl independently is unsubstituted, mono-, or di-substituted wherein the substituents are independently selected from the group consisting of $(C_{1-4})$alkyl; $(C_{1-4})$alkoxy; $(C_{1-3})$fluoroalkyl; $(C_{1-3})$fluoroalkoxy; halogen; and cyano;

$R^4$ and $R^{4'}$ independently represent hydrogen, $(C_{1-4})$alkyl, $(C_{1-3})$alkoxy-$(C_{1-4})$alkyl;

$R^{12}R^{13}N$—$(CH_2)$, wherein $R^{12}$ and $R^{13}$ independently represent $(C_{1-3})$alkyl; or $R^4$ and $R^{4'}$ together form a bridge —$(CH_2)_m$—, wherein m represents the integer 1 or 2;

p represents the integer 1, or 2; and $R^5$ represents aryl or 5- to 10-membered heteroaryl, wherein said aryl or heteroaryl independently is unsubstituted, or mono-, di-, or tri-substituted, wherein the substituents are independently selected from the group consisting of $(C_{1-4})$alkyl; $(C_{1-4})$alkoxy; $(C_{1-3})$fluoroalkyl; $(C_{1-3})$fluoroalkoxy; halogen; cyano; $(C_{1-3})$alkoxy-$(C_{1-4})$alkyl; $(C_{1-3})$alkoxy-$(C_{2-4})$alkoxy; hydroxy; —CO—$(C_{1-4})$alkoxy; hydroxy-$(C_{1-4})$alkyl; —$(C_{1-3})$alkylene-$NR^{10}R^{11}$ wherein $R^{10}$ and $R^{11}$ independently represent $(C_{1-3})$alkyl; phenyl; 5-membered heteroaryl; and heterocyclyl, wherein the heterocyclyl is a 5- to 7-membered mono-cyclic saturated ring containing one or two nitrogen atoms, wherein said heterocyclyl is optionally substituted on a nitrogen having a free valency with $(C_{1-4})$alkyl;

or $R^5$ represents 9- or 10-membered partially aromatic bicyclic heterocyclyl; wherein said heterocyclyl consists of a phenyl or 5- or 6-membered heteroaryl ring (especially a phenyl, pyridine, pyrazole or imidazole ring) which is fused to a 5- or 6-membered saturated or partially unsaturated non-aromatic ring containing one or two heteroatoms independently selected from the group consisting of oxygen, sulphur and nitrogen; wherein said heterocyclyl is unsubstituted, or mono-, di- or tri-substituted, wherein the substituents are independently selected from $(C_{1-4})$alkyl, $(C_{1-4})$alkoxy, halogen and oxo.

2) In a second embodiment, the present invention relates to compounds of Formula (I) which are also compounds of Formula (II)

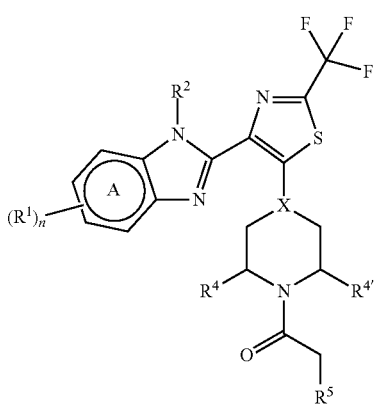

Formula (II)

wherein
ring A represents a benzene, pyridine, or pyrimidine ring;
$(R^1)_n$ represents one or two optional substituents each independently selected from the group consisting of $(C_{1-4})$alkyl; $(C_{1-4})$alkoxy; $(C_{1-3})$fluoroalkyl; $(C_{1-3})$fluoroalkoxy; halogen; cyano; $(C_{3-6})$cycloalkyl optionally mono-substituted with hydroxy; $(C_{1-3})$alkoxy-$(C_{1-4})$alkyl; $(C_{1-3})$alkoxy-$(C_{2-4})$alkoxy; hydroxy-$(C_{1-4})$alkyl; hydroxy-$(C_{2-4})$alkoxy; hydroxy; $(C_{1-4})$alkyl-sulfonyl; phenyl; 5-membered heteroaryl optionally substituted with $(C_{1-4})$alkyl; —CO—$(C_{1-4})$alkyl; —CO—$(C_{1-4})$alkoxy; —$(CH_2)_q$—$NR^6R^7$, wherein $R^6$ and $R^7$ independently represent hydrogen or $(C_{1-4})$alkyl; and q represents the integer 0, 1, or 2; and -L-heterocyclyl, wherein -L- represents —O— or —$(CH_2)_r$— wherein r represents the integer 0, 1, or 2; and the heterocyclyl independently is a 4- to 7-membered mono-cyclic saturated ring containing one or two heteroatoms independently selected from nitrogen and oxygen, wherein said heterocyclyl is optionally substituted with one substituent independently selected from $(C_{1-4})$alkyl, $(C_{1-4})$alkoxy, and oxo;
$R^2$ represents hydrogen, $(C_{1-4})$alkyl, or $(C_{1-3})$alkoxy-$(C_{2-4})$alkyl;
$R^4$ represents hydrogen; and $R^{4'}$ represents methyl; wherein the carbon atom to which $R^{4'}$ is attached to is preferably in absolute (R)-configuration; or
$R^4$ and $R^{4'}$ both represent hydrogen; and
$R^5$ represents
aryl, wherein said aryl is unsubstituted, or mono-, di-, or tri-substituted, wherein the substituents are independently selected from the group consisting of $(C_{1-4})$alkyl; $(C_{1-4})$alkoxy; $(C_{1-3})$fluoroalkyl; $(C_{1-3})$fluoroalkoxy; halogen; cyano; $(C_{1-3})$alkoxy-$(C_{1-4})$alkyl; $(C_{1-3})$alkoxy-$(C_{2-4})$alkoxy; hydroxy; hydroxy-$(C_{1-4})$alkyl; 5-membered heteroaryl; and heterocyclyl, wherein the heterocyclyl is a 5- to 7-membered mono-cyclic saturated ring containing one or two nitrogen atoms, wherein said heterocyclyl is optionally substituted on a nitrogen having a free valency with $(C_{1-4})$alkyl; or
5- or 6-membered heteroaryl, wherein said heteroaryl independently is unsubstituted, or mono-, di-, or tri-substituted, wherein the substituents are independently selected from the group consisting of $(C_{1-4})$alkyl; $(C_{1-4})$alkoxy; $(C_{1-3})$fluoroalkyl; $(C_{1-3})$fluoroalkoxy; halogen; cyano; $(C_{1-3})$alkoxy-$(C_{1-4})$alkyl; $(C_{1-3})$alkoxy-$(C_{2-4})$alkoxy; hydroxy; —CO—$(C_{1-4})$alkoxy; hydroxy-$(C_{1-4})$alkyl; —$(C_{1-3})$alkylene-$NR^{10}R^{11}$ wherein $R^{16}$ and $R^{11}$ independently represent $(C_{1-3})$alkyl; phenyl; and heterocyclyl, wherein the heterocyclyl is a 5- to 7-membered mono-cyclic saturated ring containing one or two nitrogen atoms, wherein said heterocyclyl is optionally substituted on a nitrogen having a free valency with $(C_{1-4})$alkyl; or 9- or 10-membered heteroaryl, wherein said heteroaryl independently is unsubstituted, or mono-, di-, or tri-substituted, wherein the substituents are independently selected from the group consisting of $(C_{1-4})$alkyl; $(C_{1-4})$alkoxy; $(C_{1-3})$fluoroalkyl; $(C_{1-3})$fluoroalkoxy; halogen; cyano; $(C_{1-3})$alkoxy-$(C_{1-4})$alkyl; $(C_{1-3})$alkoxy-$(C_{2-4})$alkoxy; hydroxy; and hydroxy-$(C_{1-4})$alkyl; or
9- or 10-membered partially aromatic bicyclic heterocyclyl; wherein said heterocyclyl consists of a phenyl or 6-membered heteroaryl ring (especially a phenyl or pyridine ring) which is fused to a 5- or 6-membered saturated or partially unsaturated non-aromatic ring containing one nitrogen atom, and optionally one further heteroatom selected from the group consisting of oxygen and nitrogen; wherein said heterocyclyl is attached to the rest of the molecule through said non-aromatic nitrogen atom; wherein said heterocyclyl group is unsubstituted, or mono-, di- or tri-substituted, wherein the substituents are independently selected from $(C_{1-4})$alkyl, $(C_{1-4})$alkoxy, halogen and oxo; or
9-membered partially aromatic bicyclic heterocyclyl; wherein said heterocyclyl consists of a pyrazole or imidazole ring which is fused to a 6-membered saturated or partially unsaturated non-aromatic ring containing one or two heteroatoms independently selected from the group consisting of oxygen and nitrogen; wherein said heterocyclyl is attached to the rest of the molecule through an aromatic nitrogen atom of said pyrazole or imidazole ring; wherein said heterocyclyl group is unsubstituted, or mono-, or di-substituted, wherein the substituents are independently selected from $(C_{1-4})$alkyl, and oxo; or
9- or 10-membered partially aromatic bicyclic heterocyclyl; wherein said heterocyclyl consists of a phenyl or 6-membered heteroaryl ring (especially a phenyl, or pyridine ring) which is fused to a 5- or 6-membered saturated or partially unsaturated non-aromatic ring containing one or two heteroatoms independently selected from the group consisting of oxygen, sulphur and nitrogen; wherein said heterocyclyl is attached to the rest of the molecule through an aromatic carbon atom; wherein said heterocyclyl group is unsubstituted, or mono-, or di-substituted, wherein the substituents are independently selected from $(C_{1-4})$alkyl, $(C_{1-4})$alkoxy, halogen and oxo.

3) In a third embodiment, the present invention relates to compounds of Formula (I) which are also compounds of Formula (III)

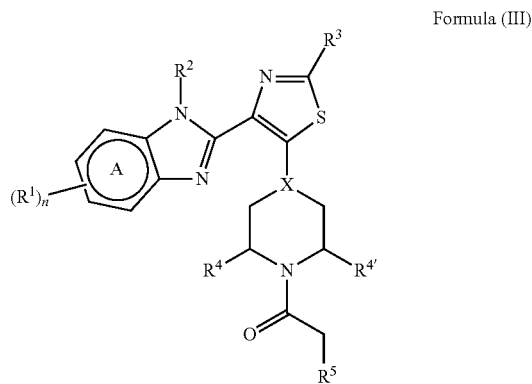

Formula (III)

wherein
ring A represents a benzene, pyridine, or pyrimidine ring;
$(R^1)_n$ represents one or two optional substituents each independently selected from the group consisting of $(C_{1-4})$alkyl; methoxy; trifluoromethyl; trifluoromethoxy; halogen; cyano; cyclopropyl optionally mono-substituted with hydroxy; methoxy-ethoxy; hydroxy-$(C_{1-2})$alkyl; hydroxy-ethoxy; hydroxy; methyl-sulfonyl; phenyl; 5-membered heteroaryl selected from triazolyl, and oxadiazolyl which is optionally substituted with methyl; —CO-methyl; —CO-methoxy; —$(CH_2)_q$—$NR^6R^7$, wherein $R^6$ and $R^7$ independently represent hydrogen or methyl; and q represents the integer 0, 1, or 2; —O-(azetidin-3-yl); and —$(CH_2)_r$-heterocyclyl, wherein r represents the integer 0, 1 or 2, and wherein the heterocyclyl is independently selected from pyrrolidinyl, piperidinyl, morpholinyl, piperazinyl, and tetrahydropyranyl, and wherein said heterocyclyl is optionally substituted with one substituent independently selected from methyl, methoxy, and oxo;

$R^2$ represents hydrogen, methyl, or 2-methoxy-ethyl;

$R^3$ represents hydrogen, methyl, ethyl, trifluoromethyl; chloro; bromo; cyclopropyl; oxetanyl; hydroxy-$(C_{1-2})$alkyl; —$(CH_2)$—$N(CH_3)_2$; or phenyl, which is unsubstituted, or mono-substituted wherein the substituent is selected from the group consisting of methyl; methoxy; and fluoro; (especially $R^3$ represents hydrogen or trifluoromethyl; notably trifluoromethyl);

$R^4$ represents hydrogen; and $R^{4'}$ represents hydrogen, methyl, ethyl, methoxy-methyl, or dimethylamino-methyl; or both $R^4$ and $R^{4'}$ represent methyl; and $R^5$ represents aryl or 5-, 6-, 9, or 10-membered heteroaryl, wherein said aryl or heteroaryl independently is unsubstituted, or mono-, di-, or tri-substituted, wherein the substituents are independently selected from the group consisting of unsubstituted, or mono-, di-, or tri-substituted, wherein the substituents are independently selected from the group consisting of methyl; methoxy; trifluoromethyl; halogen; cyano; hydroxy-methyl; —$CH_2N(CH_3)_2$; phenyl; and piperidin-4-yl optionally substituted on the nitrogen with methyl;

or $R^5$ represents 9- or 10-membered partially aromatic bicyclic heterocyclyl; wherein said heterocyclyl consists of a phenyl, pyridine, pyrazole or imidazole ring which is fused to a 5- or 6-membered saturated or partially unsaturated non-aromatic ring containing one or two heteroatoms independently selected from the group consisting of oxygen and nitrogen; wherein said heterocyclyl is unsubstituted, or mono-, di- or tri-substituted, wherein the substituents are independently selected from methyl, halogen and oxo.

4) In a fourth embodiment, the present invention relates to compounds of Formula (I) which are also compounds of Formula (IV)

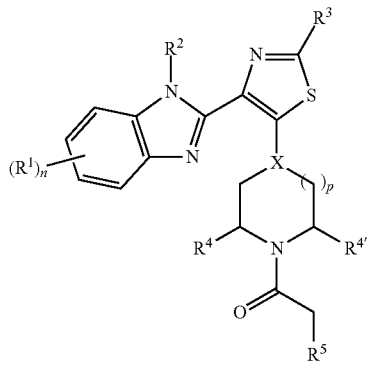

Formula (IV)

wherein
X represents CH, or (especially) N;
$(R^1)_n$ represents one or two optional substituents each independently selected from the group consisting of $(C_{1-4})$alkyl; $(C_{1-4})$alkoxy; $(C_{1-3})$fluoroalkyl; $(C_{1-3})$fluoroalkoxy; halogen; cyano; $(C_{3-6})$cycloalkyl; $(C_{1-3})$alkoxy-$(C_{1-4})$alkyl; $(C_{1-3})$alkoxy-$(C_{2-4})$alkoxy; hydroxy-$(C_{1-4})$alkyl; hydroxy-$(C_{2-4})$alkoxy; hydroxy; $(C_{1-4})$alkyl-sulfonyl; and phenyl;

$R^2$ represents hydrogen, $(C_{1-4})$alkyl, $(C_{1-3})$fluoroalkyl; $(C_{1-3})$alkoxy-$(C_{2-4})$alkyl; or hydroxy-$(C_{2-4})$alkyl;

$R^3$ represents hydrogen, $(C_{1-4})$alkyl, $(C_{1-4})$alkoxy; $(C_{1-3})$fluoroalkyl; halogen; $(C_{3-6})$cycloalkyl, wherein optionally one ring carbon atom may be replaced by oxygen; $(C_{1-3})$alkoxy-$(C_{1-4})$alkyl; hydroxy-$(C_{1-4})$alkyl; or 5- or 6-membered monocyclic heteroaryl or phenyl, wherein said 5- or 6-membered monocyclic heteroaryl or phenyl independently is unsubstituted, mono-, or di-substituted wherein the substituents are independently selected from the group consisting of $(C_{1-4})$alkyl; $(C_{1-4})$alkoxy; $(C_{1-3})$fluoroalkyl; $(C_{1-3})$fluoroalkoxy; halogen; and cyano;

$R^4$ and $R^{4'}$ independently represent hydrogen, $(C_{1-4})$alkyl, $(C_{1-3})$alkoxy-$(C_{1-4})$alkyl; or $R^4$ and $R^{4'}$ together form a bridge —$(CH_2)_m$—, wherein m represents the integer 1 or 2;

p represents the integer 1, or 2; and $R^5$ represents aryl or 5- to 10-membered heteroaryl, wherein said aryl or heteroaryl independently is unsubstituted, or mono-, di-, or tri-substituted, wherein the substituents are independently selected from the group consisting of $(C_{1-4})$alkyl; $(C_{1-4})$alkoxy; $(C_{1-3})$fluoroalkyl; $(C_{1-3})$fluoroalkoxy; halogen; cyano; $(C_{1-3})$alkoxy-$(C_{1-4})$alkyl; $(C_{1-3})$alkoxy-$(C_{2-4})$alkoxy; hydroxy;

or $R^5$ represents 9- or 10-membered partially aromatic bicyclic heterocyclyl; wherein said heterocyclyl is a phenyl or 6-membered heteroaryl ring (especially a phenyl or pyridine ring) which is fused to a 5- or 6-membered saturated or partially unsaturated non-aromatic ring containing one or two heteroatoms independently selected from the group consisting of oxygen, sulphur and nitrogen; wherein said heterocyclyl is unsubstituted, or mono-, or di-substituted, wherein the substituents are independently selected from $(C_{1-4})$alkyl, $(C_{1-4})$alkoxy, halogen and oxo.

5) In a fifth embodiment, the present invention relates to compounds of Formula (I) which are also compounds of Formula (V)

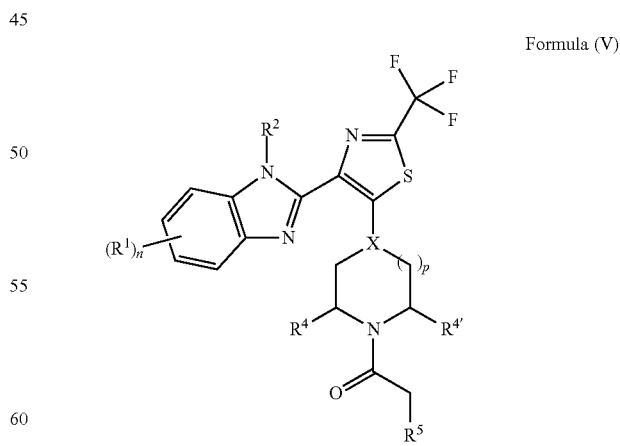

Formula (V)

wherein
X represents N; and $R^4$ and $R^{4'}$ both represent hydrogen; or
X represents N; and $R^4$ and $R^{4'}$ both represent methyl; or
X represents N; $R^4$ represents hydrogen; and $R^{4'}$ represents methyl.

$(R^1)_n$ represents one or two optional substituents each independently selected from the group consisting of $(C_{1-4})$alkyl; $(C_{1-4})$alkoxy; $(C_{1-3})$fluoroalkyl; $(C_{1-3})$fluoroalkoxy; halogen; cyano; $(C_{3-6})$cycloalkyl; $(C_{1-3})$alkoxy-$(C_{1-4})$alkyl; $(C_{1-3})$alkoxy-$(C_{2-4})$alkoxy; hydroxy-$(C_{1-4})$alkyl; hydroxy-$(C_{2-4})$alkoxy; hydroxy; $(C_{1-4})$alkyl-sulfonyl; and phenyl;

$R^2$ represents hydrogen, or $(C_{1-4})$alkyl; and $R^5$ represents 5- to 10-membered heteroaryl, wherein said heteroaryl independently is unsubstituted, or mono-, di-, or tri-substituted, wherein the substituents are independently selected from the group consisting of $(C_{1-4})$alkyl; $(C_{1-4})$alkoxy; $(C_{1-3})$ fluoroalkyl; $(C_{1-3})$fluoroalkoxy; halogen; cyano; $(C_{1-3})$alkoxy-$(C_{1-4})$alkyl; $(C_{1-3})$ alkoxy-$(C_{2-4})$alkoxy; and hydroxy; or $R^5$ represents 9- or 10-membered partially aromatic bicyclic heterocyclyl; wherein said heterocyclyl is attached to the rest of the molecule through a non-aromatic nitrogen atom; wherein said heterocyclyl group is unsubstituted, or mono-, or di-substituted, wherein the substituents are independently selected from $(C_{1-4})$alkyl, $(C_{1-4})$alkoxy, halogen and oxo; or $R^5$ represents 9- or 10-membered partially aromatic bicyclic heterocyclyl; wherein said heterocyclyl is attached to the rest of the molecule through an aromatic carbon atom; wherein said heterocyclyl group is unsubstituted, or mono-, or di-substituted, wherein the substituents are independently selected from $(C_{1-4})$alkyl, $(C_{1-4})$alkoxy, halogen and oxo.

Definitions provided herein are intended to apply uniformly to the compounds of formulae (I), (II), (III) (IV) and (V) as defined in any one of embodiments 1) to 47), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein.

The compounds of Formula (I) as defined in any one of embodiments 1) to 47), may contain one or more stereogenic or asymmetric centers, such as one or more asymmetric carbon atoms. The compounds of Formula (I) as defined in any one of embodiments 1) to 47), may thus be present as mixtures of stereoisomers or in stereoisomerically enriched form, preferably as pure stereoisomers. Mixtures of stereoisomers may be separated in a manner known to a person skilled in the art.

The term "enriched", for example when used in the context of enantiomers is understood in the context of the present invention to mean especially that the respective enantiomer is present in a ratio (mutatis mutandis:purity) of at least 70:30, and notably of at least 90:10 (mutatis mutandis:purity of 70%/90%) with respect to the respective other enantiomer. Preferably the term refers to the respective essentially pure enantiomer. The term "essentially", for example when used in a term such as "essentially pure" is understood in the context of the present invention to mean especially that the respective stereoisomer/composition/compound etc. consists in an amount of at least 90, especially of at least 95, and notably of at least 99 percent by weight of the respective pure stereoisomer/composition/compound etc.

In this patent application, a bond drawn as a dotted line shows the point of attachment of the radical drawn. For example, the radical drawn below

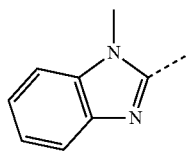

is the 1-methyl-1H-benzoimidazol-2-yl group.

In some instances, the compounds of formulae (I), (II), (III) and (IV) may contain tautomeric forms. Such tautomeric forms are encompassed in the scope of the present invention. For example, in case the present compounds contain heteroaromatic aromatic rings containing unsubstituted ring nitrogen atoms having a free valency such as imidazolyl, benzoimidazolyl, or [1,2,4]-triazolyl, such rings may be present in tautomeric forms. For example, the group benzoimidazol-2-yl represents the tautomeric forms 1H-benzoimidazol-2-yl and 3H-benzoimidazol-2-yl.

For avoidance of any doubt, the term "$(R^1)_n$ representing one or two optional substituents" means that n represents the integer 0 (i.e. $(R^1)_n$ is absent), 1 (i.e. one $R^1$ is present), or 2 (i.e. two $R^1$ are present). A substituent $R^1$ may be attached to ring A in ortho or meta position to one of the bridgehead atoms. In case a substituent $R^1$ is referred to as being in ortho-position to one of the bridgehead atoms, this means that said substituent is attached in position 4 or 7 of, for example, a benzoimidazole moiety. Likewise, if a substituent $R^1$ is referred to as being in meta-position to one of the bridgehead atoms, this means that said substituent is attached in position 5 or 6 of a benzoimidazole moiety. It is understood that, in case $R^2$ represents hydrogen, for example, a benzoimidazol-2-yl moiety of the present compounds may be present in the tautomeric forms 1H-benzoimidazol-2-yl and 3H-benzoimidazol-2-yl. Thus, the ortho positions 4 and 7, respectively the two meta positions 5 and 6, of such benzoimidazol-2-yl moiety are considered identical. For example, the group 4-methyl-1H-benzoimidazol-2-yl is understood to be the same as 7-methyl-1H-benzoimidazol-2-yl and 4-methyl-3H-benzoimidazol-2-yl and 7-methyl-3H-benzoimidazol-2-yl. Likewise 1H-imidazo[4,5-b]pyridin-2-yl is tautomeric to 3H-imidazo[4,5-b]pyridin-2-yl; 1H-imidazo[4,5-c]pyridin-2-yl is tautomeric to 3H-imidazo[4,5-c]pyridin-2-yl; and 7H-purin-8-yl is tautomeric to 9H-purin-8-yl.

The term "halogen" means fluorine, chlorine, or bromine, preferably fluorine or chlorine.

The term "alkyl", used alone or in combination, refers to a straight or branched saturated hydrocarbon chain containing one to six carbon atoms. The term "$(C_{x-y})$alkyl" (x and y each being an integer), refers to an alkyl group as defined before containing x to y carbon atoms. For example a $(C_{1-4})$alkyl group contains from one to four carbon atoms. Examples of $(C_{1-4})$alkyl groups are methyl, ethyl, propyl, isopropyl, n-butyl, isobutyl, sec.-butyl and tert.-butyl. Preferred are methyl and ethyl. Most preferred is methyl. For the substituents $R^6$, $R^7$, $R^8$, $R^9$, $R^{10}$, $R^{11}$, $R^{12}$ and $R^{13}$ the term "$(C_{1-4})$alkyl" preferably means methyl. For substituents of aryl, heteroaryl, or heterocyclyl groups, the term "$(C_{1-4})$alkyl" preferably means methyl.

The term "$(C_{1-3})$alkylene", used alone or in combination, refers to a bivalent straight or branched saturated hydrocarbon chain containing one to three carbon atoms. Examples are bivalent methylene (—$CH_2$—), ethylene (—$CH_2$—$CH_2$—) or propylene (—$CH_2$—$CH_2$—$CH_2$—) groups.

The term "—$(CH_2)_m$—, wherein m represents the integer 1 or 2" refers to a bivalent methylene (—$CH_2$—), or ethylene (—$CH_2$—$CH_2$—) group.

The term "alkoxy", used alone or in combination, refers to an alkyl-O— group wherein the alkyl group is as defined before. The term "$(C_{x-y})$alkoxy" (x and y each being an integer) refers to an alkoxy group as defined before containing x to y carbon atoms. For example a $(C_{1-4})$alkoxy group means a group of the formula $(C_{1-4})$alkyl-O— in which the term "$(C_{1-4})$alkyl" has the previously given significance. Examples of $(C_{1-4})$alkoxy groups are methoxy, ethoxy, n-propoxy, isopropoxy, n-butoxy, isobutoxy, sec.-butoxy and tert.-butoxy. Preferred is methoxy. For substituents of aryl, heteroaryl, or heterocyclyl groups, the term "$(C_{1-4})$alkoxy" preferably means methoxy.

The term "$(C_{1-3})$fluoroalkyl" refers to an alkyl group as defined before containing one to three carbon atoms in which one or more (and possibly all) hydrogen atoms have been replaced with fluorine. The term "$(C_{x-y})$fluoroalkyl" (x and y each being an integer) refers to a fluoroalkyl group as defined before containing x to y carbon atoms. For example a $(C_{1-3})$ fluoroalkyl group contains from one to three carbon atoms in which one to seven hydrogen atoms have been replaced with fluorine. Representative examples of $(C_{1-3})$fluoroalkyl groups include trifluoromethyl, 2-fluoroethyl, 2,2-difluoroethyl, 2,2,2-trifluoroethyl, and difluoromethyl. Preferred are $(C_1)$fluoroalkyl groups such as trifluoromethyl or difluoromethyl.

The term "$(C_{1-3})$fluoroalkoxy" refers to an alkoxy group as defined before containing one to three carbon atoms in which one or more (and possibly all) hydrogen atoms have been replaced with fluorine. The term "$(C_{x-y})$fluoroalkoxy" (x and y each being an integer) refers to a fluoroalkoxy group as defined before containing x to y carbon atoms. For example a $(C_{1-3})$ fluoroalkoxy group contains from one to three carbon atoms in which one to seven hydrogen atoms have been replaced with fluorine. Representative examples of $(C_{1-3})$ fluoroalkoxy groups include trifluoromethoxy, difluoromethoxy and 2,2,2-trifluoroethoxy. Preferred are $(C_1)$fluoroalkoxy groups such as trifluoromethoxy and difluoromethoxy. Most preferred is trifluoromethoxy.

The term "cycloalkyl", used alone or in combination, refers to a saturated carbocyclic ring containing three to seven carbon atoms. The term "$(C_{x-y})$cycloalkyl" (x and y each being an integer), refers to a cycloalkyl group as defined before containing x to y carbon atoms. For example a $(C_{3-7})$cycloalkyl group contains from three to seven carbon atoms. Examples of cycloalkyl groups are cyclopropyl, cyclobutyl, cyclopentyl, cyclohexyl, and cycloheptyl. Preferred are cyclopropyl, cyclopentyl and cyclohexyl.

The term "cycloalkyl, wherein optionally one ring carbon atom may be replaced by oxygen", refers to a cycloalkyl group as defined before. In addition, one ring carbon atom of said cycloalkyl may be replaced by an oxygen atom, such as in an oxetan-3-yl group.

The term "cycloalkyl, optionally mono-substituted with hydroxy", refers to a cycloalkyl group as defined before. In addition, one ring carbon atom of said cycloalkyl may be substituted with a hydroxy group. An example is 1-hydroxy-cyclopropyl-1-yl.

The term "aryl", used alone or in combination, means phenyl or naphthyl. The above-mentioned aryl groups are unsubstituted or substituted as explicitly defined.

For the substituent "$R^5$" representing aryl, the term especially means phenyl. Such aryl group is unsubstituted, or mono-, di-, or tri-substituted hydroxyl as explicitly defined. Especially such aryl group is unsubstituted, or mono-, di-, or tri-substituted, wherein the substituents are independently selected from the group consisting of $(C_{1-4})$alkyl; $(C_{1-4})$alkoxy; $(C_{1-3})$fluoroalkyl; $(C_{1-3})$fluoroalkoxy; halogen; cyano; $(C_{1-3})$alkoxy-$(C_{1-4})$alkyl; $(C_{1-3})$alkoxy-$(C_{2-4})$alkoxy; hydroxy; —CO—$(C_{1-4})$alkoxy; hydroxy-$(C_{1-4})$alkyl; 5-membered heteroaryl; and heterocyclyl, wherein the heterocyclyl is a 5- to 7-membered mono-cyclic saturated ring containing one or two nitrogen atoms, wherein said heterocyclyl is optionally substituted on a nitrogen having a free valency with $(C_{1-4})$alkyl (notably it is unsubstituted, or mono-, or di-substituted, wherein the substituents are independently selected from the group consisting of $(C_{1-4})$alkyl; $(C_{1-4})$alkoxy; and halogen). Examples of "$R^5$" representing aryl are 2-fluoro-4-methoxy-phenyl, naphthalen-2-yl, naphthalen-1-yl, 2-(4-methyl-piperazin-1-yl)-phenyl, 2-([1,2,3]-triazol-2-yl)-phenyl, 3-([1,2,3]-triazol-2-yl)-phenyl, and 2-(pyrazol-1-yl)-phenyl.

Examples of "$R^3$" representing "phenyl which is unsubstituted, mono-, or di-substituted wherein the substituents are independently selected from the group consisting of $(C_{1-4})$ alkyl; $(C_{1-4})$alkoxy; $(C_{1-3})$fluoroalkyl; $(C_{1-3})$fluoroalkoxy; halogen; and cyano" are especially phenyl groups which are unsubstituted, or mono-substituted wherein the substituents are selected from the group consisting of $(C_{1-4})$alkyl; $(C_{1-4})$ alkoxy; $(C_{1-3})$fluoroalkyl; $(C_{1-3})$fluoroalkoxy; and halogen (especially $(C_{1-4})$alkyl; $(C_{1-4})$alkoxy). Examples are phenyl, 2-methylphenyl, 3-methylphenyl, 4-methylphenyl, 2-fluorophenyl, and 2-methoxyphenyl.

The term "heteroaryl", used alone or in combination, means a 5- to 10-membered monocyclic or bicyclic aromatic ring containing one to a maximum of four heteroatoms, each independently selected from oxygen, nitrogen and sulfur. Examples of such heteroaryl groups are furanyl, oxazolyl, isoxazolyl, oxadiazolyl, thiophenyl, thiazolyl, isothiazolyl, thiadiazolyl, pyrrolyl, imidazolyl, pyrazolyl, triazolyl, pyridinyl, pyrimidinyl, pyridazinyl, pyrazinyl, indolyl, isoindolyl, benzofuranyl, isobenzofuranyl, benzothiophenyl, indazolyl, benzoimidazolyl, benzoxazolyl, benzisoxazolyl, benzothiazolyl, benzoisothiazolyl, benzotriazolyl, benzoxadiazolyl, benzothiadiazolyl, quinolinyl, isoquinolinyl, naphthyridinyl, cinnolinyl, quinazolinyl, quinoxalinyl, phthalazinyl, pyrrolopyridinyl, pyrazolopyridinyl, pyrazolopyrimidinyl, pyrrolopyrazinyl, imidazopyridinyl, imidazopyridazinyl, and imidazothiazolyl. The above-mentioned heteroaryl groups are unsubstituted or substituted as explicitly defined.

In case a substitutent "$R^1$" represents "5-membered heteroaryl optionally substituted with $(C_{1-4})$alkyl", the term "heteroaryl" means the above-mentioned 5-membered groups. Examples of such 5-membered heteroaryl groups as used for $R^1$ are especially nitrogen containing 5-membered heteroaryl groups such as for example oxazolyl, isoxazolyl, oxadiazolyl, thiazolyl, isothiazolyl, thiadiazolyl, pyrrolyl, imidazolyl, pyrazolyl, and triazolyl; wherein said groups are optionally substituted with $(C_{1-4})$alkyl (especially methyl). Especially such groups are oxadiazolyl optionally substituted with $(C_{1-4})$alkyl (notably [1,2,4]-oxadiazol-3-yl optionally substituted with methyl, in particular 5-methyl-[1,2,4]-oxadiazol-3-yl), and triazolyl optionally substituted with $(C_{1-4})$ alkyl (in particular [1H-[1,2,4]-triazol-1-yl).

In case "$R^5$" represents "heteroaryl", the term means the above-mentioned groups. In one embodiment, the term especially refers to pyrazolyl (especially pyrazol-1-yl), triazolyl (especially [1,2,4]-triazol-1-yl, [1,2,3]-triazol-1-yl, [1,2,3]-triazol-2-yl), indazolyl (especially indazol-1-yl, indazol-3-yl), pyrrolopyridinyl (especially pyrrolo[2,3-c]pyridin-1-yl, pyrrolo[2,3-b]pyridin-1-yl), indolyl (especially indol-1-yl, 1H-indol-3-yl, 1H-indol-4-yl), imidazopyridinyl (especially imidazo[4,5-c]pyridin-1-yl, imidazo[4,5-c]pyridin-3-yl, imidazo[4,5-b]pyridin-3-yl, imidazo[1,2-a]pyridin-3-yl), benzoimidazolyl (especially benzoimidazol-1-yl, benzoimidazol-2-yl), imidazopyridazinyl (especially imidazo[1,2-b]pyridazin-2-yl), pyrazolopyridinyl (especially pyrazolo[3,4-b]pyridin-1-yl, pyrazolo[3,4-b]pyridin-1-yl), pyrrolopyrazinyl (especially pyrrolo[2,3-b]pyrazin-5-yl); and in addition, the term refers to thiazolyl (especially thiazol-4-yl, thiazol-5-yl), pyridinyl (especially pyridin-3-yl, pyridine-2-yl, pyridine-4-yl), benzothiophenyl (especially benzo[b]thiophen-3-yl), benzofuranyl (especially benzofuran-3-yl), benzoisoxazolyl (especially benzo[d]isoxazol-3-yl), quinolinyl (especially quinolin-7-yl, quinolin-8-yl), quinoxalinyl (especially quinoxalin-6-yl); and in addition: oxadiazolyl (especially [1,3,4]oxadiazol-3-yl).

In a further sub-embodiment of "$R^5$" representing "heteroaryl", the term preferably means a 5-membered monocyclic or a 9-membered bicyclic aromatic ring containing one to (a maximum of) three (especially 1 or 2) heteroatoms, wherein one of said heteroatoms is nitrogen, and the remaining heteroatoms, if present, are independently selected from oxygen, nitrogen and sulfur. In a further sub-embodiment, such heteroaryl as used for the substituent "$R^5$" is preferably attached to the rest of the molecule at said nitrogen atom. Examples of such particular heteroaryl groups are pyrazol-1-yl, [1,2,4]-triazol-1-yl, indazol-1-yl, pyrrolo[2,3-c]pyridin-1-yl, pyrrolo[2,3-b]pyridin-1-yl, indol-1-yl, imidazo[4,5-c]pyridin-1-yl, imidazo[4,5-c]pyridin-3-yl, imidazo[4,5-b]pyridin-3-yl, benzoimidazol-1-yl, pyrazolo[3,4-b]pyridin-1-yl, pyrazolo[3,4-b]pyridin-2-yl, and pyrrolo[2,3-b]pyrazin-5-yl. The above-mentioned heteroaryl groups as used for the substitutent "$R^5$" are unsubstituted or substituted as explicitly defined. In particular, the above-mentioned heteroaryl groups are unsubstituted, or mono-, di-, or tri-substituted (especially unsubstituted, or mono-, or di-substituted), wherein the substituents are independently selected from the group consisting of $(C_{1-4})$alkyl; $(C_{1-4})$alkoxy; $(C_{1-3})$fluoroalkyl; $(C_{1-3})$fluoroalkoxy; halogen; cyano; $(C_{1-3})$alkoxy-$(C_{1-4})$alkyl; $(C_{1-3})$alkoxy-$(C_{2-4})$alkoxy; and hydroxy. In a sub-embodiment, substituents are selected from the group consisting of $(C_{1-4})$alkyl; $(C_{1-4})$alkoxy; $(C_{1-3})$fluoroalkyl; halogen; and cyano. In another embodiment, the substituents are selected from the group consisting of $(C_{1-4})$alkyl and halogen.

Particular examples of heteroaryl groups as used for the substitutent "$R^5$" are 3-methyl-pyrazol-1-yl, 3,5-dimethyl-pyrazol-1-yl, 3-trifluoromethyl-pyrazol-1-yl, 3,5-dimethyl-[1,2,4]triazol-1-yl, indazol-1-yl, pyrrolo[2,3-c]pyridin-1-yl, pyrrolo[2,3-b]pyridin-1-yl, 6-chloro-pyrrolo[2,3-b]pyridin-1-yl, 7-chloro-pyrrolo[2,3-c]pyridin-1-yl, 3-chloro-pyrrolo[2,3-b]pyridin-1-yl, 2-methyl-pyrrolo[2,3-b]pyridin-1-yl, 3-methyl-pyrrolo[2,3-b]pyridin-1-yl, 6-methyl-pyrrolo[2,3-b]pyridin-1-yl, 6-methoxy-pyrrolo[2,3-b]pyridin-1-yl, indol-1-yl, 5-fluoro-indol-1-yl, 6-fluoro-indol-1-yl, 7-fluoro-indol-1-yl, 4-chloro-indol-1-yl, 2-methyl-indol-1-yl, 7-methyl-indol-1-yl, 3-cyano-indol-1-yl, 7-cyano-indol-1-yl, 5-fluoro-3-methyl-indol-1-yl, 5,6-dichloro-indol-1-yl, 4-methoxy-indol-1-yl, 5-chloro-6-methoxy-indol-1-yl, 6-trifluoromethyl-indol-1-yl, imidazo[4,5-c]pyridin-1-yl, imidazo[4,5-c]pyridin-3-yl, imidazo[4,5-b]pyridin-3-yl, pyrazolo[3,4-b]pyridin-1-yl, pyrazolo[3,4-b]pyridin-2-yl, 3-chloro-pyrrolo[2,3-b]pyrazin-5-yl, benzoimidazol-1-yl, 2-methyl-benzoimidazol-1-yl, and 2-trifluoromethyl-benzoimidazol-1-yl; and, in addition, 2-methyl-thiazol-4-yl, 2,4-dimethyl-thiazol-5-yl, 1H-indazol-3-yl, indol-3-yl, indol-4-yl, 5-chloro-1H-indol-3-yl, 5-fluoro-1H-indol-3-yl, 1-methyl-1H-indol-3-yl, 5-methoxy-1H-indol-3-yl, 5-chloro-1H-benzoimidazol-2-yl, pyridin-3-yl, 6-methoxy-benzofuran-3-yl, benzo[b]thiophen-3-yl, 5-chloro-benzo[b]thiophen-3-yl, benzo[d]isoxazol-3-yl, 5-methoxy-benzo[d]isoxazol-3-yl, 5-methyl-benzo[d]isoxazol-3-yl, quinoxalin-6-yl, quinolin-7-yl, quinolin-8-yl, 2-methyl-imidazo[1,2-a]pyridin-3-yl, and 6-chloro-imidazo[1,2-b]pyridazin-2-yl. Further particular examples are pyrazol-1-yl, 4-chloro-pyrazol-1-yl, 5-methyl-pyrazol-1-yl, 4-methyl-pyrazol-1-yl, 3-methoxycarbonyl-pyrazol-1-yl, 4-dimethylaminomethyl-3-methyl-pyrazol-1-yl, 4-dimethylaminomethyl-3,5-dimethyl-pyrazol-1-yl, 3-phenyl-pyrazol-1-yl, 5-phenyl-pyrazol-1-yl, 4-piperidin-4-yl-pyrazol-1-yl, 4-(1-methyl-piperidin-4-yl)-pyrazol-1-yl, [1,2,4]triazol-1-yl, 3-bromo-[1,2,4]triazol-1-yl, 3-methyl-[1,2,4]triazol-1-yl, 5-methyl-[1,2,4]triazol-1-yl, 3-dimethylaminomethyl-5-methyl-[1,2,4]triazol-1-yl, [1,2,3]triazol-2-yl, 4-phenyl-[1,2,3]triazol-1-yl, and 2-hydroxymethyl-pyrrolo[2,3-b]pyridin-1-yl; and, in addition, 5-methyl-[1,3,4]oxadiazol-3-yl, 5-phenyl-[1,3,4]oxadiazol-3-yl, 2-methyl-pyridin-5-yl, 2,6-dimethyl-pyridin-4-yl, and 4,6-dimethyl-pyridin-2-yl.

The term "heterocyclyl", wherein "heterocyclyl independently is a 4- to 7-membered mono-cyclic saturated ring containing one or two heteroatoms independently selected from nitrogen and oxygen", as used for substituents $R^1$, means for example azetidinyl, pyrrolidinyl, piperidinyl, piperazinyl, morpholinyl, and tetrahydropyran-4-yl groups; wherein said heterocyclyl is optionally substituted with one substituent independently selected from $(C_{1-4})$alkyl, $(C_{1-4})$alkoxy, and oxo. Particular examples are azetidin-3-yl, pyrrolidin-1-yl, 3-methoxy-pyrrolidin-1-yl, 2-oxo-pyrrolidin-1-yl, piperidin-4-yl, 1-methyl-piperidin-4-yl, piperidin-1-yl, 4-methyl-piperazin-1-yl, morpholin-4-yl, and tetrahydropyran-4-yl.

The term "heterocyclyl", wherein "heterocyclyl is a 5- to 7-membered mono-cyclic saturated ring containing one or two nitrogen atoms", as used for substituents of aromatic groups $R^5$, means for example pyrrolidinyl, piperidinyl, and piperazinyl groups, notably piperidinyl and piperazinyl groups; wherein said heterocyclyl is optionally substituted on a nitrogen having a free valency with $(C_{1-4})$alkyl (especially methyl). Particular examples are pyrrolidin-1-yl, 1-methyl-pyrrolidin-3-yl, and notably the 6-membered heterocyclyl groups piperidin-4-yl, 1-methyl-piperidin-4-yl, piperidin-1-yl, and 4-methyl-piperazin-1-yl.

The term "heterocyclyl", wherein "heterocyclyl" is a "9- or 10-membered partially aromatic bicyclic heterocyclyl", as used for the substituent $R^5$, means a phenyl or 5- or 6-membered heteroaryl ring (notably containing one or two nitrogen atoms) as defined before (especially a phenyl, pyridine, pyrazole or imidazole ring) which is fused to a 5- or 6-membered saturated or partially unsaturated non-aromatic ring containing one or two heteroatoms independently selected from the group consisting of oxygen, sulphur and nitrogen (especially oxygen and nitrogen). Examples of such groups comprising a phenyl or 6-membered heteroaryl ring are 2,3-dihydro-benzofuranyl, 4H-benzo[1,3]dioxinyl, benzo[1,3]dioxolyl, 2,3-dihydro-benzo[1,4]dioxinyl, 2H-chromenyl, chromanyl, and especially the nitrogen containing groups 1,3-dihydroindol-1-yl, 1,3-dihydro-benzoimidazol-1-yl, 3H-benzooxazol-3-yl, 3,4-dihydro-1H-quinolin-1-yl, 2,3-dihydro-4H-benzo[1,4]oxazin-4-yl, 1,3-dihydro-imidazo[4,5-b]pyridin-3-yl, and 3H-oxazolo[4,5-b]pyridine-3-yl. In addition, examples of such heterocyclyl comprising a 5-membered heteroaryl ring are 1,4,6,7-tetrahydro-pyrazolo[4,3-c]pyridinyl and 4,5,6,7-tetrahydro-imidazo[4,5-c]pyridinyl groups such as especially 4,5,6,7-tetrahydro-pyrazolo[4,3-c]pyridin-1-yl, 4,5,6,7-tetrahydro-pyrazolo[4,3-c]pyridin-2-yl, 4,5,6,7-tetrahydro-imidazo[4,5-c]pyridin-3-yl, and 4,5,6,7-tetrahydro-imidazo[4,5-c]pyridin-1-yl. For avoidance of any doubt, in case a saturated 5- or 6-membered non-aromatic ring is fused to said phenyl or 5- or 6-membered heteroaryl ring, it is understood that such ring comprises the aromatic bond between the bridgehead atoms but no further unsaturated bond; whereas in case a partially unsaturated 5- or 6-membered non-aromatic ring is fused to said phenyl or 5- or 6-membered heteroaryl ring, it is understood that such ring comprises the aromatic bond between the bridgehead atoms and at least one further unsaturated bond. Preferred are those groups wherein within the above meaning the fused ring is saturated.

Particular examples of fragments forming a saturated or partially unsaturated non-aromatic 5- or 6-membered ring fused to a phenyl or a 6-membered heteroaryl ring are —$(CH_2)_s$—O—, wherein s represents the integer 2 or 3; —CH=CH—$CH_2$—O—; —O—$(CH_2)_t$—O—, wherein t represents the integer 1 or 2; —O—CH=CH—O—; and especially the nitrogen containing fragments —$(CH_2)_u$—N—, wherein u represents the integer 2 or 3; —$(CH_2)_v$—(CO)—N—, wherein v represents the integer 1 or 2; —(CO)—$(CH_2)_2$—N—; —O—$(CH_2)_2$—N—; —N—(CO)—N—; —O—(CO)—N—; —O—$(CH_2)$—(CO)—N—. In addition, a particular example of a fragment forming a saturated or partially unsaturated non-aromatic 6-membered ring fused to a 5-membered heteroaryl ring is —$(CH_2)_2$—N—$(CH_2)$—. Especially, fragments forming a saturated or partially unsaturated non-aromatic 5- or 6-membered ring are —$(CH_2)$—N—, wherein u represents the integer 2 or 3; —$(CH_2)_v$—(CO)—N—, wherein v represents the integer 1 or 2; —(CO)—$(CH_2)_2$—N—; —O—$(CH_2)_2$—N—; —N—(CO)—N—; —O—(CO)—N—; —O—$(CH_2)$—(CO)—N, and, in addition, —$(CH_2)_2$—N—$(CH_2)$—. It is well understood that in the above fragments, if present, a nitrogen atom having a free valency may be attached to the rest of the molecule, or may be unsubstituted (i.e. it is NH) or substituted (especially with $(C_{1-4})$alkyl) as explicitly defined. Preferably, a heterocyclyl group as defined before may be attached to the rest of the molecule either through an aromatic carbon atom part of a phenyl or 6-membered heteroaryl ring, or through an aromatic nitrogen atom part of a 5-membered heteroaryl ring, or through a non-aromatic nitrogen atom part of said 5- or 6-membered saturated or partially unsaturated non-aromatic ring.

In a further preferred embodiment, the term "9- or 10-membered partially aromatic bicyclic heterocyclyl" as used for the substituent $R^5$ refers to a 9- or 10-membered partially aromatic bicyclic heterocyclyl; wherein said heterocyclyl is attached to the rest of the molecule either through an aromatic nitrogen atom part of a 5-membered heteroaryl ring (i.e. said 5-membered heteroaryl group which is fused to the 6-membered saturated or partially unsaturated non-aromatic ring contains at least one aromatic nitrogen atom having a free valency, wherein said nitrogen atom is attached through the —$CH_2$-group to the rest of the molecule); or through a non-aromatic nitrogen atom (i.e. said fused 5- or 6-membered saturated or partially unsaturated non-aromatic ring contains at least one nitrogen atom, wherein said nitrogen atom is attached through the —$CH_2$-group to the rest of the molecule; wherein, in a sub-embodiment, said nitrogen is preferably in alpha position to the aromatic ring; in a further sub-embodiment the aromatic moiety of such heterocyclyl linked through a non-aromatic nitrogen atom to the rest of the molecule is preferably phenyl or pyridine, especially phenyl). Examples of the first sort of such groups are 4,5,6,7-tetrahydro-pyrazolo[4,3-c]pyridin-1-yl, 4,5,6,7-tetrahydro-pyrazolo[4,3-c]pyridin-2-yl, 4,5,6,7-tetrahydro-imidazo[4,5-c]pyridin-3-yl, and 4,5,6,7-tetrahydro-imidazo[4,5-c]pyridin-1-yl; examples of the latter are 1,3-dihydroindol-1-yl, 1,3-dihydro-benzoimidazol-1-yl, 3H-benzooxazol-3-yl, 3,4-dihydro-quinolin-1-yl, 2,3-dihydro-benzo[1,4]oxazin-4-yl, 1,3-dihydro-imidazo[4,5-b]pyridin-3-yl, and 3H-oxazolo[4,5-b]pyridine-3-yl. The above mentioned heterocyclyl groups are unsubstituted, or mono-, di- or tri-substituted as explicitly defined.

In case an oxo substituent is present, such oxo substituent is preferably in alpha position to a non-aromatic heteroatom, especially in alpha position to a non-aromatic nitrogen which is attached to the rest of the molecule. In case said fused 5- or 6-membered saturated or partially unsaturated non-aromatic ring contains two heteroatoms which are separated by one carbon atom (e.g. 1,3-dihydro-benzoimidazol-1-yl, 3H-benzooxazol-3-yl, or 1,3-dihydro-imidazo[4,5-b]pyridin-3-yl), preferably an oxo substituent is present on said separating carbon atom, wherein the remaining substituents, if present, are selected from $(C_{1-4})$alkyl, $(C_{1-4})$alkoxy, and halogen (notably $(C_{1-4})$alkyl).

Notably, the above mentioned heterocyclyl groups are unsubstituted, or mono-substituted with oxo in alpha position to a non-aromatic nitrogen which is attached to the rest of the molecule, or, in case a ring nitrogen atom having a free valency is present, mono-substituted with $(C_{1-4})$alkyl on said nitrogen atom, or di-substituted, wherein one substituent is oxo in alpha position to a non-aromatic nitrogen which is attached to the rest of the molecule, and the remaining substituent is selected from $(C_{1-4})$alkyl, $(C_{1-4})$alkoxy, and halogen (notably $(C_{1-4})$alkyl, especially on a nitrogen atom having a free valency), or tri-substituted, wherein one substituent is oxo in alpha position to a non-aromatic nitrogen which is attached to the rest of the molecule, and the remaining substituents are both methyl or both fluoro in alpha position to said oxo substituent. In case said heterocyclyl comprises a 5-membered heteroaryl ring such groups are preferably substituted with $(C_{1-4})$alkyl on a non-aromatic nitrogen atom.

Particular examples of such heterocyclyl groups are 3H-benzooxazol-2-one-3-yl, 2,3-dihydro-pyrrolo[2,3-b]pyridin-1-yl, 1,3-dihydro-imidazo[4,5-b]pyridin-2-one-3-yl, 1,3-dihydro-benzoimidazol-2-one-1-yl, 3-methyl-1,3-dihydro-benzoimidazol-2-one-1-yl, 2,3-dihydro-indol-1-yl, 1,3-dihydro-indol-2-one-1-yl, 2,3-dihydro-benzo[1,4]oxazin-4-yl, 4H-benzo[1,4]oxazin-3-one-4-yl, 3,4-dihydro-2H-quinolin-1-yl, 3,4-dihydro-1H-quinolin-2-one-1-yl, and 2,3-dihydro-1H-quinolin-4-one-1-yl; and, in addition, 2,3-dihydro-benzofuran-5-yl, 4H-benzo[1,4]oxazin-3-one-6-yl. Further particular examples are 5-methyl-4,5,6,7-tetrahydropyrazolo[4,3-c]pyridin-1-yl, 5-methyl-4,5,6,7-tetrahydropyrazolo[4,3-c]pyridin-2-yl, 5-methyl-4,5,6,7-tetrahydroimidazo[4,5-c]pyridin-3-yl, 5-methyl-4,5,6,7-tetrahydroimidazo[4,5-c]pyridin-1-yl, 2-oxo-3H-oxazolo[4,5-b]pyridin-3-yl, 4-fluoro-2-oxo-3H-benzooxazol-3-yl, 2,3-dioxo-1H-indol-1-yl, 4-methyl-2-oxo-3H-benzooxazol-3-yl, 3,3-difluoro-2-oxo-1,3-dihydro-indol-1-yl, and 3,3-dimethyl-2-oxo-1,3-dihydro-indol-1-yl.

The term "cyano" refers to a group —CN.

The term "oxo" refers to the group =O, i.e. a carbon atom substituted with oxo is a carbonyl group —(C=O)—.

The term "$(C_{x-y})$alkoxy-$(C_{x'-y'})$alkyl" refers to a $(C_{x-y})$alkyl-O—$(C_{x'-y'})$alkyl group wherein the alkyl groups are as defined before. An example is 2-methoxy-ethyl.

The term "$(C_{x-y})$alkoxy-$(C_{x'-y'})$alkoxy" refers to a $(C_{x-y})$alkyl-O—$(C_{x'-y'})$alkyl-O— group wherein the alkyl groups are as defined before. An example is 2-methoxy-ethoxy.

An example of a —CO—$(C_{1-4})$alkyl group is —CO—$CH_3$; likewise, an example of a —CO—$(C_{1-4})$alkoxy group is; —CO—$OCH_3$.

Further embodiments of the invention are described hereinafter:

6) A further embodiment of the invention relates to compounds of Formula (I) according to embodiments 1) or 4), wherein X represents N.

7) Another embodiment relates to compounds according to any one of embodiments 1) to 6), wherein $(R^1)_n$ represents one or two optional substituents each independently selected from the group consisting of $(C_{1-4})$alkyl; $(C_{1-4})$alkoxy; $(C_{1-3})$fluoroalkyl; $(C_{1-3})$fluoroalkoxy; halogen; cyano; hydroxy; $(C_{1-3})$alkoxy-$(C_{2-4})$alkoxy; hydroxy-$(C_{1-4})$alkyl; hydroxy-$(C_{2-4})$alkoxy; $(C_{1-4})$alkyl-sulfonyl; and phenyl.

8) Another embodiment relates to compounds according to any one of embodiments 1) to 6), wherein $(R^1)_n$ represents one or two optional substituents (especially one optional substituent) each independently selected from the group consisting of $(C_{1-4})$alkyl; $(C_{1-4})$alkoxy; $(C_{1-3})$fluoroalkyl; $(C_{1-3})$fluoroalkoxy; halogen; cyano; hydroxy; and hydroxy-$(C_{1-4})$alkyl (especially methyl, chloro, hydroxy, and hydroxymethyl).

9) Another embodiment relates to compounds according to any one of embodiments 1) to 6), wherein $(R^1)_n$ represents one or two optional substituents (especially one optional substituent) each independently selected from the group consisting of $(C_{1-4})$alkyl; $(C_{1-4})$alkoxy; halogen; hydroxy; and hydroxy-$(C_{1-4})$alkyl (especially methyl, chloro, hydroxy, and hydroxymethyl).

10) Another embodiment relates to compounds according to any one of embodiments 1) to 3), or 6), wherein
  A. $(R^1)_n$ is absent, or
  B. $(R^1)_n$ represents one or two substituents; wherein
     one of said substituents is attached in meta position to one of the bridgehead atoms of ring A, wherein such meta substituent is independently selected from the group consisting of $(C_{1-4})$alkyl; $(C_{1-4})$alkoxy; $(C_{1-3})$fluoroalkyl; $(C_{1-3})$ fluoroalkoxy; halogen; cyano; $(C_{3-6})$cycloalkyl optionally mono-substituted with hydroxy; $(C_{1-3})$alkoxy-$(C_{1-4})$alkyl; $(C_{1-3})$alkoxy-$(C_{2-4})$alkoxy; hydroxy-$(C_{1-4})$alkyl; hydroxy-$(C_{2-4})$alkoxy; hydroxy; $(C_{1-4})$alkyl-sulfonyl; phenyl; 5-membered heteroaryl optionally substituted with $(C_{1-4})$alkyl; —CO—$(C_{1-4})$alkyl; —CO—$(C_{1-4})$alkoxy; —$(CH_2)_q$—$NR^6R^7$, wherein $R^6$ and $R^7$ independently represent hydrogen or $(C_{1-4})$alkyl; and q represents the integer 0, 1, or 2; and -L-heterocyclyl, wherein -L- represents —O— or —$(CH_2)_r$— wherein r represents the integer 0, 1, or 2; and the heterocyclyl independently is a 4- to 7-membered mono-cyclic saturated ring containing one or two heteroatoms independently selected from nitrogen and oxygen, wherein said heterocyclyl is optionally substituted with one substituent independently selected from $(C_{1-4})$alkyl, $(C_{1-4})$alkoxy, and oxo;
     and the other of said substituents, if present, is attached in the other meta or in ortho position to the bridgehead atoms of ring A, wherein such substituent in meta or ortho position is independently selected from the group consisting of $(C_{1-4})$alkyl; $(C_{1-4})$alkoxy; $(C_{1-3})$ fluoroalkyl; halogen; and cyano; or
  C. $(R^1)_n$ represents one substituent; wherein said substituent is attached in ortho position to one of the bridgehead atoms of ring A, wherein said ortho substituent is selected from the group consisting of $(C_{1-4})$alkyl; $(C_{1-4})$alkoxy; $(C_{1-3})$fluoroalkyl; halogen; and hydroxy.

11) Another embodiment relates to compounds according to any one of embodiments 1) to 3), or 6), wherein
  A. $(R^1)_n$ is absent, or
  B. $(R^1)_n$ represents one or two substituents; wherein
     one of said substituents is attached in meta position to one of the bridgehead atoms of ring A, wherein such meta substituent is independently selected from the group consisting of $(C_{1-4})$alkyl; methoxy; trifluoromethyl; trifluoromethoxy; halogen; cyano; cyclopropyl optionally mono-substituted with hydroxy; methoxy-ethoxy; hydroxy-$(C_{1-2})$alkyl; hydroxy-ethoxy; hydroxy; methyl-sulfonyl; phenyl; 5-membered heteroaryl selected from triazolyl, and oxadiazolyl which is optionally substituted with methyl; —CO-methyl; —CO-methoxy; —$(CH_2)_q$—$NR^6R^7$, wherein $R^6$ and $R^7$ independently represent hydrogen or methyl; and q represents the integer 0, 1, or 2; —O-(azetidin-3-yl); and —$(CH_2)_r$-heterocyclyl, wherein r represents the integer 0, 1 or 2, and wherein the heterocyclyl is independently selected from pyrrolidinyl, piperidinyl, morpholinyl, piperazinyl, and tetrahydropyranyl, and wherein said heterocyclyl is optionally substituted with one substituent independently selected from methyl, methoxy, and oxo;
     and the other of said substituents, if present, is attached in the other meta or in ortho position to one of the bridgehead atoms of ring A, wherein such substituent in meta or ortho position is independently selected from the group consisting of methyl; methoxy; trifluoromethyl; and halogen; or
  C. $(R^1)_n$ represents one substituent; wherein said substituent is attached in ortho position to one of the bridgehead atoms of ring A, wherein said ortho substituent is selected from the group consisting of methyl; methoxy; trifluoromethyl; fluoro; chloro; and hydroxy.

12) Another embodiment relates to compounds according to any one of embodiments 1) to 3), or 6), wherein
  A. $(R^1)_n$ is absent, or
  B. $(R^1)_n$ represents one substituent; wherein said substituent is attached in meta position to one of the bridgehead atoms of ring A; wherein said meta substituent is independently selected from the group consisting of $(C_{1-3})$ fluoroalkyl; $(C_{1-3})$ fluoroalkoxy; halogen; $(C_{3-6})$cycloalkyl optionally mono-substituted with hydroxy; $(C_{1-3})$alkoxy-$(C_{2-4})$alkoxy; hydroxy-$(C_{1-4})$alkyl; hydroxy-$(C_{2-4})$alkoxy; 5-membered heteroaryl optionally substituted with $(C_{1-4})$alkyl; —$(CH_2)_q$—$NR^6R^7$, wherein $R^6$ and $R^7$ independently represent hydrogen or $(C_{1-4})$alkyl; and q represents the integer 0, 1, or 2; and -L-heterocyclyl, wherein -L- represents —O— or —$(CH_2)_r$— wherein r represents the integer 0, 1, or 2; and the heterocyclyl independently is a 4- to 7-membered mono-cyclic saturated ring containing one or two heteroatoms independently selected from nitrogen and oxygen, wherein said heterocyclyl is optionally substituted with one substituent independently selected from $(C_{1-4})$alkyl, $(C_{1-4})$alkoxy, and oxo; or
  C. $(R^1)_n$ represents two halogen substituents; or
  D. $(R^1)_n$ represents one substituent; wherein said substituent is attached in ortho position to one of the bridgehead atoms of ring A, wherein said ortho substituent is selected from the group consisting of $(C_{1-4})$alkyl; $(C_{1-4})$alkoxy; $(C_{1-3})$fluoroalkyl; halogen; and hydroxy.

13) Another embodiment relates to compounds according to any one of embodiments 1) to 3), or 6), wherein the group

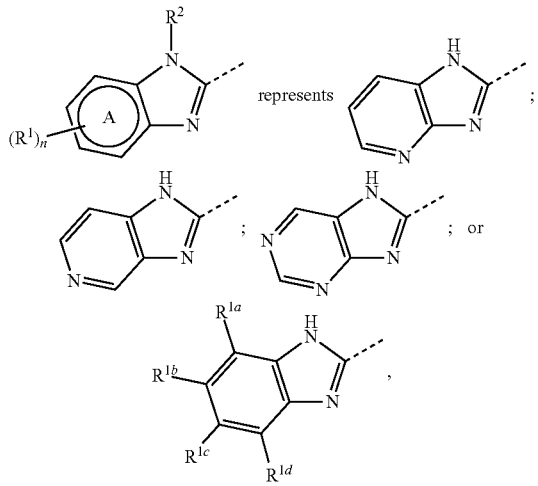

represents wherein
$R^{1a}$, $R^{1b}$, $R^{1c}$ and $R^{1d}$ all represent hydrogen;
or
$R^{1a}$ and $R^{1d}$ both represent hydrogen;
one of $R^{1b}$ and $R^{1c}$ is selected from the group consisting of $(C_{1-4})$alkyl; $(C_{1-4})$alkoxy; $(C_{1-3})$fluoroalkyl; $(C_{1-3})$fluoroalkoxy; halogen; cyano; $(C_{3-6})$cycloalkyl optionally mono-substituted with hydroxy; $(C_{1-3})$alkoxy-$(C_{1-4})$alkyl; $(C_{1-3})$alkoxy-$(C_{2-4})$alkoxy; hydroxy-$(C_{1-4})$alkyl; hydroxy-$(C_{2-4})$alkoxy; hydroxy; $(C_{1-4})$alkyl-sulfonyl; phenyl; 5-membered heteroaryl optionally substituted with $(C_{1-4})$alkyl; —CO—$(C_{1-4})$alkyl; —CO—$(C_{1-4})$alkoxy; —$(CH_2)_q$—$NR^6R^7$, wherein $R^6$ and $R^7$ independently represent hydrogen or $(C_{1-4})$alkyl; and q represents the integer 0, 1, or 2; and -L-heterocyclyl, wherein -L- represents —O— or —$(CH_2)_r$— wherein r represents the integer 0, 1, or 2; and the heterocyclyl independently is a 4- to 7-membered mono-cyclic saturated ring containing one or two heteroatoms independently selected from nitrogen and oxygen, wherein said heterocyclyl is optionally substituted with one substituent independently selected from $(C_{1-4})$alkyl, $(C_{1-4})$alkoxy, and oxo;
and the other of $R^{1b}$ and $R^{1c}$ is selected from the group consisting of hydrogen, $(C_{1-4})$alkyl; $(C_{1-4})$alkoxy; $(C_{1-3})$fluoroalkyl; and halogen;
or
one of $R^{1a}$ and $R^{1d}$ is halogen; and the remaining of $R^{1a}$, $R^{1b}$, $R^{1c}$ and $R^{1d}$ all represent hydrogen.

14) Another embodiment relates to compounds according to any one of embodiments 1) to 3), or 6), wherein the group

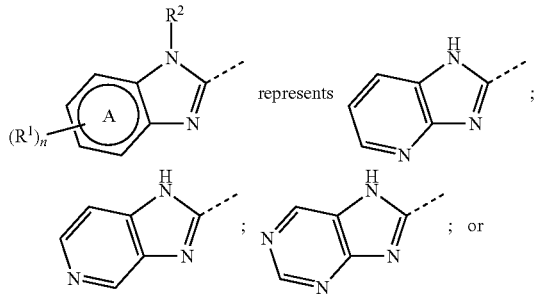

represents

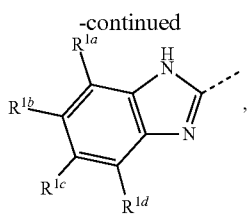

wherein
$R^{1a}$, $R^{1b}$, $R^{1c}$ and $R^{1d}$ all represent hydrogen;
or
one of $R^{1b}$ and $R^{1c}$ is selected from the group consisting of $(C_{1-4})$alkyl; methoxy; trifluoromethyl; trifluoromethoxy; halogen; cyano; cyclopropyl optionally mono-substituted with hydroxy; methoxy-ethoxy; hydroxy-$(C_{1-2})$alkyl; hydroxy-ethoxy; hydroxy; methyl-sulfonyl; phenyl; 5-membered heteroaryl selected from triazolyl, and oxadiazolyl which is optionally substituted with methyl; —CO-methyl; —CO-methoxy; —$(CH_2)_q$—$NR^6R^7$, wherein $R^6$ and $R^7$ independently represent hydrogen or methyl; and q represents the integer 0, 1, or 2; —O-(azetidin-3-yl); and —$(CH_2)_r$-heterocyclyl, wherein r represents the integer 0, 1 or 2, and wherein the heterocyclyl is independently selected from pyrrolidinyl, piperidinyl, morpholinyl, piperazinyl, and tetrahydropyranyl, and wherein said heterocyclyl is optionally substituted with one substituent independently selected from methyl, methoxy, and oxo;
and the remaining of $R^{1a}$, $R^{1b}$, $R^{1c}$ and $R^{1d}$ all represent hydrogen
or
one of $R^{1b}$ and $R^{1c}$ is selected from the group consisting of methyl; methoxy; and halogen;
one of $R^{1a}$ and $R^{1d}$, or the other of $R^{1b}$ and $R^{1c}$ is selected from the group consisting of methyl; methoxy; and halogen;
and the remaining of $R^{1a}$, $R^{1b}$, $R^{1c}$ and $R^{1d}$ all represent hydrogen;
or
one of $R^{1a}$ and $R^{1d}$ is selected from the group consisting of methyl; methoxy; trifluoromethyl; halogen and hydroxy;
and the remaining of $R^{1a}$, $R^{1b}$, $R^{1c}$ and $R^{1d}$ all represent hydrogen.

15) Another embodiment relates to compounds according to any one of embodiments 1) to 14), wherein $R^2$ represents hydrogen, or $(C_{1-4})$alkyl.

16) Another embodiment relates to compounds according to any one of embodiments 1) to 14), wherein $R^2$ represents hydrogen.

17) Another embodiment relates to compounds according to any one of embodiments 1) to 3) or 6) to 15), wherein the ring A is selected from a benzene, pyridine, or a pyrimidine ring such that the group

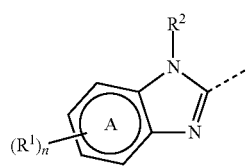

represents a benzoimidazol-2-yl, an imidazo[4,5-b]pyridin-2-yl, an imidazo[4,5-c]pyridin-2-yl, or a purin-8-yl group; wherein said groups independently are unsubstituted or substituted with $R^2$ and/or $(R^1)_n$ as explicitly defined (wherein, in a sub-embodiment, imidazo[4,5-b]pyridin-2-yl, imidazo[4,5-c]pyridin-2-yl, and purin-8-yl groups are especially unsubstituted).

18) Another embodiment relates to compounds according to any one of embodiments 1) to 3), or 6), wherein the group

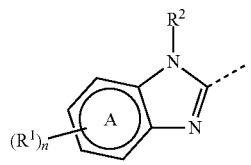

represents a group independently selected from any one of the following groups A, B, C, and D:

A.

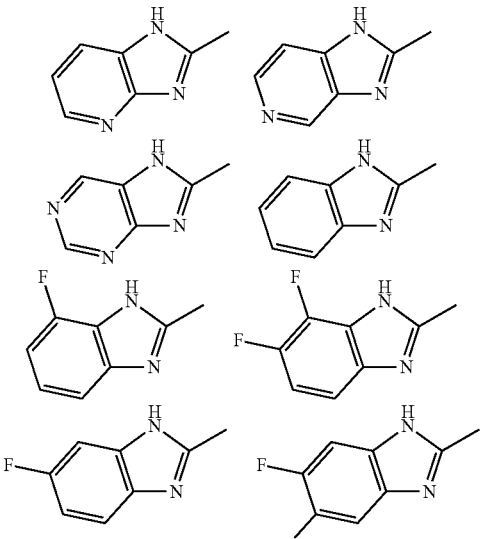

B.

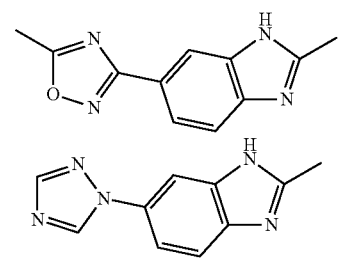

C.

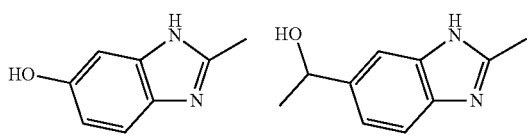

D.

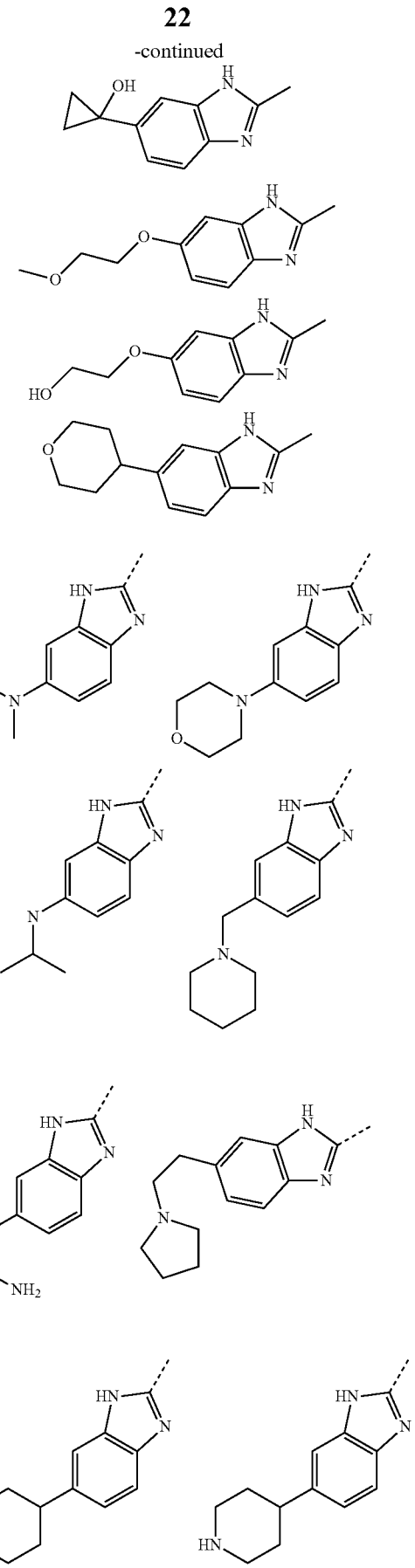

-continued

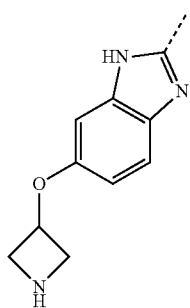

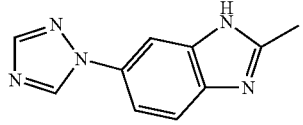

wherein it is understood that the above-listed benzoimidazole, imidazo[4,5-b]pyridine and purine moieties may be present in tautomeric forms.

20) Another embodiment relates to compounds according to any one of embodiments 1) to 6), wherein the group

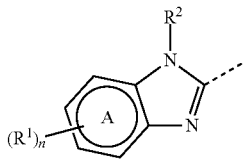

respectively the group wherein it is understood that the above-listed benzoimidazole, imidazo[4,5-b]pyridine, imidazo[4,5-c]pyridine and purine moieties may be present in tautomeric forms.

19) Another embodiment relates to compounds according to any one of embodiments 1) to 3), or 6), wherein the group represents a group independently selected from any one of the following groups A, B, and C:

A.

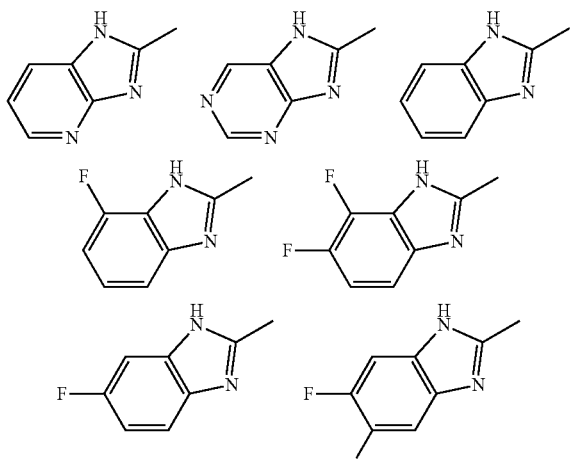

B.

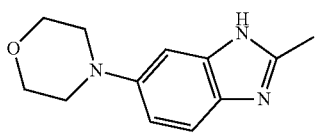

C.

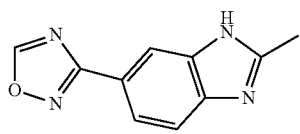

is a group selected from the group consisting of benzoimidazol-2-yl, 4-fluoro-1H-benzoimidazol-2-yl, 5-fluoro-1H-benzoimidazol-2-yl, 4,5-difluoro-1H-benzoimidazol-2-yl, 5,6-difluoro-1H-benzoimidazol-2-yl, 5-chloro-1H-benzoimidazol-2-yl, 5,6-dichloro-1H-benzoimidazol-2-yl, 5-chloro-6-fluoro-1H-benzoimidazol-2-yl, 5-chloro-6-methyl-1H-benzoimidazol-2-yl, 5-chloro-4-methyl-1H-benzoimidazol-2-yl, 5-chloro-6-trifluoromethyl-1H-benzoimidazol-2-yl, 5-methoxy-1H-benzoimidazol-2-yl, 7-methoxy-1H-benzoimidazol-2-yl, 5,6-dimethoxy-1H-benzoimidazol-2-yl, 1-methyl-1H-benzoimidazol-2-yl, 4-methyl-1H-benzoimidazol-2-yl, 5-methyl-1H-benzoimidazol-2-yl, 5-ethyl-1H-benzoimidazol-2-yl, 5-isopropyl-1H-benzoimidazol-2-yl, 5-tert.-butyl-1H-benzoimidazol-2-yl, 4-trifluoromethyl-1H-benzoimidazol-2-yl, 5-trifluoromethyl-1H-benzoimidazol-2-yl, 5-trifluoromethoxy-1H-benzoimidazol-2-yl, 4-hydroxy-1H-benzoimidazol-2-yl, 5-cyano-1H-benzoimidazol-2-yl, 5-methanesulfonyl-1H-benzoimidazol-2-yl, 5-(2-hydroxyethoxy)-1H-benzoimidazol-2-yl, 5-(2-methoxy-ethoxy)-1H-benzoimidazol-2-yl, 5-(hydroxymethyl)-1H-benzoimidazol-2-yl, and 5-phenyl-1H-benzoimidazol-2-yl.

21) Another embodiment relates to compounds according to any one of embodiments 1) to 20), wherein $R^3$ represents hydrogen, $(C_{1-4})$alkyl, $(C_{1-3})$fluoroalkyl; halogen; $(C_{3-6})$cycloalkyl, wherein optionally one ring carbon atom may be replaced by oxygen; hydroxy-$(C_{1-4})$alkyl; or phenyl, which is unsubstituted, or mono- or di-substituted wherein the substituents independently are selected from the group consisting of $(C_{1-4})$alkyl, $(C_{1-4})$alkoxy, $(C_{1-3})$ fluoroalkyl, $(C_{1-3})$ fluoroalkoxy, halogen, and cyano (especially unsubstituted, or mono-substituted with $(C_{1-4})$alkyl or $(C_{1-4})$alkoxy).

22) Another embodiment relates to compounds according to any one of embodiments 1) to 20), wherein $R^3$ represents 23) Another embodiment relates to compounds according to any one of embodiments 1) to 20), wherein $R^3$ represents hydrogen, methyl, ethyl, chloro, bromo, phenyl, 2-methyl-phenyl, 2-methoxy-phenyl, 1-hydroxyethyl, isopropyl, trifluoromethyl, cyclopropyl, or oxetan-3-yl (especially hydrogen or trifluoromethyl).

24) Another embodiment relates to compounds according to any one of embodiments 1) to 20), wherein $R^3$ represents trifluoromethyl.

25) Another embodiment relates to compounds according to any one of embodiments 1) to 24), wherein $R^4$ and $R^{4'}$ independently represent hydrogen, $(C_{1-4})$alkyl, $(C_{1-3})$alkoxy-$(C_{1-4})$alkyl; $R^{12}R^{13}N$—$(CH_2)$—, wherein $R^{12}$ and $R^{13}$ independently represent $(C_{1-3})$alkyl; or $R^4$ and $R^{4'}$ together form an ethylene bridge.

26) Another embodiment relates to compounds according to any one of embodiments 1) to 24), wherein
- X represents CH, or (especially) N; p represents the integer 1, or 2 (especially p is 1); and $R^4$ and $R^{4'}$ both represent hydrogen; or
- X represents N; p represents the integer 1; and $R^4$ and $R^{4'}$ both represent $(C_{1-4})$alkyl; or
- X represents N; p represents the integer 1 or 2 (especially p is 1); $R^4$ represents hydrogen; and $R^{4'}$ represents $(C_{1-3})$alkoxy-$(C_{1-4})$alkyl; $R^{12}R^{13}N$—$(CH_2)$—, wherein $R^{12}$ and $R^{13}$ independently represent $(C_{1-3})$alkyl; or (especially) $(C_{1-4})$alkyl; or
- X represents N; p represents the integer 1; and $R^4$ and $R^{4'}$ together form an ethylene bridge.

27) Another embodiment relates to compounds according to any one of embodiments 1) to 24), wherein p represents the integer 1; and
- X represents CH, or (especially) N; and $R^4$ and $R^{4'}$ both represent hydrogen; or
- X represents N; and $R^4$ and $R^{4'}$ both represent methyl; or
- X represents N; $R^4$ represents hydrogen; and $R^{4'}$ represents methyl.

28) Another embodiment relates to compounds according to any one of embodiments 1) to 24), wherein p represents the integer 1; and
- $R^4$ and $R^{4'}$ both represent hydrogen; or
- $R^4$ represents hydrogen; and $R^{4'}$ represents methyl; wherein the carbon atom to which $R^{4'}$ is attached to is preferably in absolute (R)-configuration.

29) Another embodiment relates to compounds according to any one of embodiments 1) to 24), wherein p represents the integer 1; and
- $R^4$ represents hydrogen; and $R^{4'}$ represents methyl; wherein the carbon atom to which $R^{4'}$ is attached to is preferably in absolute (R)-configuration.

30) Another embodiment relates to compounds according to any one of embodiments 1), 2), or 4) to 29), wherein
- $R^5$ represents aryl, wherein said aryl is unsubstituted, or mono-, di-, or tri-substituted, wherein the substituents are independently selected from the group consisting of $(C_{1-4})$alkyl; $(C_{1-4})$alkoxy; $(C_{1-3})$fluoroalkyl; $(C_{1-3})$fluoroalkoxy; halogen; cyano; $(C_{1-3})$alkoxy-$(C_{1-4})$alkyl; $(C_{1-3})$alkoxy-$(C_{2-4})$alkoxy; and hydroxy; or
- $R^5$ represents 5- to 10-membered heteroaryl, wherein said heteroaryl independently is unsubstituted, or mono-, di-, or tri-substituted, wherein the substituents are independently selected from the group consisting of $(C_{1-4})$alkyl; $(C_{1-4})$alkoxy; $(C_{1-3})$ fluoroalkyl; $(C_{1-3})$fluoroalkoxy; halogen; cyano; $(C_{1-3})$alkoxy-$(C_{1-4})$alkyl; $(C_{1-3})$alkoxy-$(C_{2-4})$alkoxy; and hydroxy; or
- $R^5$ represents 9- or 10-membered partially aromatic bicyclic heterocyclyl; wherein said heterocyclyl group is unsubstituted, or mono-, or di-, or tri-substituted (notably unsubstituted, or mono-, or di-substituted), wherein the substituents are independently selected from $(C_{1-4})$alkyl, $(C_{1-4})$alkoxy, halogen and oxo.

31) Another embodiment relates to compounds according to any one of embodiments 1), 2), or 4) to 29), wherein
- $R^5$ represents 5- to 10-membered heteroaryl, wherein said heteroaryl independently is unsubstituted, or mono-, di-, or tri-substituted, wherein the substituents are independently selected from the group consisting of $(C_{1-4})$alkyl; $(C_{1-4})$alkoxy; $(C_{1-3})$ fluoroalkyl; $(C_{1-3})$fluoroalkoxy; halogen; cyano; $(C_{1-3})$alkoxy-$(C_{1-4})$alkyl; $(C_{1-3})$alkoxy-$(C_{2-4})$alkoxy; hydroxy; or
- $R^5$ represents 9- or 10-membered partially aromatic bicyclic heterocyclyl; wherein said heterocyclyl is attached to the rest of the molecule through a non-aromatic nitrogen atom; wherein said heterocyclyl group is unsubstituted, or mono-, or di-, or tri-substituted (notably unsubstituted, or mono-, or di-substituted), wherein the substituents are independently selected from $(C_{1-4})$alkyl, $(C_{1-4})$alkoxy, halogen and oxo; or
- $R^5$ represents 9- or 10-membered partially aromatic bicyclic heterocyclyl; wherein said heterocyclyl is attached to the rest of the molecule through an aromatic carbon atom; wherein said heterocyclyl group is unsubstituted, or mono-, or di-substituted, wherein the substituents are independently selected from $(C_{1-4})$alkyl, $(C_{1-4})$alkoxy, halogen and oxo.

32) Another embodiment relates to compounds according to any one of embodiments 1), 2), or 4) to 29), wherein
- $R^5$ represents 5- to 10-membered heteroaryl, wherein said heteroaryl is unsubstituted, or mono-, or di-substituted, wherein the substituents are independently selected from the group consisting of $(C_{1-4})$alkyl; $(C_{1-4})$alkoxy; $(C_{1-3})$ fluoroalkyl; halogen; and cyano; or
- $R^5$ represents 9- or 10-membered partially aromatic bicyclic heterocyclyl; wherein said heterocyclyl is attached to the rest of the molecule through a non-aromatic nitrogen atom; wherein said heterocyclyl group is unsubstituted, or mono-, or di-, or tri-substituted (notably unsubstituted, or mono-, or di-substituted), wherein the substituents are independently selected from $(C_{1-4})$alkyl, $(C_{1-4})$alkoxy, halogen and oxo (especially unsubstituted or mono-substituted with $(C_{1-4})$alkyl or oxo).

33) Another embodiment relates to compounds according to any one of embodiments 1), 2), or 4) to 29), wherein
- $R^5$ represents 5- or 9-membered heteroaryl, wherein said heteroaryl is a 5-membered monocyclic or a 9-membered bicyclic aromatic ring each independently containing one to three heteroatoms, wherein one of said heteroatoms is nitrogen, and the remaining heteroatoms, if present, are independently selected from oxygen, nitrogen and sulfur; wherein said heteroaryl is attached to the rest of the molecule at said nitrogen atom; wherein said heteroaryl is unsubstituted, or mono-, or di-substituted, wherein the substituents are independently selected from the group consisting of $(C_{1-4})$alkyl; $(C_{1-4})$alkoxy; $(C_{1-3})$fluoroalkyl; halogen; and cyano; or
- $R^5$ represents 9- or 10-membered partially aromatic bicyclic heterocyclyl; wherein said heterocyclyl is attached to the rest of the molecule through a non-aromatic nitrogen atom which is in alpha position to the aromatic ring; wherein said heterocyclyl group is unsubstituted, or mono-, or di-, or tri-substituted (notably unsubstituted, or mono-, or di-substituted), wherein the substituents are independently selected from $(C_{1-4})$alkyl, $(C_{1-4})$alkoxy, halogen and oxo (especially unsubstituted or mono-substituted with $(C_{1-4})$alkyl or oxo).

34) Another embodiment relates to compounds according to any one of embodiments 1), 2), or 6) to 29), wherein
- $R^5$ represents aryl, wherein said aryl is unsubstituted, or mono-, di-, or tri-substituted, wherein the substituents are independently selected from the group consisting of $(C_{1-4})$alkyl; $(C_{1-4})$alkoxy; $(C_{1-3})$fluoroalkyl; $(C_{1-3})$fluoroalkoxy; halogen; cyano; $(C_{1-3})$alkoxy-$(C_{1-4})$alkyl; $(C_{1-3})$alkoxy-$(C_{2-4})$alkoxy; hydroxy; hydroxy-$(C_{1-4})$alkyl; 5-membered heteroaryl; and heterocyclyl, wherein the heterocyclyl is a 5- to 7-membered mono-cyclic saturated ring containing one or two nitrogen atoms, wherein said heterocyclyl is optionally substituted on a nitrogen having a free valency with $(C_{1-4})$alkyl; or
- $R^5$ represents 5- or 6-membered heteroaryl, wherein said heteroaryl independently is unsubstituted, or mono-, di-, or tri-substituted, wherein the substituents are independently selected from the group consisting of $(C_{1-4})$alkyl; $(C_{1-4})$alkoxy; $(C_{1-3})$ fluoroalkyl; $(C_{1-3})$fluoroalkoxy; halogen; cyano; $(C_{1-3})$alkoxy-$(C_{1-4})$alkyl; $(C_{1-3})$alkoxy-$(C_{2-4})$alkoxy; hydroxy; —CO—$(C_{1-4})$alkoxy; hydroxy-$(C_{1-4})$alkyl; —$(C_{1-3})$alkylene-$NR^{10}R^{11}$ wherein $R^{10}$ and $R^{11}$ independently represent $(C_{1-3})$alkyl; phenyl; and heterocyclyl, wherein the heterocyclyl is a 5- to 7-membered mono-cyclic saturated ring containing one or two nitrogen atoms, wherein said heterocyclyl is optionally substituted on a nitrogen having a free valency with $(C_{1-4})$alkyl; or
- $R^5$ represents 9- or 10-membered heteroaryl, wherein said heteroaryl independently is unsubstituted, or mono-, di-, or tri-substituted, wherein the substituents are independently selected from the group consisting of $(C_{1-4})$alkyl; $(C_{1-4})$alkoxy; $(C_{1-3})$ fluoroalkyl; $(C_{1-3})$fluoroalkoxy; halogen; cyano; $(C_{1-3})$alkoxy-$(C_{1-4})$alkyl; $(C_{1-3})$alkoxy-$(C_{2-4})$alkoxy; hydroxy; and hydroxy-$(C_{1-4})$alkyl; or
- $R^5$ represents 9- or 10-membered partially aromatic bicyclic heterocyclyl; wherein said heterocyclyl consists of a phenyl or 6-membered heteroaryl ring (especially a phenyl or pyridine ring) which is fused to a 5- or 6-membered saturated or partially unsaturated non-aromatic ring containing one nitrogen atom, and optionally one further heteroatom selected from the group consisting of oxygen and nitrogen; wherein said heterocyclyl is attached to the rest of the molecule through said non-aromatic nitrogen atom; wherein said heterocyclyl group is unsubstituted, or mono-, di- or tri-substituted, wherein the substituents are independently selected from $(C_{1-4})$alkyl, $(C_{1-4})$alkoxy, halogen and oxo; or
- $R^5$ represents 9-membered partially aromatic bicyclic heterocyclyl; wherein said heterocyclyl consists of a pyrazole or imidazole ring which is fused to a 6-membered saturated or partially unsaturated non-aromatic ring containing one or two heteroatoms independently selected from the group consisting of oxygen and nitrogen; wherein said heterocyclyl is attached to the rest of the molecule through an aromatic nitrogen atom of said pyrazole or imidazole ring; wherein said heterocyclyl group is unsubstituted, or mono-, or di-substituted, wherein the substituents are independently selected from $(C_{1-4})$alkyl, and oxo; or
- $R^5$ represents 9- or 10-membered partially aromatic bicyclic heterocyclyl; wherein said heterocyclyl consists of a phenyl or 6-membered heteroaryl ring (especially a phenyl, or pyridine ring) which is fused to a 5- or 6-membered saturated or partially unsaturated non-aromatic ring containing one or two heteroatoms independently selected from the group consisting of oxygen, sulphur and nitrogen; wherein said heterocyclyl is attached to the rest of the molecule through an aromatic carbon atom; wherein said heterocyclyl group is unsubstituted, or mono-, or di-substituted, wherein the substituents are independently selected from $(C_{1-4})$alkyl, $(C_{1-4})$alkoxy, halogen and oxo.

35) Another embodiment relates to compounds according to any one of embodiments 1), 2), or 6) to 29), wherein
- $R^5$ represents 5-membered heteroaryl, wherein said heteroaryl contains one to three nitrogen atoms; wherein said heteroaryl is attached to the rest of the molecule at one of said nitrogen atoms; wherein said heteroaryl independently is unsubstituted, or mono-, di-, or tri-substituted, wherein the substituents are independently selected from the group consisting of $(C_{1-4})$alkyl; $(C_{1-4})$alkoxy; $(C_{1-3})$fluoroalkyl; $(C_{1-3})$ fluoroalkoxy; halogen; cyano; $(C_{1-3})$alkoxy-$(C_{1-4})$alkyl; $(C_{1-3})$alkoxy-$(C_{2-4})$alkoxy; hydroxy; —CO—$(C_{1-4})$alkoxy; hydroxy-$(C_{1-4})$alkyl; —$(C_{1-3})$alkylene-$NR^{10}R^{11}$ wherein $R^{10}$ and $R^{11}$ independently represent $(C_{1-3})$alkyl; phenyl; and heterocyclyl, wherein the heterocyclyl is a 5- to 7-membered mono-cyclic saturated ring containing one or two nitrogen atoms, wherein said heterocyclyl is optionally substituted on a nitrogen having a free valency with $(C_{1-4})$alkyl; or
- $R^5$ represents 5- or 6-membered heteroaryl, wherein said heteroaryl contains one to three heteroatoms independently selected from oxygen, sulphur and nitrogen; wherein said heteroaryl is attached to the rest of the molecule at a ring carbon atom; wherein said heteroaryl independently is unsubstituted, or mono-, or di-substituted, wherein the substituents are independently selected from the group consisting of $(C_{1-4})$alkyl; $(C_{1-4})$alkoxy; $(C_{1-3})$fluoroalkyl; halogen; and phenyl; or
- $R^5$ represents 9- or 10-membered heteroaryl, wherein said heteroaryl contains one to three heteroatoms independently selected from oxygen, sulphur and nitrogen; wherein said heteroaryl is attached to the rest of the molecule at a ring carbon atom; wherein said heteroaryl independently is unsubstituted, or mono-, or di-substituted, wherein the substituents are independently selected from the group consisting of $(C_{1-4})$alkyl; $(C_{1-4})$alkoxy; $(C_{1-3})$fluoroalkyl; and halogen; or
- $R^5$ represents 9-membered heteroaryl, wherein said heteroaryl is a bicyclic aromatic ring containing one to three nitrogen atoms, wherein said heteroaryl is attached to the rest of the molecule at one of said nitrogen atoms; wherein said heteroaryl independently is unsubstituted, or mono-, di-, or tri-substituted, wherein the substituents are independently selected from the group consisting of $(C_{1-4})$alkyl; $(C_{1-4})$alkoxy; $(C_{1-3})$fluoroalkyl; $(C_{1-3})$fluoroalkoxy; halogen; cyano; $(C_{1-3})$alkoxy-$(C_{1-4})$alkyl; $(C_{1-3})$alkoxy-$(C_{2-4}$ alkoxy; hydroxy; and hydroxy-$(C_{1-4})$alkyl; or
- $R^5$ represents 9- or 10-membered partially aromatic bicyclic heterocyclyl; wherein said heterocyclyl consists of a phenyl or 6-membered heteroaryl ring (especially a phenyl or pyridine ring) which is fused to a 5- or 6-membered saturated or partially unsaturated non-aromatic ring containing one nitrogen atom and optionally one further heteroatom selected from the group consisting of oxygen and nitrogen; wherein said heterocyclyl is attached to the rest of the molecule through said non-aromatic nitrogen atom; wherein said heterocyclyl group is unsubstituted, or mono-, di- or tri-substituted, wherein the substituents are independently selected from $(C_{1-4})$alkyl, $(C_{1-4})$alkoxy, halogen and oxo; or $R^5$ represents 9-membered partially aromatic bicyclic heterocyclyl; wherein said heterocyclyl consists of a pyrazole or imidazole ring which is fused to a 6-membered saturated or partially unsaturated non-aromatic ring containing one or two heteroatoms independently selected from the group consisting of oxygen and nitrogen; wherein said heterocyclyl is attached to the rest of the molecule through an aromatic nitrogen atom of said pyrazole or imidazole ring; wherein said heterocyclyl group is unsubstituted, or mono-, or di-substituted, wherein the substituents are independently selected from $(C_{1-4})$alkyl, and oxo.

36) Another embodiment relates to compounds according to any one of embodiments 1) to 29), wherein $R^5$ represents 5-membered heteroaryl selected from pyrazolyl and triazolyl; wherein said heteroaryl is attached to the rest of the molecule at one of the aromatic nitrogen atoms; wherein said heteroaryl independently is unsubstituted, or mono-, di-, or tri-substituted, wherein the substituents are independently selected from the group consisting of methyl; trifluoromethyl; halogen; —CH$_2$—N(CH$_3$)$_2$; phenyl; and piperidin-4-yl optionally substituted on the nitrogen with methyl [especially methyl, halogen and trifluoromethyl]; or $R^5$ represents 9-membered heteroaryl selected from indazolyl, pyrrolopyridinyl, indolyl, imidazopyridinyl, benzoimidazolyl, and imidazopyridazinyl; wherein said heteroaryl is attached to the rest of the molecule at one of the aromatic nitrogen atoms; wherein said heteroaryl independently is unsubstituted, or mono-, or di-substituted, wherein the substituents are independently selected from the group consisting of methyl; methoxy; trifluoromethyl; halogen; cyano; and hydroxy-methyl; [especially such 9-membered heteroaryl is unsubstituted]; or $R^5$ represents 9- or 10-membered partially aromatic bicyclic heterocyclyl; wherein said heterocyclyl consists of a phenyl or pyridine ring which is fused to a 5-membered saturated or partially unsaturated non-aromatic ring containing one nitrogen atom and optionally one further heteroatom selected from the group consisting of oxygen and nitrogen; wherein said heterocyclyl is attached to the rest of the molecule through said non-aromatic nitrogen atom; wherein said heterocyclyl group is unsubstituted, or mono-, di- or tri-substituted, wherein the substituents are independently selected from $(C_{1-4})$alkyl, $(C_{1-4})$alkoxy, halogen and oxo; or $R^5$ represents 9-membered partially aromatic bicyclic heterocyclyl; wherein said heterocyclyl consists of a pyrazole or imidazole ring which is fused to a 6-membered saturated or partially unsaturated non-aromatic ring containing one or two heteroatoms independently selected from the group consisting of oxygen and nitrogen; wherein said heterocyclyl is attached to the rest of the molecule through an aromatic nitrogen atom of said pyrazole or imidazole ring; wherein said heterocyclyl group is unsubstituted, or mono-, or di-substituted, wherein the substituents are independently selected from $(C_{1-4})$alkyl, and oxo.

37) Another embodiment relates to compounds according to any one of embodiments 1) to 36), wherein, in case $R^5$ represents 5- to 10-membered heteroaryl, said heteroaryl is selected from the group consisting of pyrazolyl, triazolyl, indazolyl, pyrrolopyridinyl, indolyl, imidazopyridinyl, benzoimidazolyl, and imidazopyridazinyl; wherein said heteroaryl is unsubstituted or substituted as explicitly defined (especially it is unsubstituted, or mono-, or di-substituted, wherein the substituents are independently selected from the group consisting of $(C_{1-4})$alkyl; $(C_{1-4})$alkoxy; $(C_{1-3})$fluoroalkyl; halogen; and cyano).

38) Another embodiment relates to compounds according to any one of embodiments 1) to 36), wherein, in case $R^5$ represents 5- to 10-membered heteroaryl, said heteroaryl is selected from the group consisting of pyrazolyl (especially pyrazol-1-yl), triazolyl (especially [1,2,4]-triazol-1-yl, [1,2,3]-triazol-1-yl, [1,2,3]-triazol-2-yl), oxadiazolyl (especially [1,3,4]oxadiazol-3-yl), indazolyl (especially indazol-1-yl, indazol-3-yl), pyrrolopyridinyl (especially pyrrolo[2,3-c]pyridin-1-yl, pyrrolo[2,3-b]pyridin-1-yl), indolyl (especially indol-1-yl, 1H-indol-3-yl, 1H-indol-4-yl), imidazopyridinyl (especially imidazo[4,5-c]pyridin-1-yl, imidazo[4,5-c]pyridin-3-yl, imidazo[4,5-b]pyridin-3-yl, imidazo[1,2-a]pyridin-3-yl), benzoimidazolyl (especially benzoimidazol-1-yl, benzoimidazol-2-yl), imidazopyridazinyl (especially imidazo[1,2-b]pyridazin-2-yl), pyrazolopyridinyl (especially pyrazolo[3,4-b]pyridin-1-yl, pyrazolo[3,4-b]pyridin-2-yl), pyrrolopyrazinyl (especially pyrrolo[2,3-b]pyrazin-5-yl); and in addition, the term refers to thiazolyl (especially thiazol-4-yl, thiazol-5-yl), pyridinyl (especially pyridin-3-yl, pyridine-2-yl, pyridine-4-yl), benzothiophenyl (especially benzo[b]thiophen-3-yl), benzofuranyl (especially benzofuran-3-yl), benzoisoxazolyl (especially benzo[d]isoxazol-3-yl), quinolinyl (especially quinolin-7-yl, quinolin-8-yl), and quinoxalinyl (especially quinoxalin-6-yl); wherein said heteroaryl is unsubstituted or substituted as explicitly defined (especially it is unsubstituted, or mono-, or di-substituted, wherein the substituents are independently selected from the group consisting of $(C_{1-4})$alkyl; $(C_{1-4})$alkoxy; $(C_{1-3})$fluoroalkyl; halogen; and cyano).

39) Another embodiment relates to compounds according to any one of embodiments 1) to 36), wherein, in case $R^5$ represents 5- to 10-membered heteroaryl, said heteroaryl is independently selected from any one of the following groups A, B, C, and D:

A. 3-methyl-pyrazol-1-yl, 3,5-dimethyl-pyrazol-1-yl, 3-trifluoromethyl-pyrazol-1-yl, 3,5-dimethyl-[1,2,4]triazol-1-yl, indazol-1-yl, pyrrolo[2,3-c]pyridin-1-yl, pyrrolo[2,3-b]pyridin-1-yl, 6-chloro-pyrrolo[2,3-b]pyridin-1-yl, 7-chloro-pyrrolo[2,3-c]pyridin-1-yl, 3-chloro-pyrrolo[2,3-b]pyridin-1-yl, 2-methyl-pyrrolo[2,3-b]pyridin-1-yl, 3-methyl-pyrrolo[2,3-b]pyridin-1-yl, 6-methyl-pyrrolo[2,3-b]pyridin-1-yl, 6-methoxy-pyrrolo[2,3-b]pyridin-1-yl, indol-1-yl, 5-fluoro-indol-1-yl, 6-fluoro-indol-1-yl, 7-fluoro-indol-1-yl, 4-chloro-indol-1-yl, 2-methyl-indol-1-yl, 7-methyl-indol-1-yl, 3-cyano-indol-1-yl, 7-cyano-indol-1-yl, 5-fluoro-3-methyl-indol-1-yl, 5,6-dichloro-indol-1-yl, 4-methoxy-indol-1-yl, 5-chloro-6-methoxy-indol-1-yl, 6-trifluoromethyl-indol-1-yl, imidazo[4,5-c]pyridin-1-yl, imidazo[4,5-c]pyridin-3-yl, imidazo[4,5-b]pyridin-3-yl, pyrazolo[3,4-b]pyridin-1-yl, pyrazolo[3,4-b]pyridin-2-yl, 3-chloro-pyrrolo[2,3-b]pyrazin-5-yl, benzoimidazol-1-yl, 2-methyl-benzoimidazol-1-yl, 2-trifluoromethyl-benzoimidazol-1-yl;

B. pyrazol-1-yl, 4-chloro-pyrazol-1-yl, 5-methyl-pyrazol-1-yl, 4-methyl-pyrazol-1-yl, 3-methoxycarbonyl-pyrazol-1-yl, 4-dimethylaminomethyl-3-methyl-pyrazol-1-yl, 4-dimethylaminomethyl-3,5-dimethyl-pyrazol-1-yl, 3-phenyl-pyrazol-1-yl, 5-phenyl-pyrazol-1-yl, 4-piperidin-4-yl-pyrazol-1-yl, 4-(1-methyl-piperidin-4-yl)-pyrazol-1-yl, [1,2,4]triazol-1-yl, 3-bromo-[1,2,4]triazol-1-yl, 3-methyl-[1,2,4]triazol-1-yl, 5-methyl-[1,2,4]triazol-1-yl, 3-dimethylaminomethyl-5-methyl-[1,2,4]triazol-1-yl, [1,2,3]triazol-2-yl, 4-phenyl-[1,2,3]triazol-1-yl, 2-hydroxymethyl-pyrrolo[2,3-b]pyridin-1-yl;

C. 5-methyl-[1,3,4]oxadiazol-3-yl, 5-phenyl-[1,3,4]oxadiazol-3-yl, 2-methyl-pyridin-5-yl, 2,6-dimethyl-pyridin-4-yl, 4,6-dimethyl-pyridin-2-yl;

D. 2-methyl-thiazol-4-yl, 2,4-dimethyl-thiazol-5-yl, 1H-indazol-3-yl, indol-3-yl, indol-4-yl, 5-chloro-1H-indol-3-yl, 5-fluoro-1H-indol-3-yl, 1-methyl-1H-indol-3-yl, 5-methoxy-1H-indol-3-yl, 5-chloro-1H-benzoimidazol-2-yl, pyridin-3-yl, 6-methoxy-benzofuran-3-yl, benzo[b]thiophen-3-yl, 5-chloro-benzo[b]thiophen-3-yl, benzo[d]isoxazol-3-yl, 5-methoxy-benzo[d]isoxazol-3-yl, 5-methyl-benzo[d]isoxazol-3-yl, quinoxalin-6-yl, quinolin-7-yl, quinolin-8-yl, 2-methyl-imidazo[1,2-a]pyridin-3-yl, 6-chloro-imidazo[1,2-b]pyridazin-2-yl.

40) Another embodiment relates to compounds according to any one of embodiments 1) to 39), wherein, in case $R^5$ represents 9- or 10-membered partially aromatic bicyclic heterocyclyl, said heterocyclyl is selected from the group consisting of 1,3-dihydroindol-1-yl, 1,3-dihydro-benzoimidazol-1-yl, 3H-benzooxazol-3-yl, 3,4-dihydro-1H-quinolin-1-yl, 3,4-dihydro-4H-benzo[1,4]oxazin-4-yl, and 1,3-dihydro-imidazo[4,5-b]pyridin-3-yl; wherein said heteroaryl is unsubstituted or substituted as explicitly defined [especially it is unsubstituted, or mono-, or di-substituted, wherein the substituents are independently selected from $(C_{1-4})$alkyl, $(C_{1-4})$alkoxy, halogen and oxo (notably unsubstituted, or mono-, or di-substituted, wherein the substituents are independently selected from $(C_{1-4})$alkyl and oxo; wherein an oxo substituent, if present, is in alpha position to the nitrogen which is attached to the rest of the molecule)].

41) Another embodiment relates to compounds according to any one of embodiments 1) to 39), wherein, in case $R^5$ represents 9- or 10-membered partially aromatic bicyclic heterocyclyl, said heterocyclyl is selected from the group consisting of 1,3-dihydroindol-1-yl, 1,3-dihydro-benzoimidazol-1-yl, 3H-benzooxazol-3-yl, 3,4-dihydro-1H-quinolin-1-yl, 3,4-dihydro-4H-benzo[1,4]oxazin-4-yl, and 1,3-dihydro-imidazo[4,5-b]pyridin-3-yl; wherein said heteroaryl is unsubstituted or substituted as explicitly defined [especially it is unsubstituted, or mono-substituted with oxo in alpha position to the nitrogen which is attached to the rest of the molecule, or di-substituted, wherein one substituent is oxo in alpha position to the nitrogen which is attached to the rest of the molecule, and the remaining substituent is selected from $(C_{1-4})$alkyl, $(C_{1-4})$alkoxy, and halogen (notably $(C_{1-4})$alkyl)].

42) Another embodiment relates to compounds according to any one of embodiments 1) to 39), wherein, in case $R^5$ represents 9- or 10-membered partially aromatic bicyclic heterocyclyl, said heterocyclyl is selected from the group consisting of 3H-benzooxazol-2-one-3-yl, 2,3-dihydro-pyrrolo[2,3-b]pyridin-1-yl, 1,3-dihydro-imidazo[4,5-b]pyridin-2-one-3-yl, 1,3-dihydro-benzoimidazol-2-one-1-yl, 3-methyl-1,3-dihydro-benzoimidazol-2-one-1-yl, 2,3-dihydro-indol-1-yl, 1,3-dihydro-indol-2-one-1-yl, 2,3-dihydro-benzo[1,4]oxazin-4-yl, 4H-benzo[1,4]oxazin-3-one-4-yl, 3,4-dihydro-2H-quinolin-1-yl, 3,4-dihydro-1H-quinolin-2-one-1-yl, 2,3-dihydro-1H-quinolin-4-one-1-yl, 2,3-dihydro-benzofuran-5-yl, and 4H-benzo[1,4]oxazin-3-one-6-yl.

43) Another embodiment relates to compounds according to any one of embodiments 1) to 39), wherein, in case $R^5$ represents 9- or 10-membered partially aromatic bicyclic heterocyclyl, said heterocyclyl is selected from the group consisting of 1,3-dihydroindol-1-yl, 1,3-dihydro-benzoimidazol-1-yl, 3H-benzooxazol-3-yl, 3,4-dihydro-1H-quinolin-1-yl, 3,4-dihydro-4H-benzo[1,4]oxazin-4-yl, 1,3-dihydro-imidazo[4,5-b]pyridin-3-yl, 4,5,6,7-tetrahydro-pyrazolo[4,3-c]pyridin-1-yl, 4,5,6,7-tetrahydro-pyrazolo[4,3-c]pyridin-2-yl, 4,5,6,7-tetrahydro-imidazo[4,5-c]pyridin-3-yl, and 4,5,6,7-tetrahydro-imidazo[4,5-c]pyridin-1-yl; wherein said heteroaryl is unsubstituted or substituted as explicitly defined [especially it is unsubstituted, or mono-substituted with oxo in alpha position to the nitrogen which is attached to the rest of the molecule, or di-substituted, wherein one substituent is oxo in alpha position to the nitrogen which is attached to the rest of the molecule, and the remaining substituent is selected from $(C_{1-4})$alkyl, $(C_{1-4})$alkoxy, and halogen (notably $(C_{1-4})$alkyl)].

44) Another embodiment relates to compounds according to any one of embodiments 1) to 39), wherein, in case $R^5$ represents 9- or 10-membered partially aromatic bicyclic heterocyclyl, said heterocyclyl is independently selected from any one of the following groups A and B:

A. 3H-benzooxazol-2-one-3-yl, 2,3-dihydro-pyrrolo[2,3-b]pyridin-1-yl, 1,3-dihydro-imidazo[4,5-b]pyridin-2-one-3-yl, 1,3-dihydro-benzoimidazol-2-one-1-yl, 3-methyl-1,3-dihydro-benzoimidazol-2-one-1-yl, 2,3-dihydro-indol-1-yl, 1,3-dihydro-indol-2-one-1-yl, 2,3-dihydro-benzo[1,4]oxazin-4-yl, 4H-benzo[1,4]oxazin-3-one-4-yl, 3,4-dihydro-2H-quinolin-1-yl, 3,4-dihydro-1H-quinolin-2-one-1-yl, 2,3-dihydro-1H-quinolin-4-one-1-yl, 2,3-dihydro-benzofuran-5-yl, 4H-benzo[1,4]oxazin-3-one-6-yl;

B. 5-methyl-4,5,6,7-tetrahydro-pyrazolo[4,3-c]pyridin-1-yl, 5-methyl-4,5,6,7-tetrahydro-pyrazolo[4,3-c]pyridin-2-yl, 5-methyl-4,5,6,7-tetrahydro-imidazo[4,5-c]pyridin-3-yl, and 5-methyl-4,5,6,7-tetrahydro-imidazo[4,5-c]pyridin-1-yl, 2-oxo-3H-oxazolo[4,5-b]pyridin-3-yl, 4-fluoro-2-oxo-3H-benzooxazol-3-yl, 2,3-dioxo-1H-indol-1-yl, 4-methyl-2-oxo-3H-benzooxazol-3-yl, 3,3-difluoro-2-oxo-1,3-dihydro-indol-1-yl, 3,3-dimethyl-2-oxo-1,3-dihydro-indol-1-yl.

45) Another embodiment relates to compounds according to any one of embodiments 1) to 29), wherein $R^5$ represents a group independently selected from any one of the following groups A, B, C, and D:

A

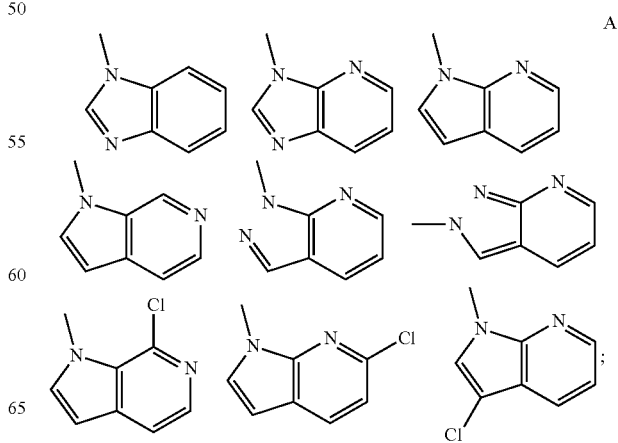

-continued

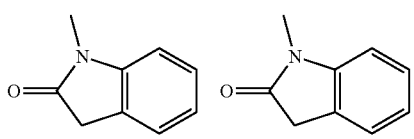
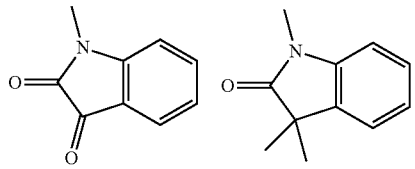
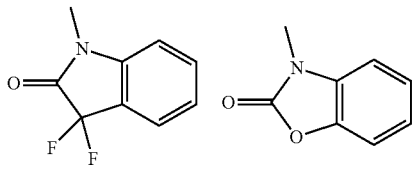
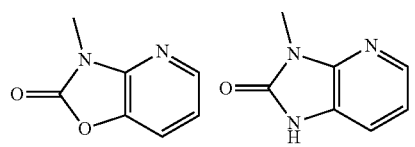
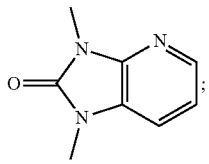
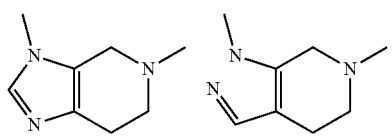
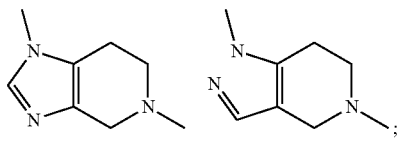
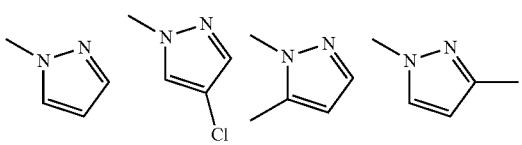
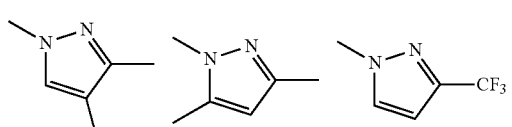
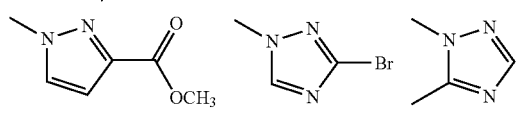
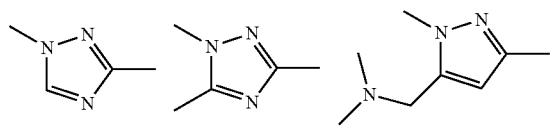

-continued

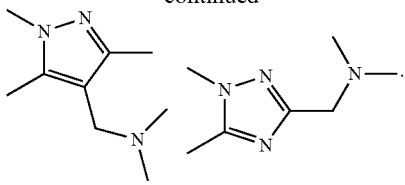

46) Another embodiment relates to compounds according to any one of embodiments 1) to 29), wherein $R^5$ represents a group selected from the group consisting of:

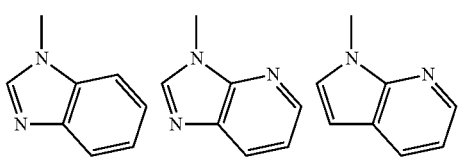
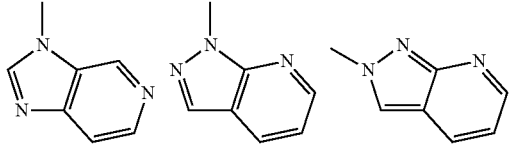
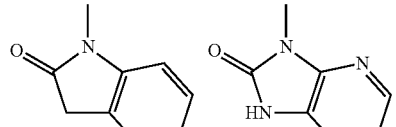
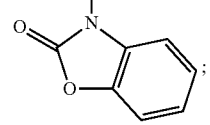

wherein each of the above groups (and among these, especially the heteroaryl groups) may optionally be mono-substituted with chloro.

47) The invention, thus, relates to compounds of the formula (I) as defined in embodiment 1), compounds of the formula (II) as defined in embodiment 2), compounds of the formula (III) as defined in embodiment 3), compounds of the formula (IV) as defined in embodiment 4); compounds of the formula (V) as defined in embodiment 5), and to such compounds further limited by the characteristics of any one of embodiments 6) to 46), under consideration of their respective dependencies; to pharmaceutically acceptable salts thereof; and to the use of such compounds as medicaments especially in the treatment of disorders relating to a dysfunction of the CXCR3 receptor or dysfunction of ligands signalling through CXCR3, such as especially autoimmune disorders, inflammatory diseases, infectious diseases, transplant rejection, fibrosis, neurodegenerative disorders and cancer. Especially the following embodiments relating to the compounds of formulae (I), (II), (III), (IV), and (V) are thus possible and intended and herewith specifically disclosed in individualized form:

1, 6+1, 13+1, 13+6+1, 16+1, 16+6+1, 16+13+1, 16+13+6+1, 17+1, 17+6+1, 17+13+1, 17+13+6+1, 17+16+1, 17+16+6+1, 17+16+13+1, 17+16+13+6+1, 18+1, 18+6+1, 28+1, 28+6+1, 28+13+1, 28+13+6+1, 28+16+1, 28+16+6+1, 28+16+13+1, 28+16+13+6+1, 28+17+1, 28+17+6+1, 28+17+13+1, 28+17+13+6+1, 28+17+16+1, 28+17+16+6+1, 28+17+16+13+1, 28+17+16+13+6+1, 28+18+1, 28+18+

6+1, 35+1, 35+6+1, 35+13+1, 35+13+6+1, 35+16+1, 35+16+6+1, 35+16+13+1, 35+16+13+6+1, 35+17+1, 35+17+6+1, 35+17+13+1, 35+17+13+6+1, 35+17+16+1, 35+17+16+6+1, 35+17+16+13+1, 35+17+16+13+6+1, 35+18+1, 35+18+6+1, 35+28+1, 35+28+6+1, 35+28+13+1, 35+28+13+6+1, 35+28+16+1, 35+28+16+6+1, 35+28+16+13+1, 35+28+16+13+6+1, 35+28+17+1, 35+28+17+6+1, 35+28+17+13+1, 35+28+17+13+6+1, 35+28+17+16+1, 35+28+17+16+6+1, 35+28+17+16+13+1, 35+28+17+16+13+6+1, 35+28+18+1, 35+28+18+6+1, 39+1, 39+6+1, 39+13+1, 39+13+6+1, 39+16+1, 39+16+6+1, 39+16+13+1, 39+16+13+6+1, 39+17+1, 39+17+6+1, 39+17+13+1, 39+17+13+6+1, 39+17+16+1, 39+17+16+6+1, 39+17+16+13+1, 39+17+16+13+6+1, 39+18+1, 39+18+6+1, 39+28+1, 39+28+6+1, 39+28+13+1, 39+28+13+6+1, 39+28+16+1, 39+28+16+6+1, 39+28+16+13+1, 39+28+16+13+6+1, 39+28+17+1, 39+28+17+6+1, 39+28+17+13+1, 39+28+17+13+6+1, 39+28+17+16+1, 39+28+17+16+6+1, 39+28+17+16+13+1, 39+28+17+16+13+6+1, 39+28+18+1, 39+28+18+6+1, 39+35+1, 39+35+6+1, 39+35+13+1, 39+35+13+6+1, 39+35+16+1, 39+35+16+6+1, 39+35+16+13+1, 39+35+16+13+6+1, 39+35+17+1, 39+35+17+6+1, 39+35+17+13+1, 39+35+17+13+6+1, 39+35+17+16+1, 39+35+17+16+6+1, 39+35+17+16+13+1, 39+35+17+16+13+6+1, 39+35+18+1, 39+35+18+6+1, 39+35+28+1, 39+35+28+6+1, 39+35+28+13+1, 39+35+28+13+6+1, 39+35+28+16+1, 39+35+28+16+6+1, 39+35+28+16+13+1, 39+35+28+16+13+6+1, 39+35+28+17+1, 39+35+28+17+6+1, 39+35+28+17+13+1, 39+35+28+17+13+6+1, 39+35+28+17+16+1, 39+35+28+17+16+6+1, 39+35+28+17+16+13+1, 39+35+28+17+16+13+6+1, 39+35+28+18+1, 39+35+28+18+6+1, 44+1, 44+6+1, 44+13+1, 44+13+6+1, 44+16+1, 44+16+6+1, 44+16+13+1, 44+16+13+6+1, 44+17+1, 44+17+6+1, 44+17+13+1, 44+17+13+6+1, 44+17+16+1, 44+17+16+6+1, 44+17+16+13+1, 44+17+16+13+6+1, 44+18+1, 44+18+6+1, 44+28+1, 44+28+6+1, 44+28+13+1, 44+28+13+6+1, 44+28+16+1, 44+28+16+6+1, 44+28+16+13+1, 44+28+16+13+6+1, 44+28+17+1, 44+28+17+6+1, 44+28+17+13+1, 44+28+17+13+6+1, 44+28+17+16+1, 44+28+17+16+6+1, 44+28+17+16+13+1, 44+28+17+16+13+6+1, 44+28+18+1, 44+28+18+6+1, 44+35+1, 44+35+6+1, 44+35+13+1, 44+35+13+6+1, 44+35+16+1, 44+35+16+6+1, 44+35+16+13+1, 44+35+16+13+6+1, 44+35+17+1, 44+35+17+6+1, 44+35+17+13+1, 44+35+17+13+6+1, 44+35+17+16+1, 44+35+17+16+6+1, 44+35+17+16+13+1, 44+35+17+16+13+6+1, 44+35+18+1, 44+35+18+6+1, 44+35+28+1, 44+35+28+6+1, 44+35+28+13+1, 44+35+28+13+6+1, 44+35+28+16+1, 44+35+28+16+6+1, 44+35+28+16+13+1, 44+35+28+16+13+6+1, 44+35+28+17+1, 44+35+28+17+6+1, 44+35+28+17+13+1, 44+35+28+17+13+6+1, 44+35+28+17+16+1, 44+35+28+17+16+6+1, 44+35+28+17+16+13+1, 44+35+28+17+16+13+6+1, 44+35+28+18+1, 44+35+28+18+6+1, 44+39+1, 44+39+6+1, 44+39+13+1, 44+39+13+6+1, 44+39+16+1, 44+39+16+6+1, 44+39+16+13+1, 44+39+16+13+6+1, 44+39+17+1, 44+39+17+6+1, 44+39+17+13+1, 44+39+17+13+6+1, 44+39+17+16+1, 44+39+17+16+6+1, 44+39+17+16+13+1, 44+39+17+16+13+6+1, 44+39+18+1, 44+39+18+6+1, 44+39+28+1, 44+39+28+6+1, 44+39+28+13+1, 44+39+28+13+6+1, 44+39+28+16+1, 44+39+28+16+6+1, 44+39+28+16+13+1, 44+39+28+16+13+6+1, 44+39+28+17+1, 44+39+28+17+6+1, 44+39+28+17+13+1, 44+39+28+17+13+6+1, 44+39+28+17+16+1, 44+39+28+17+16+6+1, 44+39+28+17+16+13+1, 44+39+28+17+16+13+6+1, 44+39+28+18+1, 44+39+28+18+6+1, 44+39+35+1, 44+39+35+6+1, 44+39+35+13+1, 44+39+35+13+6+1, 44+39+35+16+1, 44+39+35+16+6+1, 44+39+35+16+13+1, 44+39+35+16+13+6+1, 44+39+35+17+1, 44+39+35+17+6+1, 44+39+35+17+13+1, 44+39+35+17+13+6+1, 44+39+35+17+16+1, 44+39+35+17+16+6+1, 44+39+35+17+16+13+1, 44+39+35+17+16+13+6+1, 44+39+35+18+1, 44+39+35+18+6+1, 44+39+35+28+1, 44+39+35+28+6+1, 44+39+35+28+13+1, 44+39+35+28+13+6+1, 44+39+35+28+16+1, 44+39+35+28+16+6+1, 44+39+35+28+16+13+1, 44+39+35+28+16+13+6+1, 44+39+35+28+17+1, 44+39+35+28+17+6+1, 44+39+35+28+17+13+1, 44+39+35+28+17+13+6+1, 44+39+35+28+17+16+1, 44+39+35+28+17+16+6+1, 44+39+35+28+17+16+13+1, 44+39+35+28+17+16+13+6+1, 44+39+35+28+18+1, 44+39+35+28+18+6+1, 45+1, 45+6+1, 45+13+1, 45+13+6+1, 45+16+1, 45+16+6+1, 45+16+13+1, 45+16+13+6+1, 45+17+1, 45+17+6+1, 45+17+13+1, 45+17+13+6+1, 45+17+16+1, 45+17+16+6+1, 45+17+16+13+1, 45+17+16+13+6+1, 45+18+1, 45+18+6+1, 45+28+1, 45+28+6+1, 45+28+13+1, 45+28+13+6+1, 45+28+16+1, 45+28+16+6+1, 45+28+16+13+1, 45+28+16+13+6+1, 45+28+17+1, 45+28+17+6+1, 45+28+17+13+1, 45+28+17+13+6+1, 45+28+17+16+1, 45+28+17+16+6+1, 45+28+17+16+13+1, 45+28+17+16+13+6+1, 45+28+18+1, 45+28+18+6+1;

2, 13+2, 16+2, 16+13+2, 17+2, 17+13+2, 17+16+2, 17+16+13+2, 18+2, 35+2, 35+13+2, 35+16+2, 35+16+13+2, 35+17+2, 35+17+13+2, 35+17+16+2, 35+17+16+13+2, 35+18+2, 36+2, 36+13+2, 36+16+2, 36+16+13+2, 36+17+2, 36+17+13+2, 36+17+16+2, 36+17+16+13+2, 36+18+2, 39+2, 39+13+2, 39+16+2, 39+16+13+2, 39+17+2, 39+17+13+2, 39+17+16+2, 39+17+16+13+2, 39+18+2, 39+35+2, 39+35+13+2, 39+35+16+2, 39+35+16+13+2, 39+35+17+2, 39+35+17+13+2, 39+35+17+16+2, 39+35+17+16+13+2, 39+35+18+2, 39+36+2, 39+36+13+2, 39+36+16+2, 39+36+16+13+2, 39+36+17+2, 39+36+17+13+2, 39+36+17+16+2, 39+36+17+16+13+2, 39+36+18+2, 44+2, 44+13+2, 44+16+2, 44+16+13+2, 44+17+2, 44+17+13+2, 44+17+16+2, 44+17+16+13+2, 44+18+2, 44+35+2, 44+35+13+2, 44+35+16+2, 44+35+16+13+2, 44+35+17+2, 44+35+17+13+2, 44+35+17+16+2, 44+35+17+16+13+2, 44+35+18+2, 44+36+2, 44+36+13+2, 44+36+16+2, 44+36+16+13+2, 44+36+17+2, 44+36+17+13+2, 44+36+17+16+2, 44+36+17+16+13+2, 44+36+18+2, 44+39+2, 44+39+13+2, 44+39+16+2, 44+39+16+13+2, 44+39+17+2, 44+39+17+13+2, 44+39+17+16+2, 44+39+17+16+13+2, 44+39+18+2, 44+39+35+2, 44+39+35+13+2, 44+39+35+16+2, 44+39+35+16+13+2, 44+39+35+17+2, 44+39+35+17+13+2, 44+39+35+17+16+2, 44+39+35+17+16+13+2, 44+39+35+18+2, 44+39+36+2, 44+39+36+13+2, 44+39+36+16+2, 44+39+36+16+13+2, 44+39+36+17+2, 44+39+36+17+13+2, 44+39+36+17+16+2, 44+39+36+17+16+13+2, 44+39+36+18+2, 45+2, 45+13+2, 45+16+2, 45+16+13+2, 45+17+2, 45+17+13+2, 45+17+16+2, 45+17+16+13+2, 45+18+2;

3, 18+3, 24+3, 24+18+3, 28+3, 28+18+3, 28+24+3, 28+24+18+3, 45+3, 45+18+3, 45+24+3, 45+24+18+3, 45+28+3, 45+28+18+3, 45+28+24+3, 45+28+24+18+3;

4, 6+4, 7+4, 7+6+4, 16+7+4, 16+7+6+4, 20+4, 20+6+4, 24+16+7+4, 24+16+7+6+4, 24+20+4, 24+20+6+4, 26+6+4, 26+16+7+4, 26+16+7+6+4, 26+20+4, 26+20+6+4, 26+24+16+7+4, 26+24+16+7+6+4, 26+24+20+4, 26+24+20+6+4, 32+4, 32+6+4, 32+7+4, 32+7+6+4, 32+16+7+4, 32+16+7+6+4, 32+20+4, 32+20+6+4, 32+24+16+7+4, 32+24+16+7+6+4, 32+24+20+4, 32+24+20+6+4, 32+26+6+4, 32+26+16+7+4, 32+26+16+7+6+4, 32+26+20+4, 32+26+20+6+4, 32+26+24+16+7+4, 32+26+24+16+7+6+4, 32+26+24+20+4, 32+26+24+20+6+4, 37+32+4, 37+32+6+4, 37+32+7+4,

37+32+7+6+4, 37+32+16+7+4, 37+32+16+7+6+4, 37+32+20+4, 37+32+20+6+4, 37+32+24+16+7+4, 37+32+24+16+7+6+4, 37+32+24+20+4, 37+32+24+20+6+4, 37+32+26+6+4, 37+32+26+16+7+4, 37+32+26+16+7+6+4, 37+32+26+20+4, 37+32+26+20+6+4, 37+32+26+24+16+7+4, 37+32+26+24+16+7+6+4, 37+32+26+24+20+4, 37+32+26+24+20+6+4, 42+32+4, 42+32+6+4, 42+32+7+4, 42+32+7+6+4, 42+32+16+7+4, 42+32+16+7+6+4, 42+32+20+4, 42+32+20+6+4, 42+32+24+16+7+4, 42+32+24+16+7+6+4, 42+32+24+20+4, 42+32+24+20+6+4, 42+32+26+6+4, 42+32+26+16+7+4, 42+32+26+16+7+6+4, 42+32+26+20+4, 42+32+26+20+6+4, 42+32+26+24+16+7+4, 42+32+26+24+16+7+6+4, 42+32+26+24+20+4, 42+32+26+24+20+6+4, 42+37+32+4, 42+37+32+6+4, 42+37+32+7+4, 42+37+32+7+6+4, 42+37+32+16+7+4, 42+37+32+16+7+6+4, 42+37+32+20+4, 42+37+32+20+6+4, 42+37+32+24+16+7+4, 42+37+32+24+16+7+6+4, 42+37+32+24+20+4, 42+37+32+24+20+6+4, 42+37+32+26+6+4, 42+37+32+26+16+7+4, 42+37+32+26+16+7+6+4, 42+37+32+26+20+4, 42+37+32+26+20+6+4, 42+37+32+26+24+16+7+4, 42+37+32+26+24+16+7+6+4, 42+37+32+26+24+20+4, 42+37+32+26+24+20+6+4, 46+4, 46+6+4, 46+7+4, 46+7+6+4, 46+16+7+4, 46+16+7+6+4, 46+20+4, 46+20+6+4, 46+24+16+7+4, 46+24+16+7+6+4, 46+24+20+4, 46+24+20+6+4, 46+26+6+4, 46+26+16+7+4, 46+26+16+7+6+4, 46+26+20+4, 46+26+20+6+4, 46+26+24+16+7+4, 46+26+24+16+7+6+4, 46+26+24+20+4, 46+26+24+20+6+4;

5, 20+5, 46+5, 46+20+5.

In the list above the numbers refer to the embodiments according to their numbering provided hereinabove whereas "+" indicates the dependency from another embodiment. The different individualized embodiments are separated by commas. In other words, "45+18+1" for example refers to embodiment 45) depending on embodiment 18), depending on embodiment 1), i.e. embodiment "45+18+1" corresponds to the compounds of embodiment 1) further limited by the features of the embodiments 18) and 45).

48) Examples of compounds of Formula (I) according to embodiment 1) are selected from the group consisting of:
2-Benzoimidazol-1-yl-1-{4-[4-(1H-benzoimidazol-2-yl)-thiazol-5-yl]-piperazin-1-yl}-ethanone;
1-{4-[4-(1H-Benzoimidazol-2-yl)-thiazol-5-yl]-piperazin-1-yl}-2-(2-methyl-benzoimidazol-1-yl)-ethanone;
1-(2-{4-[4-(1H-Benzoimidazol-2-yl)-thiazol-5-yl]-piperazin-1-yl}-2-oxo-ethyl)-3-methyl-1,3-dihydro-benzoimidazol-2-one;
1-{4-[4-(1H-Benzoimidazol-2-yl)-thiazol-5-yl]-piperazin-1-yl}-2-indol-1-yl-ethanone;
1-{4-[4-(1H-Benzoimidazol-2-yl)-thiazol-5-yl]-piperazin-1-yl}-2-(3-trifluoromethyl-pyrazol-1-yl)-ethanone;
1-{4-[4-(1H-Benzoimidazol-2-yl)-thiazol-5-yl]-piperazin-1-yl}-2-(3-methyl-pyrazol-1-yl)-ethanone;
1-{4-[4-(1H-Benzoimidazol-2-yl)-thiazol-5-yl]-piperazin-1-yl}-2-(2-methyl-thiazol-4-yl)-ethanone;
1-{4-[4-(1H-Benzoimidazol-2-yl)-thiazol-5-yl]-piperazin-1-yl}-2-(6-chloro-imidazo[1,2-b]pyridazin-2-yl)-ethanone;
1-{4-[4-(1H-Benzoimidazol-2-yl)-thiazol-5-yl]-piperazin-1-yl}-2-(2-methyl-imidazo[1,2-a]pyridin-3-yl)-ethanone;
1-{4-[4-(1H-Benzoimidazol-2-yl)-thiazol-5-yl]-piperazin-1-yl}-2-(3,5-dimethyl-[1,2,4]triazol-1-yl)-ethanone;
1-{4-[4-(1H-Benzoimidazol-2-yl)-thiazol-5-yl]-piperazin-1-yl}-2-(2,4-dimethyl-thiazol-5-yl)-ethanone;
1-{4-[4-(1H-Benzoimidazol-2-yl)-thiazol-5-yl]-piperazin-1-yl}-2-(5-methoxy-benzo[d]isoxazol-3-yl)-ethanone;
1-{4-[4-(1H-Benzoimidazol-2-yl)-thiazol-5-yl]-piperazin-1-yl}-2-(3,5-dimethyl-pyrazol-1-yl)-ethanone;
1-{4-[4-(1H-Benzoimidazol-2-yl)-thiazol-5-yl]-piperazin-1-yl}-2-imidazo[4,5-b]pyridin-3-yl-ethanone;
1-{4-[4-(1H-Benzoimidazol-2-yl)-thiazol-5-yl]-piperazin-1-yl}-2-pyrrolo[2,3-b]pyridin-1-yl-ethanone;
1-{(R)-4-[4-(1H-Benzoimidazol-2-yl)-thiazol-5-yl]-2-methyl-piperazin-1-yl}-2-pyrrolo[2,3-b]pyridin-1-yl-ethanone;
1-{(R)-4-[4-(1H-Benzoimidazol-2-yl)-thiazol-5-yl]-2-methyl-piperazin-1-yl}-2-imidazo[4,5-b]pyridin-3-yl-ethanone;
1-{(R)-4-[4-(1H-Benzoimidazol-2-yl)-thiazol-5-yl]-2-ethyl-piperazin-1-yl}-2-pyrrolo[2,3-b]pyridin-1-yl-ethanone;
1-{(R)-4-[4-(1H-Benzoimidazol-2-yl)-thiazol-5-yl]-2-methoxymethyl-piperazin-1-yl}-2-pyrrolo[2,3-b]pyridin-1-yl-ethanone;
1-{(R)-4-[4-(1H-Benzoimidazol-2-yl)-thiazol-5-yl]-2-methoxymethyl-piperazin-1-yl}-2-imidazo[4,5-b]pyridin-3-yl-ethanone;
1-{(R)-4-[4-(4-Fluoro-1H-benzoimidazol-2-yl)-thiazol-5-yl]-2-methyl-piperazin-1-yl}-2-pyrrolo[2,3-b]pyridin-1-yl-ethanone;
1-{(R)-2-Methyl-4-[4-(4-methyl-1H-benzoimidazol-2-yl)-thiazol-5-yl]-piperazin-1-yl}-2-pyrrolo[2,3-b]pyridin-1-yl-ethanone;
1-{(R)-4-[4-(6-Chloro-1H-benzoimidazol-2-yl)-thiazol-5-yl]-2-methyl-piperazin-1-yl}-2-pyrrolo[2,3-b]pyridin-1-yl-ethanone;
1-{(R)-4-[4-(6-tert-Butyl-1H-benzoimidazol-2-yl)-thiazol-5-yl]-2-methyl-piperazin-1-yl}-2-pyrrolo[2,3-b]pyridin-1-yl-ethanone;
1-{(R)-4-[4-(5-Methanesulfonyl-1H-benzoimidazol-2-yl)-thiazol-5-yl]-2-methyl-piperazin-1-yl}-2-pyrrolo[2,3-b]pyridin-1-yl-ethanone;
1-{(R)-4-[4-(5-Chloro-6-fluoro-1H-benzoimidazol-2-yl)-thiazol-5-yl]-2-methyl-piperazin-1-yl}-2-pyrrolo[2,3-b]pyridin-1-yl-ethanone;
1-{(R)-4-[4-(5-Chloro-6-methyl-1H-benzoimidazol-2-yl)-thiazol-5-yl]-2-methyl-piperazin-1-yl}-2-pyrrolo[2,3-b]pyridin-1-yl-ethanone;
1-{(R)-4-[4-(4,5-Difluoro-1H-benzoimidazol-2-yl)-thiazol-5-yl]-2-methyl-piperazin-1-yl}-2-pyrrolo[2,3-b]pyridin-1-yl-ethanone;
1-(2-{4-[4-(4-Chloro-1H-benzoimidazol-2-yl)-thiazol-5-yl]-piperazin-1-yl}-2-oxo-ethyl)-3-methyl-1,3-dihydro-benzoimidazol-2-one;
1-(2-{4-[4-(7-Methoxy-1H-benzoimidazol-2-yl)-thiazol-5-yl]-piperazin-1-yl}-2-oxo-ethyl)-3-methyl-1,3-dihydro-benzoimidazol-2-one;
1-Methyl-3-(2-{4-[4-(5-methyl-1H-benzoimidazol-2-yl)-thiazol-5-yl]-piperazin-1-yl}-2-oxo-ethyl)-1,3-dihydro-benzoimidazol-2-one;
1-Methyl-3-(2-oxo-2-{4-[4-(5-trifluoromethyl-1H-benzoimidazol-2-yl)-thiazol-5-yl]-piperazin-1-yl}-ethyl)-1,3-dihydro-benzoimidazol-2-one;
1-(2-{4-[4-(5-Methoxy-1H-benzoimidazol-2-yl)-thiazol-5-yl]-piperazin-1-yl}-2-oxo-ethyl)-3-methyl-1,3-dihydro-benzoimidazol-2-one;
1-(2-{4-[4-(6-Fluoro-1H-benzoimidazol-2-yl)-thiazol-5-yl]-piperazin-1-yl}-2-oxo-ethyl)-3-methyl-1,3-dihydro-benzoimidazol-2-one;
1-(2-{4-[4-(5,6-Dichloro-1H-benzoimidazol-2-yl)-thiazol-5-yl]-piperazin-1-yl}-2-oxo-ethyl)-3-methyl-1,3-dihydro-benzoimidazol-2-one;

1-(2-{4-[4-(5,6-Dimethoxy-1H-benzoimidazol-2-yl)-thiazol-5-yl]-piperazin-1-yl}-2-oxo-ethyl)-3-methyl-1,3-dihydro-benzoimidazol-2-one;
1-(2-{4-[4-(6-Chloro-7-methyl-1H-benzoimidazol-2-yl)-thiazol-5-yl]-piperazin-1-yl}-2-oxo-ethyl)-3-methyl-1,3-dihydro-benzoimidazol-2-one;
1-{4-[4-(1H-Benzoimidazol-2-yl)-2-bromo-thiazol-5-yl]-piperazin-1-yl}-2-pyrrolo[2,3-b]pyridin-1-yl-ethanone;
1-{4-[4-(1H-Benzoimidazol-2-yl)-2-ethyl-thiazol-5-yl]-piperazin-1-yl}-2-pyrrolo[2,3-b]pyridin-1-yl-ethanone;
1-{4-[4-(1H-Benzoimidazol-2-yl)-2-methyl-thiazol-5-yl]-piperazin-1-yl}-2-pyrrolo[2,3-b]pyridin-1-yl-ethanone;
1-{4-[4-(1H-Benzoimidazol-2-yl)-2-phenyl-thiazol-5-yl]-piperazin-1-yl}-2-pyrrolo[2,3-b]pyridin-1-yl-ethanone;
1-{4-[4-(1H-Benzoimidazol-2-yl)-2-chloro-thiazol-5-yl]-piperazin-1-yl}-2-pyrrolo[2,3-b]pyridin-1-yl-ethanone;
1-{4-[4-(1H-Benzoimidazol-2-yl)-2-(1-hydroxy-ethyl)-thiazol-5-yl]-piperazin-1-yl}-2-pyrrolo[2,3-b]pyridin-1-yl-ethanone;
1-{4-[4-(1H-Benzoimidazol-2-yl)-thiazol-5-yl]-[1,4]diazepan-1-yl}-2-pyrrolo[2,3-b]pyridin-1-yl-ethanone;
1-{4-[4-(1H-Benzoimidazol-2-yl)-thiazol-5-yl]-[1,4]diazepan-1-yl}-2-imidazo[4,5-b]pyridin-3-yl-ethanone;
1-{(S)-4-[4-(1H-Benzoimidazol-2-yl)-thiazol-5-yl]-2-methyl-piperazin-1-yl}-2-pyrrolo[2,3-b]pyridin-1-yl-ethanone;
1-{(S)-4-[4-(1H-Benzoimidazol-2-yl)-thiazol-5-yl]-2-methyl-piperazin-1-yl}-2-imidazo[4,5-b]pyridin-3-yl-ethanone;
1-{4-[4-(1H-Benzoimidazol-2-yl)-thiazol-5-yl]-piperidin-1-yl}-2-imidazo[4,5-b]pyridin-3-yl-ethanone;
1-{(R)-4-[4-(1H-Benzoimidazol-2-yl)-thiazol-5-yl]-2-ethyl-piperazin-1-yl}-2-imidazo[4,5-b]pyridin-3-yl-ethanone;
1-{(R)-4-[4-(1H-Benzoimidazol-2-yl)-2-isopropyl-thiazol-5-yl]-2-methyl-piperazin-1-yl}-2-imidazo[4,5-b]pyridin-3-yl-ethanone;
1-{(R)-4-[4-(1H-Benzoimidazol-2-yl)-2-trifluoromethyl-thiazol-5-yl]-2-methyl-piperazin-1-yl}-2-imidazo[4,5-b]pyridin-3-yl-ethanone;
1-{4-[4-(1H-Benzoimidazol-2-yl)-thiazol-5-yl]-piperazin-1-yl}-2-(4-methoxy-indol-1-yl)-ethanone;
1-{4-[4-(1H-Benzoimidazol-2-yl)-thiazol-5-yl]-piperazin-1-yl}-2-(5,6-dichloro-indol-1-yl)-ethanone;
1-{4-[4-(1H-Benzoimidazol-2-yl)-thiazol-5-yl]-piperazin-1-yl}-2-(6-trifluoromethyl-indol-1-yl)-ethanone;
1-{4-[4-(1H-Benzoimidazol-2-yl)-thiazol-5-yl]-piperazin-1-yl}-2-(5-fluoro-indol-1-yl)-ethanone;
1-{4-[4-(1H-Benzoimidazol-2-yl)-thiazol-5-yl]-piperazin-1-yl}-2-(6-fluoro-indol-1-yl)-ethanone;
1-{4-[4-(1H-Benzoimidazol-2-yl)-thiazol-5-yl]-piperazin-1-yl}-2-(7-methyl-indol-1-yl)-ethanone;
1-{4-[4-(1H-Benzoimidazol-2-yl)-thiazol-5-yl]-piperazin-1-yl}-2-(2-methyl-indol-1-yl)-ethanone;
1-(2-{4-[4-(1H-Benzoimidazol-2-yl)-thiazol-5-yl]-piperazin-1-yl}-2-oxo-ethyl)-1H-indole-3-carbonitrile;
1-{4-[4-(1H-Benzoimidazol-2-yl)-thiazol-5-yl]-piperazin-1-yl}-2-(4-chloro-indol-1-yl)-ethanone;
1-(2-{4-[4-(1H-Benzoimidazol-2-yl)-thiazol-5-yl]-piperazin-1-yl}-2-oxo-ethyl)-1H-indole-7-carbonitrile;
1-{4-[4-(1H-Benzoimidazol-2-yl)-thiazol-5-yl]-piperazin-1-yl}-2-(5-chloro-6-methoxy-indol-1-yl)-ethanone;
1-{4-[4-(1H-Benzoimidazol-2-yl)-thiazol-5-yl]-piperazin-1-yl}-2-(5-fluoro-3-methyl-indol-1-yl)-ethanone;
1-{4-[4-(1H-Benzoimidazol-2-yl)-thiazol-5-yl]-piperazin-1-yl}-2-(2-trifluoromethyl-benzoimidazol-1-yl)-ethanone;
1-{4-[4-(1H-Benzoimidazol-2-yl)-thiazol-5-yl]-piperazin-1-yl}-2-(6-chloro-pyrrolo[2,3-b]pyridin-1-yl)-ethanone;
1-{4-[4-(1H-Benzoimidazol-2-yl)-thiazol-5-yl]-piperazin-1-yl}-2-(2-methyl-pyrrolo[2,3-b]pyridin-1-yl)-ethanone;
1-{4-[4-(1H-Benzoimidazol-2-yl)-thiazol-5-yl]-piperazin-1-yl}-2-(3-methyl-pyrrolo[2,3-b]pyridin-1-yl)-ethanone;
1-(2-{4-[4-(1H-Benzoimidazol-2-yl)-thiazol-5-yl]-piperazin-1-yl}-2-oxo-ethyl)-1,3-dihydro-indol-2-one;
1-{4-[4-(1H-Benzoimidazol-2-yl)-thiazol-5-yl]-piperazin-1-yl}-2-(6-methoxy-pyrrolo[2,3-b]pyridin-1-yl)-ethanone;
1-{4-[4-(1H-Benzoimidazol-2-yl)-thiazol-5-yl]-piperazin-1-yl}-2-(6-methyl-pyrrolo[2,3-b]pyridin-1-yl)-ethanone;
3-(2-{4-[4-(1H-Benzoimidazol-2-yl)-thiazol-5-yl]-piperazin-1-yl}-2-oxo-ethyl)-1,3-dihydro-imidazo[4,5-b]pyridin-2-one;
1-{(2S,6R)-4-[4-(5-Chloro-1H-benzoimidazol-2-yl)-thiazol-5-yl]-2,6-dimethyl-piperazin-1-yl}-2-imidazo[4,5-b]pyridin-3-yl-ethanone;
1-{(R)-4-[4-(1H-Benzoimidazol-2-yl)-2-cyclopropyl-thiazol-5-yl]-2-methyl-piperazin-1-yl}-2-imidazo[4,5-b]pyridin-3-yl-ethanone;
1-Methyl-3-(2-oxo-2-{4-[4-(6-trifluoromethoxy-1H-benzoimidazol-2-yl)-thiazol-5-yl]-piperazin-1-yl}-ethyl)-1,3-dihydro-benzoimidazol-2-one;
2-(5-{4-[2-(3-Methyl-2-oxo-2,3-dihydro-benzoimidazol-1-yl)-acetyl]-piperazin-1-yl}-thiazol-4-yl)-1H-benzoimidazole-5-carbonitrile;
1-(2-{4-[4-(6-Hydroxymethyl-1H-benzoimidazol-2-yl)-thiazol-5-yl]-piperazin-1-yl}-2-oxo-ethyl)-3-methyl-1,3-dihydro-benzoimidazol-2-one;
1-(2-{4-[4-(1H-Benzoimidazol-2-yl)-thiazol-5-yl]-piperazin-1-yl}-2-oxo-ethyl)-3,4-dihydro-1H-quinolin-2-one;
4-(2-{4-[4-(1H-Benzoimidazol-2-yl)-thiazol-5-yl]-piperazin-1-yl}-2-oxo-ethyl)-4H-benzo[1,4]oxazin-3-one;
1-{(1S*,5R*)-3-[4-(1H-Benzoimidazol-2-yl)-thiazol-5-yl]-3,8-diaza-bicyclo[3.2.1]oct-8-yl}-2-imidazo[4,5-b]pyridin-3-yl-ethanone;
1-{(R)-4-[4-(1H-Benzoimidazol-2-yl)-2-bromo-thiazol-5-yl]-2-methyl-piperazin-1-yl}-2-imidazo[4,5-b]pyridin-3-yl-ethanone;
1-{(R)-4-[4-(1H-Benzoimidazol-2-yl)-2-o-tolyl-thiazol-5-yl]-2-methyl-piperazin-1-yl}-2-imidazo[4,5-b]pyridin-3-yl-ethanone;
1-{(R)-4-[4-(1H-Benzoimidazol-2-yl)-2-(2-methoxy-phenyl)-thiazol-5-yl]-2-methyl-piperazin-1-yl}-2-imidazo[4,5-b]pyridin-3-yl-ethanone;
1-{(R)-4-[4-(6-Chloro-1H-benzoimidazol-2-yl)-thiazol-5-yl]-2-methyl-piperazin-1-yl}-2-imidazo[4,5-b]pyridin-3-yl-ethanone;
3-(2-{(R)-4-[4-(5-Chloro-1H-benzoimidazol-2-yl)-thiazol-5-yl]-2-methyl-piperazin-1-yl}-2-oxo-ethyl)-3H-benzooxazol-2-one;
2-Imidazo[4,5-b]pyridin-3-yl-1-{(R)-2-methyl-4-[4-(5-methyl-1H-benzoimidazol-2-yl)-thiazol-5-yl]-piperazin-1-yl}-ethanone;
1-{(R)-4-[4-(5-tert-Butyl-1H-benzoimidazol-2-yl)-thiazol-5-yl]-2-methyl-piperazin-1-yl}-2-imidazo[4,5-b]pyridin-3-yl-ethanone;
1-{(R)-4-[4-(5-Chloro-6-methyl-1H-benzoimidazol-2-yl)-thiazol-5-yl]-2-methyl-piperazin-1-yl}-2-imidazo[4,5-b]pyridin-3-yl-ethanone;
2-Imidazo[4,5-b]pyridin-3-yl-1-{(R)-4-[4-(6-isopropyl-1H-benzoimidazol-2-yl)-thiazol-5-yl]-2-methyl-piperazin-1-yl}-ethanone;

1-{(R)-4-[4-(5-Chloro-6-fluoro-1H-benzoimidazol-2-yl)-thiazol-5-yl]-2-methyl-piperazin-1-yl}-2-imidazo[4,5-b]pyridin-3-yl-ethanone;
1-{(R)-4-[4-(4,5-Difluoro-1H-benzoimidazol-2-yl)-thiazol-5-yl]-2-methyl-piperazin-1-yl}-2-imidazo[4,5-b]pyridin-3-yl-ethanone;
1-{(R)-4-[4-(5,6-Difluoro-1H-benzoimidazol-2-yl)-thiazol-5-yl]-2-methyl-piperazin-1-yl}-2-imidazo[4,5-b]pyridin-3-yl-ethanone;
2-Imidazo[4,5-b]pyridin-3-yl-1-{(R)-2-methyl-4-[4-(5-trifluoromethyl-1H-benzoimidazol-2-yl)-thiazol-5-yl]-piperazin-1-yl}-ethanone;
1-{(R)-4-[4-(5-Chloro-6-trifluoromethyl-1H-benzoimidazol-2-yl)-thiazol-5-yl]-2-methyl-piperazin-1-yl}-2-imidazo[4,5-b]pyridin-3-yl-ethanone;
1-{(R)-4-[4-(5-Chloro-4-methyl-1H-benzoimidazol-2-yl)-thiazol-5-yl]-2-methyl-piperazin-1-yl}-2-imidazo[4,5-b]pyridin-3-yl-ethanone;
2-Imidazo[4,5-b]pyridin-3-yl-1-{(R)-2-methyl-4-[4-(4-trifluoromethyl-1H-benzoimidazol-2-yl)-thiazol-5-yl]-piperazin-1-yl}-ethanone;
1-{(R)-4-[4-(5-Fluoro-1H-benzoimidazol-2-yl)-thiazol-5-yl]-2-methyl-piperazin-1-yl}-2-imidazo[4,5-b]pyridin-3-yl-ethanone;
1-{(R)-4-[4-(4-Fluoro-1H-benzoimidazol-2-yl)-thiazol-5-yl]-2-methyl-piperazin-1-yl}-2-imidazo[4,5-b]pyridin-3-yl-ethanone;
2-Imidazo[4,5-b]pyridin-3-yl-1-{(R)-2-methyl-4-[4-(1-methyl-1H-benzoimidazol-2-yl)-thiazol-5-yl]-piperazin-1-yl}-ethanone;
1-{(R)-4-[4-(6-Ethyl-1H-benzoimidazol-2-yl)-thiazol-5-yl]-2-methyl-piperazin-1-yl}-2-imidazo[4,5-b]pyridin-3-yl-ethanone;
2-Imidazo[4,5-b]pyridin-3-yl-1-{(R)-2-methyl-4-[4-(6-phenyl-1H-benzoimidazol-2-yl)-thiazol-5-yl]-piperazin-1-yl}-ethanone;
1-[2-(4-{(R)-4-[5-(2-Hydroxy-ethoxy)-1H-benzoimidazol-2-yl]-thiazol-5-yl}-piperazin-1-yl)-2-oxo-ethyl]-3-methyl-1,3-dihydro-benzoimidazol-2-one;
1-[2-(4-{(R)-4-[5-(2-Methoxy-ethoxy)-1H-benzoimidazol-2-yl]-thiazol-5-yl}-piperazin-1-yl)-2-oxo-ethyl]-3-methyl-1,3-dihydro-benzoimidazol-2-one;
1-(2-{(R)-4-[4-(1H-Benzoimidazol-2-yl)-2-trifluoromethyl-thiazol-5-yl]-2-methyl-piperazin-1-yl}-2-oxo-ethyl)-1,3-dihydro-indol-2-one;
3-(2-{(R)-4-[4-(1H-Benzoimidazol-2-yl)-2-trifluoromethyl-thiazol-5-yl]-2-methyl-piperazin-1-yl}-2-oxo-ethyl)-1,3-dihydro-imidazo[4,5-b]pyridin-2-one;
1-{4-[4-(1H-Benzoimidazol-2-yl)-thiazol-5-yl]-piperazin-1-yl}-2-(3,4-dihydro-2H-quinolin-1-yl)-ethanone;
1-{4-[4-(1H-Benzoimidazol-2-yl)-thiazol-5-yl]-piperazin-1-yl}-2-(2,3-dihydro-benzo[1,4]oxazin-4-yl)-ethanone;
1-(2-{4-[4-(1H-Benzoimidazol-2-yl)-thiazol-5-yl]-piperazin-1-yl}-2-oxo-ethyl)-2,3-dihydro-1H-quinolin-4-one;
1-{4-[4-(1H-Benzoimidazol-2-yl)-thiazol-5-yl]-piperazin-1-yl}-2-(7-fluoro-indol-1-yl)-ethanone;
1-{4-[4-(1H-Benzoimidazol-2-yl)-thiazol-5-yl]-piperazin-1-yl}-2-indazol-1-yl-ethanone;
1-{4-[4-(1H-Benzoimidazol-2-yl)-thiazol-5-yl]-piperazin-1-yl}-2-pyridin-3-yl-ethanone;
1-{4-[4-(1H-Benzoimidazol-2-yl)-thiazol-5-yl]-piperazin-1-yl}-2-(2-fluoro-4-methoxy-phenyl)-ethanone;
1-(2-{4-[4-(4-Hydroxy-1H-benzoimidazol-2-yl)-thiazol-5-yl]-piperazin-1-yl}-2-oxo-ethyl)-3-methyl-1,3-dihydro-benzoimidazol-2-one; and
1-{(R)-4-[4-(1H-Benzoimidazol-2-yl)-2-oxetan-3-yl-thiazol-5-yl]-2-methyl-piperazin-1-yl}-2-imidazo[4,5-b]pyridin-3-yl-ethanone.

49) In addition to the above-listed compounds, further examples of compounds of Formula (I) according to embodiment 1) are selected from the group consisting of:
1-{(R)-4-[4-(1H-Benzoimidazol-2-yl)-2-ethyl-thiazol-5-yl]-2-methyl-piperazin-1-yl}-2-imidazo[4,5-b]pyridin-3-yl-ethanone;
1-{(R)-4-[4-(5-Chloro-1H-benzoimidazol-2-yl)-2-trifluoromethyl-thiazol-5-yl]-2-methyl-piperazin-1-yl}-2-imidazo[4,5-b]pyridin-3-yl-ethanone;
1-{(R)-4-[4-(1H-Benzoimidazol-2-yl)-2-(2-fluoro-phenyl)-thiazol-5-yl]-2-methyl-piperazin-1-yl}-2-imidazo[4,5-b]pyridin-3-yl-ethanone;
1-{(R)-4-[4-(1H-Benzoimidazol-2-yl)-2-m-tolyl-thiazol-5-yl]-2-methyl-piperazin-1-yl}-2-imidazo[4,5-b]pyridin-3-yl-ethanone;
1-{(R)-4-[4-(1H-Benzoimidazol-2-yl)-2-p-tolyl-thiazol-5-yl]-2-methyl-piperazin-1-yl}-2-imidazo[4,5-b]pyridin-3-yl-ethanone;
1-(2-{(R)-4-[4-(1H-Benzoimidazol-2-yl)-thiazol-5-yl]-2-methyl-piperazin-1-yl}-2-oxo-ethyl)-3,3-dimethyl-1,3-dihydro-indol-2-one;
3-(2-{(R)-4-[4-(1H-Benzoimidazol-2-yl)-thiazol-5-yl]-2-methyl-piperazin-1-yl}-2-oxo-ethyl)-4-methyl-3H-benzooxazol-2-one;
3-(2-{(R)-4-[4-(1H-Benzoimidazol-2-yl)-thiazol-5-yl]-2-methyl-piperazin-1-yl}-2-oxo-ethyl)-4-fluoro-3H-benzooxazol-2-one;
1-{(R)-4-[4-(5,6-Dimethoxy-1H-benzoimidazol-2-yl)-thiazol-5-yl]-2-methyl-piperazin-1-yl}-2-imidazo[4,5-b]pyridin-3-yl-ethanone;
1-{(R)-4-[4-(1H-Benzoimidazol-2-yl)-thiazol-5-yl]-2-methyl-piperazin-1-yl}-2-(2-hydroxymethyl-pyrrolo[2,3-b]pyridin-1-yl)-ethanone;
1-{(R)-4-[4-(6-Hydroxymethyl-1H-benzoimidazol-2-yl)-2-trifluoromethyl-thiazol-5-yl]-2-methyl-piperazin-1-yl}-2-imidazo[4,5-b]pyridin-3-yl-ethanone;
1-{(R)-4-[4-(5,6-Dimethoxy-1H-benzoimidazol-2-yl)-2-trifluoromethyl-thiazol-5-yl]-2-methyl-piperazin-1-yl}-2-imidazo[4,5-b]pyridin-3-yl-ethanone;
1-{4-[4-(1H-Benzoimidazol-2-yl)-2-trifluoromethyl-thiazol-5-yl]-piperazin-1-yl}-2-imidazo[4,5-b]pyridin-3-yl-ethanone;
3-{4-(1H-Benzoimidazol-2-yl)-5-[(R)-3-methyl-4-(2-pyrrolo[2,3-b]pyridin-1-yl-acetyl)-piperazin-1-yl]-thiazol-2-yl}-propionic acid;
3-(2-{(R)-4-[4-(1H-Benzoimidazol-2-yl)-thiazol-5-yl]-2-methyl-piperazin-1-yl}-2-oxo-ethyl)-3H-oxazolo[4,5-b]pyridin-2-one;
4-(2-{(R)-4-[4-(1H-Benzoimidazol-2-yl)-thiazol-5-yl]-2-methyl-piperazin-1-yl}-2-oxo-ethyl)-4H-oxazolo[4,5-b]pyridin-2-one;
1-{(R)-4-[4-(6-Cyclopropyl-1H-benzoimidazol-2-yl)-thiazol-5-yl]-2-methyl-piperazin-1-yl}-2-imidazo[4,5-b]pyridin-3-yl-ethanone;
1-{(R)-4-[4-(1H-Benzoimidazol-2-yl)-thiazol-5-yl]-2-methyl-piperazin-1-yl}-2-(4-phenyl-[1,2,3]triazol-1-yl)-ethanone;
1-{(R)-4-[4-(6-Hydroxymethyl-1H-benzoimidazol-2-yl)-thiazol-5-yl]-2-methyl-piperazin-1-yl}-2-imidazo[4,5-b]pyridin-3-yl-ethanone;
1-{(R)-4-[4-(1H-Benzoimidazol-2-yl)-thiazol-5-yl]-2-methyl-piperazin-1-yl}-2-(2-[1,2,3]triazol-2-yl-phenyl)-ethanone;

1-(2-{(R)-4-[4-(1H-Benzoimidazol-2-yl)-thiazol-5-yl]-2-methyl-piperazin-1-yl}-2-oxo-ethyl)-1H-indole-2,3-dione;

2-Benzoimidazol-1-yl-1-{(R)-4-[4-(1H-benzoimidazol-2-yl)-2-trifluoromethyl-thiazol-5-yl]-2-methyl-piperazin-1-yl}-ethanone;

1-{(R)-4-[4-(1H-Benzoimidazol-2-yl)-2-trifluoromethyl-thiazol-5-yl]-2-methyl-piperazin-1-yl}-2-pyrazol-1-yl-ethanone;

1-{(R)-4-[4-(1H-Benzoimidazol-2-yl)-2-trifluoromethyl-thiazol-5-yl]-2-methyl-piperazin-1-yl}-2-(3-methyl-pyrazol-1-yl)-ethanone;

1-{(R)-4-[4-(1H-Benzoimidazol-2-yl)-2-trifluoromethyl-thiazol-5-yl]-2-methyl-piperazin-1-yl}-2-(4-chloro-pyrazol-1-yl)-ethanone;

1-{(R)-4-[4-(1H-Benzoimidazol-2-yl)-2-trifluoromethyl-thiazol-5-yl]-2-methyl-piperazin-1-yl}-2-(5-methyl-pyrazol-1-yl)-ethanone;

1-{(R)-4-[4-(1H-Benzoimidazol-2-yl)-2-trifluoromethyl-thiazol-5-yl]-2-methyl-piperazin-1-yl}-2-(3-phenyl-pyrazol-1-yl)-ethanone;

1-{(R)-4-[4-(1H-Benzoimidazol-2-yl)-2-trifluoromethyl-thiazol-5-yl]-2-methyl-piperazin-1-yl}-2-(3,5-dimethyl-[1,2,4]triazol-1-yl)-ethanone;

1-{(R)-4-[4-(1H-Benzoimidazol-2-yl)-2-trifluoromethyl-thiazol-5-yl]-2-methyl-piperazin-1-yl}-2-(2-[1,2,3]triazol-2-yl-phenyl)-ethanone;

1-{(R)-4-[4-(1H-Benzoimidazol-2-yl)-2-trifluoromethyl-thiazol-5-yl]-2-methyl-piperazin-1-yl}-2-(3-[1,2,3]triazol-2-yl-phenyl)-ethanone;

1-{(R)-4-[4-(1H-Benzoimidazol-2-yl)-2-hydroxymethyl-thiazol-5-yl]-2-methyl-piperazin-1-yl}-2-imidazo[4,5-b]pyridin-3-yl-ethanone;

1-{(R)-4-[4-(5-Acetyl-1H-benzoimidazol-2-yl)-2-trifluoromethyl-thiazol-5-yl]-2-methyl-piperazin-1-yl}-2-imidazo[4,5-b]pyridin-3-yl-ethanone;

1-{(R)-4-[4-(1H-Benzoimidazol-2-yl)-2-trifluoromethyl-thiazol-5-yl]-2-methyl-piperazin-1-yl}-2-quinolin-8-yl-ethanone;

1-((R)-4-{4-[5-(1-Hydroxy-ethyl)-1H-benzoimidazol-2-yl]-2-trifluoromethyl-thiazol-5-yl}-2-methyl-piperazin-1-yl)-2-imidazo[4,5-b]pyridin-3-yl-ethanone;

1-{(R)-4-[4-(1H-Benzoimidazol-2-yl)-2-trifluoromethyl-thiazol-5-yl]-2-methyl-piperazin-1-yl}-2-(4-phenyl-[1,2,3]triazol-1-yl)-ethanone;

1-{(R)-4-[4-(1H-Benzoimidazol-2-yl)-2-dimethylaminomethyl-thiazol-5-yl]-2-methyl-piperazin-1-yl}-2-imidazo[4,5-b]pyridin-3-yl-ethanone;

1-{(R)-4-[4-(1H-Benzoimidazol-2-yl)-2-trifluoromethyl-thiazol-5-yl]-2-methyl-piperazin-1-yl}-2-pyrazolo[3,4-b]pyridin-2-yl-ethanone;

1-{(R)-4-[4-(1H-Benzoimidazol-2-yl)-2-trifluoromethyl-thiazol-5-yl]-2-methyl-piperazin-1-yl}-2-(2-pyrazol-1-yl-phenyl)-ethanone;

1-{(R)-4-[4-(1H-Benzoimidazol-2-yl)-2-trifluoromethyl-thiazol-5-yl]-2-methyl-piperazin-1-yl}-2-(5-phenyl-pyrazol-1-yl)-ethanone;

1-(2-{(R)-4-[4-(1H-Benzoimidazol-2-yl)-thiazol-5-yl]-2-methyl-piperazin-1-yl}-2-oxo-ethyl)-3,3-difluoro-1,3-dihydro-indol-2-one;

2-{5-[(R)-4-(2-Imidazo[4,5-b]pyridin-3-yl-acetyl)-3-methyl-piperazin-1-yl]-2-trifluoromethyl-thiazol-4-yl}-1H-benzoimidazole-5-carboxylic acid methyl ester;

1-{(R)-4-[4-(1H-Benzoimidazol-2-yl)-2-trifluoromethyl-thiazol-5-yl]-2-methyl-piperazin-1-yl}-2-imidazo[4,5-c]pyridin-1-yl-ethanone;

2-Imidazo[4,5-b]pyridin-3-yl-1-((R)-4-{4-[5-(2-methoxy-ethoxy)-1H-benzoimidazol-2-yl]-2-trifluoromethyl-thiazol-5-yl}-2-methyl-piperazin-1-yl)-ethanone;

1-((R)-4-{4-[5-(2-Hydroxy-ethoxy)-1H-benzoimidazol-2-yl]-2-trifluoromethyl-thiazol-5-yl}-2-methyl-piperazin-1-yl)-2-imidazo[4,5-b]pyridin-3-yl-ethanone;

1-((R)-4-{4-[5-(1-Hydroxy-cyclopropyl)-1H-benzoimidazol-2-yl]-2-trifluoromethyl-thiazol-5-yl}-2-methyl-piperazin-1-yl)-2-imidazo[4,5-b]pyridin-3-yl-ethanone;

1-(2-{(R)-4-[4-(1H-Benzoimidazol-2-yl)-2-trifluoromethyl-thiazol-5-yl]-2-methyl-piperazin-1-yl}-2-oxo-ethyl)-3,3-difluoro-1,3-dihydro-indol-2-one;

1-{(R)-4-[4-(1H-Benzoimidazol-2-yl)-2-trifluoromethyl-thiazol-5-yl]-2-methyl-piperazin-1-yl}-2-(3-bromo-[1,2,4]triazol-1-yl)-ethanone;

1-{(R)-4-[4-(1H-Benzoimidazol-2-yl)-2-trifluoromethyl-thiazol-5-yl]-2-methyl-piperazin-1-yl}-2-(4-methyl-pyrazol-1-yl)-ethanone;

1-{(R)-4-[4-(1H-Benzoimidazol-2-yl)-2-trifluoromethyl-thiazol-5-yl]-2-methyl-piperazin-1-yl}-2-(3,5-dimethyl-pyrazol-1-yl)-ethanone;

1-{(R)-4-[4-(1H-Benzoimidazol-2-yl)-2-trifluoromethyl-thiazol-5-yl]-2-methyl-piperazin-1-yl}-2-(3-trifluoromethyl-pyrazol-1-yl)-ethanone;

1-{(R)-4-[4-(1H-Benzoimidazol-2-yl)-2-trifluoromethyl-thiazol-5-yl]-2-methyl-piperazin-1-yl}-2-[1,2,4]triazol-1-yl-ethanone;

1-{(R)-4-[4-(1H-Benzoimidazol-2-yl)-2-trifluoromethyl-thiazol-5-yl]-2-methyl-piperazin-1-yl}-2-[2-(4-methyl-piperazin-1-yl)-phenyl]-ethanone;

1-{(R)-4-[4-(1H-Benzoimidazol-2-yl)-2-trifluoromethyl-thiazol-5-yl]-2-methyl-piperazin-1-yl}-2-(5-methyl-[1,3,4]oxadiazol-2-yl)-ethanone;

1-{(R)-4-[4-(1H-Benzoimidazol-2-yl)-2-trifluoromethyl-thiazol-5-yl]-2-methyl-piperazin-1-yl}-2-(5-phenyl-[1,3,4]oxadiazol-2-yl)-ethanone;

1-{(R)-4-[4-(1H-Benzoimidazol-2-yl)-2-trifluoromethyl-thiazol-5-yl]-2-methyl-piperazin-1-yl}-2-[1,2,3]triazol-2-yl-ethanone;

1-(2-{(R)-4-[4-(1H-Benzoimidazol-2-yl)-2-trifluoromethyl-thiazol-5-yl]-2-methyl-piperazin-1-yl}-2-oxo-ethyl)-1H-pyrazole-3-carboxylic acid methyl ester;

1-((R)-2-Methyl-4-{4-[6-(4-methyl-piperazin-1-yl)-1H-benzoimidazol-2-yl]-2-trifluoromethyl-thiazol-5-yl}-piperazin-1-yl)-2-pyrazol-1-yl-ethanone;

1-{(R)-4-[4-(6-Dimethylamino-1H-benzoimidazol-2-yl)-2-trifluoromethyl-thiazol-5-yl]-2-methyl-piperazin-1-yl}-2-pyrazol-1-yl-ethanone;

2-Imidazo[4,5-b]pyridin-3-yl-1-{(R)-4-[4-(3H-imidazo[4,5-b]pyridin-2-yl)-2-trifluoromethyl-thiazol-5-yl]-2-methyl-piperazin-1-yl}-ethanone;

1-{(R)-2-Methyl-4-[4-(1-methyl-1H-benzoimidazol-2-yl)-2-trifluoromethyl-thiazol-5-yl]-piperazin-1-yl}-2-pyrazol-1-yl-ethanone;

1-((R)-4-{4-[1-(2-Methoxy-ethyl)-1H-benzoimidazol-2-yl]-2-trifluoromethyl-thiazol-5-yl}-2-methyl-piperazin-1-yl)-2-pyrazol-1-yl-ethanone;

2-Imidazo[4,5-b]pyridin-3-yl-1-{(R)-4-[4-(3H-imidazo[4,5-c]pyridin-2-yl)-2-trifluoromethyl-thiazol-5-yl]-2-methyl-piperazin-1-yl}-ethanone;

2-Imidazo[4,5-b]pyridin-3-yl-1-{(R)-2-methyl-4-[4-(9H-purin-8-yl)-2-trifluoromethyl-thiazol-5-yl]-piperazin-1-yl}-ethanone;

1-{(R)-4-[4-(1H-Benzoimidazol-2-yl)-2-trifluoromethyl-thiazol-5-yl]-2-methyl-piperazin-1-yl}-2-(6-methyl-pyridin-3-yl)-ethanone;

1-{(R)-4-[4-(1H-Benzoimidazol-2-yl)-2-trifluoromethyl-thiazol-5-yl]-2-methyl-piperazin-1-yl}-2-(2,6-dimethyl-pyridin-4-yl)-ethanone;
1-{(R)-4-[4-(1H-Benzoimidazol-2-yl)-2-trifluoromethyl-thiazol-5-yl]-2-methyl-piperazin-1-yl}-2-(5-methyl-4,5,6,7-tetrahydro-imidazo[4,5-c]pyridin-1-yl)-ethanone;
1-{(R)-4-[4-(1H-Benzoimidazol-2-yl)-2-trifluoromethyl-thiazol-5-yl]-2-methyl-piperazin-1-yl}-2-(4-dimethylaminomethyl-3-methyl-pyrazol-1-yl)-ethanone;
1-{(R)-2-Methyl-4-[4-(6-piperidin-1-ylmethyl-1H-benzoimidazol-2-yl)-2-trifluoromethyl-thiazol-5-yl]-piperazin-1-yl}-2-pyrazol-1-yl-ethanone;
1-{(R)-4-[4-(1H-Benzoimidazol-2-yl)-2-trifluoromethyl-thiazol-5-yl]-2-methyl-piperazin-1-yl}-2-(5-methyl-[1,2,4]triazol-1-yl)-ethanone;
1-{(R)-4-[4-(1H-Benzoimidazol-2-yl)-2-trifluoromethyl-thiazol-5-yl]-2-methyl-piperazin-1-yl}-2-(3-methyl-[1,2,4]triazol-1-yl)-ethanone;
1-{(R)-4-[4-(6-Dimethylaminomethyl-1H-benzoimidazol-2-yl)-2-trifluoromethyl-thiazol-5-yl]-2-methyl-piperazin-1-yl}-2-pyrazol-1-yl-ethanone;
1-((R)-4-{4-[6-(3-Methoxy-pyrrolidin-1-ylmethyl)-1H-benzoimidazol-2-yl]-2-trifluoromethyl-thiazol-5-yl}-2-methyl-piperazin-1-yl)-2-pyrazol-1-yl-ethanone;
1-{(R)-4-[4-(1H-Benzoimidazol-2-yl)-2-trifluoromethyl-thiazol-5-yl]-2-methyl-piperazin-1-yl}-2-(4,6-dimethyl-pyridin-2-yl)-ethanone;
1-{(R)-4-[4-(1H-Benzoimidazol-2-yl)-thiazol-5-yl]-2-dimethylaminomethyl-piperazin-1-yl}-2-imidazo[4,5-b]pyridin-3-yl-ethanone;
2-(3,5-Dimethyl-[1,2,4]triazol-1-yl)-1-((R)-2-methyl-4-{4-[6-(1-methyl-piperidin-4-yl)-1H-benzoimidazol-2-yl]-2-trifluoromethyl-thiazol-5-yl}-piperazin-1-yl)-ethanone;
2-(3,5-Dimethyl-[1,2,4]triazol-1-yl)-1-((R)-2-methyl-4-{4-[6-(tetrahydro-pyran-4-yl)-1H-benzoimidazol-2-yl]-2-trifluoromethyl-thiazol-5-yl}-piperazin-1-yl)-ethanone;
1-((R)-4-{4-[5-(2-Amino-ethyl)-1H-benzoimidazol-2-yl]-2-trifluoromethyl-thiazol-5-yl}-2-methyl-piperazin-1-yl)-2-(3,5-dimethyl-[1,2,4]triazol-1-yl)-ethanone;
1-{(R)-4-[4-(1H-Benzoimidazol-2-yl)-2-trifluoromethyl-thiazol-5-yl]-2-methyl-piperazin-1-yl}-2-(4-piperidin-4-yl-pyrazol-1-yl)-ethanone;
1-{(R)-4-[4-(1H-Benzoimidazol-2-yl)-2-trifluoromethyl-thiazol-5-yl]-2-methyl-piperazin-1-yl}-2-[4-(1-methyl-piperidin-4-yl)-pyrazol-1-yl]-ethanone;
1-{(R)-4-[4-(1H-Benzoimidazol-2-yl)-2-trifluoromethyl-thiazol-5-yl]-2-methyl-piperazin-1-yl}-2-(5-methyl-4,5,6,7-tetrahydro-imidazo[4,5-c]pyridin-3-yl)-ethanone;
2-(3,5-Dimethyl-[1,2,4]triazol-1-yl)-1-((R)-2-methyl-4-{4-[6-(2-pyrrolidin-1-yl-ethyl)-1H-benzoimidazol-2-yl]-2-trifluoromethyl-thiazol-5-yl}-piperazin-1-yl)-ethanone;
1-{(R)-4-[4-(1H-Benzoimidazol-2-yl)-2-trifluoromethyl-thiazol-5-yl]-2-methyl-piperazin-1-yl}-2-(5-methyl-4,5,6,7-tetrahydro-pyrazolo[4,3-c]pyridin-2-yl)-ethanone;
1-{(R)-4-[4-(1H-Benzoimidazol-2-yl)-2-trifluoromethyl-thiazol-5-yl]-2-methyl-piperazin-1-yl}-2-(5-methyl-4,5,6,7-tetrahydro-pyrazolo[4,3-c]pyridin-1-yl)-ethanone;
1-{(R)-4-[4-(1H-Benzoimidazol-2-yl)-2-trifluoromethyl-thiazol-5-yl]-2-methyl-piperazin-1-yl}-2-(1,4,6,7-tetrahydro-pyrazolo[4,3-c]pyridin-5-yl)-ethanone;
1-{(R)-4-[4-(1H-Benzoimidazol-2-yl)-2-trifluoromethyl-thiazol-5-yl]-2-dimethylaminomethyl-piperazin-1-yl}-2-(3,5-dimethyl-[1,2,4]triazol-1-yl)-ethanone;
1-{(R)-4-[4-(1H-Benzoimidazol-2-yl)-2-trifluoromethyl-thiazol-5-yl]-2-methyl-piperazin-1-yl}-2-(4-dimethylaminomethyl-3,5-dimethyl-pyrazol-1-yl)-ethanone;
1-{(R)-4-[4-(1H-Benzoimidazol-2-yl)-2-trifluoromethyl-thiazol-5-yl]-2-dimethylaminomethyl-piperazin-1-yl}-2-imidazo[4,5-b]pyridin-3-yl-ethanone;
1-{(R)-4-[4-(1H-Benzoimidazol-2-yl)-2-trifluoromethyl-thiazol-5-yl]-2-methyl-piperazin-1-yl}-2-(3-dimethylaminomethyl-5-methyl-[1,2,4]triazol-1-yl)-ethanone;
2-(3,5-Dimethyl-[1,2,4]triazol-1-yl)-1-{(R)-2-methyl-4-[4-(5-trifluoromethoxy-1H-benzoimidazol-2-yl)-2-trifluoromethyl-thiazol-5-yl]-piperazin-1-yl}-ethanone;
2-(3,5-Dimethyl-[1,2,4]triazol-1-yl)-1-{(R)-2-methyl-4-[4-(6-morpholin-4-yl-1H-benzoimidazol-2-yl)-2-trifluoromethyl-thiazol-5-yl]-piperazin-1-yl}-ethanone;
1-((R)-4-{4-[6-(Azetidin-3-yloxy)-1H-benzoimidazol-2-yl]-2-trifluoromethyl-thiazol-5-yl}-2-methyl-piperazin-1-yl)-2-(3,5-dimethyl-[1,2,4]triazol-1-yl)-ethanone;
2-(3,5-Dimethyl-[1,2,4]triazol-1-yl)-1-{(R)-2-methyl-4-[4-(6-piperidin-4-yl-1H-benzoimidazol-2-yl)-2-trifluoromethyl-thiazol-5-yl]-piperazin-1-yl}-ethanone;
2-(3,5-Dimethyl-[1,2,4]triazol-1-yl)-1-{(R)-2-methyl-4-[4-(6-[1,2,4]triazol-1-yl-1H-benzoimidazol-2-yl)-2-trifluoromethyl-thiazol-5-yl]-piperazin-1-yl}-ethanone;
1-[2-(5-{(R)-4-[2-(3,5-Dimethyl-[1,2,4]triazol-1-yl)-acetyl]-3-methyl-piperazin-1-yl}-2-trifluoromethyl-thiazol-4-yl)-3H-benzoimidazol-5-yl]-pyrrolidin-2-one;
1-{(S)-4-[4-(1H-Benzoimidazol-2-yl)-2-trifluoromethyl-thiazol-5-yl]-2-methyl-piperazin-1-yl}-2-(3,5-dimethyl-[1,2,4]triazol-1-yl)-ethanone;
2-(3,5-Dimethyl-[1,2,4]triazol-1-yl)-1-((R)-2-methyl-4-{4-[6-(5-methyl-[1,2,4]oxadiazol-3-yl)-1H-benzoimidazol-2-yl]-2-trifluoromethyl-thiazol-5-yl}-piperazin-1-yl)-ethanone;
2-(3,5-Dimethyl-[1,2,4]triazol-1-yl)-1-{(R)-4-[4-(4-fluoro-1H-benzoimidazol-2-yl)-2-trifluoromethyl-thiazol-5-yl]-2-methyl-piperazin-1-yl}-ethanone;
1-{(R)-4-[4-(4,5-Difluoro-1H-benzoimidazol-2-yl)-2-trifluoromethyl-thiazol-5-yl]-2-methyl-piperazin-1-yl}-2-(3,5-dimethyl-[1,2,4]triazol-1-yl)-ethanone; and
2-(3,5-Dimethyl-[1,2,4]triazol-1-yl)-1-{(R)-2-methyl-4-[2-trifluoromethyl-4-(4-trifluoromethyl-1H-benzoimidazol-2-yl)-thiazol-5-yl]-piperazin-1-yl}-ethanone.

Where the plural form is used for compounds, salts, pharmaceutical compositions, diseases or the like, this is intended to mean also a single compound, salt, disease or the like.

Any reference to a compound of Formulae (I) as defined in any one of embodiments 1) to 49) is to be understood as referring also to the salts (and especially the pharmaceutically acceptable salts) of such compounds, as appropriate and expedient.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

The present invention also includes isotopically labelled, especially $^2$H (deuterium) labelled compounds of formula (I), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

Besides, the term "room temperature" as used herein refers to a temperature of 25° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

The compounds of formula (I) as defined in any one of embodiments 1) to 49) and their pharmaceutically acceptable salts can be used as medicaments, e.g. in the form of pharmaceutical compositions for enteral (such especially oral) or parenteral administration (including topical application or inhalation).

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I) as defined in any one of embodiments 1) to 49). In a preferred embodiment of the invention, the administered amount is comprised between 1 mg and 1000 mg per day, particularly between 5 mg and 500 mg per day, more particularly between 25 mg and 400 mg per day, especially between 50 mg and 200 mg per day.

For avoidance of any doubt, if compounds are described as useful for the prevention or treatment of certain diseases, such compounds are likewise suitable for use in the preparation of a medicament for the prevention or treatment of said diseases.

Another aspect of the invention concerns a method for the prevention or the treatment of a disease or disorder as mentioned above in a patient comprising the administration to said patient of a pharmaceutically active amount of a compound of Formula (I) as defined in any one of embodiments 1) to 49) or a pharmaceutically acceptable salt thereof.

The compounds according to formula (I) as defined in any one of embodiments 1) to 49) [and especially those comprising the characteristics defined in embodiment 24)] are useful for the prevention or treatment of disorders relating to a dysfunction of the CXCR3 receptor or dysfunction of ligands signalling through CXCR3.

Such disorders relating to a dysfunction of the CXCR3 receptor or its ligands are diseases or disorders where a modulator of a human CXCR3 receptor is required. The above mentioned disorders may in particular be defined as comprising autoimmune disorders, inflammatory diseases, infectious diseases, transplant rejection, fibrosis, neurodegenerative disorders and cancer.

Autoimmune disorders may be defined as comprising rheumatoid arthritis (RA); multiple sclerosis (MS); inflammatory bowel disease (IBD; comprising Crohn's disease and ulcerative colitis); systemic lupus erythematosus (SLE); psoriasis; psoriatic arthritis; lupus nephritis; interstitial cystitis; celiac disease; antiphospholipid syndrome; thyroiditis such as Hashimoto's thyroiditis; lymphocytic thyroiditis; myasthenia gravis; type I diabetes; uveitis; episcleritis; scleritis; Kawasaki's disease, uveo-retinitis; posterior uveitis; uveitis associated with Behcet's disease; uveomeningitis syndrome; allergic encephalomyelitis; atopic diseases such as rhinitis, conjunctivitis, dermatitis; and post-infectious autoimmune diseases including rheumatic fever and post-infectious glomerulonephritis. In a sub-embodiment, autoimmune disorders include rheumatoid arthritis (RA); multiple sclerosis (MS); inflammatory bowel disease comprising Crohn's disease and ulcerative colitis; systemic lupus erythematosus (SLE); lupus nephritis; interstitial cystitis; celiac disease; and type I diabetes.

Inflammatory diseases may be defined as comprising asthma; COPD, atherosclerosis; myocarditis; dry eye disease; inflammatory myopathies; sarcoidosis; pulmonary artherial hypertension, especially associated with sarcoidosis; and obesity.

Infectious diseases may be defined as comprising diseases mediated by various infectious agents and complications resulting therefrom; such as malaria, cerebral malaria, leprosy, tuberculosis, influenza, *toxoplasma gondii*, dengue, hepatitis B and C, herpes simplex, *leishmania, chlamydia trachomatis*, lyme disease, west nile virus.

Transplant rejection may be defined as comprising rejection of transplanted organs such as kidney, liver, heart, lung, pancreas, cornea, and skin; graft-versus-host diseases brought about by stem cell transplantation; and chronic allograft vasculopathy.

Fibrosis may be defined as comprising liver cirrhosis, idiopathic pulmonary fibrosis, renal fibrosis, endomyocardial fibrosis, systemic sclerosis, and arthrofibrosis.

Neurodegenerative disorders may be defined as comprising neurodegeneration and conditions involving neuronal death such as multiple sclerosis (including relapsing remitting multiple sclerosis and progressive multiple sclerosis), Alzheimer's disease, Parkinson's disease, Huntington's chorea, HIV associated dementia, prion mediated neurodegeneration, epilepsy, stroke, cerebral ischemia, cerebral palsy, neuromyelitis optica, clinically isolated syndrome, Alpers' disease, amyotrophic lateral sclerosis (ALS), senile dementia, dementia with Lewy bodies, Rett syndrome, spinal cord trauma, traumatic brain injury, trigeminal neuralgia, chronic inflammatory demyelinating polyneuropathy, Guillain-Barré syndrome, glossopharyngeal neuralgia, mild cognitive decline, cognitive decline, spinal muscular atrophy, and cerebral malaria.

Cancer may be defined as comprising all sorts of cancers such as large intestine cancer, rectal cancer, breast cancer, lung cancer, non-small cell lung cancer, prostate cancer, esophagal cancer, stomach cancer, liver cancer, bile duct cancer, spleen cancer, kidney cancer, urinary bladder cancer, uterine cancer, ovarian cancer, cervical cancer, testicular cancer, thyroid cancer, pancreas cancer, brain tumor, blood tumor, basophil adenoma, prolactinoma, hyperprolactinemia, adenomas, endometrial cancer, colon cancer; chronic lymphocytic leukemia (CLL); and especially the metastatic spread of those cancers.

Preparation of Compounds of Formula (I)

A further aspect of the invention is a process for the preparation of compounds of formula (I). Compounds according to formula (I) of the present invention can be prepared from commercially available or well known starting materials according to the methods described in the experimental part, by analogous methods; or according to the general sequence of reactions outlined below, wherein ring A, X, $(R^1)_n$, $R^2$, $R^3$, $R^4$, $R^{4'}$, $R^5$, m, n, and p are as defined for formula (I). Other abbreviations used herein are explicitly defined, or are as defined in the experimental section. In some instances the generic groups $(R^1)_n$, $R^2$, $R^3$, $R^4$, $R^{4'}$, and $R^5$ might be incompatible with the assembly illustrated in the schemes below and so will require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups as necessary are in place. The compounds obtained may also be converted into salts, especially pharmaceutically acceptable salts thereof in a manner known per se.

General Preparation Routes:
Preparation of the Compounds of Formula (I)

or N-methylmorpholine and in a suitable solvent such as DCM, THF, DMF or a mixture thereof, preferably at a temperature about RT.

Alternatively, the compounds of formula (I) can be obtained as described in Scheme 2.

Scheme 2

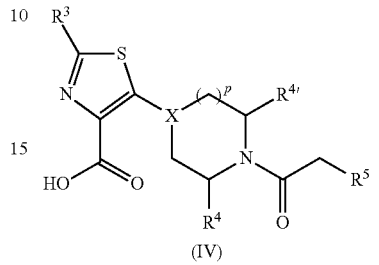

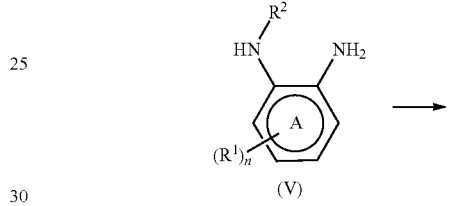

A compound of structure IV can be coupled to a compound of structure V using standard methods for an amide coupling such as those previously described for the synthesis of the compounds of formula (I) (Scheme 1). The obtained intermediate can be directly engaged in the next cyclization step by heating in acidic medium, preferably refluxing in acetic acid, $POCl_3$ or aqueous HCl, to yield the compounds of formula (I). The intermediate can also be worked-up before cyclization, with $NaHSO_4$ and/or $NaHCO_3$ or a polymer supported form thereof, or purified by preparative LC-MS.

Another possible route to access the compounds of formula (I) wherein $R^3$ is methyl, ethyl or phenyl is shown in Scheme 3. A compound of formula (I) wherein $R^3$ is bromine can be converted into a compound of formula (I) wherein $R^3$ is phenyl, using a reagent of formula $R^3$—B—$(OR)_2$, R being hydrogen or alkyl, using Suzuki conditions such as $K_3PO_4$, $Pd(OAc)_2$, in the presence of a ligand such as tricyclohexylphosphine, in water/toluene and heating at a temperature about 100° C.

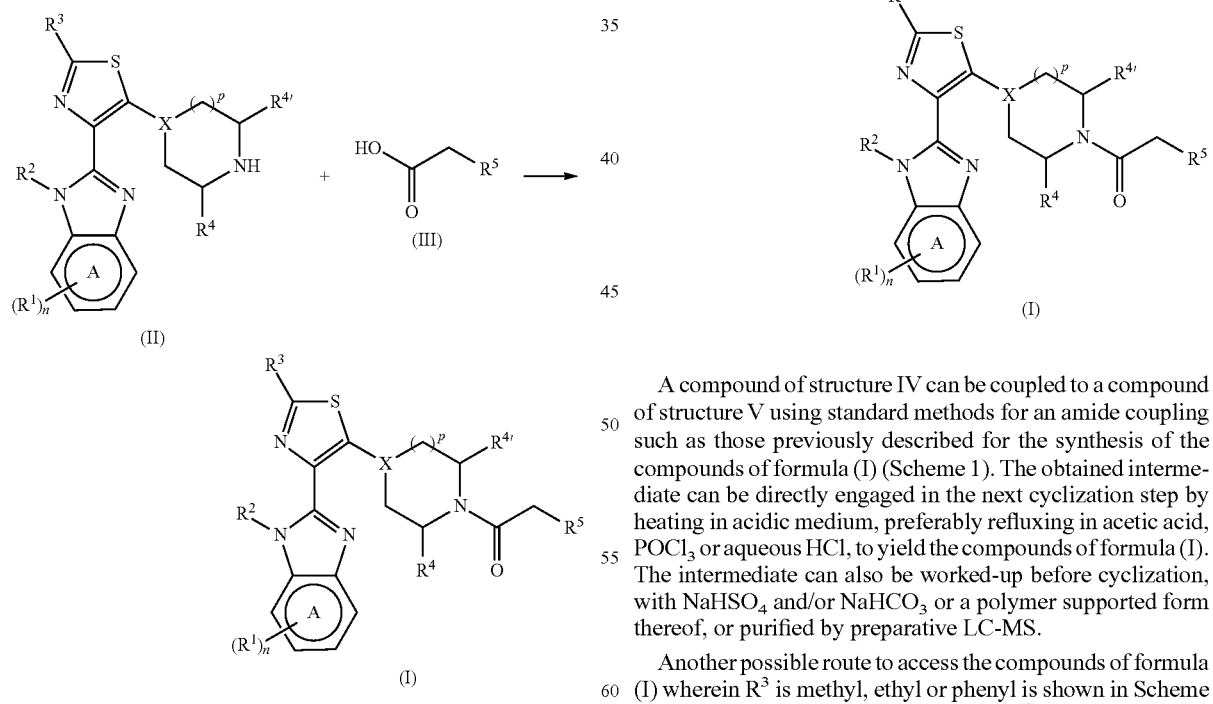

The compounds of formula (I) can be prepared (Scheme 1) by coupling a compound of structure II with a compound of structure III using standard peptide coupling methods such as HOBT, EDCI, DCC, HATU, PyBOP, TBTU, HOAT, or a combination thereof, or a polymer supported form thereof, optionally in presence of a suitable base such as TEA, DIPEA Scheme 3

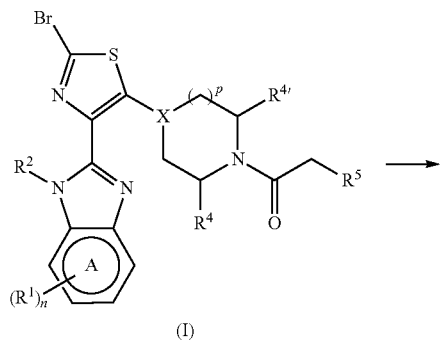
(I)

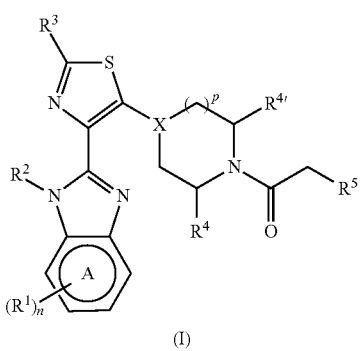
(I)

Moreover, a compound of formula (I) wherein R³ is bromine can be converted into a compound of formula (I) wherein R³ is methyl or ethyl, using a reagent of formula Zn—(R³)₂, using standard conditions for a Negishi reaction, in presence of a suitable palladium catalyst such as 1,1'-bis(diphenylphosphin)ferrocene dichloropalladium-(II)-chlorid complex, in a suitable solvent such as dioxane, and preferably heating between 90° C. and 110° C.

Alternatively, the compounds of formula (I) wherein R³ is aryl or 1-hydroxy-ethyl can be obtained by the synthetic route shown in Scheme 4.

-continued

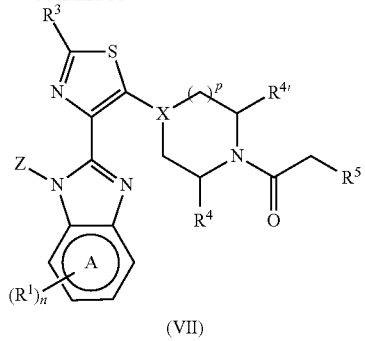
(VII)

The intermediate of structure VI wherein Z is a suitable protecting group for a benzimidazole ring such as SEM can be converted into an intermediate of structure VII wherein R³ is aryl, using a reagent of formula R³—B—(OR)₂, R being hydrogen or alkyl, using standard conditions for a Suzuki reaction, in presence of a suitable base such as aq. Na₂CO₃ or K₂CO₃, in presence of a suitable palladium catalyst such as Pd(PPh₃)₄ or Pd(PPh₃)₂Cl₂, in a suitable solvent such as MeCN, and preferably heating between 80° C. and 100° C. The SEM protecting group can be subsequently cleaved using TBAF to lead to the compounds of formula (I) wherein R³ is aryl.

Besides, the intermediate of structure VI can also be converted into an intermediate of structure VII wherein R³ is 1-hydroxy-ethyl, using standard conditions for a Stille reaction, using tributyl(1-ethoxyvinyl)tin and Pd(PPh₃)₂Cl₂ in toluene and heating at about 95° C. The resulting acetoxy derivative can be reduced using NaBH₄ in MeOH at a temperature about RT. Subsequent cleavage of the Z group leads to the compounds of formula (I) wherein R³ is 1-hydroxy-ethyl.

Alternatively, the compounds of formula (I) wherein R² is not hydrogen can be prepared (see Scheme 5) by alkylation reaction of a compound of formula I wherein R² is hydrogen, using a reagent such as R$^{2X}$, X being iodine, bromine or chlorine, using a base such as NaH, in a suitable solvent such as THF or DMF and at a temperature between RT and reflux.

Scheme 4

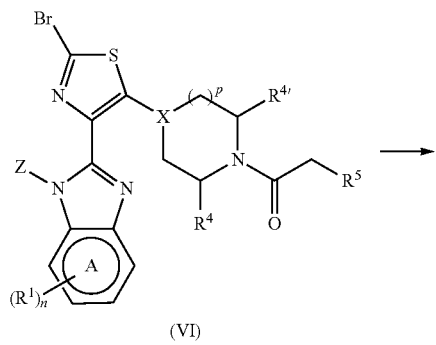
(VI)

Scheme 5

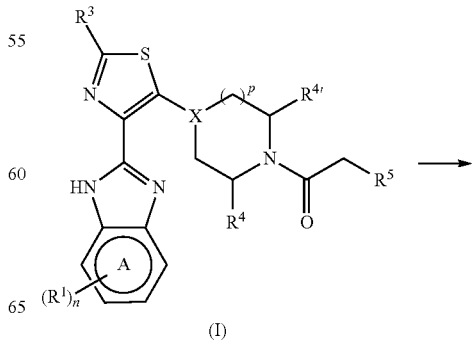
(I)

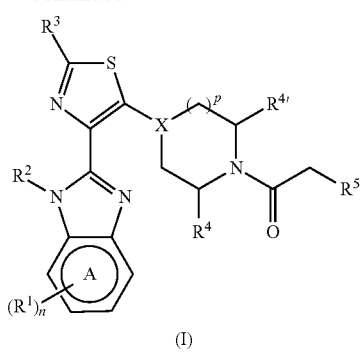

(I)

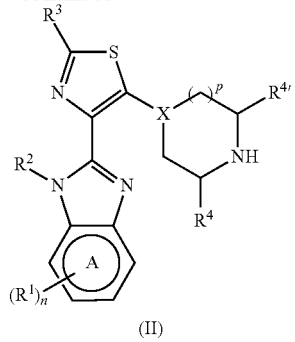

(II)

Preparation of the Compounds of Structure II

The compounds of structure II can be prepared using the route shown in Scheme 6.

Scheme 6

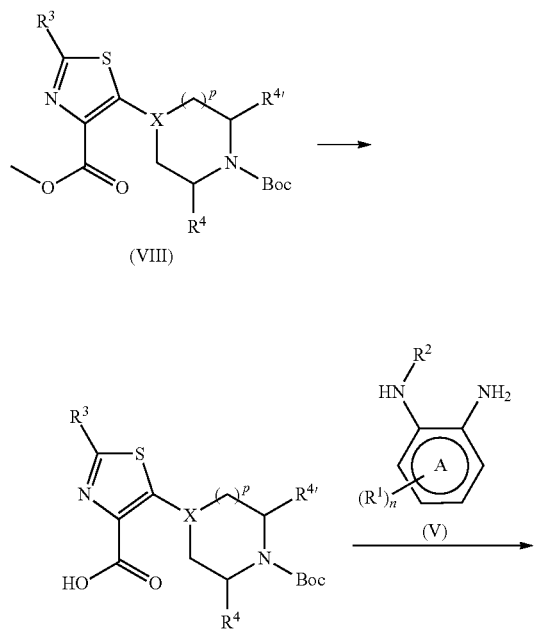

The methyl ester function of the compound of structure VIII can be cleaved under standard basic conditions, preferably using NaOH or LiOH, in a suitable solvent such as EtOH, MeOH, THF, water or a mixture thereof and at a temperature between RT and 60° C. The intermediate of structure IX can be coupled to a diamine compound of structure V followed by cyclization according to the procedure described for the synthesis of the compounds of formula (I) in Scheme 2. The Boc protecting group of the intermediate of structure X can be subsequently cleaved under standard acidic conditions, preferably using HCl in a suitable solvent such as EA, dioxane, Et$_2$O, EtOH or a mixture thereof, or using TFA in DCM, and at a temperature about RT to give the compound of structure II.

Preparation of the Compounds of Structure III

The compounds of structure III are either commercially available, or, for $R^5$ representing a nitrogen-linked heterocyclyl ring, can be synthesized following the route shown hereafter (Scheme 7).

Scheme 7

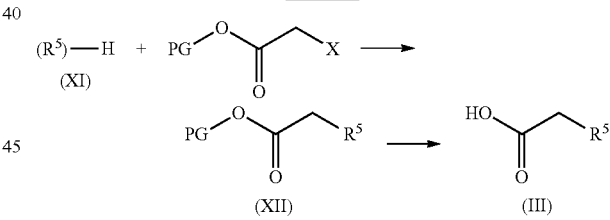

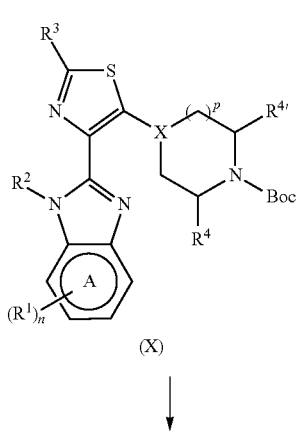

A compound of structure XI, ($R^5$)—H, representing a heterocyclyl ring bearing a free NH, can be alkylated using an acetic acid derivative of formula X—CH$_2$—COO(PG) wherein X is Cl or Br and PG is a protecting group suitable for an acid function, in presence of a base such as Cs$_2$CO$_3$, K$_2$CO$_3$ or NaH, in a suitable solvent such as THF or DMF, and at a temperature between RT and 120° C. Deprotection of the intermediate of structure XII leads to the compound of structure III. Suitable acid function protecting groups and protection and deprotection methods are well known to one skilled in the art (see notably "Protective groups in organic synthesis", Greene T. W. and Wuts P. G. M., Wiley-Interscience, 1999).

Preparation of the Compounds of Structure IV

The compounds of structure IV can be prepared according to the route described in Scheme 8 hereafter using reaction conditions described before.

Scheme 8

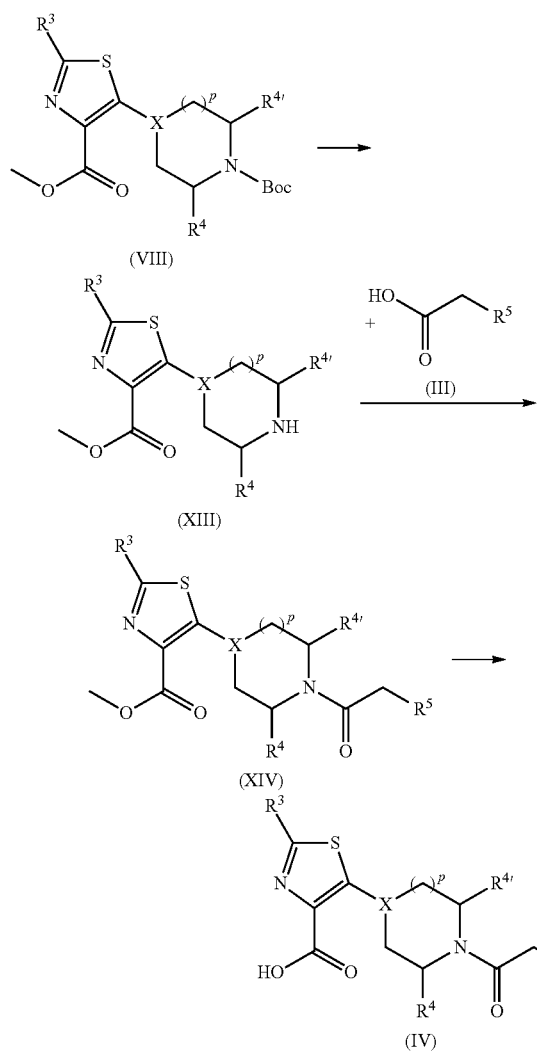

Starting from the compound of structure VIII, the cleavage of the Boc can be performed, followed by amide coupling with a compound of structure III. Finally, the cleavage of the methyl ester leads to the compound of structure IV.

Preparation of the Compounds of Structure V

The compounds of structure V are either commercially available, or can be prepared according to literature procedures, or in analogy. Non-commercially available 1,2-diamines substituted once in position 4 can be prepared by nitration of the corresponding para-substituted amine, using acetic anhydride and nitric acid at a temperature between 10° C. and RT followed by heating in dioxane and 6M HCl at a temperature about 70° C. Starting from the para-substituted acetamide, nitration can be performed using a mixture of nitric acid and sulphuric acid at 0° C., followed by acetate cleavage in acidic or basic conditions according to methods well known to one skilled in the art. The resulting 1-amino-2-nitro derivative can be reduced to the 1,2-diamino compound of structure V using standard conditions such as ammonium formate or hydrogen and Pd/C in a suitable solvent such as EtOH or MeOH optionally in presence of water at a temperature about RT. Alternatively, the nitro group can be reduced in presence of zinc and ammonium chloride in MeOH at a temperature around RT Alternatively, 1,2-diamines substituted once in position 4 can be prepared by performing a Suzuki reaction with the appropriate boronic acid or ester and 4-bromo-2-nitroaniline, in presence of a suitable palladium catalyst such as palladium acetate, using a suitable ligand such as tricyclohexylphosphine, in presence of a suitable base such as $K_3PO_4$, in toluene/water and heating at about 100° C. Or the Suzuki reaction can be performed with 3,4-diaminophenylboronic acid pinacol ester and an appropriate reagent, in presence of a suitable palladium catalyst such as dichloro(1,1'-bis(diphenylphosphino) ferrocene) palladium (II) dichloromethane adduct, in presence of a suitable base such as $K_3PO_4$, in DMF and heating at about 85° C.

Another route towards 1,2-diamines substituted once in position 4 consists in performing a reductive amination reaction with 4-acetamidobenzaldehyde, using standard conditions such as sodium triacetoxyborohydride in DCM in presence of DIPEA at around RT.

1,2-diamines substituted once in position 4 can also be prepared by performing a nucleophilic aromatic substitution with the appropriate amine or alcohol derivative and 5-chloro-2-nitroaniline or 5-fluoro-2-nitroaniline, in presence of a base such as TEA or NaH, in a suitable solvent such as DMF and at a temperature between 100° C. and 120° C.

Preparation of the Compounds of Structure VIII

Methyl 5-bromo-1,3-thiazole-4-carboxylate can be reacted with the derivative of structure XV, in an aromatic nucleophilic substitution type reaction, in presence of a suitable base such as $K_2CO_3$, DIPEA or DBU, in a suitable solvent such as MeCN, DMSO or NMP, and at a temperature between 80° C. and 120° C. (see Scheme 9 hereafter).

Scheme 9

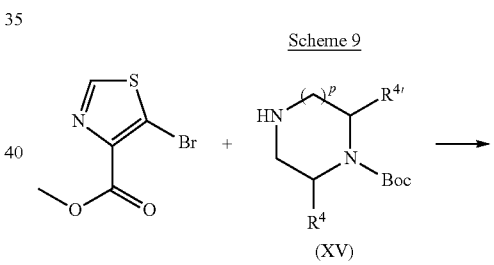

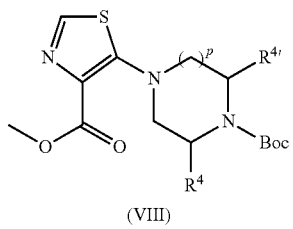

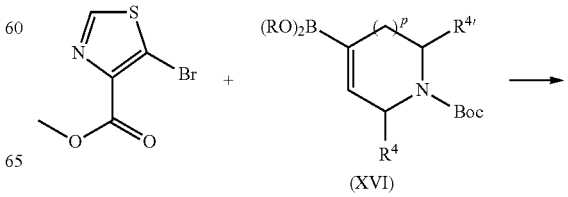

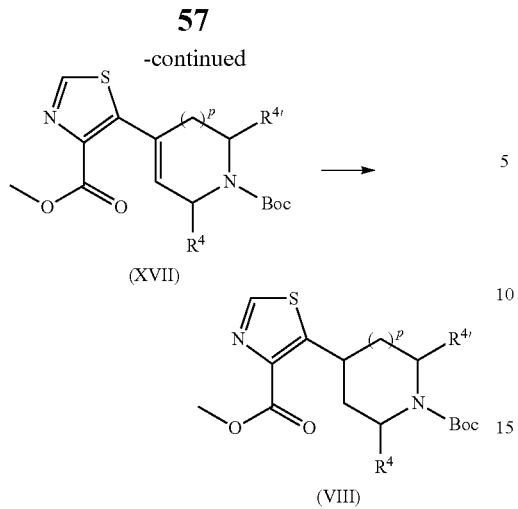

(XVII)

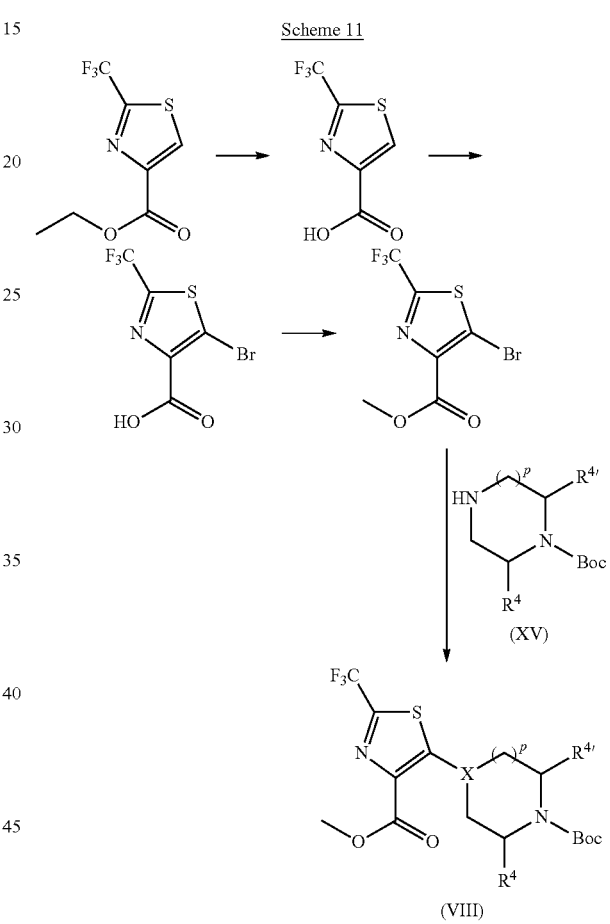

Alternatively, methyl 5-bromo-1,3-thiazole-4-carboxylate can be reacted with the boronic acid derivative of formula XVI wherein R is hydrogen or alkyl, in a Suzuki type reaction, in presence of a suitable base such as aq. $K_2CO_3$, in presence of a suitable palladium catalyst such as $Pd(PPh_3)_4$, in a suitable solvent such as dioxane, and preferably heating at about 100° C. The resulting intermediate of structure XVII can be further transformed into a compound of structure VIII by using standard conditions for the reduction of an alkene moiety, such as Pd/C in EtOH/AcOH under a hydrogen atmosphere and heating at about 50° C.

Scheme 10

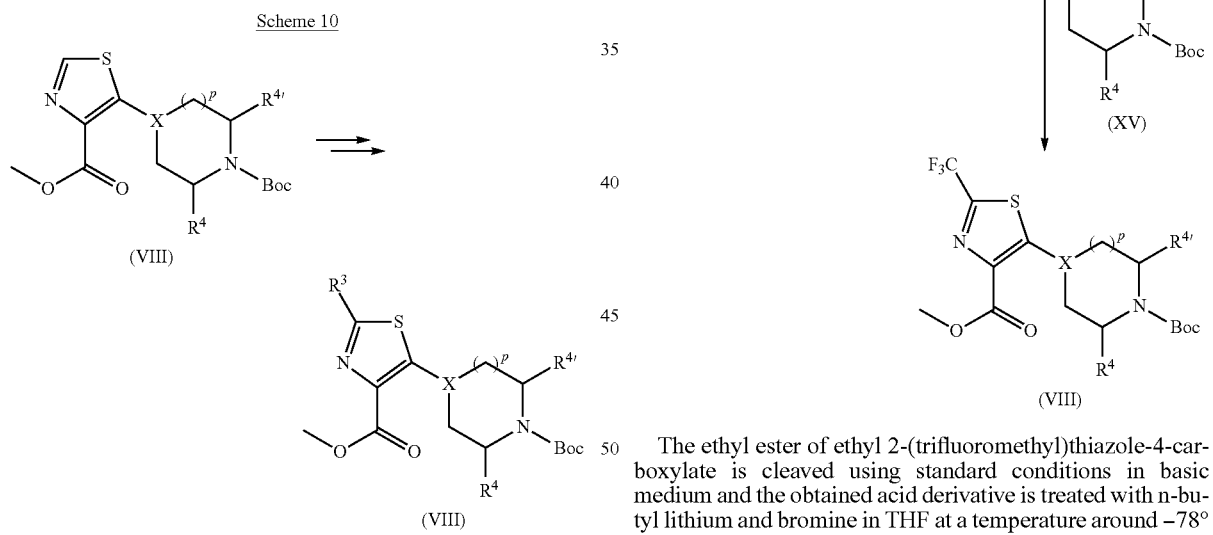

The compound of structure VIII wherein $R^3$ is hydrogen can be further transformed into a compound of structure VIII wherein $R^3$ is bromine or chloride, using NBS or NCS respectively, in a suitable solvent such as MeCN, preferably at a temperature about 50° C. (See Scheme 10). The compound of structure VIII wherein $R^3$ is —$CH_2$—N-(Me)$_2$ can be synthesized by reacting the compound of structure VIII wherein $R^3$ is H with the Eschenmoser's salt in a mixture of MeCN and DMF at a temperature around 90° C.

The compound of structure VIII wherein $R^3$ is —$CH_2$—OH can be prepared by reacting the compound of structure VIII wherein $R^3$ is H with DMF, in presence of a base such as lithium diisopropylamide, in a suitable solvent such as THF and at a temperature around −78° C. The resulting aldehyde derivative can be subsequently reduced using standard reducing agents such as $NaBH_4$.

The compound of structure VIII wherein $R^3$ is trifluoromethyl can be obtained by treating the compound of structure VIII wherein $R^3$ is bromine with methyl 2,2-difluoro-2-(fluorosulfonyl)acetate, in presence of CuI, $AsPh_3$ and tris(dibenzylideneacetone)dipalladium-(0)-chloroform adduct in DMF, heating at a temperature about 100° C.

Another route to prepare the compounds of structure VIII wherein $R^3$ is trifluoromethyl is described in Scheme 11 hereafter.

The ethyl ester of ethyl 2-(trifluoromethyl)thiazole-4-carboxylate is cleaved using standard conditions in basic medium and the obtained acid derivative is treated with n-butyl lithium and bromine in THF at a temperature around −78° C. The resulting brominated compound can be esterified using sulphuric acid in MeOH and heating at a temperature around 70° C. Nucleophilic aromatic substitution using conditions already described with a compound of structure XV leads to the compounds of structure VIII wherein $R^3$ is trifluoromethyl.

In addition, the compound of structure VIII wherein $R^3$ is cyclopropyl can be obtained by treating the compound of structure VIII wherein $R^3$ is bromine, in a Suzuki type reaction, using the conditions already described in Scheme 3.

Besides, the compound of structure VIII wherein $R^3$ is isopropyl can be obtained by a Suzuki reaction, treating a compound of structure VIII wherein $R^3$ is bromine with isopropenylboronic acid pinacol ester, $Na_2CO_3$, $Pd(PPh_3)_2Cl_2$ in a mixture of water and MeCN, heating at a temperature about 80° C. The isopropenyl group can be further reduced to yield the compound of structure VIII wherein $R^3$ is isopropyl using standard conditions for the reduction of an alkene moeity, such as Pd/C in MeOH under a hydrogen atmosphere.

Alternatively, the compound of structure VIII wherein $R^3$ is hydrogen can be transformed into a compound of structure VIII wherein $R^3$ is oxetane by a Minisci reaction, using 3-iodo-oxetane as reagent, in presence of $Fe(II)SO_4$, $H_2SO_4$ and $H_2O_2$, in a suitable solvent such as DMSO, and preferably at a temperature about RT.

Preparation of the Compounds of Structure IX

The compound of structure IX wherein $R^3$ is bromine can be converted into a compound of structure IX wherein $R^3$ is aryl, using a reagent of formula $R^3$—B—$(OR)_2$, R being hydrogen or alkyl, using standard conditions for a Suzuki reaction such as those described in Scheme 4. (See Scheme 12).

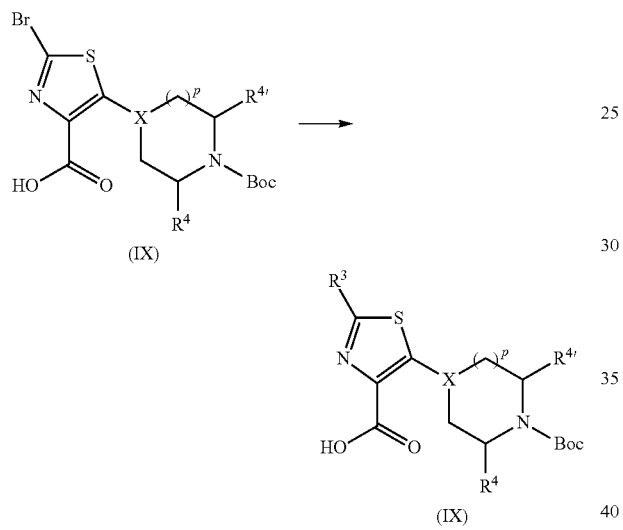

Preparation of the Compounds of Structure X

In the case of $R^3$ being trifluoromethyl, the compounds of structure X can be prepared using the route shown in Scheme 13. 5-Bromo-2-trifluoromethyl-thiazole-4-carboxylic acid is reacted with a compound of structure V according to standard protocols for an amide coupling reaction. The resulting amide of structure XVIII is then submitted to a nucleophilic aromatic substitution reaction with a compound of structure XV to afford a compound of structure XIX. Cyclisation reaction yields to the benzimidazole derivative of structure X, using conditions described previously.

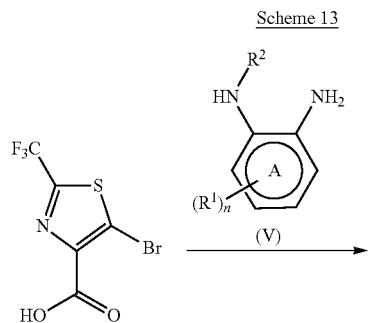

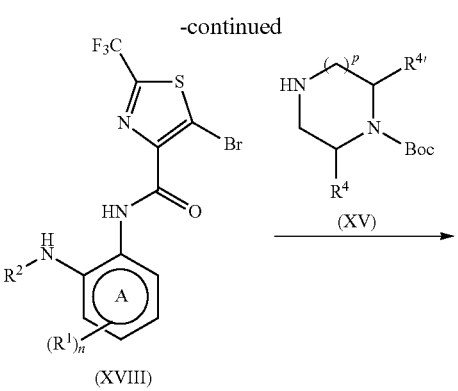

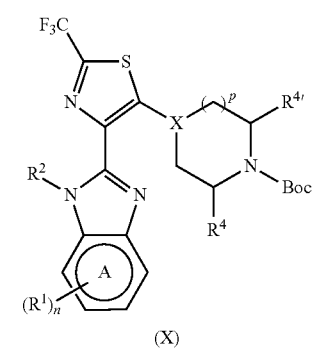

The compound of structure X wherein $R^3$ is —$CH_2$—$CH_2$—COOH can be prepared as described in Scheme 14, by reacting a compound of structure IX wherein $R^3$ is Br with a compound of structure V to give an amide derivative of structure XX, using standard conditions for an amide coupling reaction. The compound of structure XX can be submitted to conditions for a Suzuki reaction, using 2-ethoxycarbonylvinylboronic acid pinacol ester, in presence of a palladium catalyst such as $Pd(PPh_3)_2Cl_2$, in a mixture of aqueous sodium carbonate and DMF and heating at a temperature around 100° C. Subsequent reduction of the double bond (hydrogen, palladium on charcoal in EtOH) followed by cyclisation reaction yields to the benzimidazole derivative of structure X wherein $R^3$ is —$CH_2$—$CH_2$—COOH, using conditions described previously.

Scheme 14

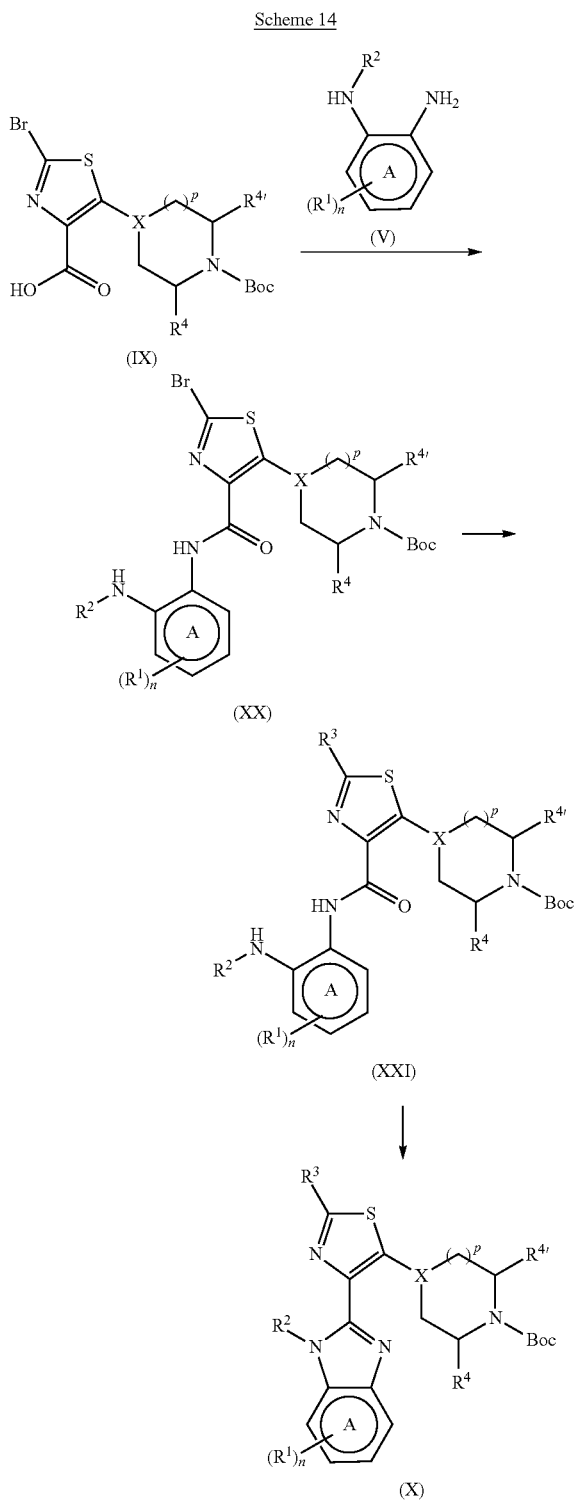

Preparation of the Compounds of Structure XI, XV, and XVI

The compounds of structure XI, XV and XVI are either commercially available, or can be prepared according to literature procedures, or in analogy.

Whenever the compounds of formula (I) are obtained in the form of mixtures of enantiomers, the enantiomers can be separated using methods known to one skilled in the art: e.g. by formation and separation of diastereomeric salts or by HPLC over a chiral stationary phase such as a Regis Whelk-O1(R,R) (10 µm) column, a Daicel ChiralCel OD-H (5-10 µm) column, or a Daicel ChiralPak IA (10 µm) or AD-H (5 µm) column. Typical conditions of chiral HPLC are an isocratic mixture of eluent A (EtOH or iPrOH, in presence or absence of an amine such as TEA, diethylamine) and eluent B (hexane), at a flow rate of 0.8 to 150 mL/min.

Experimental Section

Abbreviations (as used herein and in the description above):

Ac acetyl
aq. aqueous
Boc tert.-butyloxycarbonyl
Br broad
Brine saturated aqueous NaCl solution
BSA Bovine serum albumine
Bu butyl (such as in tBuLi=tert.-BuLi=tertiary butyl lithium)
Cbz benzyloxycarbonyl
CC column chromatography on silica gel
CDI 1,1'-carbonyldiimidazole
CHO Chinese hamster ovary
conc. concentrated
CV column volume
d doublet
dba dibenzylideneacetone
DBU 1,8-Diazabicyclo[5.4.0]undec-7-ene
DCC 1,3-dicyclohexylcarbodiimide
DCM dichloromethane
DEA diethylamine
DETA diethylenetriamine
DIPEA N-ethyldiisopropylamine
DMAP 4-dimethylaminopyridine
DME 1,2-dimethoxyethane
DMF dimethylformamide
DMP Dess-Martin periodinane
DMSO dimethylsulfoxide
Dppf 1,1'-bis(diphenylphosphanyl) ferrocene
EA ethyl acetate
EDCI N-(3-dimethylaminopropyl)-N'-ethylcarbodiimide (as HCl salt)
Eq equivalent
Et ethyl
EtOH ethanol
FBS fetal bovine serum
FLIPR Fluorescent imaging plate reader
Fluo-4-AM 2-{[2-(2-{5-[bis(carboxymethyl)amino]-2-methylphenoxy}ethoxy)-4-(2,7-difluoro-6-hydroxy-3-oxo-3H-xanthen-9-yl)phenyl]carboxymethyl)amino}acetic acid
G418 (2R,3S,4R,5R,6S)-5-amino-6-[(1R,2S,3S,4R,6S)-4,6-diamino-3-[(2R,3R,4R,5R)-3,5-dihydroxy-5-methyl-4-methylaminooxan-2-yl]oxy-2-hydroxycyclohexyl]oxy-2-(1-hydroxyethyl)oxane-3,4-diol
h hour(s)
HATU 2-(7-Aza-1H-benzotriazole-1-yl)-1,1,3,3-tetramethyluronium hexafluorophosphate
HBSS Hank's balanced salt solution
HEPES 4-(2-hydroxyethyl)-piperazine-1-ethanesulfonic acid
Hept heptane
Hex hexane
HOAT 7-aza-1-hydroxybenzotriazole
HOBT 1-hydroxybenzotriazole, hydrate
HPLC high performance liquid chromatography
iPr isopropyl
iPrOH iso-propanol
LC liquid chromatography
M molarity [mol L$^{-1}$]

Me methyl
MeCN acetonitrile
MeOH methanol
MS mass spectroscopy
min. minute(s)
N normality
NaOtBu sodium tert. (tertiary) butoxide
NBS N-bromo-succinimide
NCS N-chloro-succinimide
NMP 1-methyl-2-pyrrolidone
org. organic
Pd/C palladium on carbon
PG protecting group
Ph phenyl
PL- Polymer supported
PL-HCO$_3$ StratoSpheres™ Solid Phase Extraction cartridges containing a HCO3⁻ quaternary amine salt
PyBOP benzotriazole-1-yl-oxy-tris-pyrrolidino-phosphonium hexafluorophosphate
q quadruplet
RT room temperature
s singulet
Sat. Saturated
sec secondary
SEMCl (2-chloromethoxyethyl)-trimethylsilane
Si-DCC Silicabond DCC
t triplet
TBAF tetrabutylammonium fluoride
TBTU O-benzotriazol-1-yl-N,N,N',N'-tetramethyluronium tetrafluoroborate
tBu tert-butyl
TEA triethylamine
TFA trifluoroacetic acid
THF tetrahydrofuran
$t_R$ retention time I. Chemistry The following examples illustrate the preparation of biologically active compounds of the invention but do not at all limit the scope thereof.

General:

All temperatures are stated in degrees Celsius (° C.). Unless otherwise indicated, the reactions take place at RT under an argon atmosphere and are run in a flame dried round-bottomed flask equipped with a magnetic stir bar.

Characterization Methods Used:

The LC-MS retention times have been obtained using the following elution conditions:

A) LC-MS (A):

Acquity UPLC BEH C18 1.7 μm 2.1×50 mm ID column from Waters, thermostated in the Acquity UPLC Column Manager (60° C.) was used. The two elution solvents were as follows: solvent A=water+0.05% TFA; solvent B=acetonitrile+0.045% TFA. The eluent flow rate was 1.2 mL/min and the characteristics of the eluting mixture proportion in function of the time t from start of the elution are summarized in the table below (a linear gradient being used between two consecutive time points):

|  | t (min) | | | |
| --- | --- | --- | --- | --- |
|  | 0 | 1.4 | 1.9 | 2.0 |
| Solvent A (%) | 98 | 2 | 2 | 98 |
| Solvent B (%) | 2 | 98 | 98 | 2 |

B) LC-MS (B):

Zorbax SB-Aq, 3.5 μm, 4.6×50 mm column thermostated at 40° C. The two elution solvents were as follows: solvent A=water+0.04% TFA; solvent B=acetonitrile. The eluent flow rate was 4.5 mL/min and the characteristics of the eluting mixture proportion in function of the time t from start of the elution are summarized in the table below (a linear gradient being used between two consecutive time points):

|  | t (min) | | | |
| --- | --- | --- | --- | --- |
|  | 0 | 1.0 | 1.45 | 1.55 |
| Solvent A (%) | 95 | 5 | 5 | 95 |
| Solvent B (%) | 5 | 95 | 95 | 5 |

C) LC-MS (C):

Waters XBridge C18, 2.5 μm, 4.6×30 mm column thermostated at 40° C. The two elution solvents were as follows: solvent A=water+0.04% TFA; solvent B=acetonitrile. The eluent flow rate was 4.5 mL/min and the characteristics of the eluting mixture proportion in function of the time t from start of the elution are summarized in the table below (a linear gradient being used between two consecutive time points):

|  | t (min) | | | |
| --- | --- | --- | --- | --- |
|  | 0 | 1.0 | 1.45 | 1.55 |
| Solvent A (%) | 95 | 5 | 5 | 95 |
| Solvent B (%) | 5 | 95 | 95 | 5 |

D) LC-MS (D):

Ascentis Express C18, 2.7 μm, 2.1×50 mm column thermostated at 50° C. The two elution solvents were as follows: solvent A=acetonitrile; solvent B=water+0.05% NH$_4$OH+2% acetonitrile. The eluent flow rate was 1.4 mL/min and the characteristics of the eluting mixture proportion in function of the time t from start of the elution are summarized in the table below (a linear gradient being used between two consecutive time points):

|  | t (min) | | | | |
| --- | --- | --- | --- | --- | --- |
|  | 0 | 2.0 | 2.3 | 2.35 | 2.50 |
| Solvent A (%) | 5 | 95 | 95 | 5 | 5 |
| Solvent B (%) | 95 | 5 | 5 | 95 | 95 |

E) LC-MS (E):

Zorbax Extend-C18, 5 μm, 4.6×50 mm column not thermostated. The two elution solvents were as follows: solvent A=water+0.1% NH$_4$OH; solvent B=acetonitrile. The eluent flow rate was 4.5 mL/min and the characteristics of the eluting mixture proportion in function of the time t from start of the elution are summarized in the table below (a linear gradient being used between two consecutive time points):

|  | t (min) | | | | |
| --- | --- | --- | --- | --- | --- |
|  | 0 | 0.8 | 1.2 | 1.45 | 1.55 |
| Solvent A (%) | 98 | 60 | 5 | 5 | 98 |
| Solvent B (%) | 2 | 40 | 95 | 95 | 2 |

F) LC-MS (F):

Waters XBridge C18, 5 μm, 4.6×50 mm column not thermostated. The two elution solvents were as follows: solvent A=water+0.1% NH$_4$OH; solvent B=acetonitrile. The eluent flow rate was 4.5 mL/min and the characteristics of the eluting mixture proportion in function of the time t from start of the elution are summarized in the table below (a linear gradient being used between two consecutive time points):

| t (min)      | 0  | 0.75 | 1.45 | 1.55 |
|--------------|----|------|------|------|
| Solvent A (%) | 95 | 5    | 5    | 98   |
| Solvent B (%) | 5  | 95   | 95   | 2    |

G) LC-MS (G):

Acquity UPLC BEH C18 1.7 μm 2.1×50 mm ID column from Waters, thermostated in the Acquity UPLC Column Manager (60° C.) was used. The two elution solvents were as follows: solvent A=water+0.05% TFA; solvent B=acetonitrile+0.045% TFA. The eluent flow rate was 1 mL/min and the characteristics of the eluting mixture proportion in function of the time t from start of the elution are summarized in the table below (a linear gradient being used between two consecutive time points):

| t (min)       | 0  | 1.4 | 1.8 | 1.9 | 2.0 |
|---------------|----|-----|-----|-----|-----|
| Solvent A (%) | 98 | 5   | 2   | 2   | 98  |
| Solvent B (%) | 2  | 95  | 98  | 98  | 2   |

Preparative LC-MS Methods Used:

The purifications by preparative LC-MS have been performed using the conditions described hereafter.

I) Preparative LC-MS (I):

A X-Bridge column (Waters C18, 10 μm OBD, 30×75 mm) was used. The two elution solvents were as follows: solvent A=water+0.5% NH$_4$OH; solvent B=acetonitrile. The eluent flow rate was 75 mL/min and the characteristics of the eluting mixture proportion in function of the time t from start of the elution are summarized in the tables below (a linear gradient being used between two consecutive time points):

| t (min)       | 0  | 4.0 | 6.0 | 6.4 |
|---------------|----|-----|-----|-----|
| Solvent A (%) | 80 | 5   | 5   | 80  |
| Solvent B (%) | 20 | 95  | 95  | 20  |

II) Preparative LC-MS (II):

A X-Bridge column (Waters Prep C18, 5 μm OBD, 19×50 mm) was used. The two elution solvents were as follows: solvent A=water+0.1% NH$_4$OH; solvent B=acetonitrile+0.1% NH4OH. The eluent flow rate was 40 mL/min and the characteristics of the eluting mixture proportion in function of the time t from start of the elution are summarized in the tables below (a linear gradient being used between two consecutive time points):

| t (min)       | 0  | 0.2 | 0.3 | 3.2 | 3.3 | 4.3 | 4.4 |
|---------------|----|-----|-----|-----|-----|-----|-----|
| Solvent A (%) | 90 | 90  | 80  | 50  | 5   | 5   | 95  |
| Solvent B (%) | 10 | 10  | 20  | 50  | 95  | 95  | 5   |

III) Preparative LC-MS (III):

A Gemini column (Phenomenex NX 10 μm, 30×1000 mm) was used. The two elution solvents were as follows: solvent A=water+0.5% NH$_4$OH; solvent B=acetonitrile. The eluent flow rate was 100 mL/min and the characteristics of the eluting mixture proportion in function of the time t from start of the elution are summarized in the tables below (a linear gradient being used between two consecutive time points):

| t (min)       | 0  | 0.6 | 7.8 | 9.2 | 9.5 | 10.0 |
|---------------|----|-----|-----|-----|-----|------|
| Solvent A (%) | 90 | 90  | 5   | 5   | 90  | 90   |
| Solvent B (%) | 10 | 10  | 95  | 95  | 10  | 10   |

IV) Preparative LC-MS (IV):

A XBridge column (Waters Prep C18 5 μm, 19×50 mm) was used. The two elution solvents were as follows: solvent A=water+0.1% NH$_4$OH; solvent B=acetonitrile+0.1% NH$_4$OH. The eluent flow rate was 40 mL/min and the characteristics of the eluting mixture proportion in function of the time t from start of the elution are summarized in the tables below (a linear gradient being used between two consecutive time points):

| t (min)       | 0  | 0.2 | 0.3 | 3.2 | 3.3 | 4.3 | 4.4 |
|---------------|----|-----|-----|-----|-----|-----|-----|
| Solvent A (%) | 75 | 75  | 65  | 35  | 95  | 95  | 5   |
| Solvent B (%) | 25 | 25  | 35  | 65  | 5   | 5   | 95  |

V) Preparative LC-MS (V):

A Gemini column (Phenomenex NX 10 μm, 30×1000 mm) was used. The two elution solvents were as follows: solvent A=water+0.5% formic acid; solvent B=acetonitrile. The eluent flow rate was 100 mL/min and the characteristics of the eluting mixture proportion in function of the time t from start of the elution are summarized in the tables below (a linear gradient being used between two consecutive time points):

| t (min)       | 0  | 0.6 | 7.8 | 9.2 | 9.5 | 10.0 |
|---------------|----|-----|-----|-----|-----|------|
| Solvent A (%) | 90 | 90  | 5   | 5   | 90  | 90   |
| Solvent B (%) | 10 | 10  | 95  | 95  | 10  | 10   |

VI) Preparative LC-MS (VI):

A Gemini column (Phenomenex NX 10 μm, 30×1000 mm) was used. The two elution solvents were as follows: solvent A=water+0.5% NH$_4$OH; solvent B=acetonitrile. The eluent flow rate was 100 mL/min and the characteristics of the eluting mixture proportion in function of the time t from start of the elution are summarized in the tables below (a linear gradient being used between two consecutive time points):

| t (min)       | 0  | 0.6 | 7.8 | 9.2 | 9.5 | 10.0 |
|---------------|----|-----|-----|-----|-----|------|
| Solvent A (%) | 80 | 80  | 5   | 5   | 80  | 80   |
| Solvent B (%) | 20 | 20  | 95  | 95  | 20  | 20   |

VII) Preparative LC-MS (VII):

A Gemini column (Phenomenex NX 10 μm, 30×1000 mm) was used. The two elution solvents were as follows: solvent A=water+0.5% NH$_4$OH; solvent B=acetonitrile. The eluent flow rate was 100 mL/min and the characteristics of the eluting mixture proportion in function of the time t from start of the elution are summarized in the tables below (a linear gradient being used between two consecutive time points):

| t (min)       | 0  | 0.6 | 7.8 | 9.2 | 9.5 | 10.0 |
|---------------|----|-----|-----|-----|-----|------|
| Solvent A (%) | 60 | 60  | 5   | 5   | 60  | 60   |
| Solvent B (%) | 40 | 40  | 95  | 95  | 40  | 40   |

VIII) Preparative LC-MS (VIII):

A XBridge column (Waters Prep C18 5 µm, 19×50 mm) was used. The two elution solvents were as follows: solvent A=water+0.1% NH₄OH; solvent B=acetonitrile+0.1% NH₄OH. The eluent flow rate was 40 mL/min and the characteristics of the eluting mixture proportion in function of the time t from start of the elution are summarized in the tables below (a linear gradient being used between two consecutive time points):

| t (min)       | 0  | 0.2 | 0.3 | 4.4 | 4.5 | 5.6 | 5.7 | 6.5 |
|---------------|----|-----|-----|-----|-----|-----|-----|-----|
| Solvent A (%) | 75 | 75  | 65  | 65  | 5   | 5   | 95  | 95  |
| Solvent B (%) | 25 | 25  | 35  | 35  | 95  | 95  | 5   | 5   |

IX) Preparative LC-MS (IX):

A Gemini column (Phenomenex Phenyl C6, 5 µm, 30×750 mm) was used. The two elution solvents were as follows: solvent A=water+0.5% NH₄OH; solvent B=acetonitrile. The eluent flow rate was 100 mL/min and the characteristics of the eluting mixture proportion in function of the time t from start of the elution are summarized in the tables below (a linear gradient being used between two consecutive time points):

| t (min)       | 0  | 0.6 | 5.85 | 6.90 | 7.30 | 7.50 |
|---------------|----|-----|------|------|------|------|
| Solvent A (%) | 95 | 95  | 10   | 5    | 90   | 90   |
| Solvent B (%) | 5  | 5   | 90   | 95   | 10   | 10   |

X) Preparative LC-MS (X):

A Gemini column (Phenomenex NX, 10 µm, 30×1000 mm) was used. The two elution solvents were as follows: solvent A=water+0.5% formic acid; solvent B=acetonitrile. The eluent flow rate was 100 mL/min and the characteristics of the eluting mixture proportion in function of the time t from start of the elution are summarized in the tables below (a linear gradient being used between two consecutive time points):

| t (min)       | 0  | 0.6 | 6.66 | 7.80 | 8.53 |
|---------------|----|-----|------|------|------|
| Solvent A (%) | 95 | 95  | 80   | 5    | 5    |
| Solvent B (%) | 5  | 5   | 20   | 95   | 95   |

XI) Preparative LC-MS (XI):

A Gemini column (Phenomenex NX, 10 µm, 30×1000 mm) was used. The two elution solvents were as follows: solvent A=water+0.5% formic acid; solvent B=acetonitrile. The eluent flow rate was 100 mL/min and the characteristics of the eluting mixture proportion in function of the time t from start of the elution are summarized in the tables below (a linear gradient being used between two consecutive time points):

| t (min)       | 0  | 0.6 | 6.66 | 7.80 | 8.53 |
|---------------|----|-----|------|------|------|
| Solvent A (%) | 95 | 95  | 60   | 5    | 5    |
| Solvent B (%) | 5  | 5   | 40   | 95   | 95   |

Preparative HPLC Methods Used:

The purifications by preparative HPLC have been performed using the conditions described hereafter.

I) Preparative HPLC (I):

A Macherey-Nagel column (Nucleosil 50-10 10 mm, 21×100 mm) was used. The three elution solvents were as follows: solvent A=Hept; solvent B=EA; solvent C=MeOH. The eluent flow rate was 40 mL/min and the characteristics of the eluting mixture proportion in function of the time t from start of the elution are summarized in the tables below (a linear gradient being used between two consecutive time points):

| t (min)       | 0  | 0.5 | 7  | 7.5 | 8.3 | 8.4 | 9.7 |
|---------------|----|-----|----|-----|-----|-----|-----|
| Solvent A (%) | 90 | 90  | 60 | 0   | 0   | 0   | 0   |
| Solvent B (%) | 10 | 10  | 40 | 50  | 50  | 30  | 30  |
| Solvent C (%) | 0  | 0   | 0  | 50  | 50  | 70  | 70  |

Preparative Chiral HPLC Methods Used:

The purifications by preparative chiral HPLC have been performed using the conditions described hereafter.

I) Preparative chiral HPLC (I):

A ChiralPak IA column (5 µm, 21×100 mm) was used. The elution solvent was Hept/EtOH/DEA 50/50/0.1, run for 15 min and at a flow rate of 18 mL/min.

II) Preparative chiral HPLC (II):

A ChiralCel OD-H column (5 µm, 20×250 mm) was used. The elution solvent was Hept/EtOH/DEA 50/50/0.1, run for 120 min and at a flow rate of 16 mL/min.

EXAMPLE 1

2-Benzoimidazol-1-yl-1-{4-[4-(1H-benzoimidazol-2-yl)-thiazol-5-yl]-piperazin-1-yl}-ethanone 1.1. 4-(4-Methoxycarbonyl-thiazol-5-yl)-piperazine-1-carboxylic acid tert-butyl ester To a solution of methyl 5-bromo-1,3-thiazole-4-carboxylate (10 g) in MeCN (120 mL) was added 1-Boc-piperazine (8.56 g) followed by DBU (10.1 mL). The resulting solution was stirred at 80° C. for 5 h. The reaction mixture was diluted with EA and water. The layers were separated and the org. phase was further washed with water. The combined aq. layers were extracted with EA. The combined org. layers were dried over Na₂SO₄, filtrated off and evaporated in vacuo. The crude was purified by CC (Biotage, SNAP 100 g cartridge, solvent A: Hept; solvent B: EA; gradient in % B: 10 for 2CV, 10 to 50 over 12CV, 50 for 3CV) to afford 7.65 g of yellow oil. LC-MS (B): $t_R$=0.79 min; [M+H]⁺: 328.37.

1.2. 4-(4-Carboxy-thiazol-5-yl)-piperazine-1-carboxylic acid tert-butyl ester

To a solution of intermediate 1.1 (7650 mg) in EtOH (60 ml) was added NaOH 2M (40 ml). The mixture was stirred for 1 h. The solvent was removed in vacuo and 2M HCl (35 mL) were added leading to pH 5. Water and DCM were added. The aq phase was further extracted with DCM. Combined org. layers were dried (Na₂SO₄) and evaporated off to give 6.03 g of pale yellow powder. LC-MS (B): $t_R$=0.69 min; [M+H]⁺: 314.35.

1.3. 4-[4-(1H-Benzoimidazol-2-yl)-thiazol-5-yl]-piperazine-1-carboxylic acid tert-butyl ester To a solution of intermediate 1.2 (6.03 g) in DCM (150 mL) was added HOBT (2.86 g) followed by EDCI (4.04 g) and DIPEA (9.88 mL). The resulting mixture was stirred for 20 min. o-Phenylenediamine (2.12 g) was added and the resulting mixture was stirred at RT for 20 h. The reaction mixture was diluted with water. The layers were separated and the aq. phase was extracted twice with DCM. The combined org. layers were dried over $Na_2SO_4$, filtrated off and evaporated in vacuo. The resulting yellow oil was taken up in acetic acid (50 mL) and the mixture was stirred at 80° C. for 2.5 h. Toluene was added and the mixture was evaporated in reduced pressure. The crude was purified by CC (Biotage, SNAP 100 g cartridge, solvent A: Hept; solvent B: EA; gradient in % B: 5 to 25 over 10CV, 25 for 3CV, 25 to 45 over 6CV, 45 for 5CV) to afford 2.45 g of fine pale yellow needles. LC-MS (B): $t_R$=0.71 min; $[M+H]^+$: 386.32.

1.4. 2-(5-Piperazin-1-yl-thiazol-4-yl)-1H-benzoimidazole, double hydrochloride salt To a suspension of intermediate 1.3 (2.35 g) in EA (15 ml) was added HCl 3M in EA (40 ml). The suspension immediately turned into an orange solution. Precipitation started to occur after 5 min. The suspension was stirred at rt for 4.5 h. HCl was partially removed under a stream of air. The solvent was removed in reduced pressure and the residue was dried in high vacuo to afford 2.36 g of yellow powder. LC-MS (B): $t_R$=0.40 min; $[M+H]^+$: 286.34.

1.5. 2-Benzoimidazol-1-yl-1-{4-[4-(1H-benzoimidazol-2-yl)-thiazol-5-yl]-piperazin-1-yl}-ethanone A mixture of intermediate 1.4 (25 mg), benzoimidazol-1-yl-acetic acid (11.2 mg), HATU (26.5 mg) and DIPEA (54 μL) in DCM (1 mL) was stirred for 2.5 h. The solvent was removed under reduced pressure, the residue was taken up in DMF and purified by preparative LC-MS (I) to afford 13 mg of beige solid. LC-MS (A): $t_R$=0.44 min; $[M+H]^+$: 444.2.

Example 2 to Example 7 were synthesized starting from the appropriate acid derivative and following the procedure described in Example 1, step 1.5. LC-MS data of Example 2 to Example 7 are listed in the table below. The LC-MS conditions used were LC-MS (A).

| Example No | Name | $t_R$ | $[M+H]^+$ |
| --- | --- | --- | --- |
| 2 | 1-{4-[4-(1H-Benzoimidazol-2-yl)-thiazol-5-yl]-piperazin-1-yl}-2-(2-methyl-benzoimidazol-1-yl)-ethanone | 0.45 | 458.3 |
| 3 | 1-(2-{4-[4-(1H-Benzoimidazol-2-yl)-thiazol-5-yl]-piperazin-1-yl}-2-oxo-ethyl)-3-methyl-1,3-dihydro-benzoimidazol-2-one | 0.61 | 474.3 |
| 4 | 1-{4-[4-(1H-Benzoimidazol-2-yl)-thiazol-5-yl]-piperazin-1-yl}-2-indol-1-yl-ethanone | 0.71 | 443.2 |
| 5 | 1-{4-[4-(1H-Benzoimidazol-2-yl)-thiazol-5-yl]-piperazin-1-yl}-2-(3-trifluoromethyl-pyrazol-1-yl)-ethanone | 0.66 | 462.2 |
| 6 | 1-{4-[4-(1H-Benzoimidazol-2-yl)-thiazol-5-yl]-piperazin-1-yl}-2-(3-methyl-pyrazol-1-yl)-ethanone | 0.51 | 408.2 |
| 7 | 1-{4-[4-(1H-Benzoimidazol-2-yl)-thiazol-5-yl]-piperazin-1-yl}-2-(2-methyl-thiazol-4-yl)-ethanone | 0.51 | 425.2 |

EXAMPLE 8

1-{4-[4-(1H-Benzoimidazol-2-yl)-thiazol-5-yl]-piperazin-1-yl}-2-(6-chloro-imidazo[1,2-b]pyridazin-2-yl)-ethanone To 6-chloroimidazo[1,2-b]pyridazine-2-yl)acetic acid (12.7 mg) were added a solution of intermediate 1.4 (20.8 mg) in DMF/DIPEA (0.5 mL, 5/1) and a solution of HOAT (8.17 mg) in DMF (0.5 mL), followed by Si-DCC (0.96 mmol/g, 180 mg). The reaction mixture was stirred at 40° C. for 24 h. PL-$HCO_3$ (2.06 mmol/g, 120 mg) and PL-DETA (7.99 mmol/g, 23 mg) were added and the reaction mixture was further stirred for 3 h. The resins were filtered, washed five times with 1 mL DCM/MeOH 1:1 and the resulting solution was evaporated in vacuo. The residue was taken up in DMSO/MeCN 1:4 (0.5 mL) and purified by preparative LC-MS (II) to afford 14 mg of white solid. LC-MS (A): $t_R$=0.57 min; $[M+H]^+$: 479.2.

Example 9 to Example 13 were synthesized starting from the appropriate acid derivative and following the procedure described in Example 8. LC-MS data of Example 9 to Example 13 are listed in the table below. The LC-MS conditions used were LC-MS (A).

| Example No | Name | $t_R$ | $[M+H]^+$ |
| --- | --- | --- | --- |
| 9 | 1-{4-[4-(1H-Benzoimidazol-2-yl)-thiazol-5-yl]-piperazin-1-yl}-2-(2-methyl-imidazo[1,2-a]pyridin-3-yl)-ethanone | 0.42 | 458.2 |
| 10 | 1-{4-[4-(1H-Benzoimidazol-2-yl)-thiazol-5-yl]-piperazin-1-yl}-2-(3,5-dimethyl-[1,2,4]triazol-1-yl)-ethanone | 0.41 | 423.2 |
| 11 | 1-{4-[4-(1H-Benzoimidazol-2-yl)-thiazol-5-yl]-piperazin-1-yl}-2-(2,4-dimethyl-thiazol-5-yl)-ethanone | 0.44 | 438.9 |
| 12 | 1-{4-[4-(1H-Benzoimidazol-2-yl)-thiazol-5-yl]-piperazin-1-yl}-2-(5-methoxy-benzo[d]isoxazol-3-yl)-ethanone | 0.67 | 475.2 |
| 13 | 1-{4-[4-(1H-Benzoimidazol-2-yl)-thiazol-5-yl]-piperazin-1-yl}-2-(3,5-dimethyl-pyrazol-1-yl)-ethanone | 0.52 | 422.2 |

EXAMPLE 14

1-{4-[4-(1H-Benzoimidazol-2-yl)-thiazol-5-yl]-piperazin-1-yl}-2-imidazo[4,5-b]pyridin-3-yl-ethanone

14.1. Imidazo[4,5-b]pyridin-3-yl-acetic acid benzyl ester

To a brown solution of 4-azabenzimidazole (4.75 g) in DMF (80 mL) was added benzyl bromoacetate (6.58 mL) followed by $Cs_2CO_3$ (25.9 g). The resulting light brown suspension was stirred overnight. The reaction mixture was diluted with EA and washed twice with water and aq. sat. $NH_4Cl$. The aq. layers were extracted twice with EA. The combined org. layers were dried over $MgSO_4$, filtrated off and evaporated in reduced pressure. The crude was purified by CC (Biotage, SNAP 100 g cartridge, solvent A: DCM; solvent B: DCM/MeOH 8:2; gradient in % B: 0 to 5 over 3CV, 5 for 5CV, 5 to 15 over 5CV, 15% B for 3CV) to afford 4.99 g of the desired compound as yellow solid. LC-MS (C): $t_R$=0.59 min; $[M+H]^+$: 267.86.

14.2. Imidazo[4,5-b]pyridin-3-yl-acetic acid

To a yellow suspension of intermediate 14.1 (4.99 g) in MeOH (30 mL) and acetic acid (0.3 mL) was added Pd/C (10%, 994 mg) under argon. The flask was evacuated and backfilled with argon three times, then evacuated and backfilled with hydrogen twice. The reaction mixture was stirred at RT under hydrogen for 5 h, filtrated over celite and the celite was washed with MeOH. The filtrate was evaporated and dried in vacuo to afford 2.41 g of off-white solid that was used without purification. LC-MS (C): $t_R$=0.15 min; [M+H]$^+$: 178.24.

14.3. 1-{4-[4-(1H-Benzoimidazol-2-yl)-thiazol-5-yl]-piperazin-1-yl}-2-imidazo[4,5-b]pyridin-3-yl-ethanone This compound was prepared using a method analogous to that of Example 1 step 1.5, intermediate 14.2 replacing benzoimidazol-1-yl-acetic acid. LC-MS (A): $t_R$=0.45 min; [M+H]$^+$: 445.1.

EXAMPLE 15

1-{4-[4-(1H-Benzoimidazol-2-yl)-thiazol-5-yl]-piperazin-1-yl}-2-pyrrolo[2,3-b]pyridin-1-yl-ethanone This compound was prepared using a method analogous to that of Example 1 step 1.5, 2-(1H-pyrrolo[2,3-b]pyridin-1-yl)acetic acid replacing benzoimidazol-1-yl-acetic acid. LC-MS (A): $t_R$=0.55 min; [M+H]$^+$: 444.2.

EXAMPLE 16

1-{(R)-4-[4-(1H-Benzoimidazol-2-yl)-thiazol-5-yl]-2-methyl-piperazin-1-yl}-2-pyrrolo[2,3-b]pyridin-1-yl-ethanone

16.1. (R)-4-(4-Methoxycarbonyl-thiazol-5-yl)-2-methyl-piperazine-1-carboxylic acid tert-butyl ester To a solution of methyl 5-bromo-1,3-thiazole-4-carboxylate (3 g) in NMP (30 mL) was added (R)-1-N-Boc-2-methylpiperazine (2.76 g) followed by DIPEA (10.1 mL). The resulting solution was stirred at 120° C. for 1.5 d, at RT over weekend and at 120° C. for 7 h. After cooling down, the reaction mixture was diluted with EA and washed with sat. aq. NaHCO3, 1M HCl and sat. aq NaCl. The aq. phases were extracted with EA. The combined org. layers were dried over Na$_2$SO$_4$, filtrated off and evaporated in vacuo. The crude was purified by CC (Biotage, SNAP 100 g cartridge, solvent A: Hept; solvent B: EA; gradient in % B: 0 for 10CV, 0 to 10 over 5CV, 10 for 5CV, 10 to 20 over 5CV, 20 for 5CV, 20 to 30 over 5CV, 30 for 5CV) to afford 1.42 g of yellow oil. LC-MS (B): $t_R$=0.84 min; [M+H]$^+$: 342.08.

16.2. (R)-4-(4-Carboxy-thiazol-5-yl)-2-methyl-piperazine-1-carboxylic acid tert-butyl ester This compound was prepared using a method analogous to that of Example 1 step 1.2, intermediate 16.1 replacing intermediate 1.1, and using 1M NaOH instead of 2M NaOH. LC-MS (B): $t_R$=0.69 min; [M+H]$^+$: 314.35.

16.3. (R)-4-[4-(1H-Benzoimidazol-2-yl)-thiazol-5-yl]-2-methyl-piperazine-1-carboxylic acid tert-butyl ester To a solution of intermediate 16.2 (540 mg) in DCM (10 mL) was added o-phenylenediamine (202 mg) followed by HATU (941 mg) and DIPEA (367 μL). The resulting mixture was stirred for 2.5 h. The reaction mixture was diluted with DCM and washed with sat. aq. NaHCO$_3$, and water. The aq. phases were extracted with DCM. The combined org. layers were dried over Na$_2$SO$_4$, filtrated off and concentrated in vacuo. The residue was purified by CC (Biotage, SNAP 25 g cartridge, solvent A: DCM; solvent B: MeOH; gradient in % B: 0 for 5CV, 0 to 3 over 5CV, 3 for 10CV). The resulting orange oil (850 mg) was taken up in acetic acid (5 mL), the mixture was stirred at 90° C. for 5 h and evaporated in vacuo. The residue was taken up in DCM and washed with sat. aq. NH$_4$Cl and sat. aq. NaHCO$_3$. The aq. phases were extracted with DCM. The combined org. layers were dried over Na$_2$SO$_4$, filtrated off and concentrated in vacuo. The crude was purified by CC (30 g silica gel, eluent Hept/EA 7/3+0.1% TEA) to afford 280 mg of yellow solid. LC-MS (B): $t_R$=0.72 min; [M+H]$^+$: 400.03.

16.4. 2-[5-((R)-3-Methyl-piperazin-1-yl)-thiazol-4-yl]-1H-benzoimidazole, double hydrochloride salt A suspension of intermediate 16.3 (280 mg) in 4M HCl in dioxane (5 ml) was stirred at RT for 1 h. The solvent was removed in reduced pressure to afford 260 mg of beige solid. LC-MS (B): $t_R$=0.42 min; [M+H]$^+$: 300.02.

16.5. 1-{(R)-4-[4-(1H-Benzoimidazol-2-yl)-thiazol-5-yl]-2-methyl-piperazin-1-yl}-2-pyrrolo[2,3-b]pyridin-1-yl-ethanone This compound was prepared using a method analogous to that of Example 1 step 1.5, intermediate 16.4 replacing intermediate 1.4 and 2-(1H-pyrrolo[2,3-b]pyridin-1-yl)acetic acid replacing benzoimidazol-1-yl-acetic acid. LC-MS (A): $t_R$=0.58 min; [M+H]$^+$: 458.2.

EXAMPLE 17

1-{(R)-4-[4-(1H-Benzoimidazol-2-yl)-thiazol-5-yl]-2-methyl-piperazin-1-yl}-2-imidazo[4,5-b]pyridin-3-yl-ethanone This compound was prepared using a method analogous to that of Example 1 step 1.5, intermediate 16.4 replacing intermediate 1.4 and intermediate 14.2 replacing benzoimidazol-1-yl-acetic acid. LC-MS (A): $t_R$=0.47 min; [M+H]$^+$: 459.3.

EXAMPLE 18

1-{(R)-4-[4-(1H-Benzoimidazol-2-yl)-thiazol-5-yl]-2-ethyl-piperazin-1-yl}-2-pyrrolo[2,3-b]pyridin-1-yl-ethanone

18.1. 2-[5-((R)-3-Ethyl-piperazin-1-yl)-thiazol-4-yl]-1H-benzoimidazole, double hydrochloride salt This compound was prepared in four steps following the method described in Example 16, from step 16.1 to 16.4, (R)-1-N-Boc-2-ethylpiperazine replacing (R)-1-N-Boc-2-methylpiperazine in step 16.1. LC-MS (B): $t_R$=0.45 min; [M+H]$^+$: 314.18.

18.2. 1-{(R)-4-[4-(1H-Benzoimidazol-2-yl)-thiazol-5-yl]-2-ethyl-piperazin-1-yl}-2-pyrrolo[2,3-b]pyridin-1-yl-ethanone This compound was prepared using a method analogous to that of Example 1 step 1.5, intermediate 18.1 replacing intermediate 1.4 and 2-(1H-pyrrolo[2,3-b]pyridin-1-yl)acetic acid replacing benzoimidazol-1-yl-acetic acid. LC-MS (A): $t_R$=0.63 min; [M+H]$^+$: 472.3.

EXAMPLE 19

1-{(R)-4-[4-(1H-Benzoimidazol-2-yl)-thiazol-5-yl]-2-methoxymethyl-piperazin-1-yl}-2-pyrrolo[2,3-b]pyridin-1-yl-ethanone

19.1. 2-[5-((R)-3-Methoxymethyl-piperazin-1-yl)-thiazol-4-yl]-1H-benzoimidazole, double hydrochloride salt This compound was prepared in four steps following the method described in Example 16, from step 16.1 to 16.4, (R)-1-N-Boc-2-methoxymethylpiperazine replacing (R)-1-N-Boc-2-methylpiperazine in step 16.1. LC-MS (B): $t_R$=0.43 min; [M+H]$^+$: 329.97.

19.2. 1-{(R)-4-[4-(1H-Benzoimidazol-2-yl)-thiazol-5-yl]-2-methoxymethyl-piperazin-1-yl}-2-pyrrolo[2,3-b]pyridin-1-yl-ethanone This compound was prepared using a method analogous to that of Example 1 step 1.5, intermediate 19.1 replacing intermediate 1.4 and 2-(1H-pyrrolo[2,3-b]pyridin-1-yl)acetic acid replacing benzoimidazol-1-yl-acetic acid. LC-MS (A): $t_R$=0.6 min; [M+H]$^+$: 488.3.

EXAMPLE 20

1-{(R)-4-[4-(1H-Benzoimidazol-2-yl)-thiazol-5-yl]-2-methoxymethyl-piperazin-1-yl}-2-pyrrolo[2,3-b]pyridin-1-yl-ethanone This compound was prepared using a method analogous to that of Example 1 step 1.5, intermediate 19.1 replacing intermediate 1.4 and intermediate 14.2 replacing benzoimidazol-1-yl-acetic acid. LC-MS (A): $t_R$=0.5 min; [M+H]$^+$: 489.1.

EXAMPLE 21

1-{(R)-4-[4-(4-Fluoro-1H-benzoimidazol-2-yl)-thiazol-5-yl]-2-methyl-piperazin-1-yl}-2-pyrrolo[2,3-b]pyridin-1-yl-ethanone

21.1. 5-((R)-3-Methyl-piperazin-1-yl)-thiazole-4-carboxylic acid methyl ester, hydrochloride salt This compound was prepared using a method analogous to that of Example 1 step 1.4, intermediate 16.1 replacing intermediate 1.3. LC-MS (B): $t_R$=0.39 min; [M+H]$^+$: 242.10.

21.2. 5-[(R)-3-Methyl-4-(2-pyrrolo[2,3-b]pyridin-1-yl-acetyl)-piperazin-1-yl]-thiazole-4-carboxylic acid methyl ester To a solution of 2-(1H-pyrrolo[2,3-b]pyridin-1-yl)acetic acid (592 mg) in DCM (5 mL) was added HOBT (499 mg) followed by EDCI (709 mg) and DIPEA (1.21 mL). The resulting mixture was stirred for 5 min. Intermediate 21.1 (933 mg) was added and the resulting mixture was stirred at RT for 20 h. The reaction mixture was diluted with 1M NaHCO$_3$ (30 mL). The layers were separated and the org. phase was washed with water, dried over Na$_2$SO$_4$, filtrated off and evaporated in vacuo. The crude was purified by CC (Biotage, SNAP 50 g cartridge, solvent A: DCM; solvent B: MeOH; gradient in % B: 0 to 15 over 16CV) to afford 1.29 g of brown oil. LC-MS (B): $t_R$=0.64 min; [M+H]$^+$: 400.31.

21.3. 5-[(R)-3-Methyl-4-(2-pyrrolo[2,3-b]pyridin-1-yl-acetyl)-piperazin-1-yl]-thiazole-4-carboxylic acid This compound was prepared using a method analogous to that of Example 16 step 16.2, intermediate 21.2 replacing intermediate 16.1. LC-MS (B): $t_R$=0.56 min; [M+H]$^+$: 385.91.

21.4. 1-{(R)-4-[4-(4-Fluoro-1H-benzoimidazol-2-yl)-thiazol-5-yl]-2-methyl-piperazin-1-yl}-2-pyrrolo[2,3-b]pyridin-1-yl-ethanone A suspension of 3-fluorobenzene-1,2-diamine (13.5 mg), intermediate 21.3 (40.1 mg), HATU (39.5 mg) and DIPEA (55 µL) in DCM (1 mL) was stirred at RT for 20 h. PL-HCO$_3$ (500 mg, 2.11 mmol/g) was added and the mixture was further stirred for 1 h. The resin was filtered off, washed with DCM and the resulting solution was evaporated in vacuo. The residue was dissolved in AcOH (3 mL) and heated at 70° C. for 20 h. The reaction mixture was concentrated under reduced pressure and purified by preparative LC-MS (III) to afford 10 mg of white solid. LC-MS (A): $t_R$=0.69 min; [M+H]$^+$: 476.3.

Example 22 to Example 28 were synthesized starting from the appropriate diamine derivative and following the procedure described in Example 21. LC-MS data of Example 22 to Example 28 are listed in the table below. The LC-MS conditions used were LC-MS (A).

| Example No | Name | $t_R$ | [M + H]$^+$ |
|---|---|---|---|
| 22 | 1-{(R)-2-Methyl-4-[4-(4-methyl-1H-benzoimidazol-2-yl)-thiazol-5-yl]-piperazin-1-yl}-2-pyrrolo[2,3-b]pyridin-1-yl-ethanone | 0.62 | 472.3 |
| 23 | 1-{(R)-4-[4-(6-Chloro-1H-benzoimidazol-2-yl)-thiazol-5-yl]-2-methyl-piperazin-1-yl}-2-pyrrolo[2,3-b]pyridin-1-yl-ethanone | 0.7 | 492.3 |
| 24 | 1-{(R)-4-[4-(6-tert-Butyl-1H-benzoimidazol-2-yl)-thiazol-5-yl]-2-methyl-piperazin-1-yl}-2-pyrrolo[2,3-b]pyridin-1-yl-ethanone | 0.77 | 514.3 |
| 25 | 1-{(R)-4-[4-(5-Methanesulfonyl-1H-benzoimidazol-2-yl)-thiazol-5-yl]-2-methyl-piperazin-1-yl}-2-pyrrolo[2,3-b]pyridin-1-yl-ethanone | 0.63 | 536.2 |
| 26 | 1-{(R)-4-[4-(5-Chloro-6-fluoro-1H-benzoimidazol-2-yl)-thiazol-5-yl]-2-methyl-piperazin-1-yl}-2-pyrrolo[2,3-b]pyridin-1-yl-ethanone | 0.79 | 510.2 |
| 27 | 1-{(R)-4-[4-(5-Chloro-6-methyl-1H-benzoimidazol-2-yl)-thiazol-5-yl]-2-methyl-piperazin-1-yl}-2-pyrrolo[2,3-b]pyridin-1-yl-ethanone | 0.73 | 506.2 |
| 28 | 1-{(R)-4-[4-(4,5-Difluoro-1H-benzoimidazol-2-yl)-thiazol-5-yl]-2-methyl-piperazin-1-yl}-2-pyrrolo[2,3-b]pyridin-1-yl-ethanone | 0.81 | 494.2 |

EXAMPLE 29

1-(2-{4-[4-(4-Chloro-1H-benzoimidazol-2-yl)-thiazol-5-yl]-piperazin-1-yl}-2-oxo-ethyl)-3-methyl-1,3-dihydro-benzoimidazol-2-one

29.1. 5-{4-[2-(3-Methyl-2-oxo-2,3-dihydro-benzoimidazol-1-yl)-acetyl]-piperazin-1-yl}-thiazole-4-carboxylic acid This compound was prepared in three steps following the method described in Example 21, from step 21.1 to 21.3, starting with intermediate 1.1 instead of intermediate 16.1 in step 21.1 and using (3-methyl-2-oxo-2,3-dihydro-benzoimidazol-1-yl)-acetic acid instead of 2-(1H-pyrrolo[2,3-b]pyridin-1-yl)acetic acid in step 21.2. LC-MS (B): $t_R$=0.60 min; [M+H]$^+$: 402.11.

29.2. 1-(2-{4-[4-(4-Chloro-1H-benzoimidazol-2-yl)-thiazol-5-yl]-piperazin-1-yl}-2-oxo-ethyl)-3-methyl-1,3-dihydro-benzoimidazol-2-one This compound was prepared using a method analogous to that of Example 21 step 21.4, intermediate 29.1 replacing intermediate 21.3 and 3-chloro-benzene-1,2-diamine replacing 3-fluorobenzene-1,2-diamine. LC-MS (A): $t_R$=0.75 min; [M+H]$^+$: 508.2.

Example 30 to Example 37 were synthesized starting from the appropriate diamine derivative and following the procedure described in Example 29 step 29.2. LC-MS data of Example 30 to Example 37 are listed in the table below. The LC-MS conditions used were LC-MS(A).

stirred at 50° C. for 1 h. The reaction mixture was evaporated to dryness. The crude was diluted with EA and Hept was added. The resulting suspension was filtered off, the powder was washed with Hept and the filtrate was evaporated in vacuo to afford 4.71 g (80% pure) of brown resin. LC-MS (B): $t_R$=0.90 min; [M+H]$^+$: 407.96.

38.2. 4-(2-Bromo-4-carboxy-thiazol-5-yl)-piperazine-1-carboxylic acid tert-butyl ester This compound was prepared using a method analogous to that of Example 16 step 16.2, intermediate 38.1 replacing intermediate 16.1 and using as solvent MeOH/THF (2/1) instead of MeOH. LC-MS (B): $t_R$=0.79 min; [M+H]$^+$: 393.84.

38.3. 2-(2-Bromo-5-piperazin-1-yl-thiazol-4-yl)-1H-benzoimidazole, double hydrochloride salt This compound was prepared using a method analogous to that of Example 16 step 16.3, intermediate 38.2 replacing intermediate 16.2. LC-MS (B): $t_R$=0.46 min; [M+H]$^+$: 365.97.

38.4. 1-{4-[4-(1H-Benzoimidazol-2-yl)-2-bromo-thiazol-5-yl]-piperazin-1-yl}-2-pyrrolo[2,3-b]pyridin-1-yl-ethanone This compound was prepared using a method analogous to that of Example 1 step 1.5, intermediate 38.3 replacing inter-

| Example No | Name | $t_R$ | [M + H]$^+$ |
|---|---|---|---|
| 30 | 1-(2-{4-[4-(7-Methoxy-1H-benzoimidazol-2-yl)-thiazol-5-yl]-piperazin-1-yl}-2-oxo-ethyl)-3-methyl-1,3-dihydro-benzoimidazol-2-one | 0.63 | 504.3 |
| 31 | 1-Methyl-3-(2-{4-[4-(5-methyl-1H-benzoimidazol-2-yl)-thiazol-5-yl]-piperazin-1-yl}-2-oxo-ethyl)-1,3-dihydro-benzoimidazol-2-one | 0.65 | 488.3 |
| 32 | 1-Methyl-3-(2-oxo-2-{4-[4-(5-trifluoromethyl-1H-benzoimidazol-2-yl)-thiazol-5-yl]-piperazin-1-yl}-ethyl)-1,3-dihydro-benzoimidazol-2-one | 0.79 | 542.2 |
| 33 | 1-(2-{4-[4-(5-Methoxy-1H-benzoimidazol-2-yl)-thiazol-5-yl]-piperazin-1-yl}-2-oxo-ethyl)-3-methyl-1,3-dihydro-benzoimidazol-2-one | 0.63 | 504.2 |
| 34 | 1-(2-{4-[4-(6-Fluoro-1H-benzoimidazol-2-yl)-thiazol-5-yl]-piperazin-1-yl}-2-oxo-ethyl)-3-methyl-1,3-dihydro-benzoimidazol-2-one | 0.64 | 492.2 |
| 35 | 1-(2-{4-[4-(5,6-Dichloro-1H-benzoimidazol-2-yl)-thiazol-5-yl]-piperazin-1-yl}-2-oxo-ethyl)-3-methyl-1,3-dihydro-benzoimidazol-2-one | 0.84 | 542.1 |
| 36 | 1-(2-{4-[4-(5,6-Dimethoxy-1H-benzoimidazol-2-yl)-thiazol-5-yl]-piperazin-1-yl}-2-oxo-ethyl)-3-methyl-1,3-dihydro-benzoimidazol-2-one | 0.62 | 534.3 |
| 37 | 1-(2-{4-[4-(6-Chloro-7-methyl-1H-benzoimidazol-2-yl)-thiazol-5-yl]-piperazin-1-yl}-2-oxo-ethyl)-3-methyl-1,3-dihydro-benzoimidazol-2-one | 0.75 | 522.2 |

EXAMPLE 38

1-{4-[4-(1H-Benzoimidazol-2-yl)-2-bromo-thiazol-5-yl]-piperazin-1-yl}-2-pyrrolo[2,3-b]pyridin-1-yl-ethanone

38.1. 4-(2-Bromo-4-methoxycarbonyl-thiazol-5-yl)-piperazine-1-carboxylic acid tert-butyl ester To a brown solution of intermediate 1.1 (3.94 g) in MeCN (60 mL) was added NBS (2.21 g). The resulting solution was mediate 1.4 and 2-(1H-pyrrolo[2,3-b]pyridin-1-yl)acetic acid replacing benzoimidazol-1-yl-acetic acid. LC-MS (A): $t_R$=0.63 min; [M+H]$^+$: 522.2.

EXAMPLE 39

1-{4-[4-(1H-Benzoimidazol-2-yl)-2-ethyl-thiazol-5-yl]-piperazin-1-yl}-2-pyrrolo[2,3-b]pyridin-1-yl-ethanone A vial was charged with Example 38 (50 mg), 1,1'-bis(diphenylphosphin)ferrocen dichloropalladium-(II)-chlorid complex (in DCM 1/1, 3.91 mg) and dioxane (1.5 mL) at RT under argon, sealed and evacuated and backfilled with argon three times. Diethylzinc (1.5M in toluene) was added. The resulting orange suspension was shaken at 100° C. for 1.5 h. The reaction mixture was allowed to cool down, was quenched with water (0.5 mL) dropwise and evaporated to dryness. The resulting brown solid was purified by preparative LC-MS (I) to afford 17 mg of beige solid. LC-MS (A): $t_R$=0.65 min; [M+H]$^+$: 472.3.

EXAMPLE 40

1-{4-[4-(1H-Benzoimidazol-2-yl)-2-methyl-thiazol-5-yl]-piperazin-1-yl}-2-pyrrolo[2,3-b]pyridin-1-yl-ethanone This compound was prepared using a method analogous to that of Example 39, dimethylzinc (2M in toluene) replacing diethylzinc (1.5M in toluene). LC-MS (A): $t_R$=0.6 min; [M+H]$^+$: 458.2.

EXAMPLE 41

1-{4-[4-(1H-Benzoimidazol-2-yl)-2-phenyl-thiazol-5-yl]-piperazin-1-yl}-2-pyrrolo[2,3-b]pyridin-1-yl-ethanone

41.1. 1-(4-{2-Bromo-4-[1-(2-trimethylsilanyl-ethoxymethyl)-1H-benzoimidazol-2-yl]-thiazol-5-yl}-piperazin-1-yl)-2-pyrrolo[2,3-b]pyridin-1-yl-ethanone To a yellow solution of Example 38 (542 mg) in THF (6 mL) was added NaH (62 mg, 60% in mineral oil) at 0° C. The resulting pale yellow foaming suspension was stirred at 0° C. for 15 min under argon, then SEMCl (182 mg) was added and stirring was continued for 1.25 h. The reaction mixture was quenched by addition of water. Phases were separated and the org. layer was washed with water and brine. The aq. layers were extracted twice with EA. The combined org. layers were dried over MgSO$_4$, filtrated off, evaporated and dried in high vacuo. The crude was purified by CC (Biotage, SNAP 25 g cartridge, solvent A: DCM; solvent B: DCM/MeOH 8/2; gradient in % B: 5 for 4CV, 5 to 15 over 6CV, 15 for 3CV) to afford 530 mg of light yellow solid. LC-MS (B): $t_R$=0.91 min; [M+H]$^+$: 652.48.

41.2. 1-(4-{2-Phenyl-4-[1-(2-trimethylsilanyl-ethoxymethyl)-1H-benzoimidazol-2-yl]-thiazol-5-yl}-piperazin-1-yl)-2-pyrrolo[2,3-b]pyridin-1-yl-ethanone A mixture of intermediate 41.1 (50 mg), phenylboronic acid (9.83 mg), Pd(PPh$_3$)$_2$Cl$_2$ (2.69 mg) in MeCN (1 mL) and 1M Na$_2$CO$_3$ (1 mL) was stirred at 80° C. for 24 h. The reaction mixture was allowed to cool down, diluted with EA and washed twice with water and brine. The aq. layers were extracted twice with EA. The combined org. layers were dried over MgSO4, filtrated off and evaporated to dryness. The crude was purified by CC (Biotage, SNAP 10 g cartridge, solvent A: DCM; solvent B: DCM/MeOH 8/2; gradient in % B: 5 for 5CV, 5 to 15 over 5CV, 15 for 5CV) to afford 28 mg of brown solid. LC-MS (B): $t_R$=0.94 min; [M+H]$^+$: 650.64.

41.3. 1-{4-[4-(1H-Benzoimidazol-2-yl)-2-phenyl-thiazol-5-yl]-piperazin-1-yl}-2-pyrrolo[2,3-b]pyridin-1-yl-ethanone To a brown solution of intermediate 41.2 (26 mg) in THF (0.5 mL) was added TBAF (0.16 mL, 1M in THF) at RT. The mixture was stirred at RT for 1 h, heated at 70° C. for 20.5 h. Two additional equivalents of TBAF were added and the mixture was stirred at 70° C. for 3.5 h. After cooling down, sat. aq. NaHCO$_3$ was added and the mixture was extracted twice with DCM. The combined org. layers were dried over MgSO$_4$, filtrated off and evaporated to dryness. The crude was purified by preparative LC-MS (I) to afford 2 mg of yellow solid. LC-MS (A): $t_R$=0.76 min; [M+H]$^+$: 520.2.

EXAMPLE 42

1-{4-[4-(1H-Benzoimidazol-2-yl)-2-chloro-thiazol-5-yl]-piperazin-1-yl}-2-pyrrolo[2,3-b]pyridin-1-yl-ethanone

42.1. 4-(2-Chloro-4-methoxycarbonyl-thiazol-5-yl)-piperazine-1-carboxylic acid tert-butyl ester This compound was prepared using a method analogous to that of Example 38 step 38.1, NCS replacing NBS. LC-MS (C): $t_R$=0.85 min; [M+H]$^+$: 362.24.

42.2. 4-(4-Carboxy-2-chloro-thiazol-5-yl)-piperazine-1-carboxylic acid tert-butyl ester This compound was prepared using a method analogous to that of Example 16 step 16.2, intermediate 42.1 replacing intermediate 16.1 and using MeOH/THF 1/1 instead of EtOH. LC-MS (C): $t_R$=0.72 min; [M+H]$^+$: 348.26.

42.3. 4-[4-(1H-Benzoimidazol-2-yl)-2-chloro-thiazol-5-yl]-piperazine-1-carboxylic acid tert-butyl ester This compound was prepared using a method analogous to that of Example 16 step 16.3, intermediate 42.2 replacing intermediate 16.2. LC-MS (C): $t_R$=0.69 min; [M+H]$^+$: 420.35.

42.4. 5-[(R)-3-Methyl-4-(2-pyrrolo[2,3-b]pyridin-1-yl-acetyl)-piperazin-1-yl]-thiazole-4-carboxylic acid This compound was prepared using a method analogous to that of Example 16 step 16.4, intermediate 42.3 replacing intermediate 16.3. LC-MS (C): $t_R$=0.57 min; [M+H]$^+$: 319.96.

42.5. 1-{4-[4-(1H-Benzoimidazol-2-yl)-2-chloro-thiazol-5-yl]-piperazin-1-yl}-2-pyrrolo[2,3-b]pyridin-1-yl-ethanone This compound was prepared using a method analogous to that of Example 1 step 1.5, intermediate 42.4 replacing intermediate 1.4 and 2-(1H-pyrrolo[2,3-b]pyridin-1-yl)acetic acid replacing benzoimidazol-1-yl-acetic acid. LC-MS (A): $t_R$=0.63 min; [M+H]$^+$: 478.2.

EXAMPLE 43 rac-1-{4-[4-(1H-Benzoimidazol-2-yl)-2-(1-hydroxy-ethyl)-thiazol-5-yl]-piperazin-1-yl}-2-pyrrolo[2,3-b]pyridin-1-yl-ethanone

43.1. 1-(4-{2-Acetyl-4-[1-(2-trimethylsilanyl-ethoxymethyl)-1H-benzoimidazol-2-yl]-thiazol-5-yl}-piperazin-1-yl)-2-pyrrolo[2,3-b]pyridin-1-yl-ethanone To a solution of intermediate 41.1 (250 mg) in toluene (5 mL) was added tributyl(1-ethoxyvinyl)tin (0.163 mL) followed by Pd(PPh$_3$)$_2$Cl$_2$ (26.9 mg). The resulting yellow suspension was stirred at 95° C. under argon for 19.5 h. 1.2 equivalents of tributyl(1-ethoxyvinyl)tin and 0.1 equivalent of Pd(PPh$_3$)$_2$Cl$_2$ were added and the mixture was further stirred at 95° C. for 3.5 h. The reaction mixture was evaporated to dryness. The residue was dissolved in dioxane (3.3 mL) and 2M HCl (1.6 mL). The resulting dark brown emulsion was vigorously stirred at RT overnight. 1M NaOH (3.5 mL) was added to reach pH 9. Water was added and the mixture was extracted three times with DCM. The combined org. layers were dried over MgSO$_4$, filtrated off and evaporated to dryness. The crude was purified by CC (Biotage, SNAP 10 g cartridge, solvent A: DCM; solvent B: DCM/MeOH 8/2; gradient in % B: 5 for 5CV, 5 to 15 over 3CV, 15 for 7CV) to afford 191 mg of dark yellow solid. LC-MS (B): t$_R$=0.91 min; [M+H]$^+$: 616.63.

43.2. rac-1-(4-{2-(1-Hydroxy-ethyl)-4-[1-(2-trimethylsilanyl-ethoxymethyl)-1H-benzoimidazol-2-yl]-thiazol-5-yl}-piperazin-1-yl)-2-pyrrolo[2,3-b]pyridin-1-yl-ethanone To a yellow solution of intermediate 43.1 (40 mg) in MeOH (1 mL) was added NaBH$_4$ (2.5 mg) under argon at RT. The resulting foaming brown suspension was shaken at RT. The reaction mixture was quenched by adding water and extracted three times with DCM. The combined org. layers were evaporated and dried in high vacuo to afford 33 mg of brown solid. LC-MS (B): t$_R$=0.82 min; [M+H]$^+$: 618.05.

43.3. rac-1-{4-[4-(1H-Benzoimidazol-2-yl)-2-(1-hydroxy-ethyl)-thiazol-5-yl]-piperazin-1-yl}-2-pyrrolo[2,3-b]pyridin-1-yl-ethanone This compound was prepared using a method analogous to that of Example 41 step 41.3, intermediate 43.2 replacing intermediate 41.2. LC-MS (A): t$_R$=0.57 min; [M+H]$^+$: 488.3.

EXAMPLE 44

1-{4-[4-(1H-Benzoimidazol-2-yl)-thiazol-5-yl]-[1,4]diazepan-1-yl}-2-pyrrolo[2,3-b]pyridin-1-yl-ethanone 44.1. 4-(1H-benzo[d]imidazol-2-yl)-5-(1,4-diazepan-1-yl)thiazole, double hydrochloride salt This compound was prepared in four steps following the method described in Example 16, from step 16.1 to 16.4, tert-butyl-1,4-diazepane-1-carboxylate replacing (R)-1-N-Boc-2-methylpiperazine, DBU replacing DIPEA and heating at 80° C. in step 16.1. LC-MS (B): t$_R$=0.43 min; [M+H]$^+$: 300.00.

44.2. 1-{4-[4-(1H-Benzoimidazol-2-yl)-thiazol-5-yl]-[1,4]-diazepan-1-yl}-2-pyrrolo[2,3-b]pyridin-1-yl-ethanone This compound was prepared using a method analogous to that of Example 1 step 1.5, intermediate 44.1 replacing intermediate 1.4 and 2-(1H-pyrrolo[2,3-b]pyridin-1-yl)acetic acid replacing benzoimidazol-1-yl-acetic acid. LC-MS (A): t$_R$=0.57 min; [M+H]$^+$: 458.3.

EXAMPLE 45

1-{4-[4-(1H-Benzoimidazol-2-yl)-thiazol-5-yl]-[1,4]diazepan-1-yl}-2-imidazo[4,5-b]pyridin-3-yl-ethanone This compound was prepared using a method analogous to that of Example 1 step 1.5, intermediate 44.1 replacing intermediate 1.4 and intermediate 14.2 replacing benzoimidazol-1-yl-acetic acid. LC-MS (A): t$_R$=0.47 min; [M+H]$^+$: 459.3.

EXAMPLE 46

1-{(S)-4-[4-(1H-Benzoimidazol-2-yl)-thiazol-5-yl]-2-methyl-piperazin-1-yl}-2-pyrrolo[2,3-b]pyridin-1-yl-ethanone 46.1. 2-[5-((S)-3-Methyl-piperazin-1-yl)-thiazol-4-yl]-1H-benzoimidazole, double hydrochloride salt This compound was prepared in four steps following the method described in Example 16, from step 16.1 to 16.4, (S)-1-N-Boc-2-methylpiperazine replacing (R)-1-N-Boc-2-methylpiperazine and DBU replacing DIPEA in step 16.1 and using MeOH/THF 2.5/1 instead of EtOH in step 16.2. LC-MS (B): t$_R$=0.42 min; [M+H]$^+$: 300.02.

46.2. 1-{(S)-4-[4-(1H-Benzoimidazol-2-yl)-thiazol-5-yl]-2-methyl-piperazin-1-yl}-2-pyrrolo[2,3-b]pyridin-1-yl-ethanone This compound was prepared using a method analogous to that of Example 1 step 1.5, intermediate 46.1 replacing intermediate 1.4 and 2-(1H-pyrrolo[2,3-b]pyridin-1-yl)acetic acid replacing benzoimidazol-1-yl-acetic acid. LC-MS (A): t$_R$=0.58 min; [M+H]$^+$: 458.3.

EXAMPLE 47

1-{(S)-4-[4-(1H-Benzoimidazol-2-yl)-thiazol-5-yl]-2-methyl-piperazin-1-yl}-2-imidazo[4,5-b]pyridin-3-yl-ethanone This compound was prepared using a method analogous to that of Example 1 step 1.5, intermediate 46.1 replacing intermediate 1.4 and intermediate 14.2 replacing benzoimidazol-1-yl-acetic acid. LC-MS (A): t$_R$=0.47 min; [M+H]$^+$: 459.2.

EXAMPLE 48

1-{4-[4-(1H-Benzoimidazol-2-yl)-thiazol-5-yl]-piperidin-1-yl}-2-imidazo[4,5-b]pyridin-3-yl-ethanone 48.1. 4-(4-Methoxycarbonyl-thiazol-5-yl)-3,6-dihydro-2H-pyridine-1-carboxylic acid tert-butyl ester A mixture of methyl 5-bromo-1,3-thiazole-4-carboxylate (250 mg), tert-butyl 4-(4,4,5,5-tetramethyl-1,3,2-dioxaborolan-2-yl)-5-6-dihydropyridine-1(2H)-carboxylate (348 mg), Pd(PPh$_3$)$_4$ (67.1 mg) in sat. aq. K$_2$CO$_3$ (1.5 mL) and dioxane (3 mL) was stirred at 125° C. for 1 h under argon in the microwave. EA was added and the mixture was washed with water and brine. The aq. layers were extracted with EA. The combined org. layers were dried over MgSO$_4$, filtrated off and concentrated in vacuo. The crude was purified by CC (Biotage, SNAP 25 g cartridge, solvent A: Hept; solvent B: EA; gradient in % B: 0 for 5CV, 0 to 10 over 5CV, 10 for 5CV, 10 to 20 over 5CV, 20 for 5CV, 20 to 30 over 5CV, 30 for 10CV) to afford 187 mg of yellow oil. LC-MS (B): $t_R$=0.84 min; [M+H]$^+$: 325.05.

48.2. 4-(4-Methoxycarbonyl-thiazol-5-yl)-piperidine-1-carboxylic acid tert-butyl ester To a solution of intermediate 48.1 (180 mg) in EtOH (5 mL) was added Pd/C (10%, 29 mg) under argon. The flask was evacuated and backfilled with argon three times, then evacuated and backfilled with hydrogen twice. The reaction mixture was stirred at RT under hydrogen. After 3 h, 0.05 equivalent of Pd was added, followed by 1 equivalent of TEA 0.75 h later. After stirring for 1.5 h, the reaction mixture was heated up to 50° C. overnight. 2 equivalents of AcOH were added and the mixture was heated at 50° C. for 4 h. 0.05 equivalent of Pd was added and the heating was pursued for 20 h. The mixture was filtered over celite and the filtrate was engaged with Pd/C (10%, 29 mg) under argon. The flask was evacuated and backfilled with argon three times, then evacuated and backfilled with hydrogen twice. The reaction mixture was stirred at 50° C. under hydrogen overnight. The mixture was filtered over celite and evaporated under reduced pressure to afford 143 mg of yellow wax. LC-MS (B): $t_R$=0.85 min; [M+H]$^+$: 327.21.

48.3. 4-(4-Carboxy-thiazol-5-yl)-piperidine-1-carboxylic acid tert-butyl ester This compound was prepared using a method analogous to that of Example 16 step 16.2, intermediate 48.2 replacing intermediate 16.1. LC-MS (B): $t_R$=0.73 min; [M+H]$^+$: 313.22.

48.4. 2-(5-Piperidin-4-yl-thiazol-4-yl)-1H-benzoimidazole

This compound was prepared using a method analogous to that of Example 16 step 16.3, intermediate 48.3 replacing intermediate 16.2, however no work-up was performed after reaction with HATU. The BOC group was moreover cleaved during AcOH treatment. LC-MS (C): $t_R$=0.45 min; [M+H]$^+$: 285.14.

48.5. 1-{4-[4-(1H-Benzoimidazol-2-yl)-thiazol-5-yl]-piperidin-1-yl}-2-imidazo[4,5-b]pyridin-3-yl-ethanone This compound was prepared using a method analogous to that of Example 1 step 1.5, intermediate 48.4 replacing intermediate 1.4 and intermediate 14.2 replacing benzoimidazol-1-yl-acetic acid. LC-MS (A): $t_R$=0.51 min; [M+H]$^+$: 444.3.

EXAMPLE 49

1-{(R)-4-[4-(1H-Benzoimidazol-2-yl)-thiazol-5-yl]-2-ethyl-piperazin-1-yl}-2-imidazo[4,5-b]pyridin-3-yl-ethanone This compound was prepared using a method analogous to that of Example 1 step 1.5, intermediate 18.1 replacing intermediate 1.4 and intermediate 14.2 replacing benzoimidazol-1-yl-acetic acid. LC-MS (A): $t_R$=0.51 min; [M+H]$^+$: 473.3.

EXAMPLE 50

1-{(R)-4-[4-(1H-Benzoimidazol-2-yl)-2-isopropyl-thiazol-5-yl]-2-methyl-piperazin-1-yl}-2-imidazo[4,5-b]pyridin-3-yl-ethanone

50.1. (R)-4-(2-Bromo-4-methoxycarbonyl-thiazol-5-yl)-2-methyl-piperazine-1-carboxylic acid tert-butyl ester This compound was prepared using a method analogous to that of Example 38 step 38.1, intermediate 16.1 replacing intermediate 1.1. LC-MS (B): $t_R$=0.93 min; [M+H]$^+$: 420.30.

50.2. (R)-4-(2-Isopropenyl-4-methoxycarbonyl-thiazol-5-yl)-2-methyl-piperazine-1-carboxylic acid tert-butyl ester A mixture of isopropenylboronic acid pinacol ester (0.246 mL), Pd(PPh$_3$)$_2$Cl$_2$ (42.2 mg), intermediate 50.1 (500 mg) in MeCN (4 mL) and 1M Na$_2$CO$_3$ (4 mL) was stirred at 80° C. under argon for 2 h. The reaction mixture was allowed to cool down, was diluted with EA and washed twice with water and once with brine. The aq. layers were extracted with EA. The combined org. layers were dried over MgSO$_4$, filtrated off and evaporated to dryness to afford 575 mg of brown oil. CC (Biotage, SNAP 10 g cartridge, solvent A: Hept; solvent B: EA; gradient in % B: 10 for 6CV, 10 to 30 over 3CV, 30 for 5CV) afforded 343 mg of pale yellow wax. LC-MS (B): $t_R$=0.96 min; [M+H]$^+$: 382.03.

50.3. (R)-4-(2-Isopropyl-4-methoxycarbonyl-thiazol-5-yl)-2-methyl-piperazine-1-carboxylic acid tert-butyl ester To a flask containing intermediate 50.2 (296 mg) was added Pd/C (10%, 41 mg) under argon followed by MeOH (3 mL). The flask was evacuated and backfilled with argon three times, then evacuated and backfilled with H$_2$ three times. The reaction mixture was stirred at RT under H$_2$ for 1.75 h, filtrated over celite. The celite was washed with MeOH and the filtrate was evaporated in vacuo to afford 294 mg of white solid. LC-MS (B): $t_R$=0.94 min; [M+H]$^+$: 384.20.

50.4. (R)-4-(4-Carboxy-2-isopropyl-thiazol-5-yl)-2-methyl-piperazine-1-carboxylic acid tert-butyl ester This compound was prepared using a method analogous to that of Example 16 step 16.2, intermediate 50.3 replacing intermediate 16.1, using MeOH/THF 1:1 instead of EtOH and heating at 50° C. LC-MS (B): $t_R$=0.87 min; [M+H]$^+$: 369.78.

50.5. (R)-4-[4-(1H-Benzoimidazol-2-yl)-2-isopropyl-thiazol-5-yl]-2-methyl-piperazine-1-carboxylic acid tert-butyl ester This compound was prepared using a method analogous to that of Example 16 step 16.3, intermediate 50.4 replacing intermediate 16.2. LC-MS (B): $t_R$=0.83 min; [M+H]$^+$: 442.52

50.6. (R)-4-(1H-benzoimidazol-2-yl)-2-isopropyl-5-(3-methylpiperazin-1-yl)thiazole, double hydrochloride salt This compound was prepared using a method analogous to that of Example 16 step 16.4, intermediate 50.5 replacing intermediate 16.3. LC-MS (B): $t_R$=0.83 min; [M+H]$^+$: 442.52.

50.7. 1-{(R)-4-[4-(1H-Benzoimidazol-2-yl)-2-isopropyl-thiazol-5-yl]-2-methyl-piperazin-1-yl}-2-imidazo[4,5-b]pyridin-3-yl-ethanone This compound was prepared using a method analogous to that of Example 1 step 1.5, intermediate 50.6 replacing intermediate 1.4 and intermediate 14.2 replacing benzoimidazol-1-yl-acetic acid. LC-MS (A): $t_R$=0.61 min; [M+H]$^+$: 501.3.

EXAMPLE 51

1-{(R)-4-[4-(1H-Benzoimidazol-2-yl)-2-trifluoromethyl-thiazol-5-yl]-2-methyl-piperazin-1-yl}-2-imidazo[4,5-b]pyridin-3-yl-ethanone

51.1. (R)-4-(4-Methoxycarbonyl-2-trifluoromethyl-thiazol-5-yl)-2-methyl-piperazine-1-carboxylic acid tert-butyl ester To a solution of intermediate 50.1 (2 g) in DMF (40 mL), CuI (4.53 g), AsPh$_3$ (601 mg), tris(dibenzylidenaceton)dipalladium-(0)-chloroform adduct (246 mg) and methyl 2,2-difluoro-2-(fluorosulfonyl)acetate (4.57 g) were added in sequence. The resulting suspension was heated at 100° C. for 4 h. The mixture was allowed to cool down and was flushed with nitrogen for 30 min into an ethanolamine solution (50% in water). The residue was evaporated to dryness. CC (Biotage, SNAP 100 g cartridge, solvent A: Hept; solvent B: EA; gradient in % B: 00 for 1CV, 0 to 10 over 5CV, 10 for 3CV, 10 to over 5CV, 20 for 3CV, 20 to 30 over 5CV, 30 for 3CV, 30 to 50 over 5CV) afforded 1.26 g of yellow oil. LC-MS (B): $t_R$=0.97 min; [M+H]$^+$: 409.96.

51.2. (R)-4-(1H-benzoimidazol-2-yl)-5-(3-methylpiperazin-1-yl)-2-(trifluoromethyl)thiazole, double hydrochloride salt This compound was prepared in three steps following the method described in Example 16, from step 16.2 to 16.4, intermediate 51.1 replacing intermediate 16.1 in step 16.2. LC-MS (B): $t_R$=0.55 min; [M+H]$^+$: 367.94.

51.3. 1-{(R)-4-[4-(1H-Benzoimidazol-2-yl)-2-trifluoromethyl-thiazol-5-yl]-2-methyl-piperazin-1-yl}-2-imidazo[4,5-b]pyridin-3-yl-ethanone This compound was prepared using a method analogous to that of Example 1 step 1.5, intermediate 51.2 replacing intermediate 1.4 and intermediate 14.2 replacing benzoimidazol-1-yl-acetic acid. LC-MS (A): $t_R$=0.66 min; [M+H]$^+$: 527.2.

EXAMPLE 52

1-{4-[4-(1H-Benzoimidazol-2-yl)-thiazol-5-yl]-piperazin-1-yl}-2-(4-methoxy-indol-1-yl)-ethanone

52.1. (4-Methoxy-indol-1-yl)-acetic acid

To a solution of 4-methoxyindole (294 mg) in DMF (10 mL) was added K$_2$CO$_3$ (829 mg). After 10 min stirring, ethylchloroacetate (0.426 mL) was added. The reaction mixture was stirred overnight at 120° C., was allowed to cool down and was filtered off. The solid was washed with DCM and the filtrate was concentrated in vacuo. After CC (silica gel, EA/MeOH 9/1) followed by preparative HPLC (I), the resulting material was dissolved in 1M NaOH/THF (20 mL, 1/1). The mixture was stirred at RT overnight, neutralized with 1M HCl (8 mL) and concentrated to dryness. The residue was taken up in DCM and the resulting suspension was filtered off. The filtrate was evaporated in vacuo to afford 340 mg of beige powder. LC-MS (D): $t_R$=0.76 min; [M+H]$^+$: 206.1.

52.2. 1-{4-[4-(1H-Benzoimidazol-2-yl)-thiazol-5-yl]-piperazin-1-yl}-2-(4-methoxy-indol-1-yl)-ethanone To intermediate 52.1 (30.8 mg) were added a solution of intermediate 1.4 (35.8 mg) in DMF/DIPEA (0.54 mL, 5/1) and a solution of HOAT (20.4 mg) in DMF (0.45 mL). DMF (0.9 mL) and DIPEA (0.9 mL) were added and the mixture was heated up until complete dissolution. Si-DCC (0.93 mmol/g, 322.6 mg) was added and the reaction mixture was heated at 50° C. overnight. After cooling down, it was filtered through a PL-HCO$_3$ cartridge preconditioned with DCM/MeOH 1/1. The cartridge was further washed with DCM/MeOH 1/1 and the solvents were removed in vacuo. The crude was purified by preparative LC-MS (IV) to afford 19 mg of white solid. LC-MS (A): $t_R$=0.7 min; [M+H]$^+$: 473.3.

Example 53 to Example 64 were synthesized starting from the appropriate indole derivative and following the procedure described in Example 52, step 52.1 and 52.2. LC-MS data of Example 53 to Example 64 are listed in the table below. The LC-MS conditions used were LC-MS (A).

| Example No | Name | $t_R$ | [M + H]$^+$ |
|---|---|---|---|
| 53 | 1-{4-[4-(1H-Benzoimidazol-2-yl)-thiazol-5-yl]-piperazin-1-yl}-2-(5,6-dichloro-indol-1-yl)-ethanone | 0.86 | 511.1 |
| 54 | 1-{4-[4-(1H-Benzoimidazol-2-yl)-thiazol-5-yl]-piperazin-1-yl}-2-(6-trifluoromethyl-indol-1-yl)-ethanone | 0.84 | 511.2 |
| 55 | 1-{4-[4-(1 H-Benzoimidazol-2-yl)-thiazol-5-yl]-piperazin-1-yl}-2-(5-fluoro-indol-1-yl)-ethanone | 0.73 | 461.2 |
| 56 | 1-{4-[4-(1H-Benzoimidazol-2-yl)-thiazol-5-yl]-piperazin-1-yl}-2-(6-fluoro-indol-1-yl)-ethanone | 0.74 | 461.2 |
| 57 | 1-{4-[4-(1H-Benzoimidazol-2-yl)-thiazol-5-yl]-piperazin-1-yl}-2-(7-methyl-indol-1-yl)-ethanone | 0.74 | 457.3 |
| 58 | 1-{4-[4-(1H-Benzoimidazol-2-yl)-thiazol-5-yl]-piperazin-1-yl}-2-(2-methyl-indol-1-yl)-ethanone | 0.75 | 457.2 |
| 59 | 1-(2-{4-[4-(1H-Benzoimidazol-2-yl)-thiazol-5-yl]-piperazin-1-yl}-2-oxo-ethyl)-1H-indole-3-carbonitrile | 0.69 | 468.2 |
| 60 | 1-{4-[4-(1H-Benzoimidazol-2-yl)-thiazol-5-yl]-piperazin-1-yl}-2-(4-chloro-indol-1-yl)-ethanone | 0.79 | 477.2 |
| 61 | 1-(2-{4-[4-(1H-Benzoimidazol-2-yl)-thiazol-5-yl]-piperazin-1-yl}-2-oxo-ethyl)-1H-indole-7-carbonitrile | 0.71 | 468.2 |
| 62 | 1-{4-[4-(1H-Benzoimidazol-2-yl)-thiazol-5-yl]-piperazin-1-yl}-2-(5-chloro-6-methoxy-indol-1-yl)-ethanone | 0.78 | 507.2 |

| Example No | Name | $t_R$ | [M + H]$^+$ |
|---|---|---|---|
| 63 | 1-{4-[4-(1H-Benzoimidazol-2-yl)-thiazol-5-yl]-piperazin-1-yl}-2-(5-fluoro-3-methyl-indol-1-yl)-ethanone | 0.79 | 475.3 |
| 64 | 1-{4-[4-(1H-Benzoimidazol-2-yl)-thiazol-5-yl]-piperazin-1-yl}-2-(2-trifluoromethyl-benzoimidazol-1-yl)-ethanone | 0.67 | 512.2 |

EXAMPLE 65

1-{4-[4-(1H-Benzoimidazol-2-yl)-thiazol-5-yl]-piperazin-1-yl}-2-(6-chloro-pyrrolo[2,3-b]pyridin-1-yl)-ethanone

65.1. (6-Chloro-pyrrolo[2,3-b]pyridin-1-yl)-acetic acid tert-butyl ester

This compound was prepared following the method described in Example 14, step 14.1, 6-chloro-1H-pyrrolo[2,3-b]pyridine replacing 4-azabenzimidazole. LC-MS (B): $t_R$=0.93 min; [M+H]$^+$: 267.28

65.2. (6-Chloro-pyrrolo[2,3-b]pyridin-1-yl)-acetic acid, hydrochloride salt

This compound was prepared following the method described in Example 16, step 16.4, intermediate 65.1 replacing intermediate 16.3. LC-MS (B): $t_R$=0.68 min; [M+H]$^+$: 211.31.

65.3. 1-{4-[4-(1H-Benzoimidazol-2-yl)-thiazol-5-yl]-piperazin-1-yl}-2-(6-chloro-pyrrolo[2,3-b]pyridin-1-yl)-ethanone This compound was prepared following the method described in Example 52, step 52.2, intermediate 65.2 replacing intermediate 52.1. LC-MS (A): $t_R$=0.72 min; [M+H]$^+$: 478.2.

EXAMPLE 66

1-{4-[4-(1H-Benzoimidazol-2-yl)-thiazol-5-yl]-piperazin-1-yl}-2-(2-methyl-pyrrolo[2,3-b]pyridin-1-yl)-ethanone

66.1. (2-Methyl-pyrrolo[2,3-b]pyridin-1-yl)-acetic acid

This compound was prepared in two steps following the method described in Example 14, step 14.1 and step 14.2, 2-methyl-7-azaindole replacing 4-azabenzimidazole in step 14.1. LC-MS (B): $t_R$=0.44 min; [M+H]$^+$: 191.11.

66.2. 1-{4-[4-(1H-Benzoimidazol-2-yl)-thiazol-5-yl]-piperazin-1-yl}-2-(2-methyl-pyrrolo[2,3-b]pyridin-1-yl)-ethanone This compound was prepared following the method described in Example 52, step 52.2, intermediate 66.1 replacing intermediate 52.1. LC-MS (A): $t_R$=0.58 min; [M+H]$^+$: 458.3.

EXAMPLE 67

1-{4-[4-(1H-Benzoimidazol-2-yl)-thiazol-5-yl]-piperazin-1-yl}-2-(3-methyl-pyrrolo[2,3-b]pyridin-1-yl)-ethanone

67.1. 3-Methyl-1H-pyrrolo[2,3-b]pyridine

A mixture of 2,3-dichloropyridine (500 mg), allylamine (0.254 mL), NaOtBu (1.19 g), Pd$_2$dba$_3$ (37.9 mg), dppf (91.8 mg) in toluene (15 mL) was prepared under argon and divided into three vials. The vials were sealed and evacuated and backfilled with argon three times. The resulting green-brown suspensions were heated up to 140° C. for 19.3 h. Pd$_2$dba$_3$ (0.0125 eq) and dppf (0.05 eq) were added and the reaction mixture was further stirred at 140° C. for 25 h. After cooling down, the combined reaction mixtures were diluted with EA and washed with water and brine. The aq. layers were extracted with EA. The combined org. layers were dried over MgSO$_4$, filtrated off and evaporated to dryness. CC of the crude (Biotage, SNAP 25 g cartridge, solvent A: Hept; solvent B: EA; gradient in % B: 50 for 6CV, 50 to 70 over 3CV, 70 for 5CV, 70 to 100 over 3CV, 100 for 3CV) afforded 67 mg of brown solid. LC-MS (B): $t_R$=0.44 min; [M+H]$^+$: 133.22

67.2. (3-Methyl-pyrrolo[2,3-b]pyridin-1-yl)-acetic acid

This compound was prepared in two steps following the method described in Example 14, step 14.1 and step 14.2, intermediate 67.1 replacing 4-azabenzimidazole in step 14.1. LC-MS (B): $t_R$=0.47 min; [M+H]$^+$: 191.41.

67.3. 1-{4-[4-(1H-Benzoimidazol-2-yl)-thiazol-5-yl]-piperazin-1-yl}-2-(3-methyl-pyrrolo[2,3-b]pyridin-1-yl)-ethanone This compound was prepared following the method described in Example 52, step 52.2, intermediate 67.2 replacing intermediate 52.1. LC-MS (A): $t_R$=0.59 min; [M+H]$^+$: 458.2.

EXAMPLE 68

1-(2-{4-[4-(1H-Benzoimidazol-2-yl)-thiazol-5-yl]-piperazin-1-yl}-2-oxo-ethyl)-1,3-dihydro-indol-2-one

68.1. (2-Oxo-2,3-dihydro-indol-1-yl)-acetic acid benzyl ester

To a brown solution of oxindole (500 mg) in anhydrous THF (15 mL) was added NaH (204 mg, 60% in mineral oil) at 0° C. under argon. The resulting foaming brown suspension was stirred at 0° C. for 15 min and benzyl bromoacetate (0.602 mL) was added. The reaction mixture was stirred at RT for 4 h. Water and EA were added. The phases were separated and the aq. phase was extracted three times with EA. The org.

layers were washed with water and brine, dried over MgSO$_4$, filtrated off and evaporated in vacuo. CC of the crude (Biotage, SNAP 25 g cartridge, solvent A: Hept; solvent B: EA; gradient in % B: 10 for 6CV, 10 to 30 over 4CV, 30 for 6CV) afforded 648 mg of red wax. LC-MS (B): $t_R$=0.85 min; [M+H]$^+$: 282.38

68.2. (2-Oxo-2,3-dihydro-indol-1-yl)-acetic acid

This compound was prepared following the method described in Example 14, step 14.2, intermediate 68.1 replacing intermediate 14.1. LC-MS (B): $t_R$=0.54 min; [M+H]$^+$: 191.09.

68.3. 1-(2-{4-[4-(1H-Benzoimidazol-2-yl)-thiazol-5-yl]-piperazin-1-yl}-2-oxo-ethyl)-1,3-dihydro-indol-2-one This compound was prepared following the method described in Example 52, step 52.2, intermediate 68.2 replacing intermediate 52.1. LC-MS (A): $t_R$=0.6 min; [M+H]$^+$: 459.2.

EXAMPLE 69

1-{4-[4-(1H-Benzoimidazol-2-yl)-thiazol-5-yl]-piperazin-1-yl}-2-(6-methoxy-pyrrolo[2,3-b]pyridin-1-yl)-ethanone

69.1. (6-Methoxy-pyrrolo[2,3-b]pyridin-1-yl)-acetic acid, hydrochloride salt This compound was prepared in two steps following the method described in Example 65, step 65.1 and step 65.2, 6-methoxy-7-azaindole replacing 6-chloro-1H-pyrrolo[2,3-b]pyridine in step 65.1. LC-MS (B): $t_R$=0.68 min; [M+H]$^+$: 207.38.

69.2. 1-{4-[4-(1H-Benzoimidazol-2-yl)-thiazol-5-yl]-piperazin-1-yl}-2-(6-methoxy-pyrrolo[2,3-b]pyridin-1-yl)-ethanone This compound was prepared following the method described in Example 52, step 52.2, intermediate 69.1 replacing intermediate 52.1. LC-MS (A): $t_R$=0.7 min; [M+H]$^+$: 474.2.

EXAMPLE 70

1-{4-[4-(1H-Benzoimidazol-2-yl)-thiazol-5-yl]-piperazin-1-yl}-2-(6-methyl-pyrrolo[2,3-b]pyridin-1-yl)-ethanone

70.1. (6-Methyl-pyrrolo[2,3-b]pyridin-1-yl)-acetic acid tert-butyl ester

A vial was charged with intermediate 65.1 (250 mg), Pd(dppf)Cl$_2$.CH$_2$Cl$_2$ (38.3 mg) and dioxane (5 mL), sealed and evacuated and backfilled with argon. Dimethylzinc (2M in toluene, 1.03 mL) was subsequently added. The resulting red-brown suspension was stirred at 100° C. After 1.6 h, the reaction mixture was cooled down, quenched with water (0.8 mL) and evaporated to dryness. CC of the resulting crude (Biotage, SNAP 10 g cartridge, solvent A: Hept; solvent B: EA; gradient in % B: 5 for 5CV, 5 to 10 over 2CV, 10 for 4CV) afforded 150 mg of yellow oil. LC-MS (B): $t_R$=0.72 min; [M+H]$^+$: 247.28

70.2. (6-Methyl-pyrrolo[2,3-b]pyridin-1-yl)-acetic acid, hydrochloride salt

This compound was prepared following the method described in Example 16, step 16.4, intermediate 70.1 replacing intermediate 16.3. LC-MS (B): $t_R$=0.40 min; [M+H]$^+$: 191.39.

70.3. 1-{4-[4-(1H-Benzoimidazol-2-yl)-thiazol-5-yl]-piperazin-1-yl}-2-(6-methyl-pyrrolo[2,3-b]pyridin-1-yl)-ethanone This compound was prepared following the method described in Example 52, step 52.2, intermediate 70.2 replacing intermediate 52.1. LC-MS (A): $t_R$=0.53 min; [M+H]$^+$: 458.3.

EXAMPLE 71

3-(2-{4-[4-(1H-Benzoimidazol-2-yl)-thiazol-5-yl]-piperazin-1-yl}-2-oxo-ethyl)-1,3-dihydro-imidazo[4,5-b]pyridin-2-one

71.1. (3-Nitro-pyridin-2-ylamino)-acetic acid tert-butyl ester

To a suspension of H-Gly-OtBu.HCl (1.57 g) in MeCN (35 mL) was added 2-chloro-3-nitropyridine (1.5 g) and DIPEA (4.01 mL). The resulting yellow solution was heated up to 80° C. for 14 h. The reaction mixture was evaporated to dryness. The residue was taken up in DCM, washed with water and brine and the aq. phases were extracted with DCM. The combined org. layers were dried (MgSO$_4$), filtrated off and evaporated in vacuo to afford 2.44 g of yellow solid. LC-MS (C): $t_R$=0.81 min; [M+H]$^+$: 254.27

71.2. (3-Amino-pyridin-2-ylamino)-acetic acid tert-butyl ester

To a solution of intermediate 71.1 (1.07 g) in EtOH (15 mL) and DIPEA (0.72 mL) was added Pd/C (10%, 224 mg) under argon. The flask was evacuated and backfilled with argon three times, then evacuated and backfilled with hydrogen twice. The reaction mixture was stirred at RT under hydrogen for 5 days, filtrated over celite and the celite was washed with EtOH. The filtrate was evaporated and dried in vacuo to afford 827 mg of brown wax. LC-MS (C): $t_R$=0.38 min; [M+H]$^+$: 224.35

71.3. (2-Oxo-1,2-dihydro-imidazo[4,5-b]pyridin-3-yl)-acetic acid tert-butyl ester A solution of intermediate 71.2 (976 mg) and CDI (767 mg) in THF (20 mL) was stirred at RT for 30 min. DMAP (27.2 mg) was added and the reaction mixture was stirred at RT for 19 h. CDI (0.3 eq) and DMAP (0.5 eq) were added and the stirring was continued for 115 h. The reaction mixture was diluted with EA and washed with water and brine. The org. layers were dried (MgSO$_4$), filtrated off and evaporated in vacuo. CC (First CC: Hept/EA/NH$_3$ 7/3/0.01; second CC: DCM/MeOH/NH$_3$ 8/2/0.01) afforded 833 mg of grey powder. LC-MS (C): $t_R$=0.56 min; [M+H]$^+$: 250.04

71.4. (2-Oxo-1,2-dihydro-imidazo[4,5-b]pyridin-3-yl)-acetic acid

This compound was prepared following the method described in Example 16, step 16.4, intermediate 71.3 replacing intermediate 16.3. The compound was however purified by CC (DCM/MeOH/AcOH 9/1/0.01). LC-MS (C): $t_R$=0.27 min; [M+H]$^+$: 194.40.

71.5. 3-(2-{4-[4-(1H-Benzoimidazol-2-yl)-thiazol-5-yl]-piperazin-1-yl}-2-oxo-ethyl)-1,3-dihydro-imidazo[4,5-b]pyridin-2-one This compound was prepared following the method described in Example 52, step 52.2, intermediate 71.4 replacing intermediate 52.1. LC-MS (A): $t_R$=0.49 min; [M+H]$^+$: 461.2.

EXAMPLE 72

1-{(2S,6R)-4-[4-(5-Chloro-1H-benzoimidazol-2-yl)-thiazol-5-yl]-2,6-dimethyl-piperazin-1-yl}-2-imidazo[4,5-b]pyridin-3-yl-ethanone

72.1. 4-(5-chloro-1H-benzo[d]imidazol-2-yl)-5-((3R,5S)-3,5-dimethylpiperazin-1-yl)thiazole, double hydrochloride salt This compound was prepared in four steps following the method described in Example 1, from step 1.1 to 1.4, (2R,6S)-tert-butyl 2,6-dimethylpiperazine-1-carboxylate replacing 1-Boc-piperazine in step 1.1, and 4-chloro-1,2-phenylenediamine replacing o-phenylenediamine in step 1.3. LC-MS (C): $t_R$=0.42 min; [M+H]$^+$: 348.31.

72.2. 1-{(2S,6R)-4-[4-(5-Chloro-1H-benzoimidazol-2-yl)-thiazol-5-yl]-2,6-dimethyl-piperazin-1-yl}-2-imidazo[4,5-b]pyridin-3-yl-ethanone This compound was prepared using a method analogous to that of Example 1 step 1.5, intermediate 72.1 replacing intermediate 1.4 and intermediate 14.2 replacing benzoimidazol-1-yl-acetic acid. LC-MS (A): $t_R$=0.66 min; [M+H]$^+$: 507.2.

EXAMPLE 73

1-{(R)-4-[4-(1H-Benzoimidazol-2-yl)-2-cyclopropyl-thiazol-5-yl]-2-methyl-piperazin-1-yl}-2-imidazo[4,5-b]pyridin-3-yl-ethanone

73.1. (R)-methyl 5-(4-(tert-butoxycarbonyl)-3-methylpiperazin-1-yl)-2-cyclopropylthiazole-4-carboxylate A flask was charged with cyclopropylboronic acid (133 mg), K$_3$PO$_4$ (930 mg), tricyclohexylphosphine (33.4 mg), a solution of intermediate 50.1 (500 mg) in toluene (15 mL), water (0.75 mL) and Pd(OAc)$_2$ (13.4 mg) at RT under argon. The resulting yellow suspension was stirred at 100° C. under argon. Cyclopropylboronic acid (1.3 eq), tricyclohexylphosphine (0.1 eq), water (0.3 mL) and Pd(OAc)$_2$ (0.05 eq) were further added. The reaction mixture was evacuated and back-filled with nitrogen and stirred at 100° C. overnight. After cooling down, EA was added and the mixture was washed with water and brine. The aq. layers were extracted with EA. The combined org. layers were dried (MgSO$_4$), filtrated off and evaporated to dryness. CC (25 g silica gel, Hept/EA 7/3) afforded 283 mg of yellow oil. LC-MS (B): $t_R$=0.92 min; [M+H]$^+$: 381.98

73.2. (R)-4-(4-Carboxy-2-cyclopropyl-thiazol-5-yl)-2-methyl-piperazine-1-carboxylic acid tert-butyl ester This compound was prepared following the method described in Example 16, step 16.2, intermediate 73.1 replacing intermediate 16.1, and quenching with citric acid instead of HCl. LC-MS (C): $t_R$=0.78 min; [M+H]$^+$: 367.85

73.3. (R)-tert-butyl 4-(4-(1H-benzo[d]imidazol-2-yl)-2-cyclopropylthiazol-5-yl)-2-methylpiperazine-1-carboxylate This compound was prepared following the method described in Example 16, step 16.3, intermediate 73.2 replacing intermediate 16.2. LC-MS (B): $t_R$=0.82 min; [M+H]$^+$: 440.02

73.4. (R)-4-(1H-benzo[d]imidazol-2-yl)-2-cyclopropyl-5-(3-methylpiperazin-1-yl)thiazole hydrochloride This compound was prepared following the method described in Example 16, step 16.4, intermediate 73.3 replacing intermediate 16.3. LC-MS (B): $t_R$=0.51 min; [M+H]$^+$: 340.03.

73.5. 1-{(R)-4-[4-(1H-Benzoimidazol-2-yl)-2-cyclopropyl-thiazol-5-yl]-2-methyl-piperazin-1-yl}-2-imidazo[4,5-b]pyridin-3-yl-ethanone This compound was prepared following the method described in Example 1, step 1.5, intermediate 73.4 replacing intermediate 1.4 and intermediate 14.2 replacing benzoimidazol-1-yl-acetic acid. LC-MS (A): $t_R$=0.58 min; [M+H]$^+$: 499.3.

EXAMPLE 74

1-Methyl-3-(2-oxo-2-{4-[4-(6-trifluoromethoxy-1H-benzoimidazol-2-yl)-thiazol-5-yl]-piperazin-1-yl}-ethyl)-1,3-dihydro-benzoimidazol-2-one This compound was prepared following the method described in Example 29, step 29.2, 4-(trifluoromethoxy)benzene-1,2-diamine replacing 3-chloro-benzene-1,2-diamine. LC-MS (A): $t_R$=0.78 min; [M+H]$^+$: 558.2.

EXAMPLE 75

2-(5-{4-[2-(3-Methyl-2-oxo-2,3-dihydro-benzoimidazol-1-yl)-acetyl]-piperazin-1-yl}-thiazol-4-yl)-1H-benzoimidazole-5-carbonitrile This compound was prepared following the method described in Example 29, step 29.2, 4-cyano-benzene-1,2-diamine replacing 3-chloro-benzene-1,2-diamine. LC-MS (A): $t_R$=0.7 min; [M+H]$^+$: 499.2.

EXAMPLE 76

1-(2-{4-[4-(6-Hydroxymethyl-1H-benzoimidazol-2-yl)-thiazol-5-yl]-piperazin-1-yl}-2-oxo-ethyl)-3-methyl-1,3-dihydro-benzoimidazol-2-one This compound was prepared following the method described in Example 29, step 29.2, 3,4-diaminobenzyl alcohol replacing 3-chloro-benzene-1,2-diamine. LC-MS (A): $t_R$=0.56 min; [M+H]$^+$: 504.3.

EXAMPLE 77

1-(2-{4-[4-(1H-Benzoimidazol-2-yl)-thiazol-5-yl]-piperazin-1-yl}-2-oxo-ethyl)-3,4-dihydro-1H-quinolin-2-one

77.1. (2-Oxo-3,4-dihydro-2H-quinolin-1-yl)-acetic acid ethyl ester

To a solution of 3,4-dihydro-2(1H)-quinolinone (200 mg) and NaH (58.6 mg, 60% in mineral oil) in DMF (4 mL) was added ethyl chloroacetate (0.287 mL) under argon. The reaction mixture was stirred at RT overnight, was diluted with DCM and washed twice with sat. NH$_4$Cl. The org. layers were dried (Na$_2$SO$_4$), filtrated off and evaporated in vacuo. CC (Biotage, SNAP 25 g cartridge, solvent A: Hept; solvent B: EA; gradient in % B: 8 for 4CV, 8 to 66 over 10CV, 66 for 2CV) afforded 272 mg of yellow oil. LC-MS (B): $t_R$=0.75 min; [M+H]$^+$: 234.30

77.2. (2-Oxo-3,4-dihydro-2H-quinolin-1-yl)-acetic acid

To a solution of intermediate 77.1 (273 mg) in THF (2.7 ml) was added NaOH 1M (2.7 ml). The reaction mixture was stirred at RT overnight. 2M HCl was added leading to pH 1 and the mixture was extracted with EA. The org. layers were dried (Na$_2$SO$_4$) and evaporated off to give 227 mg of white powder. LC-MS (B): $t_R$=0.58 min; [M+H]$^+$: 206.40.

77.3. 1-(2-{4-[4-(1H-Benzoimidazol-2-yl)-thiazol-5-yl]-piperazin-1-yl}-2-oxo-ethyl)-3,4-dihydro-1H-quinolin-2-one This compound was prepared following the method described in Example 1 step 1.5, intermediate 77.2 replacing benzoimidazol-1-yl-acetic acid. LC-MS (A): $t_R$=0.63 min; [M+H]$^+$: 473.3.

EXAMPLE 78

4-(2-{4-[4-(1H-Benzoimidazol-2-yl)-thiazol-5-yl]-piperazin-1-yl}-2-oxo-ethyl)-4H-benzo[1,4]oxazin-3-one This compound was prepared in three steps following the method described in Example 77, 2H-1,4-benzoxazin-3(4H)-one replacing 3,4-dihydro-2(1H)-quinolinone. LC-MS (A): $t_R$=0.62 min; [M+H]$^+$: 475.2.

EXAMPLE 79 rac-1-{(1S*,5R*)-3-[4-(1H-Benzoimidazol-2-yl)-thiazol-5-yl]-3,8-diaza-bicyclo[3.2.1]oct-8-yl}-2-imidazo[4,5-b]pyridin-3-yl-ethanone

79.1. rac-(1S*,5R*)-8-(2-Imidazo[4,5-b]pyridin-3-yl-acetyl)-3,8-diaza-bicyclo[3.2.1]octane-3-carboxylic acid tert-butyl ester This compound was prepared following the method described in Example 1 step 1.5, tert-butyl 3,8-diazabicyclo[3.2.1]octane-3-carboxylate replacing intermediate 1.4 and intermediate 14.2 replacing benzoimidazol-1-yl-acetic acid. LC-MS (B): $t_R$=0.66 min; [M+H]$^+$: 372.36

79.2. rac-1-((1R,5S)-3,8-diazabicyclo[3.2.1]octan-8-yl)-2-(3H-imidazo[4,5-b]pyridin-3-yl)ethanone, dihydrochloride salt This compound was prepared following the method described in Example 16 step 16.4, intermediate 79.1 replacing intermediate 16.3. LC-MS (B): $t_R$=0.32 min; [M+H]$^+$: 272.36

79.3. rac-5-[(1S*,5R*)-8-(2-Imidazo[4,5-b]pyridin-3-yl-acetyl)-3,8-diaza-bicyclo[3.2.1]oct-3-yl]-thiazole-4-carboxylic acid methyl ester This compound was prepared following the method described in Example 1 step 1.1, intermediate 79.2 replacing 1-Boc-piperazine and using 3.5 eq of DBU. LC-MS (B): $t_R$=0.59 min; [M+H]$^+$: 413.00

79.4. rac-5-[(1S*,5R*)-8-(2-Imidazo[4,5-b]pyridin-3-yl-acetyl)-3,8-diaza-bicyclo[3.2.1]oct-3-yl]-thiazole-4-carboxylic acid This compound was prepared following the method described in Example 16 step 16.2, intermediate 79.3 replacing intermediate 16.1 and using MeOH instead of EtOH. LC-MS (B): $t_R$=0.52 min; [M+H]$^+$: 399.32.

79.5. rac-1-{(1S*,5R*)-3-[4-(1H-Benzoimidazol-2-yl)-thiazol-5-yl]-3,8-diaza-bicyclo[3.2.1]oct-8-yl}-2-imidazo[4,5-b]pyridin-3-yl-ethanone This compound was prepared following the method described in Example 16 step 16.3, intermediate 79.4 replacing intermediate 16.2. LC-MS (A): $t_R$=0.49 min; [M+H]$^+$: 471.2.

EXAMPLE 80

1-{(R)-4-[4-(1H-Benzoimidazol-2-yl)-2-bromo-thiazol-5-yl]-2-methyl-piperazin-1-yl}-2-imidazo[4,5-b]pyridin-3-yl-ethanone

80.1. (R)-2-bromo-5-(4-(tert-butoxycarbonyl)-3-methylpiperazin-1-yl)thiazole-4-carboxylic acid This compound was prepared following the method described in Example 73 step 73.3, intermediate 50.1 replacing intermediate 73.2. LC-MS (B): $t_R$=0.82 min; [M+H]$^+$: 406.24

80.2. (R)-tert-butyl 4-(4-(1H-benzo[d]imidazol-2-yl)-2-bromothiazol-5-yl)-2-methylpiperazine-1-carboxylate This compound was prepared following the method described in Example 16 step 16.3, intermediate 80.1 replacing intermediate 16.2. However, due to partial cleavage of the BOC group, the crude obtained after evaporation of AcOH was treated with BOC anhydride in DCM in presence of DIPEA. LC-MS (B): $t_R$=0.80 min; [M+H]$^+$: 478.42.

80.3. 2-[2-Bromo-5-((R)-3-methyl-piperazin-1-yl)-thiazol-4-yl]-1H-benzoimidazole A solution of intermediate 80.2 (1.6 g) in DCM (8 mL) and HCl 4M in dioxane (8 mL) was stirred at RT for 1 h. The reaction mixture was diluted with EA and washed with aq. sat. NaHCO$_3$. The aq. layer was extracted with EA. The combined org. layers were dried over MgSO$_4$, filtrated off and evaporated in vacuo to afford 1.07 g of pale yellow foam. LC-MS (B): $t_R$=0.48 min; [M+H]$^+$: 378.19.

80.4. 1-{(R)-4-[4-(1H-Benzoimidazol-2-yl)-2-bromo-thiazol-5-yl]-2-methyl-piperazin-1-yl}-2-imidazo[4,5-b]pyridin-3-yl-ethanone This compound was prepared following the method described in Example 1 step 1.5, intermediate 80.3 replacing intermediate 1.4 and intermediate 14.2 replacing benzoimidazol-1-yl-acetic acid. LC-MS (A): $t_R$=0.56 min; [M+H]$^+$: 537.

EXAMPLE 81

1-{(R)-4-[4-(1H-Benzoimidazol-2-yl)-2-o-tolyl-thiazol-5-yl]-2-methyl-piperazin-1-yl}-2-imidazo[4,5-b]pyridin-3-yl-ethanone This compound was prepared following the method described in Example 73 step 73.1, intermediate 80.4 replacing intermediate 50.1 and 2-tolylboronic acid replacing cyclopropylboronic acid. LC-MS (A): $t_R$=0.71 min; [M+H]$^+$: 549.2.

EXAMPLE 82

1-{(R)-4-[4-(1H-Benzoimidazol-2-yl)-2-(2-methoxy-phenyl)-thiazol-5-yl]-2-methyl-piperazin-1-yl}-2-imidazo[4,5-b]pyridin-3-yl-ethanone This compound was prepared following the method described in Example 73 step 73.1, intermediate 80.4 replacing intermediate 50.1 and 2-methoxyphenylboronic acid replacing 2-tolylboronic acid. LC-MS (A): $t_R$=0.7 min; [M+H]$^+$: 565.2.

EXAMPLE 83

1-{(R)-4-[4-(6-Chloro-1H-benzoimidazol-2-yl)-thiazol-5-yl]-2-methyl-piperazin-1-yl}-2-imidazo[4,5-b]pyridin-3-yl-ethanone

83.1. (R)-4-(5-chloro-1H-benzo[d]imidazol-2-yl)-5-(3-methylpiperazin-1-yl)thiazole, double hydrochloride salt This compound was prepared in four steps following the method described in Example 16, from step 16.1 to 16.4, 4-chloro-1,2-phenylenediamine replacing 0-phenylenediamine in step 16.3. LC-MS (B): $t_R$=0.50 min; [M+H]$^+$: 333.96.

83.2. 1-{(R)-4-[4-(6-Chloro-1H-benzoimidazol-2-yl)-thiazol-5-yl]-2-methyl-piperazin-1-yl}-2-imidazo[4,5-b]pyridin-3-yl-ethanone This compound was prepared following the method described in Example 1 step 1.5, intermediate 83.1 replacing intermediate 1.4 and intermediate 14.2 replacing replacing benzoimidazol-1-yl-acetic acid. LC-MS (A): $t_R$=0.59 min; [M+H]$^+$: 493.2.

EXAMPLE 84

3-(2-{(R)-4-[4-(5-Chloro-1H-benzoimidazol-2-yl)-thiazol-5-yl]-2-methyl-piperazin-1-yl}-2-oxo-ethyl)-3H-benzooxazol-2-one This compound was prepared following the method described in Example 83 step 83.2, (2-oxo-benzooxazol-3-yl)-acetic acid replacing intermediate 14.2. LC-MS (A): $t_R$=0.77 min; [M+H]$^+$: 509.2.

EXAMPLE 85

2-Imidazo[4,5-b]pyridin-3-yl-1-{(R)-2-methyl-4-[4-(5-methyl-1H-benzoimidazol-2-yl)-thiazol-5-yl]-piperazin-1-yl}-ethanone

85.1. 5-[(1R)-4-(2-Imidazo[4,5-b]pyridin-3-yl-acetyl)-3-methyl-piperazin-1-yl]-thiazole-4-carboxylic acid methyl ester This compound was prepared following the method described in Example 21 step 21.2, intermediate 14.2 replacing 2-(1H-pyrrolo[2,3-b]pyridin-1-yl)acetic acid. LC-MS (B): $t_R$=0.57 min; [M+H]$^+$: 401.18.

85.2. 5-[(1R)-4-(2-Imidazo[4,5-b]pyridin-3-yl-acetyl)-3-methyl-piperazin-1-yl]-thiazole-4-carboxylic acid To a solution of intermediate 85.1 (3.2 g) in EtOH (110 mL) was added 1M NaOH (8 ml) and the reaction mixture was stirred for 2 h. A second equivalent of NaOH was added (1M NaOH, 8 mL) and the stirring was pursued for 2 h. Citric acid (10%) was added to pH 3 and the mixture was extracted with EA. The org. phase was dried (Na$_2$SO$_4$) and evaporated in vacuo to afford 2.08 g of off white semi-solid containing 30% of side product (decarboxylated analog). LC-MS (B): $t_R$=0.51 min; [M+H]$^+$: 387.29.

85.3. 2-Imidazo[4,5-b]pyridin-3-yl-1-{(R)-2-methyl-4-[4-(5-methyl-1H-benzoimidazol-2-yl)-thiazol-5-yl]-piperazin-1-yl}-ethanone To a solution of intermediate 85.2 (50 mg) in DMF (1 mL) was added PyBOP (74 mg) and DIPEA (0.069 mL). After 1 h stirring, a solution of 3,4-diaminotoluene (15.9 mg) in DMF (1 mL) was added. The resulting reaction mixture was stirred for 24 h. PL-HCO$_3$ (200 mg, 2.11 mmol/g) was added and the mixture was further stirred for 1 h. The resin was filtered off, washed with DCM and the resulting solution was evaporated in vacuo. The residue was dissolved in AcOH (3 mL) and heated at 80° C. for 20 h. The reaction mixture was concentrated under reduced pressure and purified by preparative LC-MS (III followed by V) to afford 3.5 mg of white solid. LC-MS (A): $t_R$=0.52 min; [M+H]$^+$: 473.3.

Example 86 to Example 100 were synthesized starting from the appropriate diamine derivative and following the procedure described in Example 85 step 85.3. LC-MS data of Example 86 to Example 100 are listed in the table below. The LC-MS conditions used were LC-MS(A).

| Example No | Name | $t_R$ | $[M + H]^+$ |
|---|---|---|---|
| 86 | 1-{(R)-4-[4-(5-tert-Butyl-1H-benzoimidazol-2-yl)-thiazol-5-yl]-2-methyl-piperazin-1-yl}-2-imidazo[4,5-b]pyridin-3-yl-ethanone | 0.67 | 515.3 |
| 87 | 1-{(R)-4-[4-(5-Chloro-6-methyl-1H-benzoimidazol-2-yl)-thiazol-5-yl]-2-methyl-piperazin-1-yl}-2-imidazo[4,5-b]pyridin-3-yl-ethanone | 0.62 | 507.2 |
| 88 | 2-Imidazo[4,5-b]pyridin-3-yl-1-{(R)-4-[4-(6-isopropyl-1H-benzoimidazol-2-yl)-thiazol-5-yl]-2-methyl-piperazin-1-yl}-ethanone | 0.63 | 501.3 |
| 89 | 1-{(R)-4-[4-(5-Chloro-6-fluoro-1H-benzoimidazol-2-yl)-thiazol-5-yl]-2-methyl-piperazin-1-yl}-2-imidazo[4,5-b]pyridin-3-yl-ethanone | 0.69 | 511.2 |
| 90 | 1-{(R)-4-[4-(4,5-Difluoro-1H-benzoimidazol-2-yl)-thiazol-5-yl]-2-methyl-piperazin-1-yl}-2-imidazo[4,5-b]pyridin-3-yl-ethanone | 0.69 | 495.2 |
| 91 | 1-{(R)-4-[4-(5,6-Difluoro-1H-benzoimidazol-2-yl)-thiazol-5-yl]-2-methyl-piperazin-1-yl}-2-imidazo[4,5-b]pyridin-3-yl-ethanone | 0.61 | 495.3 |
| 92 | 2-Imidazo[4,5-b]pyridin-3-yl-1-{(R)-2-methyl-4-[4-(5-trifluoromethyl-1H-benzoimidazol-2-yl)-thiazol-5-yl]-piperazin-1-yl}-ethanone | 0.7 | 527.3 |
| 93 | 1-{(R)-4-[4-(5-Chloro-6-trifluoromethyl-1H-benzoimidazol-2-yl)-thiazol-5-yl]-2-methyl-piperazin-1-yl}-2-imidazo[4,5-b]pyridin-3-yl-ethanone | 0.86 | 561.2 |
| 94 | 1-{(R)-4-[4-(5-Chloro-4-methyl-1H-benzoimidazol-2-yl)-thiazol-5-yl]-2-methyl-piperazin-1-yl}-2-imidazo[4,5-b]pyridin-3-yl-ethanone | 0.64 | 507.2 |
| 95 | 2-Imidazo[4,5-b]pyridin-3-yl-1-{(R)-2-methyl-4-[4-(4-trifluoromethyl-1H-benzoimidazol-2-yl)-thiazol-5-yl]-piperazin-1-yl}-ethanone | 0.75 | 527.2 |
| 96 | 1-{(R)-4-[4-(5-Fluoro-1H-benzoimidazol-2-yl)-thiazol-5-yl]-2-methyl-piperazin-1-yl}-2-imidazo[4,5-b]pyridin-3-yl-ethanone | 0.53 | 477.2 |
| 97 | 1-{(R)-4-[4-(4-Fluoro-1H-benzoimidazol-2-yl)-thiazol-5-yl]-2-methyl-piperazin-1-yl}-2-imidazo[4,5-b]pyridin-3-yl-ethanone | 0.58 | 477.2 |
| 98 | 2-Imidazo[4,5-b]pyridin-3-yl-1-{(R)-2-methyl-4-[4-(1-methyl-1H-benzoimidazol-2-yl)-thiazol-5-yl]-piperazin-1-yl}-ethanone | 0.48 | 473.2 |
| 99 | 1-{(R)-4-[4-(6-Ethyl-1H-benzoimidazol-2-yl)-thiazol-5-yl]-2-methyl-piperazin-1-yl}-2-imidazo[4,5-b]pyridin-3-yl-ethanone | 0.58 | 487.3 |
| 100 | 2-Imidazo[4,5-b]pyridin-3-yl-1-{(R)-2-methyl-4-[4-(6-phenyl-1H-benzoimidazol-2-yl)-thiazol-5-yl]-piperazin-1-yl}-ethanone | 0.69 | 535.3 |

EXAMPLE 101

1-[2-(4-{4-[5-(2-Hydroxy-ethoxy)-1H-benzoimidazol-2-yl]thiazol-5-yl}-piperazin-1-yl)-2-oxo-ethyl]-3-methyl-1,3-dihydro-benzoimidazol-2-one

101.1. 2-(3,4-Diamino-phenoxy)-ethanol

A degassed solution of ammonium formate (1.4 g) in MeOH/water (10/1) was added to 2-(4-amino-3-nitrophenoxy)ethan-1-ol (234 mg), followed by Pd/C (10%). The flask was closed and the reaction mixture was stirred at RT for 20 h. The reaction mixture was filtered off and Pd/C was further washed with MeOH/water. The filtrate was lyophilized to afford 225 mg of black solid. $^1$H-NMR (DMSO): 8.19 (s, 1H); 6.41 (d, 1H, 8.3 Hz); 6.17 (d, 1H, 2.7 Hz); 5.98 (dd, 1H, 2.8 Hz and 8.3 Hz); 4.98 (br s, NH$_2$); 3.77 (t, 2H, 5.2 Hz); 3.63 (t, 2H, 5 Hz).

101.2. 1-[2-(4-{4-[5-(2-Hydroxy-ethoxy)-1H-benzoimidazol-2-yl]-thiazol-5-yl}-piperazin-1-yl)-2-oxo-ethyl]-3-methyl-1,3-dihydro-benzoimidazol-2-one To a solution of intermediate 29.1 (100 mg) in DMF (2 mL) was added intermediate 101.1 (41.9 mg), HATU (104 mg) and DIPEA (0.132 mL). After stirring for 24 h, AcOH (2 mL) was added and the reaction mixture was heated at 80° C. for 20 h. Toluene was added and the solution was concentrated under reduced pressure. Preparative LC-MS (III followed by V) afforded 2.4 mg of white solid. LC-MS (A): $t_R$=0.57 min; [M+H]$^+$: 534.3.

EXAMPLE 102

1-[2-(4-{4-[5-(2-Methoxy-ethoxy)-1H-benzoimidazol-2-yl]-thiazol-5-yl}-piperazin-1-yl)-2-oxo-ethyl]-3-methyl-1,3-dihydro-benzoimidazol-2-one

102.1. 4-(2-Methoxy-ethoxy)-2-nitro-phenylamine 4-(2-Methoxyethoxy)aniline (500 mg) was added to acetic anhydride (2.38 g) and the mixture was cooled down to 10° C. HNO$_3$ (65% in water, 0.62 mL) was added slowly in order to keep the temperature of the reaction mixture below 15° C. After the end of the addition, the reaction mixture was allowed to warm to RT over 1 h, was quenched with ice-cold water and stirred for 10 min. The resulting suspension was filtered off and dried in high vacuo. The resulting yellow powder was dissolved in dioxane (1.4 mL), treated with 6N HCl (1.4 mL) and the reaction mixture was stirred at 70° C. for 3 h. After cooling down to RT, water was added and the pH was adjusted to 10 with 1M NaOH. The layers were separated and the aq. phase was extracted with EA. The combined org. layers were washed with brine, dried (Na$_2$SO$_4$) and evaporated in vacuo to afford 303 mg of yellow solid. LC-MS (B): $t_R$=0.99 min; [M+H]$^+$: 213.05.

102.2. 4-(2-Methoxy-ethoxy)-benzene-1,2-diamine

This compound was prepared following the method described in Example 101 step 101.1, intermediate 102.1 replacing 2-(4-amino-3-nitrophenoxy)ethan-1-ol. LC-MS (B): $t_R$=0.43 min; [M+H]$^+$: 183.16.

102.3. 1-[2-(4-{4-[5-(2-Methoxy-ethoxy)-1H-benzoimidazol-2-yl]-thiazol-5-yl}-piperazin-1-yl)-2-oxo-ethyl]-3-methyl-1,3-dihydro-benzoimidazol-2-one This compound was prepared following the method described in Example 101 step 101.2, intermediate 102.2 replacing intermediate 101.1. LC-MS (A): $t_R$=0.64 min; [M+H]$^+$: 548.3.

EXAMPLE 103

1-(2-{(R)-4-[4-(1H-Benzoimidazol-2-yl)-2-trifluoromethyl-thiazol-5-yl]-2-methyl-piperazin-1-yl}-2-oxo-ethyl)-1,3-dihydro-indol-2-one This compound was prepared following the method described in Example 1 step 1.5, intermediate 51.2 replacing intermediate 1.4 and intermediate 68.2 replacing replacing benzoimidazol-1-yl-acetic acid. LC-MS (A): $t_R$=0.8 min; [M+H]$^+$: 541.2.

EXAMPLE 104

3-(2-{(R)-4-[4-(1H-Benzoimidazol-2-yl)-2-trifluoromethyl-thiazol-5-yl]-2-methyl-piperazin-1-yl}-2-oxo-ethyl)-1,3-dihydro-imidazo[4,5-b]pyridin-2-one This compound was prepared following the method described in Example 1 step 1.5, intermediate 51.2 replacing intermediate 1.4 and intermediate 71.4 replacing replacing benzoimidazol-1-yl-acetic acid. LC-MS (A): $t_R$=0.67 min; [M+H]$^+$: 543.2.

EXAMPLE 105

1-{4-[4-(1H-Benzoimidazol-2-yl)-thiazol-5-yl]-piperazin-1-yl}-2-(3,4-dihydro-2H-quinolin-1-yl)-ethanone 105.1. (3,4-Dihydro-2H-quinolin-1-yl)-acetic acid ethyl ester To a solution of 1,2,3,4-tetrahydro-quinoline (200 mg) and NaH (63 mg, 60% in mineral oil) in DMF (4 mL) was added ethyl chloroacetate (0.31 mL) under argon. The reaction mixture was stirred at RT overnight, at 60° C. for 6 h and at 120° C. overnight. After cooling down, the reaction mixture was diluted with DCM and washed with sat. NH$_4$Cl. The org. layer was dried (Na$_2$SO$_4$), filtrated off and evaporated in vacuo. CC (Biotage, SNAP 25 g cartridge, solvent A: Hept; solvent B: EA; gradient in % B: 8 for 4CV, 8 to 66 over 10CV, 66 for 2CV) afforded 205 mg of yellow oil. LC-MS (B): $t_R$=0.89 min; [M+H]$^+$: 220.11.

105.2. (3,4-Dihydro-2H-quinolin-1-yl)-acetic acid

This compound was prepared following the method described in Example 77 step 77.2, intermediate 105.1 replacing intermediate 77.1. However, the work-up was performed as follows: 2M HCL was added to the reaction mixture until pH 1 and the mixture was extracted with EA. The aq. phase was brought to pH 4 with 32% NaOH and was extracted with EA. Both org. phases were dried (Na$_2$SO$_4$), evaporated off and analyzed. The orange oils were combined (81 mg). LC-MS (B): $t_R$=0.71 min; [M+H]$^+$: 192.43.

105.3. 1-[2-(4-{4-[5-(2-Methoxy-ethoxy)-1H-benzoimidazol-2-yl]-thiazol-5-yl}-piperazin-1-yl)-2-oxo-ethyl]-3-methyl-1,3-dihydro-benzoimidazol-2-one This compound was prepared following the method described in Example 1 step 1.5, intermediate 105.2 replacing benzoimidazol-1-yl-acetic acid. The compound was however purified by preparative LC-MS (VI followed by VII). LC-MS (A): $t_R$=0.75 min; [M+H]$^+$: 459.3.

EXAMPLE 106

1-{4-[4-(1H-Benzoimidazol-2-yl)-thiazol-5-yl]-piperazin-1-yl}-2-(2,3-dihydro-benzo[1,4]oxazin-4-yl)-ethanone 106.1. (2,3-Dihydro-benzo[1,4]oxazin-4-yl)-acetic acid ethyl ester This compound was prepared following the method described in Example 105 step 105.1, 3,4-dihydro-2H-1,4-benzoxazine replacing 1,2,3,4-tetrahydro-quinoline, and heating at 120° C. overnight. LC-MS (B): $t_R$=0.81 min; [M+H]$^+$: 222.40.

106.2. (2,3-Dihydro-benzo[1,4]oxazin-4-yl)-acetic acid

This compound was prepared following the method described in Example 77 step 77.2, intermediate 106.1 replacing intermediate 77.1. LC-MS (B): $t_R$=0.63 min; [M+H]$^+$: 194.43.

106.3. 1-{4-[4-(1H-Benzoimidazol-2-yl)-thiazol-5-yl]-piperazin-1-yl}-2-(2,3-dihydro-benzo[1,4]oxazin-4-yl)-ethanone This compound was prepared following the method described in Example 1 step 1.5, intermediate 106.2 replacing benzoimidazol-1-yl-acetic acid. The compound was however purified by preparative LC-MS (VI). LC-MS (A): $t_R$=0.67 min; [M+H]$^+$: 461.2.

EXAMPLE 107

1-(2-{4-[4-(1H-Benzoimidazol-2-yl)-thiazol-5-yl]-piperazin-1-yl}-2-oxo-ethyl)-2,3-dihydro-1H-quinolin-4-one 107.1. (4-Oxo-3,4-dihydro-2H-quinolin-1-yl)-acetic acid ethyl ester This compound was prepared following the method described in Example 105 step 105.1, 2,3-dihydro-1H-quinolin-4-one replacing 1,2,3,4-tetrahydro-quinoline, and heating at 120° C. overnight. LC-MS (B): $t_R$=0.76 min; [M+H]$^+$: 234.24.

107.2. (4-Oxo-3,4-dihydro-2H-quinolin-1-yl)-acetic acid

This compound was prepared following the method described in Example 77 step 77.2, intermediate 107.1 replacing intermediate 77.1. LC-MS (B): $t_R$=0.58 min; [M+H]$^+$: 206.41.

107.3. 1-(2-{4-[4-(1H-Benzoimidazol-2-yl)-thiazol-5-yl]-piperazin-1-yl}-2-oxo-ethyl)-2,3-dihydro-1H-quinolin-4-one This compound was prepared following the method described in Example 1 step 1.5, intermediate 107.2 replacing benzoimidazol-1-yl-acetic acid. The compound was however purified by preparative LC-MS (VI). LC-MS (A): $t_R$=0.61 min; [M+H]$^+$: 473.3.

EXAMPLE 108

1-{4-[4-(1H-Benzoimidazol-2-yl)-thiazol-5-yl]-piperazin-1-yl}-2-(7-fluoro-indol-1-yl)-ethanone

108.1. (7-Fluoro-indol-1-yl)-acetic acid ethyl ester

To a solution of 7-fluoroindole (200 mg) and $K_2CO_3$ (589 mg) in DMF (4 mL) was added ethyl chloroacetate (0.31 mL) under argon. The reaction mixture was stirred at 120° C. overnight. After cooling down, the reaction mixture was diluted with DCM and washed with sat. $NH_4Cl$. The org. layer was dried ($Na_2SO_4$), filtrated off and evaporated in vacuo. CC (Biotage, SNAP 25 g cartridge, solvent A: Hept; solvent B: EA; gradient in % B: 8 for 4CV, 8 to 66 over 10CV, 66 for 2CV) afforded 297 mg of yellow oil. LC-MS (B): $t_R$=0.87 min; [M+H]$^+$: 222.37.

108.2. (7-Fluoro-indol-1-yl)-acetic acid

This compound was prepared following the method described in Example 77 step 77.2, intermediate 108.1 replacing intermediate 77.1. $^1$H-NMR (CDCl$_3$): 7.39 (d, 1H); 7.03 (m, 2H); 6.90 (dd, 1H); 6.58 (dd, 1H); 5.10 (s, 2H).

108.3. 1-{4-[4-(1H-Benzoimidazol-2-yl)-thiazol-5-yl]-piperazin-1-yl}-2-(7-fluoro-indol-1-yl)-ethanone This compound was prepared following the method described in Example 1 step 1.5, intermediate 108.2 replacing benzoimidazol-1-yl-acetic acid. The compound was however purified by preparative LC-MS (VI). LC-MS (A): $t_R$=0.73 min; [M+H]$^+$: 461.2.

EXAMPLE 109

1-{4-[4-(1H-Benzoimidazol-2-yl)-thiazol-5-yl]-piperazin-1-yl}-2-indazol-1-yl-ethanone

109.1. Indazol-1-yl-acetic acid ethyl ester

This compound was prepared following the method described in Example 108 step 108.1, indazole replacing 7-fluoroindole. LC-MS (B): $t_R$=075 min; [M+H]$^+$: 205.45. $^1$H-NMR (CDCl3): 8.08 (s, 1H); 7.77 (dd, 1H); 7.43 (m, 1H); 7.36 (dd, 1H); 7.20 (m, 1H); 5.18 (s, 2H); 4.24 (q, 2H); 1.27 (t, 3H).

109.2. Indazol-1-yl-acetic acid

This compound was prepared following the method described in Example 77 step 77.2, intermediate 109.1 replacing intermediate 77.1. LC-MS (B): $t_R$=0.57 min; [M+H]$^+$: 177.43.

109.3. 1-{4-[4-(1H-Benzoimidazol-2-yl)-thiazol-5-yl]-piperazin-1-yl}-2-indazol-1-yl-ethanone This compound was prepared following the method described in Example 1 step 1.5, intermediate 109.2 replacing benzoimidazol-1-yl-acetic acid. The compound was however purified by preparative LC-MS (VI). LC-MS (A): $t_R$=0.63 min; [M+H]$^+$: 444.2.

EXAMPLE 110

1-{4-[4-(1H-Benzoimidazol-2-yl)-thiazol-5-yl]-piperazin-1-yl}-2-pyridin-3-yl-ethanone This compound was prepared following the method described in Example 8, 3-pyridyl acetic acid replacing 6-chloroimidazo[1,2-b]pyridazine-2-yl)acetic acid. LC-MS (A): $t_R$=0.37 min; [M+H]$^+$: 405.2.

EXAMPLE 111

1-{4-[4-(1H-Benzoimidazol-2-yl)-thiazol-5-yl]-piperazin-1-yl}-2-(2-fluoro-4-methoxy-phenyl)-ethanone This compound was prepared following the method described in Example 8, 2-(2-fluoro-4-methoxyphenyl)acetic acid replacing 6-chloroimidazo[1,2-b]pyridazine-2-yl)acetic acid. LC-MS (A): $t_R$=0.67 min; [M+H]$^+$: 452.2.

EXAMPLE 112

1-(2-{4-[4-(4-Hydroxy-1H-benzoimidazol-2-yl)-thiazol-5-yl]-piperazin-1-yl}-2-oxo-ethyl)-3-methyl-1,3-dihydro-benzoimidazol-2-one This compound was prepared following the method described in Example 101 step 101.2, 2,3-diaminophenol replacing intermediate 101.1. LC-MS (A): $t_R$=0.60 min; [M+H]$^+$: 490.2.

EXAMPLE 113

1-{(R)-4-[4-(1H-Benzoimidazol-2-yl)-2-oxetan-3-yl-thiazol-5-yl]-2-methyl-piperazin-1-yl}-2-imidazo[4,5-b]pyridin-3-yl-ethanone

113.1. (R)-4-(4-Methoxycarbonyl-2-oxetan-3-yl-thiazol-5-yl)-2-methyl-piperazine-1-carboxylic acid tert-butyl ester To a yellow solution of intermediate 16.1 (751 mg) in DMSO (20 mL) was added 3-iodooxetane (0.398 mL), $H_2SO_4$ (0.242 mL) followed by dropwise addition of $H_2O_2$ (30% in water, 0.202 mL) at RT. After 2 min, Fe(II)SO$_4$,7H$_2$O (185 mg) was added and the resulting dark yellow suspension was stirred at RT for 18 h. 3 eq of $H_2O_2$ and 0.3 eq of $Fe(II)SO_4, 7H_2O$ were added. The reaction mixture was further stirred at RT for 21 h and was poured onto EA/0.2M NaOH. Phases were separated and the aq. layer was extracted with EA twice. The org. layers were washed with brine, combined, dried ($MgSO_4$), filtrated off and evaporated to dryness. CC (Biotage, first CC: SNAP 50 g cartridge, solvent A: Hept; solvent B: EA; gradient in % B: 50 for 5CV, 50 to 70 over 3CV, 70 for 5CV. Second CC: SNAP 10 g cartridge, solvent A: Hept; solvent B: EA; gradient in % B: 50 for 4CV, 50 to 70 over 2CV, 70 for 5CV) afforded 48 mg of yellow resin. LC-MS (B): $t_R$=0.84 min; $[M+H]^+$: 398.04.

113.2. (R)-4-(4-Carboxy-2-oxetan-3-yl-thiazol-5-yl)-2-methyl-piperazine-1-carboxylic acid tert-butyl ester This compound was prepared using a method analogous to that of Example 73 step 73.3, intermediate 113.1 replacing intermediate 73.2. LC-MS (B): $t_R$=0.75 min; $[M+H]^+$: 384.32.

113.3. (R)-4-[4-(1H-Benzoimidazol-2-yl)-2-oxetan-3-yl-thiazol-5-yl]-2-methyl-piperazine-1-carboxylic acid tert-butyl ester This compound was prepared using a method analogous to that of Example 16 step 16.3, intermediate 113.2 replacing intermediate 16.2. LC-MS (B): $t_R$=0.75 min; $[M+H]^+$: 456.53.

113.4. 2-[5-((R)-3-Methyl-piperazin-1-yl)-2-oxetan-3-yl-thiazol-4-yl]-1H-benzoimidazole A solution of intermediate 113.3 (62 mg) in TFA/DCM (1/5, 1.2 mL) was stirred at RT for 1.5 h. The reaction mixture was quenched with 1M NaOH (2.5 mL) to pH 12, diluted with DCM and washed with water and brine. The aq. layers were extracted with DCM. The combined org. layers were dried over $MgSO_4$, filtrated off and evaporated in vacuo to afford 46 mg of yellow resin which was used without further purification. LC-MS (B): $t_R$=0.46 min; $[M+H]^+$: 355.98.

113.5. 1-{(R)-4-[4-(1H-Benzoimidazol-2-yl)-2-oxetan-3-yl-thiazol-5-yl]-2-methyl-piperazin-1-yl}-2-imidazo[4,5-b]pyridin-3-yl-ethanone This compound was prepared using a method analogous to that of Example 1 step 1.5, intermediate 113.4 replacing intermediate 1.4 and intermediate 14.2 replacing benzoimidazol-1-yl-acetic acid. LC-MS (A): $t_R$=0.52 min; $[M+H]^+$: 515.3.

REFERENCE EXAMPLE 114

1-{4-[5-(1H-Benzoimidazol-2-yl)-thiazol-4-yl]-piperazin-1-yl}-2-imidazo[4,5-b]pyridin-3-yl-ethanone

114.1. 4-Bromo-thiazole-5-carbaldehyde

To a pale yellow solution of (4-bromothiazol-5-yl)methanol (870 mg) in DCM (25 mL) was added DMP (2.16 g) at RT. The resulting yellow suspension was stirred at RT under argon for 18 h. EA and aq. sat. $NaHCO_3$ were added to the reaction mixture and stirred for 5 min. Water was added and the mixture was extracted with DCM three times. The combined org. layers were dried over $MgSO_4$, filtrated off and evaporated in vacuo. CC (Biotage, SNAP 50 g cartridge, solvent A: Hept; solvent B: EA; gradient in % B: 10 for 5CV, 10 to 30 over 2CV, 30 for 3CV) afforded 708 mg of yellow solid. $^1$H-NMR ($CDCl_3$): 10.0 (s, 1H); 9.04 (s, 1H)

114.2. 4-(5-Formyl-thiazol-4-yl)-piperazine-1-carboxylic acid tert-butyl ester A solution of intermediate 114.1 (50 mg), 1-Boc-piperazine (74 mg) and DIPEA (0.067 mL) in THF (1.5 mL) was stirred at RT for 1 h, then at 50° C. for 2 days. The reaction mixture was diluted with water and extracted with DCM. The org. layers were dried ($Na_2SO_4$) and evaporated in vacuo. CC (silica gel, eluent Heptan/EA 7:3) afforded 10 mg of yellow oil. LC-MS (B): $t_R$=0.80 min; $[M+H]^+$: 298.17.

114.3. 5-(1H-benzo[d]imidazol-2-yl)-4-(piperazin-1-yl)thiazole, double hydrochloride salt A vial was charged with intermediate 114.2 (10 mg), 1,2-phenylenediamine (4 mg), DMF (0.5 mL) and sodium metabisulfite (7.5 mg) at RT. The resulting brown suspension was stirred at 80° C. for 30 min and at 90° C. for 2 h30. Water was added and the mixture was extracted with DCM. The combined org. layers were washed with brine, dried ($Na_2SO_4$), filtered off and evaporated in vacuo. The resulting residue was taken up in 4M HCl in dioxane (1 mL) and stirred for 15 min. The solvent was removed in vacuo to afford 16 mg of yellow solid. LC-MS (B): $t_R$=0.43 min; $[M+H]^+$: 286.14.

114.4. 1-{4-[5-(1H-Benzoimidazol-2-yl)-thiazol-4-yl]-piperazin-1-yl}-2-imidazo[4,5-b]pyridin-3-yl-ethanone This compound was prepared using a method analogous to that of Example 1 step 1.5, intermediate 114.3 replacing intermediate 1.4 and intermediate 14.2 replacing benzoimidazol-1-yl-acetic acid. LC-MS (A): $t_R$=0.48 min; $[M+H]^+$: 445.1.

EXAMPLE 115

1-{(R)-4-[4-(1H-Benzoimidazol-2-yl)-thiazol-5-yl]-2-methyl-piperazin-1-yl}-2-pyrazolo[3,4-b]pyridin-1-yl-ethanone

115.1. Pyrazolo[3,4-b]pyridin-1-yl-acetic acid tert-butyl ester

To a solution of 1H-pyrazolo[3,4-b]pyridine (250 mg) and NaH (60% in mineral oil, 92 mg) in DMF (5 mL) was added tert-butyl bromoacetate (0.31 mL) under argon. The reaction mixture was stirred at RT for 1 h. The reaction mixture was diluted with DCM and washed with sat. $NH_4Cl$. The org. layer was evaporated in vacuo. CC (Biotage, SNAP 25 g cartridge, solvent A: Hept; solvent B: EA; gradient in % B: 12 for 4CV, 12 to 100 over 10CV, 100 for 6CV) afforded 294 mg of yellow solid. LC-MS (B): $t_R$=0.76 min; $[M+H]^+$: 233.93. $^1$H-NMR ($CDCl_3$): 8.57 (dd, 1H, 1.5 Hz and 3.5 Hz); 8.10 (dd, 1H, 1.5 Hz and 8 Hz); 8.10 (s, 1H); 7.17 (dd, 1H, 4.5 Hz and 8 Hz); 5.24 (s, 2H); 1.47 (s, 9H).

115.2. Pyrazolo[3,4-b]pyridin-1-yl-acetic acid

This compound was prepared using a method analogous to that of Example 113 step 113.4, intermediate 115.1 replacing intermediate 113.3. LC-MS (B): $t_R$=0.45 min; $[M+H]^+$: 178.43.

115.3. 1-{(R)-4-[4-(1H-Benzoimidazol-2-yl)-thiazol-5-yl]-2-methyl-piperazin-1-yl}-2-pyrazolo[3,4-b]pyridin-1-yl-ethanone This compound was prepared using a method analogous to that of Example 1 step 1.5, intermediate 16.4 replacing intermediate 1.4 and intermediate 115.2 replacing benzoimidazol-1-yl-acetic acid. LC-MS (A): $t_R$=0.58 min; [M+H]$^+$: 459.2.

EXAMPLE 116

1-{(R)-4-[4-(1H-Benzoimidazol-2-yl)-thiazol-5-yl]-2-methyl-piperazin-1-yl}-2-pyrazolo[3,4-b]pyridin-2-yl-ethanone

116.1. Pyrazolo[3,4-b]pyridin-2-yl-acetic acid tert-butyl ester

This compound was obtained as second regioisomer in Example 115 step 115. LC-MS (B): $t_R$=0.59 min; [M+H]$^+$: 234.16. $^1$H-NMR (CDCl$_3$): 8.73 (br s, 1H); 8.07 (d, 1H, 8.3 Hz); 8.06 (s, 1H); 7.08 (dd, 1H, 4.2 Hz and 8.2 Hz); 5.17 (s, 2H); 1.51 (s, 9H).

116.2. Pyrazolo[3,4-b]pyridin-2-yl-acetic acid

This compound was prepared using a method analogous to that of Example 113 step 113.4, intermediate 116.1 replacing intermediate 113.3. LC-MS (B): $t_R$=0.22 min; [M+H]$^+$: 178.13.

116.3. 1-{(R)-4-[4-(1H-Benzoimidazol-2-yl)-thiazol-5-yl]-2-methyl-piperazin-1-yl}-2-pyrazolo[3,4-b]pyridin-2-yl-ethanone This compound was prepared using a method analogous to that of Example 1 step 1.5, intermediate 16.4 replacing intermediate 1.4 and intermediate 116.2 replacing benzoimidazol-1-yl-acetic acid. LC-MS (A): $t_R$=0.46 min; [M+H]$^+$: 459.3.

EXAMPLE 117

1-{(R)-4-[4-(1H-Benzoimidazol-2-yl)-thiazol-5-yl]-2-methyl-piperazin-1-yl}-2-naphthalen-2-yl-ethanone To 2-naphthylacetic acid (22.3 mg) were added a solution of intermediate 16.4 (37.8 mg) in DMF/DIPEA (0.54 mL, 5/1) and a solution of HOAT (16.3 mg) in DMF (0.45 mL). Si-DCC (0.93 mmol/g, 322.6 mg) was added and the reaction mixture was heated at 40° C. overnight. After cooling down, it was filtered through a PL-HCO$_3$ cartridge preconditioned with DCM/MeOH 1/1. The cartridge was further washed with DCM/MeOH 1/1 and the solvents were removed in vacuo. The crude was purified by preparative LC-MS (VIII) to afford 32 mg of white solid. LC-MS (A): $t_R$=0.80 min; [M+H]$^+$: 468.3.

Example 118 to Example 141 were synthesized starting from the appropriate acid precursor and following the procedure described in Example 117. The acid precursors were commercially available for Example 118 to 136. For Example 137 to 141, they were synthesized as follows:

PRECURSOR FOR EXAMPLE 137

Imidazo[4,5-c]pyridin-3-yl-acetic acid

This compound was prepared in two steps following the method described in Example 14, step 14.1 and step 14.2, 5-azabenzimidazole replacing 4-azabenzimidazole in step 14.1. LC-MS (C): $t_R$=0.1 min; [M+H]$^+$: 178.39. $^1$H-NMR for the benzylated intermediate (CDCl$_3$): 8.78 (s, 1H); 8.50 (d, 1H, 5.5 Hz); 8.05 (s, 1H); 7.74 (dd, 1H, 0.8 Hz and 5.5 Hz); 7.38 (m, 3H); 7.32 (m, 2H); 5.24 (s, 2H); 5.03 (s, 2H).

PRECURSOR FOR EXAMPLE 138

Imidazo[4,5-c]pyridin-1-yl-acetic acid

This compound was prepared in two steps following the method described in Example 14, step 14.1 and step 14.2, 5-azabenzimidazole replacing 4-azabenzimidazole in step 14.1. LC-MS (C): $t_R$=0.09 min; [M+H]$^+$: 178.38. $^1$H-NMR for the benzylated intermediate (CDCl$_3$): 9.17 (s, 1H); 8.48 (d, 1H, 5.5 Hz); 8.00 (s, 1H); 7.39 (m, 3H); 7.32 (m, 2H); 7.27 (d, 1H, 5.8 Hz); 5.24 (s, 2H); 4.98 (s, 2H).

PRECURSOR FOR EXAMPLE 139

(2,3-Dihydro-pyrrolo[2,3-b]pyridin-1-yl)-acetic acid

This compound was prepared in two steps according to the methods described in Example 115 step 115.1, 2,3-dihydro-7-azaindole replacing 1H-pyrazolo[3,4-b]pyridine followed by Example 1 step 1.4. LC-MS (B): $t_R$=0.45 min; [M+H]$^+$: 179.15.

PRECURSOR FOR EXAMPLE 140

(3-Chloro-pyrrolo[2,3-b]pyrazin-5-yl)-acetic acid

This compound was prepared in two steps according to the methods described in Example 115 step 115.1, 3-chloro-5H-pyrrolo[2,3-b]pyrazine replacing 1H-pyrazolo[3,4-b]pyridine followed by Example 113 step 113.4. LC-MS (B): $t_R$=0.60 min; [M+H]$^+$: 211.99.

PRECURSOR FOR EXAMPLE 141

Pyrrolo[2,3-c]pyridin-1-yl-acetic acid

This compound was prepared in two steps according to the methods described in Example 65 step 65.1, 6-azaindole replacing 6-chloro-1H-pyrrolo[2,3-b]pyridine followed by Example 1 step 1.4. LC-MS (B): $t_R$=0.28 min; [M+H]$^+$: 177.43.

LC-MS data of Example 118 to Example 141 are listed in the table below. The LC-MS conditions used were LC-MS (A).

| Example No | Name | $t_R$ | [M + H]$^+$ |
|---|---|---|---|
| 118 | 1-{(R)-4-[4-(1H-Benzoimidazol-2-yl)-thiazol-5-yl]-2-methyl-piperazin-1-yl}-2-naphthalen-1-yl-ethanone | 0.8 | 468.3 |
| 119 | 1-{(R)-4-[4-(1H-Benzoimidazol-2-yl)-thiazol-5-yl]-2-methyl-piperazin-1-yl}-2-quinolin-8-yl-ethanone | 0.58 | 469.3 |

-continued

| Example No | Name | $t_R$ | $[M + H]^+$ |
|---|---|---|---|
| 120 | 1-{(R)-4-[4-(1H-Benzoimidazol-2-yl)-thiazol-5-yl]-2-methyl-piperazin-1-yl}-2-quinolin-7-yl-ethanone | 0.48 | 469.3 |
| 121 | 1-{(R)-4-[4-(1H-Benzoimidazol-2-yl)-thiazol-5-yl]-2-methyl-piperazin-1-yl}-2-quinoxalin-6-yl-ethanone | 0.58 | 470.3 |
| 122 | 6-(2-{(R)-4-[4-(1H-Benzoimidazol-2-yl)-thiazol-5-yl]-2-methyl-piperazin-1-yl}-2-oxo-ethyl)-4H-benzo[1,4]oxazin-3-one | 0.59 | 489.3 |
| 123 | 1-{(R)-4-[4-(1H-Benzoimidazol-2-yl)-thiazol-5-yl]-2-methyl-piperazin-1-yl}-2-(1H-indol-4-yl)-ethanone | 0.64 | 457.2 |
| 124 | 1-{(R)-4-[4-(1H-Benzoimidazol-2-yl)-thiazol-5-yl]-2-methyl-piperazin-1-yl}-2-(1H-indol-3-yl)-ethanone | 0.68 | 457.3 |
| 125 | 1-{(R)-4-[4-(1H-Benzoimidazol-2-yl)-thiazol-5-yl]-2-methyl-piperazin-1-yl}-2-(1-methyl-1H-indol-3-yl)-ethanone | 0.75 | 471.3 |
| 126 | 1-{(R)-4-[4-(1H-Benzoimidazol-2-yl)-thiazol-5-yl]-2-methyl-piperazin-1-yl}-2-(5-methoxy-1H-indol-3-yl)-ethanone | 0.66 | 487.3 |
| 127 | 1-{(R)-4-[4-(1H-Benzoimidazol-2-yl)-thiazol-5-yl]-2-methyl-piperazin-1-yl}-2-(5-chloro-1H-indol-3-yl)-ethanone | 0.76 | 491.2 |
| 128 | 1-{(R)-4-[4-(1H-Benzoimidazol-2-yl)-thiazol-5-yl]-2-methyl-piperazin-1-yl}-2-(5-fluoro-1H-indol-3-yl)-ethanone | 0.7 | 475.3 |
| 129 | 1-{(R)-4-[4-(1H-Benzoimidazol-2-yl)-thiazol-5-yl]-2-methyl-piperazin-1-yl}-2-(5-chloro-1H-benzoimidazol-2-yl)-ethanone | 0.56 | 492.2 |
| 130 | 2-Benzo[d]isoxazol-3-yl-1-{(R)-4-[4-(1H-benzoimidazol-2-yl)-thiazol-5-yl]-2-methyl-piperazin-1-yl}-ethanone | 0.69 | 459.3 |
| 131 | 1-{(R)-4-[4-(1H-Benzoimidazol-2-yl)-thiazol-5-yl]-2-methyl-piperazin-1-yl}-2-(5-methyl-benzo[d]isoxazol-3-yl)-ethanone | 0.75 | 473.3 |
| 132 | 1-{(R)-4-[4-(1H-Benzoimidazol-2-yl)-thiazol-5-yl]-2-methyl-piperazin-1-yl}-2-(1H-indazol-3-yl)-ethanone | 0.63 | 458.3 |
| 133 | 2-Benzo[b]thiophen-3-yl-1-{(R)-4-[4-(1H-benzoimidazol-2-yl)-thiazol-5-yl]-2-methyl-piperazin-1-yl}-ethanone | 0.79 | 474.3 |
| 134 | 1-{(R)-4-[4-(1H-Benzoimidazol-2-yl)-thiazol-5-yl]-2-methyl-piperazin-1-yl}-2-(5-chloro-benzo[b]thiophen-3-yl)-ethanone | 0.86 | 508.2 |
| 135 | 1-{(R)-4-[4-(1H-Benzoimidazol-2-yl)-thiazol-5-yl]-2-methyl-piperazin-1-yl}-2-(6-methoxy-benzofuran-3-yl)-ethanone | 0.75 | 488.3 |
| 136 | 1-{(R)-4-[4-(1H-Benzoimidazol-2-yl)-thiazol-5-yl]-2-methyl-piperazin-1-yl}-2-(2,3-dihydro-benzofuran-5-yl)-ethanone | 0.68 | 460.3 |
| 137 | 1-{(R)-4-[4-(1H-Benzoimidazol-2-yl)-thiazol-5-yl]-2-methyl-piperazin-1-yl}-2-imidazo[4,5-c]pyridin-3-yl-ethanone | 0.4 | 459.2 |
| 138 | 1-{(R)-4-[4-(1H-Benzoimidazol-2-yl)-thiazol-5-yl]-2-methyl-piperazin-1-yl}-2-imidazo[4,5-c]pyridin-1-yl-ethanone | 0.4 | 459.3 |
| 139 | 1-{(R)-4-[4-(1H-Benzoimidazol-2-yl)-thiazol-5-yl]-2-methyl-piperazin-1-yl}-2-(2,3-dihydro-pyrrolo[2,3-b]pyridin-1-yl)-ethanone | 0.46 | 460.3 |
| 140 | 1-{(R)-4-[4-(1H-Benzoimidazol-2-yl)-thiazol-5-yl]-2-methyl-piperazin-1-yl}-2-(3-chloro-pyrrolo[2,3-b]pyrazin-5-yl)-ethanone | 0.67 | 493.2 |
| 141 | 1-{(R)-4-[4-(1H-Benzoimidazol-2-yl)-thiazol-5-yl]-2-methyl-piperazin-1-yl}-2-pyrrolo[2,3-c]pyridin-1-yl-ethanone | 0.45 | 458.2 |

EXAMPLE 142

1-{(R)-4-[4-(1H-Benzoimidazol-2-yl)-thiazol-5-yl]-2-methyl-piperazin-1-yl}-2-(7-chloro-pyrrolo[2,3-c]pyridin-1-yl)-ethanone

142.1. 7-Chloro-1H-pyrrolo[2,3-c]pyridine

To a solution of 2-chloro-3-nitropyridine (1 g) in THF (30 mL) cooled at −78° C. was slowly added vinylmagnesium bromide (1M in THF, 20.2 mL). The reaction mixture was warmed up to −30° C. and was stirred at −30° C. for 30 min. Sat. NH$_4$Cl was added and the mixture was extracted with EA twice. The combined org. layers were dried (Na$_2$SO$_4$) and evaporated in vacuo. CC (Biotage, SNAP 50 g cartridge, solvent A: Hept; solvent B: EA; gradient in % B: 8 for 4CV, 8 to 66 over 10CV, 66 for 2CV) afforded 353 mg of rosa solid. LC-MS (B): t$_R$=0.47 min; [M+H]$^+$: 153.22.

142.2. (7-Chloro-pyrrolo[2,3-c]pyridin-1-yl)-acetic acid tert-butyl ester

This compound was prepared using a method analogous to that of Example 115 step 115.1, intermediate 142.1 replacing 1H-pyrazolo[3,4-b]pyridine. LC-MS (B): t$_R$=0.83 min; [M+H]$^+$: 267.29.

142.3. (7-Chloro-pyrrolo[2,3-c]pyridin-1-yl)-acetic acid, trifluoroacetate salt This compound was prepared using a method analogous to that of Example 113 step 113.4, intermediate 142.2 replacing intermediate 113.3. LC-MS (B): t$_R$=0.50 min; [M+H]$^+$: 211.01.

142.4. 1-{(R)-4-[4-(1H-Benzoimidazol-2-yl)-thiazol-5-yl]-2-methyl-piperazin-1-yl}-2-(7-chloro-pyrrolo[2,3-c]pyridin-1-yl)-ethanone This compound was prepared using a method analogous to that of Example 117, intermediate 142.3 replacing 2-naphthylacetic acid. LC-MS (A): t$_R$=0.61 min; [M+H]$^+$: 492.2.

EXAMPLE 143

1-{(R)-4-[4-(1H-Benzoimidazol-2-yl)-thiazol-5-yl]-2-methyl-piperazin-1-yl}-2-(3-chloro-pyrrolo[2,3-b]pyridin-1-yl)-ethanone

143.1. (3-Chloro-pyrrolo[2,3-b]pyridin-1-yl)-acetic acid

To a suspension of 2-(1H-pyrrolo[2,3-b]pyridin-1-yl)acetic acid (100 mg) in MeCN (10 mL) was added NCS (91 mg) and the reaction mixture was stirred at 60° C. overnight and at 65° C. for 20 h. The solvent was removed in vacuo, the residue was taken up in DCM and the resulting precipitate was filtered off. The precipitate was further washed with DCM and dried in vacuo. 92 mg of grey solid was obtained. LC-MS (B): t$_R$=0.66 min; [M+H]$^+$: 211.02.

143.2. 1-{(R)-4-[4-(1H-Benzoimidazol-2-yl)-thiazol-5-yl]-2-methyl-piperazin-1-yl}-2-(3-chloro-pyrrolo[2,3-b]pyridin-1-yl)-ethanone This compound was prepared using a method analogous to that of Example 1 step 1.5, intermediate 16.4 replacing intermediate 1.4 and intermediate 143.1 replacing benzoimidazol-1-yl-acetic acid. LC-MS (A): t$_R$=0.76 min; [M+H]$^+$: 492.3.

EXAMPLE 144

1-{(R)-4-[4-(1H-Benzoimidazol-2-yl)-2-methyl-thiazol-5-yl]-2-methyl-piperazin-1-yl}-2-imidazo[4,5-b]pyridin-3-yl-ethanone This compound was prepared using a method analogous to that of Example 39, dimethylzinc (2M in toluene) replacing diethylzinc (1.5M in toluene) and Example 80 replacing Example 38. LC-MS (A): t$_R$=0.52 min; [M+H]$^+$: 473.3.

EXAMPLE 145

1-{(R)-4-[4-(5-Chloro-1H-benzoimidazol-2-yl)-thiazol-5-yl]-2-methyl-piperazin-1-yl}-2-(2,3-dihydro-indol-1-yl)-ethanone This compound was prepared using a method analogous to that of Example 1 step 1.5, intermediate 83.1 replacing intermediate 1.4 and 2,3-dihydro-1H-indol-1-yl-acetic acid replacing benzoimidazol-1-yl-acetic acid. LC-MS (A): t$_R$=0.86 min; [M+H]$^+$: 493.2.

EXAMPLE 146

1-{(R)-4-[4-(1H-Benzoimidazol-2-yl)-2-ethyl-thiazol-5-yl]-2-methyl-piperazin-1-yl}-2-imidazo[4,5-b]pyridin-3-yl-ethanone This compound was prepared using a method analogous to that of Example 39, Example 80 replacing Example 38. LC-MS (G): t$_R$=0.62 min; [M+H]$^+$: 487.3.

EXAMPLE 147

1-{(R)-4-[4-(5-Chloro-1H-benzoimidazol-2-yl)-2-trifluoromethyl-thiazol-5-yl]-2-methyl-piperazin-1-yl}-2-imidazo[4,5-b]pyridin-3-yl-ethanone

147.1. 5-((R)-3-Methyl-piperazin-1-yl)-2-trifluoromethyl-thiazole-4-carboxylic acid methyl ester This compound was prepared using a method analogous to that of Example 16 step 16.4, intermediate 51.1 replacing intermediate 16.3. LC-MS (B): t$_R$=0.54 min; [M+H]$^+$: 309.97.

147.2. 5-[(R)-4-(2-Imidazo[4,5-b]pyridin-3-yl-acetyl)-3-methyl-piperazin-1-yl]-2-trifluoromethyl-thiazole-4-carboxylic acid methyl ester This compound was prepared using a method analogous to that of Example 1 step 1.5, intermediate 147.1 replacing intermediate 1.4 and intermediate 14.2 replacing benzoimidazol-1-yl-acetic acid. LC-MS (B): t$_R$=0.73 min; [M+H]$^+$: 468.92.

147.3. 5-[(R)-4-(2-Imidazo[4,5-b]pyridin-3-yl-acetyl)-3-methyl-piperazin-1-yl]-2-trifluoromethyl-thiazole-4-carboxylic acid This compound was prepared using a method analogous to that of Example 16 step 16.2, intermediate 147.2 replacing intermediate 16.1. LC-MS (B): t$_R$=0.64 min; [M+H]$^+$: 454.98.

147.4. 1-{(R)-4-[4-(5-Chloro-1H-benzoimidazol-2-yl)-2-trifluoromethyl-thiazol-5-yl]-2-methyl-piperazin-1-yl}-2-imidazo[4,5-b]pyridin-3-yl-ethanone To a solution of intermediate 147.3 (70 mg) in DCM (3 mL) was added 4-chloro-1,2-phenylenediamine (22.6 mg) followed by DIPEA (344) and HATU (87.9 mg). The resulting mixture was stirred for 22 h. The reaction mixture was diluted with DCM and washed with sat. aq. NaHCO$_3$, and water. The aq. phases were extracted with DCM. The combined org. layers were dried over Na$_2$SO$_4$, filtrated off and concentrated in vacuo. The resulting orange oil (113 mg) was taken up in acetic acid (3 mL), the mixture was stirred at 90° C. for 4 h and evaporated in vacuo. The residue was taken up in DMF and purified by preparative LC-MS (I) to afford 15 mg of yellow solid. LC-MS (G): $t_R$=0.94 min; [M+H]$^+$: 561.3.

EXAMPLE 148

1-{(R)-4-[4-(1H-Benzoimidazol-2-yl)-2-(2-fluoro-phenyl)-thiazol-5-yl]-2-methyl-piperazin-1-yl}-2-imidazo[4,5-b]pyridin-3-yl-ethanone

148.1. (R)-4-[4-Carboxy-2-(2-fluoro-phenyl)-thiazol-5-yl]-2-methyl-piperazine-1-carboxylic acid tert-butyl ester This compound was prepared using a method analogous to that of Example 41 step 41.2, intermediate 80.1 replacing intermediate 41.1 and 2-fluorobenzeneboronic acid replacing phenylboronic acid. LC-MS (B): $t_R$=0.94 min; [M+H]$^+$: 422.01.

148.2. (R)-4-[4-(1H-Benzoimidazol-2-yl)-2-(2-fluoro-phenyl)-thiazol-5-yl]-2-methyl-piperazine-1-carboxylic acid tert-butyl ester This compound was prepared using a method analogous to that of Example 147 step 147.4, intermediate 148.1 replacing intermediate 147.3 and 1,2-phenylenediamine replacing 4-chloro-1,2-phenylenediamine. LC-MS (B): $t_R$=0.90 min; [M+H]$^+$: 490.02.

148.3. 2-[2-(2-Fluoro-phenyl)-5-((R)-3-methyl-piperazin-1-yl)-thiazol-4-yl]-1H-benzoimidazole This compound was prepared using a method analogous to that of Example 16 step 16.4, intermediate 148.2 replacing intermediate 16.3. LC-MS (B): $t_R$=0.59 min; [M+H]$^+$: 393.99.

148.4. 1-{(R)-4-[4-(1H-Benzoimidazol-2-yl)-2-(2-fluoro-phenyl)-thiazol-5-yl]-2-methyl-piperazin-1-yl}-2-imidazo[4,5-b]pyridin-3-yl-ethanone This compound was prepared using a method analogous to that of Example 1 step 1.5, intermediate 148.3 replacing intermediate 1.4 and intermediate 14.2 replacing benzoimidazol-1-yl-acetic acid. LC-MS (G): $t_R$=0.75 min; [M+H]$^+$: 553.3.

EXAMPLE 149

1-{(R)-4-[4-(1H-Benzoimidazol-2-yl)-2-m-tolyl-thiazol-5-yl]-2-methyl-piperazin-1-yl}-2-imidazo[4,5-b]pyridin-3-yl-ethanone This compound was prepared in four steps following the method described in Example 148, m-tolylboronic acid replacing 2-fluorobenzeneboronic in step 148.1. LC-MS (G): $t_R$=0.80 min; [M+H]$^+$: 549.3.

EXAMPLE 150

1-{(R)-4-[4-(1H-Benzoimidazol-2-yl)-2-p-tolyl-thiazol-5-yl]-2-methyl-piperazin-1-yl}-2-imidazo[4,5-b]pyridin-3-yl-ethanone This compound was prepared in four steps following the method described in Example 148, p-tolylboronic acid replacing 2-fluorobenzeneboronic acid in step 148.1. LC-MS (G): $t_R$=0.80 min; [M+H]$^+$: 549.4.

EXAMPLE 151

1-(2-{(R)-4-[4-(1H-Benzoimidazol-2-yl)-thiazol-5-yl]-2-methyl-piperazin-1-yl}-2-oxo-ethyl)-3,3-dimethyl-1,3-dihydro-indol-2-one

151.1. (3,3-Dimethyl-2-oxo-2,3-dihydro-indol-1-yl)-acetic acid benzyl ester This compound was prepared using a method analogous to that of Example 68 step 68.1, 3,3-dimethyl-1,3-dihydro-indol-2-one replacing oxindole. LC-MS (B): $t_R$=0.91 min; [M+H]$^+$: 310.42.

151.2. (3,3-Dimethyl-2-oxo-2,3-dihydro-indol-1-yl)-acetic acid

This compound was prepared using a method analogous to that of Example 14 step 14.2, intermediate 151.1 replacing intermediate 14.1 and EtOH replacing MeOH/acetic acid. LC-MS (B): $t_R$=0.65 min; [M+H]$^+$: 220.38.

151.3. 1-(2-{(R)-4-[4-(1H-Benzoimidazol-2-yl)-thiazol-5-yl]-2-methyl-piperazin-1-yl}-2-oxo-ethyl)-3,3-dimethyl-1,3-dihydro-indol-2-one This compound was prepared using a method analogous to that of Example 1 step 1.5, intermediate 16.4 replacing intermediate 1.4 and intermediate 151.2 replacing benzoimidazol-1-yl-acetic acid. LC-MS (G): $t_R$=0.80 min; [M+H]$^+$: 501.3.

EXAMPLE 152

3-(2-{(R)-4-[4-(1H-Benzoimidazol-2-yl)-thiazol-5-yl]-2-methyl-piperazin-1-yl}-2-oxo-ethyl)-4-methyl-3H-benzooxazol-2-one

152.1. 4-Methyl-3H-benzooxazol-2-one

To a solution of 2-hydroxy-6-methylaniline (583 mg) in THF (8 mL) was added 1,1'-carbonyldiimidazole (1.14 g). The reaction mixture was stirred at 70° C. for 20 h. After cooling down, DCM was added and the mixture was washed three times with 2N NaOH. The aq. phases were combined, cooled down to 0° C. and the pH was brought to 6 by addition of 2N HCl. The suspension was filtered, the resulting powder was washed with cold water and dried in high vacuo to afford 587 mg of beige solid. LC-MS (B): $t_R$=0.64 min. $^1$H-NMR (DMSO-d6): 11.7 (s, NH); 7.09 (m, 1H); 6.97 (m, 2H); 2.29 (s, 3H).

152.2. (4-Methyl-2-oxo-benzooxazol-3-yl)-acetic acid tert-butyl ester

This compound was prepared using a method analogous to that of Example 115 step 115.1, intermediate 152.1 replacing 1H-pyrazolo[3,4-b]pyridine. LC-MS (B): $t_R$=0.89 min.

152.3. (4-Methyl-2-oxo-benzooxazol-3-yl)-acetic acid

This compound was prepared using a method analogous to that of Example 113 step 113.4, intermediate 152.2 replacing intermediate 113.3. LC-MS (B): $t_R$=0.62 min.

152.4. 3-(2-{(R)-4-[4-(1H-Benzoimidazol-2-yl)-thiazol-5-yl]-2-methyl-piperazin-1-yl}-2-oxo-ethyl)-4-methyl-3H-benzooxazol-2-one This compound was prepared using a method analogous to that of Example 1 step 1.5, intermediate 16.4 replacing intermediate 1.4 and intermediate 152.3 replacing benzoimidazol-1-yl-acetic acid. The work-up was however performed by adding PL-HCO$_3$ to the reaction mixture, stirring for 1 h and filtrating off. LC-MS (G): $t_R$=0.76 min; [M+H]$^+$: 489.3.

EXAMPLE 153

3-(2-{(R)-4-[4-(1H-Benzoimidazol-2-yl)-thiazol-5-yl]-2-methyl-piperazin-1-yl}-2-oxo-ethyl)-4-fluoro-3H-benzooxazol-2-one This compound was prepared in four steps following the method described in Example 152, 2-amino-3-fluorophenol replacing 2-hydroxy-6-methylaniline in step 152.1. LC-MS (G): $t_R$=0.74 min; [M+H]$^+$: 493.3.

EXAMPLE 154

1-{(R)-4-[4-(1H-Benzoimidazol-2-yl)-thiazol-5-yl]-2-methyl-piperazin-1-yl}-2-(2-hydroxymethyl-pyrrolo[2,3-b]pyridin-1-yl)-ethanone

154.1. (1H-Pyrrolo[2,3-b]pyridin-2-yl)-methanol

To an ice-cold solution of methyl 1H-pyrrolo[2,3-b]pyridine-2-carboxylate (300 mg) in THF (4.5 mL) was added LiAlH$_4$ (1.7 mL, 1M in THF). The ice bath was removed and the reaction mixture was stirred at RT for 2 h. LiAlH$_4$ (2.8 mL, 1M in THF) was added and the stirring was pursued for 20 h at RT. DCM and 1M NaOH were added and the phases were separated. The org. layer was dried (Na$_2$SO$_4$) and evaporated in vacuo to afford 100 mg of oil. LC-MS (B): $t_R$=0.34 min; [M+H]$^+$: 149.28.

154.2. 1-{(R)-4-[4-(1H-Benzoimidazol-2-yl)-thiazol-5-yl]-2-methyl-piperazin-1-yl}-2-(2-hydroxymethyl-pyrrolo[2,3-b]pyridin-1-yl)-ethanone This compound was prepared in three steps following the method described in Example 152, step 152.2 to 152.4, intermediate 154.1 replacing intermediate 152.1 in step 152.2. LC-MS (G): $t_R$=0.59 min; [M+H]$^+$: 488.3.

EXAMPLE 155

3-(2-{(R)-4-[4-(1H-Benzoimidazol-2-yl)-thiazol-5-yl]-2-methyl-piperazin-1-yl}-2-oxo-ethyl)-3H-oxazolo[4,5-b]pyridin-2-one This compound was prepared in four steps following the method described in Example 152, 2-amino-3-hydroxypyridine replacing 2-hydroxy-6-methylaniline in step 152.1. The alkylation step performed as described in step 152.2 provided a mixture of two regioisomers that was carried through the next two steps. The two regioisomers were separated after the final step by preparative LC-MS (III followed by IX). LC-MS (B): $t_R$=0.63 min; [M+H]$^+$: 475.95. $^1$H-NMR (CDCl$_3$): 10.1 (s, NH); 8.46 (s, 1H); 8.12 (dd, 1H, 1.2 Hz and 5.2 Hz); 7.79 (s, 1H); 7.49 (d, 1H, 3.3 Hz); 7.47 (dd, 1H, 1.2 Hz and 7.8 Hz); 7.30 (m, 2H); 7.10 (dd, 1H, 5.3 Hz and 7.8 Hz); 4.89-4.79 (m, 2.5H); 4.52 (m, 0.5H); 4.23-3.96 (m, 2H); 3.78-3.54 (m, 2H); 3.03 (dd, 1H, 4 Hz and 11.3 Hz); 2.93 (s, 1H); 1.64 (d, 3H).

EXAMPLE 156

4-(2-{(R)-4-[4-(1H-Benzoimidazol-2-yl)-thiazol-5-yl]-2-methyl-piperazin-1-yl}-2-oxo-ethyl)-4H-oxazolo[4,5-b]pyridin-2-one This compound was the second regioisomer obtained during the synthesis of Example 155. LC-MS (B): $t_R$=0.55 min; [M+H]$^+$: 475.93. $^1$H-NMR (CDCl$_3$): 10.2 (s, NH); 8.45 (s, 1H); 7.77 (s, 1H); 7.48 (d, 1H, 4.5 Hz); 7.32-7.27 (m, 3H); 7.17 (d, 1H, 7.3 Hz); 6.76 (t, 1H, 7.3 Hz); 5.36 (d, 1H, 14.8 Hz); 5.05 (d, 1H, 14.5Hz); 4.88 (s, 0.5H); 4.52 (d, 0.5H, 13.5 Hz); 4.31 (s, 0.5H); 4.10 (t, 0.5H, 11.5 Hz); 3.98 (d, 0.5H, 11 Hz); 3.92 (d, 0.5H, 10.3 Hz); 3.82 (d, 0.5H, 13.5 Hz); 3.70 (m, 1H); 3.56 (m, 0.5H); 3.06-2.93 (m, 2H); 1.85 (d, 1.5H, 6.0 Hz); 1.61 (d, 1.5H, 6.5 Hz). Roesy signal seen between proton at 7.32 ppm and two protons at 5.36 and 5.05 ppm.

EXAMPLE 157

1-(2-{(R)-4-[4-(1H-Benzoimidazol-2-yl)-thiazol-5-yl]-2-methyl-piperazin-1-yl}-2-oxo-ethyl)-1H-indole-2,3-dione This compound was prepared using a method analogous to that of Example 1 step 1.5, intermediate 16.4 replacing intermediate 1.4 and (2,3-dioxo-2,3-dihydro-indol-1-yl)-acetic acid replacing benzoimidazol-1-yl-acetic acid. LC-MS (G): $t_R$=0.67 min; [M+H]$^+$: 487.3.

EXAMPLE 158

1-{(R)-4-[4-(5,6-Dimethoxy-1H-benzoimidazol-2-yl)-thiazol-5-yl]-2-methyl-piperazin-1-yl}-2-imidazo[4,5-b]pyridin-3-yl-ethanone This compound was prepared in three steps following the method described in Example 1, step 1.3 to 1.5, 4,5-dimethoxy-1,2-phenylenediamine dihydrochloride replacing phenylenediamine and intermediate 16.2 replacing intermediate 1.2 in step 1.3, and intermediate 14.2 replacing benzoimidazol-1-yl-acetic acid in step 1.5. LC-MS (G): $t_R$=0.55 min; [M+H]$^+$: 519.3.

EXAMPLE 159

1-{(R)-4-[4-(6-Hydroxymethyl-1H-benzoimidazol-2-yl)-thiazol-5-yl]-2-methyl-piperazin-1-yl}-2-imidazo[4,5-b]pyridin-3-yl-ethanone This compound was prepared in three steps following the method described in Example 1, step 1.3 to 1.5, 3,4-diaminobenzyl alcohol replacing phenylenediamine and intermediate 16.2 replacing intermediate 1.2 in step 1.3, and intermediate 14.2 replacing benzoimidazol-1-yl-acetic acid in step 1.5. LC-MS (G): $t_R$=0.85 min; [M+H]$^+$: 489.3.

EXAMPLE 160

1-{(R)-4-[4-(6-Hydroxymethyl-1H-benzoimidazol-2-yl)-2-trifluoromethyl-thiazol-5-yl]-2-methyl-piperazin-1-yl}-2-imidazo[4,5-b]pyridin-3-yl-ethanone This compound was prepared using a method analogous to that of Example 1 step 1.3, 3,4-diaminobenzyl alcohol replacing phenylenediamine and intermediate 147.3 replacing intermediate 1.2. LC-MS (G): $t_R$=0.64 min; [M+H]$^+$: 557.3.

EXAMPLE 161

1-{(R)-4-[4-(5,6-Di methoxy-1H-benzoimidazol-2-yl)-2-trifluoromethyl-thiazol-5-yl]-2-methyl-piperazin-1-yl}-2-imidazo[4,5-b]pyridin-3-yl-ethanone This compound was prepared using a method analogous to that of Example 1 step 1.3, 4,5-dimethoxy-1,2-phenylenediamine dihydrochloride replacing phenylenediamine and intermediate 147.3 replacing intermediate 1.2. LC-MS (G): $t_R$=0.68 min; [M+H]$^+$: 587.3.

EXAMPLE 162

1-{(R)-4-[4-(6-Cyclopropyl-1H-benzoimidazol-2-yl)-thiazol-5-yl]-2-methyl-piperazin-1-yl}-2-imidazo[4,5-b]pyridin-3-yl-ethanone

162.1. 4-Cyclopropyl-2-nitro-phenylamine

A flask was charged with 4-bromo-2-nitroaniline (1.95 g), cyclopropylboronic acid (1 g), Pd(OAc)$_2$ (101 mg), tricyclohexylphosphine (252 mg), K$_3$PO$_4$ (6.69 g), toluene (40 mL) and water (2 mL). The resulting yellow suspension was sonicated under argon for 5 min and heated at 100° C. for 20 h. After cooling down, DCM/water was added and the resulting biphasic mixture was filtered. The phases were separated, the org. layer was dried (MgSO$_4$), filtrated off and evaporated to dryness. CC (Biotage, SNAP 50 g cartridge, solvent A: Hept; solvent B: EA; gradient in % B: 0 to 40 over 16CV) afforded 1.3 g of orange solid. LC-MS (B): $t_R$=0.80 min; [M+H]$^+$: 179.14.

162.2. 4-Cyclopropyl-benzene-1,2-diamine

To a solution of intermediate 162.1 (1.3 g) in MeOH (42 mL) was added zinc powder (1.48 g) and NH$_4$Cl (5.85 g). The reaction mixture was stirred at RT for 3 days, filtered through celite and evaporated in vacuo to afford 960 mg of black solid. LC-MS (B): $t_R$=0.45 min; [M+H]$^+$: 149.33.

162.3. 1-{(R)-4-[4-(6-Cyclopropyl-1H-benzoimidazol-2-yl)-thiazol-5-yl]-2-methyl-piperazin-1-yl}-2-imidazo[4,5-b]pyridin-3-yl-ethanone This compound was prepared in three steps following the method described in Example 1, step 1.3 to 1.5, intermediate 162.2 replacing phenylenediamine and intermediate 16.2 replacing intermediate 1.2 in step 1.3, and intermediate 14.2 replacing benzoimidazol-1-yl-acetic acid in step 1.5. LC-MS (B): $t_R$=0.63 min; [M+H]$^+$: 499.02.

EXAMPLE 163

2-Imidazo[4,5-b]pyridin-3-yl-1-((R)-4-{4-[5-(2-methoxy-ethoxy)-1H-benzoimidazol-2-yl]-2-trifluoromethyl-thiazol-5-yl}-2-methyl-piperazin-1-yl)-ethanone To a solution of intermediate 147.3 (30 mg) in DCM (3 mL) was added HATU (27.6 mg), DIPEA (0.034 mL) and intermediate 102.2 (12 mg). After stirring 6 h at RT, HATU (27.6 mg), DIPEA (0.034 mL) and intermediate 102.2 (12 mg) were added again. The reaction mixture was further stirred at RT for 20 h. PL-HCO$_3$ (200 mg) was added, stirring was pursued for 1 h and the mixture was filtered off. After removal of the solvent, the crude was purified by preparative LC-MS (III) to afford 6 mg of beige solid. It was taken up in AcOH (0.3 mL) and heated at 80° C. for 3 days. Toluene was added and the solvents were removed in vacuo. The residue was purified by preparative LC-MS (III) to afford 1.7 mg of the final compound as white solid. LC-MS (G): $t_R$=0.73 min; [M+H]$^+$: 601.2.

EXAMPLE 164

1-((R)-4-{4-[5-(2-Hydroxy-ethoxy)-1H-benzoimidazol-2-yl]-2-trifluoromethyl-thiazol-5-yl}-2-methyl-piperazin-1-yl)-2-imidazo[4,5-b]pyridin-3-yl-ethanone This compound was prepared using a method analogous to that of Example 163, intermediate 101.1 replacing intermediate 102.2. LC-MS (G): $t_R$=0.65 min; [M+H]$^+$: 587.3.

EXAMPLE 165

1-{(R)-4-[4-(5-Acetyl-1H-benzoimidazol-2-yl)-2-trifluoromethyl-thiazol-5-yl]-2-methyl-piperazin-1-yl}-2-imidazo[4,5-b]pyridin-3-yl-ethanone

165.1. 1-(4-Amino-3-nitro-phenyl)-ethanone

This compound was prepared using a method analogous to that of Example 102 step 102.1, N-(4-acetylphenyl)acetamide replacing 4-(2-methoxyethoxy)aniline and performing the nitration reaction at a temperature below −5° C. instead of 15° C. LC-MS (B): $t_R$=0.66 min; [M+H+MeCN]$^+$: 222.19.

165.2. 1-(3,4-Diaminophenyl)-ethanone

A flask charged with a solution of intermediate 165.1 (1.46 g) in EtOH/H$_2$O (270 mL/13 mL) was evacuated and backfilled with argon three times. Pd/C (10%, 216 mg) was added and the flask was evacuated and backfilled with argon three

165.3. 1-{(R)-4-[4-(5-Acetyl-1H-benzoimidazol-2-yl)-2-trifluoromethyl-thiazol-5-yl]-2-methyl-piperazin-1-yl}-2-imidazo[4,5-b]pyridin-3-yl-ethanone This compound was prepared using a method analogous to that of Example 163, intermediate 165.2 replacing intermediate 102.2. LC-MS (G): $t_R$=0.83 min; [M+H]$^+$: 569.3.

EXAMPLE 166

1-((R)-4-{4-[5-(1-Hydroxy-ethyl)-1H-benzoimidazol-2-yl]-2-trifluoro methyl-thiazol-5-yl}-2-methyl-piperazin-1-yl)-2-imidazo[4,5-b]pyridin-3-yl-ethanone To a solution of Example 165 (40 mg) in MeOH (0.22 mL) was added NaBH$_4$ (8.25 mg). After stirring at RT for 60 min, DCM/H$_2$O was added and the phases were separated. The org. layer was evaporated in vacuo and the residue was purified by preparative LC-MS (VI) to afford 8 mg of white solid. LC-MS (B): $t_R$=0.63 min; [M+H]$^+$: 570.96.

EXAMPLE 167

2-{5-[(R)-4-(2-Imidazo[4,5-b]pyridin-3-yl-acetyl)-3-methyl-piperazin-1-yl]-2-trifluoromethyl-thiazol-4-yl}-1H-benzoimidazole-5-carboxylic acid methyl ester This compound was prepared using a method analogous to that of Example 163, methyl 3,4-diaminobenzoate replacing intermediate 102.2. LC-MS (G): $t_R$=0.89 min; [M+H]$^+$: 585.0.

EXAMPLE 168

1-((R)-4-{4-[5-(1-Hydroxy-cyclopropyl)-1H-benzoimidazol-2-yl]-2-trifluoro methyl-thiazol-5-yl}-2-methyl-piperazin-1-yl)-2-imidazo[4,5-b]pyridin-3-yl-ethanone To a solution of Example 167 (25 mg) in THF (1.15 mL) was added Ti(OiPr)$_4$ (0.0126 mL). Ethylmagnesium bromide (1M in THF, 0.513 mL) was added dropwise over 30 min at RT. The reaction mixture was stirred at RT for 20 h and diluted with DCM and 1M NaHCO$_3$. The phases were separated. The org. phase was washed with water, dried (Na$_2$SO$_4$), filtered off and evaporated in vacuo. The residue was purified by preparative LC-MS (III) to afford 1 mg of pale yellow solid. LC-MS (B): $t_R$=0.65 min; [M+H]$^+$: 583.18.

EXAMPLE 169

2-Imidazo[4,5-b]pyridin-3-yl-1-{(R)-4-[4-(3H-imidazo[4,5-b]pyridin-2-yl)-2-trifluoromethyl-thiazol-5-yl]-2-methyl-piperazin-1-yl}-ethanone To a solution of intermediate 147.3 (50 mg) in DCM (1 mL) was added HATU (46 mg), DIPEA (0.056 mL) and 2,3-diaminopyridine (18 mg). After stirring overnight at RT, additional equivalents of 2,3-diaminopyridine, DIPEA and HATU were added and stirring was pursued over weekend. The reaction mixture was diluted with DCM and 1M NaHCO$_3$. The phases were separated and the org. phase was evaporated in vacuo. The residue was purified by preparative LC-MS (VI) to afford 22 mg of pale rosa powder. It was taken up in POCl$_3$ (2 mL) and heated at 100° C. for 12 h. The reaction mixture was cooled down to 0° C. and sat. aq. NaHCO$_3$ was added followed by NaOH (32% in water) until basic pH was reached. The mixture was extracted with DCM and EA, the combined org. phases were dried (Na$_2$SO$_4$) and evaporated in vacuo. The residue was purified by preparative LC-MS (VI followed by V) to afford 7.8 mg of pale yellow powder. LC-MS (G): $t_R$=0.67 min; [M+H]$^+$: 528.3.

EXAMPLE 170

2-Imidazo[4,5-b]pyridin-3-yl-1-{(R)-4-[4-(3H-imidazo[4,5-c]pyridin-2-yl)-2-trifluoromethyl-thiazol-5-yl]-2-methyl-piperazin-1-yl}-ethanone This compound was prepared using a method analogous to that of Example 169, 3,4-diaminopyridine replacing 2,3-diaminopyridine. LC-MS (G): $t_R$=0.65 min; [M+H]$^+$: 528.3.

EXAMPLE 171

2-Imidazo[4,5-b]pyridin-3-yl-1-{(R)-2-methyl-4-[4-(9H-purin-8-yl)-2-trifluoromethyl-thiazol-5-yl]-piperazin-1-yl}-ethanone This compound was prepared using a method analogous to that of Example 169, 4,5-diaminopyrimidine replacing 2,3-diaminopyridine. LC-MS (B): $t_R$=0.55 min; [M+H]$^+$: 529.12.

Example 172 to Example 178 were synthesized following the procedure described in Example 1 step 1.5, intermediate 51.2 replacing intermediate 1.4 and the appropriate acid derivative replacing benzoimidazol-1-yl-acetic acid. LC-MS data of Example 172 to Example 178 are listed in the table below. The LC-MS conditions used were LC-MS (G).

| Example No | Name | $t_R$ | [M + H]$^+$ |
|---|---|---|---|
| 172 | 2-Benzoimidazol-1-yl-1-{(R)-4-[4-(1H-benzoimidazol-2-yl)-2-trifluoromethyl-thiazol-5-yl]-2-methyl-piperazin-1-yl}-ethanone | 0.73 | 526.3 |
| 173 | 1-{(R)-4-[4-(1H-Benzoimidazol-2-yl)-2-trifluoromethyl-thiazol-5-yl]-2-methyl-piperazin-1-yl}-2-pyrazol-1-yl-ethanone | 0.75 | 476.3 |
| 174 | 1-{(R)-4-[4-(1H-Benzoimidazol-2-yl)-2-trifluoromethyl-thiazol-5-yl]-2-methyl-piperazin-1-yl}-2-(3-methyl-pyrazol-1-yl)-ethanone | 0.79 | 490.3 |

-continued

| Example No | Name | $t_R$ | $[M + H]^+$ |
|---|---|---|---|
| 175 | 1-{(R)-4-[4-(1H-Benzoimidazol-2-yl)-2-trifluoromethyl-thiazol-5-yl]-2-methyl-piperazin-1-yl}-2-(4-chloro-pyrazol-1-yl)-ethanone | 0.86 | 510.2 |
| 176 | 1-{(R)-4-[4-(1H-Benzoimidazol-2-yl)-2-trifluoromethyl-thiazol-5-yl]-2-methyl-piperazin-1-yl}-2-(5-methyl-pyrazol-1-yl)-ethanone | 0.78 | 490.3 |
| 177 | 1-{(R)-4-[4-(1H-Benzoimidazol-2-yl)-2-trifluoromethyl-thiazol-5-yl]-2-methyl-piperazin-1-yl}-2-(3-phenyl-pyrazol-1-yl)-ethanone | 0.97 | 553.3 |
| 178 | 1-{(R)-4-[4-(1H-Benzoimidazol-2-yl)-2-trifluoromethyl-thiazol-5-yl]-2-methyl-piperazin-1-yl}-2-(3,5-dimethyl-[1,2,4]triazol-1-yl)-ethanone | 0.69 | 505.3 |

EXAMPLE 179

1-((R)-2-Methyl-4-{4-[6-(4-methyl-piperazin-1-yl)-1H-benzoimidazol-2-yl]-2-trifluoromethyl-thiazol-5-yl}-piperazin-1-yl)-2-pyrazol-1-yl-ethanone 179.1. 5-[(R)-3-Methyl-4-(2-pyrazol-1-yl-acetyl)-piperazin-1-yl]-2-trifluoromethyl-thiazole-4-carboxylic acid methyl ester This compound was prepared using a method analogous to that of Example 1 step 1.5, intermediate 147.1 replacing intermediate 1.4 and 2-(1H-pyrazol-1-yl)acetic acid replacing benzoimidazol-1-yl-acetic acid. LC-MS (B): $t_R$=0.77 min; $[M+H]^+$: 417.78.

179.2. 5-[(R)-3-Methyl-4-(2-pyrazol-1-yl-acetyl)-piperazin-1-yl]-2-trifluoromethyl-thiazole-4-carboxylic acid This compound was prepared using a method analogous to that of Example 16 step 16.2, intermediate 179.1 replacing intermediate 16.1. LC-MS (B): $t_R$=0.68 min; $[M+H]^+$: 403.86.

179.3. 5-(4-Methyl-piperazin-1-yl)-2-nitro-phenylamine

A mixture of 5-fluoro-2-nitroaniline (1 g), 1-methylpiperazine (0.752 mL) and TEA (1.86 mL) in NMP (1.5 mL) was heated at 100° C. in a microwave oven for 20 h. After cooling down, $H_2O$ (50 mL) was added, the resulting suspension was stirred for 20 min and filtrated off. The yellow solid was washed with water and dried under high vacuo (1.45 g). LC-MS (B): $t_R$=0.47 min; $[M+H]^+$: 237.19.

179.4. 4-(4-Methyl-piperazin-1-yl)-benzene-1,2-diamine

This compound was prepared using a method analogous to that of Example 165 step 165.2, intermediate 179.3 replacing intermediate 165.1. LC-MS (B): $t_R$=0.61 min; $[M+H]^+$: 207.36.

179.5. 1-((R)-2-Methyl-4-{4-[6-(4-methyl-piperazin-1-yl)-1H-benzoimidazol-2-yl]-2-trifluoromethyl-thiazol-5-yl}-piperazin-1-yl)-2-pyrazol-1-yl-ethanone This compound was prepared using a method analogous to that of Example 163, intermediate 179.4 replacing intermediate 102.2 and intermediate 179.2 replacing intermediate 147.3. LC-MS (G): $t_R$=0.61 min; $[M+H]^+$: 574.4.

EXAMPLE 180

1-{(R)-4-[4-(6-Dimethylamino-1H-benzoimidazol-2-yl)-2-trifluoromethyl-thiazol-5-yl]-2-methyl-piperazin-1-yl}-2-pyrazol-1-yl-ethanone 180.1. $N^4,N^4$-dimethylbenzene-1,2,4-triamine This compound was prepared using a method analogous to that of Example 165 step 165.2, 3-amino-N,N-dimethyl-4-nitroaniline replacing intermediate 165.1. LC-MS (E): $t_R$=0.66 min; $[M+H]^+$: 152.10.

180.2. 1-{(R)-4-[4-(6-Dimethylamino-1H-benzoimidazol-2-yl)-2-trifluoromethyl-thiazol-5-yl]-2-methyl-piperazin-1-yl}-2-pyrazol-1-yl-ethanone This compound was prepared using a method analogous to that of Example 163, intermediate 180.1 replacing intermediate 102.2 and intermediate 179.2 replacing intermediate 147.3. LC-MS (B): $t_R$=0.66 min; $[M+H]^+$: 518.94.

EXAMPLE 181

1-{(R)-2-Methyl-4-[4-(6-piperidin-1-yl methyl-1H-benzoimidazol-2-yl)-2-trifluoromethyl-thiazol-5-yl]-piperazin-1-yl}-2-pyrazol-1-yl-ethanone 181.1. N-(4-Piperidin-1-ylmethyl-phenyl)-acetamide A mixture of 4-acetamidobenzaldehyde (200 mg), piperidine (0.121 mL), $NaBH(OAc)_3$ (636 mg) and DIPEA (0.617 mL) in DCM (4 mL) was stirred at RT for 4 h. DCM and sat. $NaHCO_3$ were added. The phases were separated, the org. layer was dried ($Na_2SO_4$), filtered off and evaporated to dryness to afford 267 mg of white solid. LC-MS (B): $t_R$=0.45 min; $[M+H]^+$: 233.24.

181.2. N-(2-Nitro-4-piperidin-1-ylmethyl-phenyl)-acetamide

To a flask charged with $H_2SO_4$ (0.314 mL) cooled down to 0° C. was added intermediate 181.1 (100 mg), followed by $HNO_3$ (65% in water, 0.052 mL) dropwise. At the end of the addition, the reaction mixture was stirred for 5 min and poured onto ice. The resulting mixture was basified (1M NaOH) and extracted with DCM six times. The combined org. layers were dried (Na₂SO₄) and evaporated in vacuo to afford 228 mg of yellow oil. LC-MS (B): $t_R$=0.48 min; [M+H]⁺: 278.13.

181.3. 2-Nitro-4-piperidin-1-ylmethyl-phenylamine

A mixture of intermediate 181.2 (50 mg) in MeOH (0.5 mL) and HCl (1M, 0.5 mL) was heated at 100° C. for 30 min. The solvents were removed in vacuo to afford 42 mg of yellow oil. LC-MS (B): $t_R$=0.50 min; [M+H]⁺: 236.18.

181.4. 4-Piperidin-1-ylmethyl-benzene-1,2-diamine

This compound was prepared using a method analogous to that of Example 162 step 162.2, intermediate 181.3 replacing intermediate 162.1. LC-MS (B): $t_R$=0.21 min; [M+H]⁺: 206.36.

181.5. 1-{(R)-2-Methyl-4-[4-(6-piperidin-1-ylmethyl-1H-benzoimidazol-2-yl)-2-trifluoromethyl-thiazol-5-yl]-piperazin-1-yl}-2-pyrazol-1-yl-ethanone This compound was prepared using a method analogous to that of Example 163, intermediate 181.4 replacing intermediate 102.2 and intermediate 179.2 replacing intermediate 147.3. The work-up after the HATU coupling was however performed using sat. NaHCO₃ instead of PL-HCO₃. LC-MS (G): $t_R$=0.72 min; [M+H]⁺: 573.4.

EXAMPLE 182

1-{(R)-4-[4-(6-Dimethylaminomethyl-1H-benzoimidazol-2-yl)-2-trifluoromethyl-thiazol-5-yl]-2-methyl-piperazin-1-yl}-2-pyrazol-1-yl-ethanone 182.1. 4-Dimethylaminomethyl-2-nitro-phenylamine This compound was prepared in three steps following the method described in Example 181, step 181.1 to 181.3, dimethylamine (2M in THF) replacing piperidine. LC-MS (F): $t_R$=0.72 min; [M+H]⁺: 196.29.

182.2. 4-Dimethylaminomethyl-benzene-1,2-diamine

This compound was prepared using a method analogous to that of Example 165 step 165.2, intermediate 182.1 replacing intermediate 165.1, and using EtOH instead of EtOH/H₂O as solvent. LC-MS (B): $t_R$=0.18 min; [M+H]⁺: 166.16.

182.3. 1-{(R)-4-[4-(6-Dimethylaminomethyl-1H-benzoimidazol-2-yl)-2-trifluoromethyl-thiazol-5-yl]-2-methyl-piperazin-1-yl}-2-pyrazol-1-yl-ethanone This compound was prepared using a method analogous to that of Example 181 step 181.5, intermediate 182.2 replacing intermediate 181.4. LC-MS (F): $t_R$=0.68 min; [M+H]⁺: 533.3.

EXAMPLE 183

1-((R)-4-{4-[6-(3-Methoxy-pyrrolidin-1-ylmethyl)-1H-benzoimidazol-2-yl]-2-trifluoromethyl-thiazol-5-yl}-2-methyl-piperazin-1-yl)-2-pyrazol-1-yl-ethanone 183.1. 4-(3-Methoxy-pyrrolidin-1-ylmethyl)-2-nitro-phenylamine This compound was prepared in three steps following the method described in Example 181, step 181.1 to 181.3, 3-methoxypyrrolidine hydrochloride replacing piperidine. LC-MS (F): $t_R$=0.73 min; [M+H]⁺: 252.21.

183.2. rac-4-(3-Methoxy-pyrrolidin-1-ylmethyl)-benzene-1,2-diamine

This compound was prepared using a method analogous to that of Example 165 step 165.2, intermediate 183.1 replacing intermediate 165.1, and using EtOH instead of EtOH/H₂O as solvent. LC-MS (B): $t_R$=0.18 min; [M+H]⁺: 222.21.

183.3. 1-((R)-4-{4-[6-(3-Methoxy-pyrrolidin-1-ylmethyl)-1H-benzoimidazol-2-yl]-2-trifluoromethyl-thiazol-5-yl}-2-methyl-piperazin-1-yl)-2-pyrazol-1-yl-ethanone This compound was prepared using a method analogous to that of Example 181 step 181.5, intermediate 183.2 replacing intermediate 181.4. LC-MS (G): $t_R$=0.71 min; [M+H]⁺: 589.4.

EXAMPLE 184

1-{(R)-2-Methyl-4-[4-(1-methyl-1H-benzoimidazol-2-yl)-2-trifluoromethyl-thiazol-5-yl]-piperazin-1-yl}-2-pyrazol-1-yl-ethanone To a solution of Example 173 (30 mg) in DMF (1 mL) NaH (2.78 mg, 60% in mineral oil) was added followed by MeI (0.008 mL). The reaction mixture was stirred at RT overnight and quenched by adding sat. NH₄Cl and DCM. The phases were separated and the org. phase was evaporated to dryness. The residue was purified by preparative LC-MS (III) to afford 15 mg of white powder. LC-MS (G): $t_R$=0.78 min; [M+H]⁺: 490.3.

EXAMPLE 185

1-((R)-4-{4-[1-(2-Methoxy-ethyl)-1H-benzoimidazol-2-yl]-2-trifluoromethyl-thiazol-5-yl}-2-methyl-piperazin-1-yl)-2-pyrazol-1-yl-ethanone This compound was prepared using a method analogous to that of Example 184, 2-bromoethyl methyl ether replacing MeI. LC-MS (G): $t_R$=0.84 min; [M+H]⁺: 534.4.

EXAMPLE 186

1-{(R)-4-[4-(1H-Benzoimidazol-2-yl)-thiazol-5-yl]-2-methyl-piperazin-1-yl}-2-(2-[1,2,3]triazol-2-yl-phenyl)-ethanone 186.1. (2-[1,2,3]Triazol-2-yl-phenyl)-acetic acid To a solution of 2-iodophenylacetic acid (500 mg) in DMF (5 mL) was added 1H-1,2,3-triazole (0.214 mL), followed by Cs₂CO₃ (1.21 g) upon which the temperature increased. The reaction mixture was cooled to RT and copper iodide (17.6 mg) was added. The mixture was stirred at RT overnight and at 110° C. for 1 h30. After cooling down, H₂O/EA was added and the phases were separated. The aq. phase was acidified to pH=1 with 1M HCl and extracted with EA. The combined org. phases were dried (Na₂SO₄) and evaporated in vacuo. The residue was purified by CC (Biotage, SNAP 25 g cartridge, solvent A: Hept; solvent B: EA/AcOH 100/1; gradient in % B: 18 for 4CV, 18 to 100 over 10CV, 100 for 2CV) to afford 235 mg of white solid. LC-MS (B): $t_R$=0.60 min; [M+H]$^+$: 204.42.

186.2. 1-{(R)-4-[4-(1H-Benzoimidazol-2-yl)-thiazol-5-yl]-2-methyl-piperazin-1-yl}-2-(2-[1,2,3]triazol-2-yl-phenyl)-ethanone This compound was prepared using a method analogous to that of Example 1 step 1.5, intermediate 16.4 replacing intermediate 1.4 and intermediate 186.1 replacing benzoimidazol-1-yl-acetic acid. LC-MS (G): $t_R$=0.73 min; [M+H]$^+$: 485.3.

EXAMPLE 187

1-(2-{(R)-4-[4-(1H-Benzoimidazol-2-yl)-thiazol-5-yl]-2-methyl-piperazin-1-yl}-2-oxo-ethyl)-3,3-difluoro-1,3-dihydro-indol-2-one

187.1. 3,3-Difluoro-1,3-dihydro-indol-2-one

To a suspension of isatin (150 mg) in DCM (7 mL) was added deoxofluor (50% in THF, 1.27 mL) at RT. The reaction mixture was stirred at RT for 2 days and quenched with MeOH (0.5 mL). The mixture was washed with water, dried (MgSO$_4$), filtered off and evaporated in vacuo. The residue was purified by CC (Biotage, SNAP 10 g cartridge, solvent A: Hept; solvent B: EA; gradient in % B: 10 for 5CV, 10 to 30 over 3CV, 30 for 10CV, 30 to 50 over 5CV, 50 for 5CV) to afford 74 mg of yellow solid. LC-MS (B): $t_R$=0.69 min. $^1$H-NMR (CDCl$_3$): 8.11 (s, NH); 7.64 (d, 1H, 7.5 Hz); 7.59 (dt, 1H, 1.2 Hz and 7.8 Hz); 7.15 (t, 1H, 7.5 Hz); 6.94 (d, 1H, 7.8 Hz).

187.2. (3,3-Difluoro-2-oxo-2,3-dihydro-indol-1-yl)-acetic acid tert-butyl ester To an ice-cold solution of intermediate 187.1 (71 mg) in THF (2 mL) was added NaH (60%, 25 mg). The mixture was stirred at 0° C. for 15 min and tert-butyl bromoacetate was added. The reaction mixture was stirred at RT for 1 h30, quenched with water and extracted with EA three times. The combined org. layers were washed with water, brine, dried (MgSO$_4$), filtered off and evaporated to dryness to afford 87 mg of yellow oil. LC-MS (B): $t_R$=0.92 min. $^1$H-NMR (CDCl$_3$): 7.60 (dd, 1H, 1.5 Hz and 7.5 Hz); 7.50 (dt, 1H, 1.2 Hz and 8.0 Hz); 7.21 (t, 1H, 7.5 Hz); 6.80 (d, 1H, 8.0 Hz); 4.37 (s, 2H), 1.46 (s, 9H).

187.3. (3,3-Difluoro-2-oxo-2,3-dihydro-indol-1-yl)-acetic acid

This compound was prepared using a method analogous to that of Example 16 step 16.4, intermediate 187.2 replacing intermediate 16.3. LC-MS (B): $t_R$=0.68 min. $^1$H-NMR (CDCl$_3$): 7.62 (d, 1H, 7.8 Hz); 7.52 (t, 1H, 7.5 Hz); 7.24 (t, 1H, 7.5 Hz); 6.84 (d, 1H, 8.0 Hz); 4.53 (s, 2H)

187.4. 1-(2-{(R)-4-[4-(1H-Benzoimidazol-2-yl)-thiazol-5-yl]-2-methyl-piperazin-1-yl}-2-oxo-ethyl)-3,3-difluoro-1,3-dihydro-indol-2-one This compound was prepared using a method analogous to that of Example 1 step 1.5, intermediate 16.4 replacing intermediate 1.4 and intermediate 187.3 replacing benzoimidazol-1-yl-acetic acid. LC-MS (G): $t_R$=0.80 min; [M+H]$^+$: 509.3.

EXAMPLE 188

1-{(R)-4-[4-(1H-Benzoimidazol-2-yl)-thiazol-5-yl]-2-methyl-piperazin-1-yl}-2-(4-phenyl-[1,2,3]triazol-1-yl)-ethanone

188.1. (2-{(R)-4-[4-(1H-Benzoimidazol-2-yl)-thiazol-5-yl]-2-methyl-piperazin-1-yl}-2-oxo-ethyl)-carbamic acid tert-butyl ester This compound was prepared using a method analogous to that of Example 21 step 21.2, intermediate 16.4 replacing intermediate 21.1 and Boc-Gly-OH replacing 2-(1H-pyrrolo[2,3-b]pyridin-1-yl)acetic acid. LC-MS (B): $t_R$=0.66 min; [M+H]$^+$: 457.03.

188.2. 2-Amino-1-{(R)-4-[4-(1H-benzoimidazol-2-yl)-thiazol-5-yl]-2-methyl-piperazin-1-yl}-ethanone This compound was prepared using a method analogous to that of Example 1 step 1.4, intermediate 188.1 replacing intermediate 1.3. However, after removal of the solvents, the residue was taken up in DCM/MeOH, stirred with PL-HCO$_3$ and filtered off. LC-MS (B): $t_R$=0.42 min; [M+H]$^+$: 357.01.

188.3. 1-{(R)-4-[4-(1H-Benzoimidazol-2-yl)-thiazol-5-yl]-2-methyl-piperazin-1-yl}-2-(4-phenyl-[1,2,3]triazol-1-yl)-ethanone To an ice-cold solution of NaN$_3$ (73 mg) in water (0.2 mL) was added toluene (0.2 mL) followed by triflic anhydride (0.092 mL) dropwise. The resulting brown emulsion was vigorously stirred at 0° C. for 2 h. The phases were separated and the aq. layer was extracted with toluene (0.4 mL). The combined org. layers containing triflic azide were washed with sat. NaHCO3 and used directly in the next step. Intermediate 188.2 (80 mg), CuSO$_4$ (×5H$_2$O, 4.65 mg) and NaHCO$_3$ (15.7 mg) were suspended in water (0.4 mL) at RT and the toluene-containing triflic azide solution (0.4 mL) was added followed by iPrOH (4 mL) until the reaction mixture became homogeneous. The resulting greenish suspension was stirred at RT for 1 h30. Phenylacetylene (0.027 mL) and sodium ascorbate (3.7 mg) were added and the reaction mixture was stirred at 80° C. for 2 h. After cooling down EA was added, the phases were separated and the org. phase was washed with sat. NH$_4$Cl and brine. The aq. layers were extracted with EA. The combined org. layers were dried (MgSO$_4$), filtered off and evaporated in vacuo. The residue was purified by preparative LC-MS (VI) to afford 6.5 mg of white solid. LC-MS (G): $t_R$=0.73 min; [M+H]$^+$: 485.3.

EXAMPLE 189

1-{(R)-4-[4-(1H-Benzoimidazol-2-yl)-2-trifluoromethyl-thiazol-5-yl]-2-methyl-piperazin-1-yl}-2-(4-phenyl-[1,2,3]triazol-1-yl)-ethanone This compound was prepared in three steps following the method described in Example 188, intermediate 51.2 replacing intermediate 16.4 in step 188.1. LC-MS (G): $t_R$=0.90 min; [M+H]$^+$: 553.3.

Example 190 to Example 218 were synthesized starting from the appropriate acid precursor and following the procedure described in Example 1 step 1.5, intermediate 51.2 replacing intermediate 1.4. However, prior to the final purification by CC or preparative LC-MS, the reaction mixture was either evaporated to dryness, or was workedup with NaHCO$_3$ or PL-HCO$_3$. The acid precursors were commercially available for Example 190 to 199. For Example 200 to 218, they were synthesized as follows:

PRECURSOR FOR EXAMPLE 200

Intermediate 186.1

PRECURSOR FOR EXAMPLE 201

(3-[1,2,3]Triazol-2-yl-phenyl)-acetic acid

This compound was prepared using a method analogous to that of Example 186 step 186.1, 3-iodophenylacetic acid replacing 2-iodophenylacetic acid. LC-MS (B): $t_R$=0.66 min; [M+H+MeCN]$^+$: 245.07. $^1$H-NMR (CDCl$_3$): 8.07-8.02 (m, 2H); 7.83 (s, 2H); 7.48 (t, 1H, 7.8 Hz); 7.30 (d, 1H, 7.5 Hz); 3.77 (s, 2H).

PRECURSOR FOR EXAMPLE 202

Intermediate 116.2

PRECURSOR FOR EXAMPLE 203

(2-Pyrazol-1-yl-phenyl)-acetic acid

Step 203.1: A mixture of 1-(2-bromophenyl)-1H-pyrazole (230 mg), 2-tert-butoxy-2-oxoethylzinc chloride (0.5M in Et$_2$O, 2.2 mL), Pd(dba)$_2$ (28.8 mg) and 1,2,3,4,5-pentaphenyl-1'-(di-tert-butylphosphino)ferrocene (37.4 mg) in THF (3 mL) was degassed with argon and was stirred at 70° C. overnight. The reaction mixture was diluted with EA and washed with water and brine, dried (Na$_2$SO$_4$), filtered off and evaporated to dryness. The residue was purified by CC (Biotage, SNAP 25 g cartridge, solvent A: Hept; solvent B: EA; gradient in % B: 8 for 4CV, 8 to 66 over 10CV, 66 for 2CV, 66 to 100 over 1CV, 100 for 6CV. Second CC: SNAP 10 g cartridge, solvent A: DCM; solvent B: MeOH; gradient in % B: 0 for 15CV, 0 to 1 over 1CV, 1 for 5CV, 1 to 5 over 1CV, 5 for 2CV, 5 to 10 over 1CV, 10 for 2CV, 10 to 20 over 1CV, 20 for 2CV) to afford 33 mg of (2-pyrazol-1-yl-phenyl)-acetic acid tert-butyl ester. LC-MS (B): $t_R$=0.87 min; [M+H]$^+$: 259.34.

Step 203.2: The final compound was prepared using a method analogous to that of Example 113 step 113.4, 2-(pyrazol-1-yl-phenyl)-acetic acid tert-butyl ester replacing intermediate 113.3. LC-MS (B): $t_R$=0.61 min; [M+H]$^+$: 203.44.

PRECURSOR FOR EXAMPLE 204

(5-Phenyl-pyrazol-1-yl)-acetic acid

Step 204.1: Acetophenone (1.18 mL) and N,N-dimethylformamide diethyl acetal (1.71 mL) were dissolved in DMF (4 mL) and the resulting mixture was stirred at 120° C. for 20 h. The solvent was removed in vacuo and the residue was crystallized in Et$_2$O. The mother liquors were cooled to 0° C. and precipitation occurred. The solid was filtered off and combined with the first batch to afford (E)-3-(dimethylamino)-1-phenylprop-2-en-1-one (1.02 g of yellow solid).

Step 204.2: To a solution of ethyl hydrazinoacetate hydrochloride (866 mg) in EtOH (20 mL) was added (E)-3-(dimethylamino)-1-phenylprop-2-en-1-one (981 mg) and K$_2$CO$_3$ (774 mg). The reaction mixture was stirred at 80° C. for 20 h, cooled down and the pH was brought to 2-3 by adding 1M HCl. EA was added and the phases were separated. The org. layer was washed with brine, dried (Na$_2$SO$_4$) and evaporated in vacuo to afford 720 mg of white solid. LC-MS (B): $t_R$=0.63 min; [M+H]$^+$: 203.43.

PRECURSOR FOR EXAMPLE 205

Intermediate 187.3

PRECURSOR FOR EXAMPLE 206

Imidazo[4,5-c]pyridin-1-yl-acetic acid

See Precursor for Example 138.

PRECURSOR FOR EXAMPLE 207

(3-Bromo-[1,2,4]triazol-1-yl)-acetic acid

This compound was prepared using a method analogous to that of Example 16 step 16.2, ethyl (3-bromo-1H-1,2,4-triazol-1-yl)acetate replacing intermediate 16.1. LC-MS (B): $t_R$=0.29 min; [M+H]$^+$: 205.99.

PRECURSOR FOR EXAMPLE 208

[2-(4-Methyl-piperazin-1-yl)-phenyl]-acetic acid

Step 208.1: 1-(2-Bromophenyl)piperazine (200 mg) was dissolved in formaldehyde (36.5% in water, 0.603 mL) and the solution was stirred 3 h at RT. NaBH$_3$CN (78.2 mg) was added and the mixture was stirred at RT overnight. NaBH$_3$CN (78.2 mg) was added again and the mixture was stirred at RT for 6 h. The solvents were removed in vacuo and the residue was taken up in EA, washed with sat. NaHCO$_3$, dried (Na$_2$SO$_4$) and evaporated to dryness. The residue was purified by CC (Biotage, SNAP 25 g cartridge, solvent A: Hept; solvent B: EA; gradient in % B: 18 for 4CV, 18 to 100 over 10CV, 100 for 2CV, then MeOH flush for 4CV) to afford 1-(2-bromophenyl)-4-methylpiperazine (111 mg, colorless oil). LC-MS (B): $t_R$=0.57 min; [M+H]$^+$: 255.05.

Step 208.2: The final compound was prepared in two steps following the method described in Precursor for Example 203, 1-(2-bromo-phenyl)-4-methyl-piperazine replacing 1-(2-bromophenyl)-1H-pyrazole in step 203.1. LC-MS (B): $t_R$=0.72 min; [M+H]$^+$: 235.20.

PRECURSOR FOR EXAMPLE 209

(5-Methyl-4,5,6,7-tetrahydro-imidazo[4,5-c]pyridin-1-yl)-acetic acid

Step 209.1: To a suspension of 4,5,6,7-tetrahydro-3H-imidazo[4,5-c]pyridine hydrochloride (700 mg) was added DIPEA (2.5 mL) and Boc$_2$O (0.945 mL) at 0° C. The reaction mixture was stirred at 0° C. for 2 h, diluted with DCM and washed with water. The aq. phase was extracted with DCM. The combined org. layers were dried (MgSO$_4$), filtered off and evaporated to dryness. The residue was purified by CC (Biotage, SNAP 25 g cartridge, solvent A: DCM; solvent B: DCM/MeOH 8/2; gradient in % B: 15 for 3CV, 15 to 25 over 3CV, 25 for 5CV) to afford 1,4,6,7-tetrahydro-imidazo[4,5-c]pyridine-5-carboxylic acid tert-butyl ester (298 mg, white solid). LC-MS (B): $t_R$=0.50 min; [M+H]$^+$: 223.96.

Step 209.2: To a solution of 1,4,6,7-tetrahydro-imidazo[4,5-c]pyridine-5-carboxylic acid tert-butyl ester (279 mg) in MeCN (10 mL) was added Cs$_2$CO$_3$ (407 mg) followed by benzyl bromoacetate (0.2 mL). The resulting white suspension was stirred at RT for 48 h, diluted with EA and washed with water and brine. The aq. phases were extracted with EA. The combined org. layers were dried (MgSO$_4$), filtered off and evaporated to dryness. The residue was purified by CC (Biotage, SNAP 25 g cartridge, DCM/MeOH 97/3 for 10CV) to afford 371 mg of oil. The oil was purified by preparative chiral HPLC (I) to afford the two regioisomers, both as mixture of benzyl and ethyl ester that formed during the evaporation of the fractions after HPLC purification:

First eluting compound: 3-Benzyloxycarbonylmethyl-3,4, 6,7-tetrahydro-imidazo[4,5-c]pyridine-5-carboxylic acid tert-butyl ester (131 mg, contains 20% of the ethyl ester, brown resin). LC-MS (B): $t_R$=0.71 min; [M+H]$^+$: 371.96. $^1$H-NMR (CDCl$_3$): 7.45-7.35 (m, 6H); 5.23 (s, 1.6H, CH$_2$ of benzyl ester); 4.67-4.57 (m, 2H); 4.41 (s, 2H); 3.71 (s, 2H); 2.72 (s, 2H); 1.50 (s, 9H). Roesy signal seen between CH$_2$ at 4.67-4.57 ppm and CH$_2$ at 4.41 ppm.

Second eluting compound: 1-Benzyloxycarbonylmethyl-1,4,6,7-tetrahydro-imidazo[4,5-c]pyridine-5-carboxylic acid tert-butyl ester (200 mg, contains 65% of the ethyl ester, brown resin). LC-MS (B): $t_R$=0.71 min; [M+H]$^+$: 371.96. $^1$H-NMR (CDCl$_3$): 7.43-7.32 (m, 6H); 5.22 (s, 0.7H, CH$_2$ of benzyl ester); 4.62 (s, 0.7H); 4.58 (s, 1.3H); 4.48 (s, 2H); 3.74 (m, 2H); 2.54 (m, 2H); 1.49 (s, 9H). Roesy signal seen between CH$_2$ at 4.62 and 4.58 ppm and CH$_2$ at 2.54 ppm.

Step 209.3: The Boc protecting group of 1-benzyloxycarbonylmethyl-1,4,6,7-tetrahydro-imidazo[4,5-c]pyridine-5-carboxylic acid tert-butyl ester was cleaved using a method analogous to that of Example 16 step 16.4 to give (4,5,6,7-tetrahydro-imidazo[4,5-c]pyridin-1-yl)-acetic acid benzyl ester. LC-MS (B): $t_R$=0.44 min; [M+H]$^+$: 272.04.

Step 209.4: To a solution of (4,5,6,7-tetrahydro-imidazo[4,5-c]pyridin-1-yl)-acetic acid benzyl ester (176 mg) in MeOH was added formaldehyde (36.5% in water, 0.052 mL) followed by NaBH$_3$CN (29 mg) and AcOH (0.5 mL). The reaction mixture was stirred at RT overnight. DCM was added and the mixture was washed with sat. NaHCO$_3$. The aq. layer was extracted with DCM, the combined org. layers were dried (MgSO$_4$), filtered off and evaporated to dryness. The residue was purified by CC (Biotage, SNAP 10 g cartridge, solvent A: DCM; solvent B: DCM/MeOH 8/2; gradient in % B: 25 for 3CV, 25 to 50 over 2CV, 50 for 5CV, 50 to 100 over 3CV, 100 for 2CV) to afford (5-methyl-4,5,6,7-tetrahydro-imidazo[4,5-c]pyridin-1-yl)-acetic acid benzyl ester (39 mg, yellow oil). LC-MS (B): $t_R$=0.46 min; [M+H]$^+$: 286.16.

Step 209.5: The final compound was prepared using a method analogous to that of Example 14 step 14.2, (5-methyl-4,5,6,7-tetrahydro-imidazo[4,5-c]pyridin-1-yl)acetic acid benzyl ester replacing intermediate 14.1 and using EtOH instead of MeOH/AcOH. LC-MS (B): $t_R$=0.13 min; [M+H]$^+$: 196.31.

PRECURSOR FOR EXAMPLE 210

(5-Methyl-4,5,6,7-tetrahydro-imidazo[4,5-c]pyridin-3-yl)-acetic acid

This compound was prepared in three steps following the method described in Precursor for Example 209 step 209.3 to step 209.5, 3-benzyloxycarbonylmethyl-3,4,6,7-tetrahydro-imidazo[4,5-c]pyridine-5-carboxylic acid tert-butyl ester replacing 1-benzyloxycarbonylmethyl-1,4,6,7-tetrahydro-imidazo[4,5-c]pyridine-5-carboxylic acid tert-butyl ester in step 209.3. LC-MS (B): $t_R$=0.13 min; [M+H]$^+$: 196.28.

PRECURSOR FOR EXAMPLE 211

(4-Dimethylaminomethyl-3-methyl-pyrazol-1-yl)-acetic acid

Step 211.1: A suspension of (3-methyl-1H-pyrazol-1-yl) acetic acid (200 mg) and H$_2$SO$_4$ (0.1 mL) in EtOH (2 mL) was stirred at 80° C. for 4 h. After cooling down, the reaction mixture was diluted with DCM and washed with sat. Na$_2$CO$_3$, water and brine. The aq. layers were extracted with DCM, the combined org. layers were dried (MgSO$_4$), filtered off and evaporated in vacuo to afford ethyl 2-(3-methyl-1H-pyrazol-1-yl)acetate (101 mg, colourless liquid). LC-MS (B): $t_R$=0.57 min; [M+H]$^+$: 169.01.

Step 211.2: To a solution of ethyl 2-(3-methyl-1H-pyrazol-1-yl)acetate (94 mg) and DMF (1.5 mL) in MeCN (3 mL) was added N,N-dimethylmethyleneiminium iodide (390 mg). The reaction mixture was stirred at 90° C. overnight. After cooling down, the reaction mixture was diluted with DCM and washed with sat. NaHCO$_3$ and water. The aq. layers were extracted with DCM, the combined org. layers were dried (MgSO$_4$), filtered off and evaporated in vacuo to afford ethyl 2-(4-((dimethylamino)methyl)-3-methyl-1H-pyrazol-1-yl) acetate (112 mg, brown oil). LC-MS (B): $t_R$=0.39 min; [M+H]$^+$: 226.23.

Step 211.3: The final compound (4-dimethylaminomethyl-3-methyl-pyrazol-1-yl)-acetic acid was prepared using a method analogous to that of Example 16 step 16.2, ethyl 2-(4-((dimethylamino)methyl)-3-methyl-1H-pyrazol-1-yl) acetate replacing intermediate 16.1. LC-MS (B): $t_R$=0.20 min; [M+H]$^+$: 198.31. $^1$H-NMR (CD$_3$OD): 7.47 (s, 1H); 4.62 (s, 2H); 3.36 (s, 2H); 2.25 (s, 6H); 2.21 (s, 3H). Roesy signals seen between the proton at 7.47 ppm and the CH$_2$ at 4.62 ppm, the CH$_2$ at 3.36 ppm and the methyl group at 2.25 ppm.

PRECURSOR FOR EXAMPLE 212

(5-Methyl-[1,2,4]triazol-1-yl)-acetic acid

Step 212.1: To a solution of 3-methyl-1H-1,2,4-triazole (1 g) in MeCN (40 mL) was added Cs$_2$CO$_3$ (3.72 g) followed by benzyl bromoacetate (1.89 mL). The reaction mixture was stirred at RT for 1 h and evaporated to dryness. The residue was taken up in EA and washed with water, sat. NH$_4$Cl and brine. The aq. layers were extracted with EA, the combined org. layers were dried (MgSO$_4$), filtered off and evaporated in vacuo. The residue was purified by CC (Biotage, SNAP 100 g cartridge, solvent A: DCM; solvent B: DCM/MeOH 8/2; gradient in % B: 15 for 12CV, 15 to 25 over 2CV, 25 for 3CV) to afford 2.23 g of oil. The oil was purified by preparative chiral HPLC (II) to afford the two regioisomers, both as mixture of benzyl and ethyl ester that formed during the evaporation of the fractions after HPLC purification. The second eluting compound also contains the methyl ester analog due to the addition of MeOH to the fractions before evaporation.

First eluting compound: (5-Methyl-[1,2,4]triazol-1-yl)-acetic acid benzyl ester (1.07 g, brown oil, contains 16% of the ethyl ester analog). LC-MS (B): $t_R$=0.68 min; [M+H]$^+$: 232.16. $^1$H-NMR (CDCl$_3$): 7.83 (s, 1H); 7.40-7.33 (m, 5H); 5.23 (s, 2H); 4.93 (s, 2H); 2.43 (s, 3H). Roesy signal seen between CH$_2$ at 4.93 ppm and CH$_3$ at 2.43 ppm.

Second eluting compound: (3-Methyl-[1,2,4]triazol-1-yl)-acetic acid benzyl ester (1.15 g, yellow oil, contains 30% of the ethyl ester and 20% of the methyl ester analogs). LC-MS (B): $t_R$=0.67 min; [M+H]$^+$: 232.16. $^1$H-NMR (CDCl$_3$): 8.05 (s, 1H); 7.40-7.30 (m, 5H); 5.23 (s, 0.95H, CH$_2$ of benzyl ester); 4.93-4.88 (3s, 2H); 4.27 (q, 0.58H, CH₂ of ethyl ester); 3.81 (s, 0.65H, CH₃ of methyl ester); 2.42 (s, 3H). Roesy signal seen between CH at 8.05 ppm and CH₂ at 4.93-4.88 ppm.

Step 212.2: The final compound (5-methyl-[1,2,4]triazol-1-yl)-acetic acid was prepared using a method analogous to that of Example 14 step 14.2, (5-methyl-[1,2,4]triazol-1-yl)-acetic acid benzyl ester replacing intermediate 14.1 and using EtOH instead of MeOH/AcOH. LC-MS (B): $t_R$=0.19 min; [M+H]⁺: 142.24.

PRECURSOR FOR EXAMPLE 213

(3-Methyl-[1,2,4]triazol-1-yl)-acetic acid

This compound was prepared using a method analogous to that of Example 14 step 14.2, (3-methyl-[1,2,4]triazol-1-yl) acetic acid benzyl ester (described in Precursor for Example 212 step 212.1) replacing intermediate 14.1 and using EtOH instead of MeOH/AcOH. LC-MS (B): $t_R$=0.18 min; [M+H]⁺: 142.22.

PRECURSOR FOR EXAMPLE 214 benzyl 2-(3,5-dimethyl-1H-pyrazol-1-yl)acetate

Step 214.1: A mixture of (3,5-dimethyl-1H-pyrazol-1-yl) acetic acid (600 mg), benzyl alcohol (0.402 mL), DMAP (194 mg) and DCC (802 mg) in MeCN (40 mL) was stirred at RT overnight. The suspension was filtered off and the resulting solution was evaporated to dryness. The residue was purified by CC (Hept/EA 7/3) to afford benzyl 2-(3,5-dimethyl-1H-pyrazol-1-yl)acetate (460 mg, white solid). LC-MS (B): $t_R$=0.80 min; [M+H]⁺: 245.18.

Step 214.2: This compound was reacted with N,N-dimethylmethyleneiminium iodide following the method described in Precursor for Example 211 step 211.2 to afford benzyl 2-(4-((dimethylamino)methyl)-3,5-dimethyl-1H-pyrazol-1-yl)acetate. LC-MS (B): $t_R$=0.57 min; [M+H]⁺: 302.12. ¹H-NMR (CD₃OD): 7.35 (m, 5H); 5.20 (s, 2H); 4.94 (s, 2H); 3.28 (s, 2H); 2.21 (s, 6H); 2.20 (d, 6H).

Step 214.3: The final compound was prepared using a method analogous to that of Example 14 step 14.2, benzyl 2-(4-((dimethylamino)methyl)-3,5-dimethyl-1H-pyrazol-1-yl)acetate replacing intermediate 14.1 and using EtOH instead of MeOH/AcOH. LC-MS (B): $t_R$=0.23 min; [M+H]⁺: 212.17.

PRECURSOR FOR EXAMPLE 215

(5-Methyl-4,5,6,7-tetrahydro-pyrazolo[4,3-c]pyridin-2-yl)-acetic acid

Step 215.1: tert-Butyl 6,7-dihydro-1H-pyrazolo[4,3-c]pyridine-5(4H)-carboxylate (500 mg) was submitted to alkylation with benzyl bromoacetate, followed by cleavage of the Boc protecting group and subsequent methylation of the free amine using a method analogous to that of Precursor for Example 209 step 209.2 to step 209.4. However, the mixture of regioisomers was separated at the end of the three steps (Biotage, DCM/MeOH/TEA) to afford the two isomers:

(5-Methyl-4,5,6,7-tetrahydro-pyrazolo[4,3-c]pyridin-2-yl)-acetic acid benzyl ester (111 mg, colourless oil). LC-MS (B): $t_R$=0.54 min; [M+H]⁺: 286.16. ¹H-NMR (CDCl₃): 7.40-7.33 (m, 5H); 7.18 (s, 1H); 5.21 (s, 2H); 4.89 (s, 2H); 3.50 (s, 2H); 2.86 (t, 2H, 6.0 Hz); 2.76 (t, 2H, 5.5 Hz); 2.49 (s, 3H). Roesy signal seen between CH₂ at 4.89 ppm and CH at 7.18 ppm.

(5-Methyl-4,5,6,7-tetrahydro-pyrazolo[4,3-c]pyridin-1-yl)-acetic acid benzyl ester (45 mg, pale yellow solid). LC-MS (B): $t_R$=0.54 min; [M+H]⁺: 286.16. ¹H-NMR (CDCl₃): 7.40-7.33 (m, 6H); 5.21 (s, 2H); 4.85 (s, 2H); 3.47 (s, 2H); 2.75 (t, 2H, 6.0 Hz); 2.67 (t, 2H, 5.5 Hz); 2.49 (s, 3H). Roesy signal seen between CH₂ at 4.85 ppm and CH₂ at 2.67 ppm.

Step 215.2: The final compound was prepared using a method analogous to that of Example 14 step 14.2, (5-methyl-4,5,6,7-tetrahydro-pyrazolo[4,3-c]pyridin-2-yl)-acetic acid benzyl ester replacing intermediate 14.1 and using MeOH instead of MeOH/AcOH. LC-MS (B): $t_R$=0.17 min; [M+H]⁺: 196.29.

PRECURSOR FOR EXAMPLE 216

(5-Methyl-4,5,6,7-tetrahydro-pyrazolo[4,3-c]pyridin-1-yl)-acetic acid

This compound was prepared using a method analogous to that of Example 14 step 14.2, (5-methyl-4,5,6,7-tetrahydro-pyrazolo[4,3-c]pyridin-1-yl)-acetic acid benzyl ester (described in Precursor for Example 215) replacing intermediate 14.1 and using MeOH instead of MeOH/AcOH. LC-MS (B): $t_R$=0.16 min; [M+H]⁺: 196.27.

PRECURSOR FOR EXAMPLE 217

(1,4,6,7-Tetrahydro-pyrazolo[4,3-c]pyridin-5-yl)-acetic acid

Step 217.1: The Boc protecting group of tert-butyl 6,7-dihydro-1H-pyrazolo[4,3-c]pyridine-5(4H)-carboxylate was cleaved using a method analogous to that of Example 16 step 16.4 to give 4,5,6,7-tetrahydro-1H-pyrazolo[4,3-c]pyridine. LC-MS (B): $t_R$=0.15 min; [M+H]⁺: 124.12.

Step 217.2: To a solution of 4,5,6,7-tetrahydro-1H-pyrazolo[4,3-c]pyridine (300 mg) in MeCN (10 mL) was added Cs₂CO₃ (1.49 g) followed by benzyl bromoacetate (0.253 mL). The reaction mixture was stirred at RT overnight and evaporated to dryness. The residue was taken up in EA and washed with water and brine. The aq. layers were extracted with EA, the combined org. layers were dried (MgSO₄), filtered off and evaporated in vacuo. The residue was purified by CC (Biotage, SNAP 10 g cartridge, solvent A: DCM; solvent B: DCM/MeOH 8/2; gradient in % B: 15 for 7CV, 15 to 25 over 3CV, 25 for 5CV) to afford (1,4,6,7-tetrahydro-pyrazolo[4,3-c]pyridin-5-yl)acetic acid benzyl ester (218 mg, pale yellow oil). LC-MS (B): $t_R$=0.50 min; [M+H]⁺: 272.12. ¹H-NMR (CDCl₃): 7.40-7.33 (m, 5H); 7.30 (s, 1H); 5.21 (s, 2H); 3.73 (s, 2H); 3.52 (s, 2H); 3.50 (s, 1H); 2.98 (t, 2H, 6.0 Hz); 2.85 (t, 2H, 5.8 Hz).

Step 217.3: The final compound was prepared using a method analogous to that of Example 14 step 14.2, (1,4,6,7-tetrahydro-pyrazolo[4,3-c]pyridin-5-yl)acetic acid benzyl ester replacing intermediate 14.1 and using EtOH instead of MeOH/AcOH. LC-MS (B): $t_R$=0.15 min; [M+H]⁺: 182.30.

PRECURSOR FOR EXAMPLE 218

(3-Dimethylaminomethyl-5-methyl-[1,2,4]triazol-1-yl)-acetic acid

Step 218.1: To a suspension of ethyl acetimidate hydrochloride (492 mg) in MeCN (10 mL) was added Amberlyst A21 (1.12 g). The suspension was stirred at RT for 15 min, filtered off and tert-butyl(2-hydrazino-2-oxoethyl)methylcarbamate (0.761 mL) was added to the filtrate. The reaction mixture was stirred at 50° C. for 92 h and at 100° C. for 8 h and was evaporated to dryness. The residue was purified by CC (silica gel, EA/MeOH 1/0 to 9/1) to afford methyl-(5-methyl-1H-[1,2,4]triazol-3-ylmethyl)-carbamic acid tert-butyl ester (520 mg, yellow oil). LC-MS (B): $t_R$=0.54 min; [M+H]$^+$: 227.08.

Step 218.2: To a solution of methyl-(5-methyl-1H-[1,2,4]triazol-3-ylmethyl)-carbamic acid tert-butyl ester (470 mg) in MeCN (20 mL) was added Cs$_2$CO$_3$ (677 mg) followed by benzyl bromoacetate (0.343 mL). The reaction mixture was stirred at RT overnight and evaporated to dryness. The residue was taken up in DCM and washed with water. The aq. layers were extracted with DCM, the combined org. layers were dried (Na$_2$SO$_4$), filtered off and evaporated in vacuo. The residue was purified by CC (silica gel, Hept/EA 1/1 then DCM/MeOH 9/1) to afford benzyl 2-(3-(((tert-butoxycarbonyl)(methyl)amino)methyl)-5-methyl-1H-1,2,4-triazol-1-yl)acetate (290 mg, yellow oil). LC-MS (B): $t_R$=0.83 min; [M+H]$^+$: 375.14. $^1$H-NMR (CD$_3$OD): 7.39-7.35 (m, 5H); 5.24 (s, 2H); 5.09 (s, 2H); 4.43 (m, 2H); 2.89 (m, 3H); 2.41 (s, 3H); 1.44 (d, 9H). Roesy signal seen between CH$_2$ at 5.09 ppm and CH$_3$ at 2.41 ppm.

Step 218.3: The Boc protecting group of benzyl 2-(3-(((tert-butoxycarbonyl)(methyl)amino)methyl)-5-methyl-1H-1,2,4-triazol-1-yl)acetate was cleaved using a method analogous to that of Example 16 step 16.4 to give (5-methyl-3-methylaminomethyl-[1,2,4]triazol-1-yl)-acetic acid benzyl ester. LC-MS (B): $t_R$=0.53 min; [M+H]$^+$: 275.08.

Step 218.4: A solution of 5-methyl-3-methylaminomethyl-[1,2,4]triazol-1-yl)-acetic acid benzyl ester (250 mg) and formaldehyde (36.5% in water, 27.4 mg) in DCM (8 mL) was stirred at RT overnight. NaBH(OAc)$_3$ (272 mg) was added and the reaction mixture was stirred at RT for 1 h, diluted with DCM and washed with water. The aq. phase was extracted with DCM and evaporated in vacuo to afford (3-dimethylaminomethyl-5-methyl-[1,2,4]triazol-1-yl)-acetic acid benzyl ester (150 mg, colourless oil). LC-MS (B): $t_R$=0.54 min; [M+H]$^+$: 289.11.

Step 218.5: The final compound was prepared using a method analogous to that of Example 14 step 14.2, (3-dimethylaminomethyl-5-methyl-[1,2,4]triazol-1-yl)-acetic acid benzyl ester replacing intermediate 14.1 and using EtOH instead of MeOH/AcOH. LC-MS (B): $t_R$=0.15 min; [M+H]$^+$: 199.16.

LC-MS data of Example 190 to Example 218 are listed in the table below. The LC-MS conditions used were LC-MS (G).

| Example No | Name | $t_R$ | [M + H]$^+$ |
|---|---|---|---|
| 190 | 1-{(R)-4-[4-(1H-Benzoimidazol-2-yl)-2-trifluoromethyl-thiazol-5-yl]-2-methyl-piperazin-1-yl}-2-quinolin-8-yl-ethanone | 0.81 | 537.3 |
| 191 | 1-{(R)-4-[4-(1H-Benzoimidazol-2-yl)-2-trifluoromethyl-thiazol-5-yl]-2-methyl-piperazin-1-yl}-2-(4-methyl-pyrazol-1-yl)-ethanone | 0.80 | 490.3 |
| 192 | 1-{(R)-4-[4-(1H-Benzoimidazol-2-yl)-2-trifluoromethyl-thiazol-5-yl]-2-methyl-piperazin-1-yl}-2-(3,5-dimethyl-pyrazol-1-yl)-ethanone | 0.79 | 504.3 |
| 193 | 1-{(R)-4-[4-(1H-Benzoimidazol-2-yl)-2-trifluoromethyl-thiazol-5-yl]-2-methyl-piperazin-1-yl}-2-(3-trifluoromethyl-pyrazol-1-yl)-ethanone | 0.94 | 544.3 |
| 194 | 1-{(R)-4-[4-(1H-Benzoimidazol-2-yl)-2-trifluoromethyl-thiazol-5-yl]-2-methyl-piperazin-1-yl}-2-[1,2,4]triazol-1-yl-ethanone | 0.68 | 477.3 |
| 195 | 1-{(R)-4-[4-(1H-Benzoimidazol-2-yl)-2-trifluoromethyl-thiazol-5-yl]-2-methyl-piperazin-1-yl}-2-(5-methyl-[1,3,4]oxadiazol-2-yl)-ethanone | 0.72 | 492.3 |
| 196 | 1-{(R)-4-[4-(1H-Benzoimidazol-2-yl)-2-trifluoromethyl-thiazol-5-yl]-2-methyl-piperazin-1-yl}-2-(5-phenyl-[1,3,4]oxadiazol-2-yl)-ethanone | 0.90 | 554.3 |
| 197 | 1-{(R)-4-[4-(1H-Benzoimidazol-2-yl)-2-trifluoromethyl-thiazol-5-yl]-2-methyl-piperazin-1-yl}-2-[1,2,3]triazol-2-yl-ethanone | 0.75 | 477.3 |
| 198 | 1-(2-{(R)-4-[4-(1H-Benzoimidazol-2-yl)-2-trifluoromethyl-thiazol-5-yl]-2-methyl-piperazin-1-yl}-2-oxo-ethyl)-1H-pyrazole-3-carboxylic acid methyl ester | 0.79 | 534.3 |
| 199 | 1-{(R)-4-[4-(1H-Benzoimidazol-2-yl)-2-trifluoromethyl-thiazol-5-yl]-2-methyl-piperazin-1-yl}-2-(6-methyl-pyridin-3-yl)-ethanone | 0.65 | 501.3 |
| 200 | 1-{(R)-4-[4-(1H-Benzoimidazol-2-yl)-2-trifluoromethyl-thiazol-5-yl]-2-methyl-piperazin-1-yl}-2-(2-[1,2,3]triazol-2-yl-phenyl)-ethanone | 0.92 | 553.3 |
| 201 | 1-{(R)-4-[4-(1H-Benzoimidazol-2-yl)-2-trifluoromethyl-thiazol-5-yl]-2-methyl-piperazin-1-yl}-2-(3-[1,2,3]triazol-2-yl-phenyl)-ethanone | 0.94 | 553.3 |
| 202 | 1-{(R)-4-[4-(1H-Benzoimidazol-2-yl)-2-trifluoromethyl-thiazol-5-yl]-2-methyl-piperazin-1-yl}-2-pyrazolo[3,4-b]pyridin-2-yl-ethanone | 0.68 | 527.3 |

-continued

| Example No | Name | $t_R$ | $[M + H]^+$ |
|---|---|---|---|
| 203 | 1-{(R)-4-[4-(1H-Benzoimidazol-2-yl)-2-trifluoromethyl-thiazol-5-yl]-2-methyl-piperazin-1-yl}-2-(2-pyrazol-1-yl-phenyl)-ethanone | 0.91 | 552.3 |
| 204 | 1-{(R)-4-[4-(1H-Benzoimidazol-2-yl)-2-trifluoromethyl-thiazol-5-yl]-2-methyl-piperazin-1-yl}-2-(5-phenyl-pyrazol-1-yl)-ethanone | 0.94 | 552.3 |
| 205 | 1-(2-{(R)-4-[4-(1H-Benzoimidazol-2-yl)-2-trifluoromethyl-thiazol-5-yl]-2-methyl-piperazin-1-yl}-2-oxo-ethyl)-3,3-difluoro-1,3-dihydro-indol-2-one | 0.97 | 577.3 |
| 206 | 1-{(R)-4-[4-(1H-Benzoimidazol-2-yl)-2-trifluoromethyl-thiazol-5-yl]-2-methyl-piperazin-1-yl}-2-imidazo[4,5-c]pyridin-1-yl-ethanone | 0.63 | 527.3 |
| 207 | 1-{(R)-4-[4-(1H-Benzoimidazol-2-yl)-2-trifluoromethyl-thiazol-5-yl]-2-methyl-piperazin-1-yl}-2-(3-bromo-[1,2,4]triazol-1-yl)-ethanone | 0.80 | 555.2 |
| 208 | 1-{(R)-4-[4-(1H-Benzoimidazol-2-yl)-2-trifluoromethyl-thiazol-5-yl]-2-methyl-piperazin-1-yl}-2-[2-(4-methyl-piperazin-1-yl)-phenyl]-ethanone | 0.75 | 584.4 |
| 209 | 1-{(R)-4-[4-(1H-Benzoimidazol-2-yl)-2-trifluoromethyl-thiazol-5-yl]-2-methyl-piperazin-1-yl}-2-(5-methyl-4,5,6,7-tetrahydro-imidazo[4,5-c]pyridin-1-yl)-ethanone | 0.59 | 545.3 |
| 210 | 1-{(R)-4-[4-(1H-Benzoimidazol-2-yl)-2-trifluoromethyl-thiazol-5-yl]-2-methyl-piperazin-1-yl}-2-(5-methyl-4,5,6,7-tetrahydro-imidazo[4,5-c]pyridin-3-yl)-ethanone | 0.58 | 545.2 |
| 211 | 1-{(R)-4-[4-(1H-Benzoimidazol-2-yl)-2-trifluoromethyl-thiazol-5-yl]-2-methyl-piperazin-1-yl}-2-(4-dimethylaminomethyl-3-methyl-pyrazol-1-yl)-ethanone | 0.64 | 547.4 |
| 212 | 1-{(R)-4-[4-(1H-Benzoimidazol-2-yl)-2-trifluoromethyl-thiazol-5-yl]-2-methyl-piperazin-1-yl}-2-(5-methyl-[1,2,4]triazol-1-yl)-ethanone | 0.68 | 491.3 |
| 213 | 1-{(R)-4-[4-(1H-Benzoimidazol-2-yl)-2-trifluoromethyl-thiazol-5-yl]-2-methyl-piperazin-1-yl}-2-(3-methyl-[1,2,4]triazol-1-yl)-ethanone | 0.69 | 491.3 |
| 214 | 1-{(R)-4-[4-(1H-Benzoimidazol-2-yl)-2-trifluoromethyl-thiazol-5-yl]-2-methyl-piperazin-1-yl}-2-(4-dimethylaminomethyl-3,5-dimethyl-pyrazol-1-yl)-ethanone | 0.65 | 561.3 |
| 215 | 1-{(R)-4-[4-(1H-Benzoimidazol-2-yl)-2-trifluoromethyl-thiazol-5-yl]-2-methyl-piperazin-1-yl}-2-(5-methyl-4,5,6,7-tetrahydro-pyrazolo[4,3-c]pyridin-2-yl)-ethanone | 0.63 | 545.2 |
| 216 | 1-{(R)-4-[4-(1H-Benzoimidazol-2-yl)-2-trifluoromethyl-thiazol-5-yl]-2-methyl-piperazin-1-yl}-2-(5-methyl-4,5,6,7-tetrahydro-pyrazolo[4,3-c]pyridin-1-yl)-ethanone | 0.62 | 545.3 |
| 217 | 1-{(R)-4-[4-(1H-Benzoimidazol-2-yl)-2-trifluoromethyl-thiazol-5-yl]-2-methyl-piperazin-1-yl}-2-(1,4,6,7-tetrahydro-pyrazolo[4,3-c]pyridin-5-yl)-ethanone | 0.63 | 531.4 |
| 218 | 1-{(R)-4-[4-(1H-Benzoimidazol-2-yl)-2-trifluoromethyl-thiazol-5-yl]-2-methyl-piperazin-1-yl}-2-(3-dimethylaminomethyl-5-methyl-[1,2,4]triazol-1-yl)-ethanone | 0.64 | 548.4 |

EXAMPLE 219

1-{(R)-4-[4-(1H-Benzoimidazol-2-yl)-2-trifluoromethyl-thiazol-5-yl]-2-methyl-piperazin-1-yl}-2-(4,6-di methyl-pyridin-2-yl)-ethanone

219.1. 2-(2,6-Dimethyl-pyridin-4-yl)acetic acid

To a solution of lithium diisopropylamide (2M in THF/Hept/ethylbenzene, 5 mL) was added a solution of 2,4,6-collidine (1.26 mL) in THF (5 mL). The reaction mixture was stirred at RT for 4 h and added dropwise to a solution of diethylcarbonate (1.38 mL) in THF (5 mL) over 15 min. The resulting mixture was stirred at RT for 20 h. A LiOH solution (1M in water, 28 mL) was added, the mixture was stirred at RT for 2 h and filtered off. The filtrate was evaporated in vacuo. The residue was purified by preparative LC-MS (X) to afford 30 mg of yellow oil as mixture of two regioisomers. LC-MS (E): $t_R$=0.17 min; [M+H]$^+$: 165.97.

219.2. 1-{(R)-4-[4-(1H-Benzoimidazol-2-yl)-2-trifluoromethyl-thiazol-5-yl]-2-methyl-piperazin-1-yl}-2-(4,6-dimethyl-pyridin-2-yl)-ethanone To a mixture of intermediate 219.1 (30 mg) and intermediate 51.2 (80 mg) in DMF (3.1 mL) was added HATU (76 mg) and DIPEA (0.128 mL). The reaction mixture was stirred at RT for 20 h and PL-HCO$_3$ (1.87 mmol/g, 200 mg) was added. After stirring for 1 h, the mixture was filtered off, the resin was washed with DCM and the filtrate was evaporated in vacuo. The residue was purified by preparative LC-MS (III) to afford 5 mg of pale yellow oil. LC-MS (G): $t_R$=0.68 min; [M+H]$^+$: 515.3. $^1$H-NMR (CDCl$_3$): 10.1 (s, NH); 7.75 (d, 1H, 7.0 Hz); 7.51 (d, 1H, 6.8 Hz); 7.30 (m, 2H); 6.91 (s, 2H); 5.04 (s, 0.5H); 4.68 (d, 0.5H); 4.24-3.69 (m, 5.5H); 3.49 (m, 0.5H); 3.06 (d, 0.5H); 2.93-2.82 (m, 1H); 2.69 (m, 0.5H); 2.54 (s, 6H); 1.66 (d, 1.5H); 1.56 (d, 1.5H).

EXAMPLE 220

1-{(R)-4-[4-(1H-Benzoimidazol-2-yl)-2-trifluoromethyl-thiazol-5-yl]-2-methyl-piperazin-1-yl}-2-(2,6-di methyl-pyridin-4-yl)-ethanone This compound was obtained as second regioisomer after the purification by preparative LC-MS described in Example 219 step 219.2 (4 mg, pale yellow oil). LC-MS (G): $t_R$=0.67 min; [M+H]$^+$: 515.3. $^1$H-NMR (CDCl$_3$): 10.0 (s, NH); 7.75 (m, 1H); 7.49 (m, 1H); 7.30 (m, 2H); 7.03 (m, 1H); 6.89 (s, 1H); 5.01 (s, 0.5H); 4.66 (m, 1H); 4.15 (m, 0.5H); 4.04-3.75 (m, 4.5H); 3.46 (m, 0.5H); 2.98 (m, 0.5H); 2.89-2.79 (m, 1H); 2.72 (m, 0.5H); 2.49 (d, 3H); 2.31 (s, 3H); 1.57 (m, 3H).

EXAMPLE 221

1-{(R)-4-[4-(1H-Benzoimidazol-2-yl)-2-trifluoromethyl-thiazol-5-yl]-2-methyl-piperazin-1-yl}-2-(4-piperidin-4-yl-pyrazol-1-yl)-ethanone

221.1. 4-(1-Carboxymethyl-1H-pyrazol-4-yl)-3,6-dihydro-2H-pyridine-1-carboxylic acid tert-butyl ester A mixture of 2-(4-bromo-1H-pyrazol-1-yl)acetic acid (867 mg), tert-butyl 4-(4,4,5,5-tetramethyl-1,3,2-dioxaborolan-2-yl)-5,6-dihydropyridine-1(2H)-carboxylate (1.2 g) and Pd(PPh$_3$)$_4$ (232 mg) in dioxane (15 mL) and sat. K$_2$CO$_3$ (7.5 mL) was heated at 100° C. overnight. After cooling down, EA was added and the mixture was washed with water and brine. The combined aq. layers were acidified to pH=2 with NaHSO$_4$ and extracted with EA. The org. layers from the second extraction were dried (MgSO$_4$), filtered off and evaporated in vacuo to afford 1.05 g of brown resin that was used without purification. LC-MS (B): $t_R$=0.72 min; [M+H]$^+$: 308.26.

221.2. 2-(4-(1-(tert-butoxycarbonyl)piperidin-4-yl)-1H-pyrazol-1-yl)acetic acid This compound was prepared using a method analogous to that of Example 14 step 14.2, intermediate 221.1 replacing intermediate 14.1 and using EtOH instead of MeOH/AcOH. LC-MS (B): $t_R$=0.72 min; [M+H]$^+$: 310.10.

221.3. 4-[1-(2-{(R)-4-[4-(1H-Benzoimidazol-2-yl)-2-trifluoromethyl-thiazol-5-yl]-2-methyl-piperazin-1-yl}-2-oxo-ethyl)-1H-pyrazol-4-yl]-piperidine-1-carboxylic acid tert-butyl ester This compound was prepared using a method analogous to that of Example 1 step 1.5, intermediate 51.2 replacing intermediate 1.4 and intermediate 221.2 replacing benzoimidazol-1-yl-acetic acid. LC-MS (B): $t_R$=0.85 min; [M+H]$^+$: 658.99.

221.4. 1-{(R)-4-[4-(1H-Benzoimidazol-2-yl)-2-trifluoromethyl-thiazol-5-yl]-2-methyl-piperazin-1-yl}-2-(4-piperidin-4-yl-pyrazol-1-yl)-ethanone This compound was prepared using a method analogous to that of Example 113 step 113.4, intermediate 221.3 replacing intermediate 113.3. LC-MS (G): $t_R$=0.64 min; [M+H]$^+$: 559.4.

EXAMPLE 222

1-{(R)-4-[4-(1H-Benzoimidazol-2-yl)-2-trifluoromethyl-thiazol-5-yl]-2-methyl-piperazin-1-yl}-2-[4-(1-methyl-piperidin-4-yl)-pyrazol-1-yl]-ethanone This compound was prepared using a method analogous to that of Precursor for Example 209 step 209.4, Example 221 replacing (4,5,6,7-tetrahydro-imidazo[4,5-c]pyridin-1-yl) acetic acid benzyl ester. LC-MS (G): $t_R$=0.64 min; [M+H]$^+$: 573.5.

EXAMPLE 223

1-{(R)-4-[4-(1H-Benzoimidazol-2-yl)-2-dimethylaminomethyl-thiazol-5-yl]-2-methyl-piperazin-1-yl}-2-imidazo[4,5-b]pyridin-3-yl-ethanone

223.1. (R)-4-(2-Dimethylaminomethyl-4-methoxycarbonyl-thiazol-5-yl)-2-methyl-piperazine-1-carboxylic acid tert-butyl ester This compound was prepared using a method analogous to that of Precursor for Example 211 step 211.2, intermediate 16.1 replacing (3-methyl-pyrazol-1-yl)-acetic acid ethyl ester. CC purification (Biotage, SNAP 25 g cartridge, solvent A: DCM; solvent B: DCM/MeOH 8/2; gradient in % B: 0 for 2CV, 0 to 10 over 5CV, 10 for 3CV, 10 to 20 over 5CV, 20 for 3CV, 20 to 30 over 5CV, 30 for 3CV) was however performed. LC-MS (C): $t_R$=0.58 min; [M+H]$^+$: 399.41.

223.2. (R)-4-(4-Carboxy-2-dimethylaminomethyl-thiazol-5-yl)-2-methyl-piperazine-1-carboxylic acid tert-butyl ester To a solution of intermediate 223.1 (200 mg) in MeOH/EtOH (0.7 mL/1 mL) was added a solution of LiOH (monohydrate, 23.2 mg) in water (0.3 mL). The reaction mixture was stirred at RT for 19 h and evaporated in vacuo to afford 220 mg of beige solid that was used without further purification. LC-MS (B): $t_R$=0.59 min; [M+H]$^+$: 385.05.

223.3. (R)-4-[4-(1H-Benzoimidazol-2-yl)-2-dimethylaminomethyl-thiazol-5-yl]-2-methyl-piperazine-1-carboxylic acid tert-butyl ester This compound was prepared using a method analogous to that of Example 16 step 16.3, intermediate 223.2 replacing intermediate 16.2. LC-MS (C): $t_R$=0.54 min; [M+H]$^+$: 457.57.

223.4. [4-(1H-Benzoimidazol-2-yl)-5-((R)-3-methyl-piperazin-1-yl)-thiazol-2-ylmethyl]-dimethyl-amine This compound was prepared using a method analogous to that of Example 16 step 16.4, intermediate 223.3 replacing intermediate 16.3. LC-MS (C): $t_R$=0.27 min; [M+H]$^+$: 357.40.

223.5. 1-{(R)-4-[4-(1H-Benzoimidazol-2-yl)-2-dimethylaminomethyl-thiazol-5-yl]-2-methyl-piperazin-1-yl}-2-imidazo[4,5-b]pyridin-3-yl-ethanone This compound was prepared using a method analogous to that of Example 1 step 1.5, intermediate 223.4 replacing intermediate 1.4 and intermediate 14.2 replacing benzoimidazol-1-yl-acetic acid. LC-MS (G): $t_R$=0.47 min; [M+H]$^+$: 516.3.

EXAMPLE 224

3-{4-(1H-Benzoimidazol-2-yl)-5-[(R)-3-methyl-4-(2-pyrrolo[2,3-b]pyridin-1-yl-acetyl)-piperazin-1-yl]-thiazol-2-yl}-propionic acid

224.1. (R)-4-[4-(2-Amino-phenylcarbamoyl)-2-bromo-thiazol-5-yl]-2-methyl-piperazine-1-carboxylic acid tert-butyl ester This compound was prepared using a method analogous to that of Example 1 step 1.5, intermediate 80.1 replacing benzoimidazol-1-yl-acetic acid and o-phenylenediamine replacing intermediate 1.4. LC-MS (B): $t_R$=0.89 min; [M+H]$^+$: 496.43.

224.2. (R)-4-[4-(2-Amino-phenylcarbamoyl)-2-((E)-2-carboxy-vinyl)-thiazol-5-yl]-2-methyl-piperazine-1-carboxylic acid tert-butyl ester A mixture of (E)-ethyl 3-(4,4,5,5-tetramethyl-1,3,2-dioxaborolan-2-yl)acrylate (1.81 g), Pd(PPh$_3$)$_2$Cl$_2$ (551 mg), intermediate 224.1 (3.9 g) in DMF (70 mL) and 1M Na$_2$CO$_3$ (39.3 mL) was stirred at 100° C. under argon for 24 h. The reaction mixture was allowed to cool down, diluted with EA and washed with citric acid (10%), water and brine. The aq. layers were extracted with EA. The combined org. layers were dried over MgSO$_4$, filtrated off and evaporated to dryness to afford 6.33 g of brown oil. CC (Biotage, SNAP 100 g cartridge, solvent A: DCM; solvent B: DCM/MeOH 8/2; gradient in % B: 5 for 4CV, 5 to 15 over 4CV, 15 for 5CV; second CC: SNAP 50 g cartridge, solvent A: DCM; solvent B: DCM/MeOH 8/2; gradient in % B: 5 for 5CV, 5 to 15 over 10CV, 15 for 5CV) afforded 702 mg of brown resin. LC-MS (B): $t_R$=0.78 min; [M+H]$^+$: 488.54.

224.3. (R)-4-[4-(2-Amino-phenylcarbamoyl)-2-(2-carboxy-ethyl)-thiazol-5-yl]-2-methyl-piperazine-1-carboxylic acid tert-butyl ester This compound was prepared using a method analogous to that of Example 14 step 14.2, intermediate 224.2 replacing intermediate 14.1 and using EtOH instead of MeOH/AcOH. LC-MS (B): $t_R$=0.76 min; [M+H]$^+$: 490.56.

224.4. 3-[4-(1H-Benzoimidazol-2-yl)-5-(R)-3-methyl-piperazin-1-yl)-thiazol-2-yl]-propionic acid A solution of intermediate 224.3 (182 mg) in AcOH (2 mL) was heated at 90° C. for 17 h and evaporated to dryness. The residue was taken up in HCl (4M in dioxane, 2 mL) and water (1 mL) and stirred at RT for 1.5 h. The mixture was evaporated in vacuo to afford 157 mg of brown foam. LC-MS (B): $t_R$=0.46 min; [M+H]$^+$: 372.30.

224.5. 3-{4-(1H-Benzoimidazol-2-yl)-5-[(R)-3-methyl-4-(2-pyrrolo[2,3-b]pyridin-1-yl-acetyl)-piperazin-1-yl]-thiazol-2-yl}-propionic acid This compound was prepared using a method analogous to that of Example 219 step 219.2, intermediate 224.4 replacing intermediate 51.2 and 2-(1H-pyrrolo[2,3-b]pyridine-1-yl) acetic acid replacing intermediate 219.1. No work-up with PL-HCO$_3$ was however performed. LC-MS (G): $t_R$=0.65 min; [M+H]$^+$: 530.4.

EXAMPLE 225

1-{(R)-4-[4-(1H-Benzoimidazol-2-yl)-2-hydroxymethyl-thiazol-5-yl]-2-methyl-piperazin-1-yl}-2-imidazo[4,5-b]pyridin-3-yl-ethanone

225.1. (R)-4-(2-Hydroxymethyl-4-methoxycarbonyl-thiazol-5-yl)-2-methyl-piperazine-1-carboxylic acid tert-butyl ester A solution of intermediate 16.2 (150 mg) in THF (2 mL) under argon was cooled down to −78° C. and lithium diisopropylamide (2M in THF/Hept/ethylbenzene, 0.23 mL) was added, followed by DMF (0.068 mL) 3 min after. The resulting reaction mixture was stirred at −78° C. for 1 h and NaBH$_4$ (33.2 mg) was added portion wise. The stirring was continued at −78° C. for 1.5 h. Citric acid (10%) was added, the mixture was allowed to warm to RT and extracted with EA. The org. layers were washed with citric acid and brine, dried (MgSO$_4$), filtered off and evaporated in vacuo. CC (Biotage, SNAP 10 g cartridge, solvent A: DCM; solvent B: MeOH; gradient in % B: 1 for 5CV, 1 to 3 over 3CV, 3 for 5CV) to afford 120 mg of yellow solid (contains 65% of starting material) used without further purification. LC-MS (B): $t_R$=0.76 min; [M+H]$^+$: 372.31.

225.2. (R)-4-(4-Carboxy-2-hydroxymethyl-thiazol-5-yl)-2-methyl-piperazine-1-carboxylic acid tert-butyl ester This compound was prepared using a method analogous to that of Example 1 step 1.2, intermediate 225.1 replacing intermediate 1.1 and using MeOH instead of EtOH and 1M NaOH instead of 2M NaOH. No purification was performed and compound purity is therefore 35%. LC-MS (B): $t_R$=0.68 min; [M+H]$^+$: 358.34.

225.3. (R)-4-[4-(1H-Benzoimidazol-2-yl)-2-hydroxymethyl-thiazol-5-yl]-2-methyl-piperazine-1-carboxylic acid tert-butyl ester This compound was prepared using a method analogous to that of Example 16 step 16.3, intermediate 225.2 replacing intermediate 16.2. LC-MS (B): $t_R$=0.69 min; [M+H]$^+$: 430.49. 225.4. [4-(1H-Benzoimidazol-2-yl)-5-((R)-3-methyl-piperazin-1-yl)-thiazol-2-yl]-methanol:

This compound was prepared using a method analogous to that of Example 16 step 16.4, intermediate 225.3 replacing intermediate 16.3. LC-MS (B): $t_R$=0.41 min; [M+H]$^+$: 330.45.

225.5. 1-{(R)-4-[4-(1H-Benzoimidazol-2-yl)-2-hydroxymethyl-thiazol-5-yl]-2-methyl-piperazin-1-yl}-2-imidazo[4,5-b]pyridin-3-yl-ethanone This compound was prepared using a method analogous to that of Example 1 step 1.5, intermediate 225.4 replacing intermediate 1.4 and intermediate 14.2 replacing benzoimidazol-1-yl-acetic acid. LC-MS (G): $t_R$=0.51 min; [M+H]$^+$: 489.3.

EXAMPLE 226

1-{4-[4-(1H-Benzoimidazol-2-yl)-2-trifluoromethyl-thiazol-5-yl]-piperazin-1-yl}-2-imidazo[4,5-b]pyridin-3-yl-ethanone This compound was prepared in five steps following the method described in Example 51, intermediate 38.1 replacing intermediate 50.1 in step 51.1. LC-MS (G): $t_R$=0.66 min; [M+H]$^+$: 513.2.

EXAMPLE 227

1-{(R)-4-[4-(1H-Benzoimidazol-2-yl)-2-trifluoromethyl-thiazol-5-yl]-2-dimethylaminomethyl-piperazin-1-yl}-2-(3,5-dimethyl-[1,2,4]triazol-1-yl)-ethanone

227.1. 2-Trifluoromethyl-thiazole-4-carboxylic acid

This compound was prepared using a method analogous to that of Example 16 step 16.2, ethyl 2-(trifluoromethyl)thiazole-4-carboxylate replacing intermediate 16.1. During the work-up, the pH of the aq. phase was brought to pH=2 before extraction. LC-MS (B): $t_R$=0.66 min. $^1$H-NMR (CD$_3$OD): 8.71 (s, 1H).

227.2. 5-Bromo-2-trifluoromethyl-thiazole-4-carboxylic acid

To a solution of intermediate 227.1 (3.2 g) in anhydrous THF (60 mL) under argon cooled down to −78° C. was added butyl lithium (1.6M in hexane, 21.3 mL) dropwise over 15 min so that the internal temperature didn't rise above −60° C. A solution of bromine (0.92 mL) in cyclohexane (8 mL) was then added dropwise to keep the internal temperature below −60° C. The resulting mixture was stirred at −78° C. for 2 h and carefully quenched by addition of water (50 mL). Citric acid (10%) was added until pH=2 and the mixture was extracted with EA. The org. layers were washed with brine, dried (MgSO$_4$), filtered off and evaporated in vacuo to afford 4.15 g of brown solid, used without further purification. LC-MS (B): $t_R$=0.67 min. F-NMR (CD$_3$OD): −63.57 ppm (s).

227.3. 5-Bromo-2-trifluoromethyl-thiazole-4-carboxylic acid (2-amino-phenyl)-amide This compound was prepared using a method analogous to that of Example 1 step 1.5, intermediate 227.2 replacing benzoimidazol-1-yl-acetic acid and o-phenylenediamine replacing intermediate 1.4. LC-MS (B): $t_R$=0.80 min; [M+H]$^+$: 365.82.

227.4. (S)-2-Hydroxymethyl-piperazine-1,4-dicarboxylic acid 4-benzyl ester 1-tert-butyl ester To solution of (S)-1-Boc-2-hydroxymethyl-piperazine (500 mg) in DCM (15 mL) were added NaHCO$_3$ (369 mg), water (3 mL) and benzyl chloroformate (0.464 mL) at RT. The resulting emulsion was vigorously stirred at RT overnight. The mixture was diluted with water and extracted with DCM. The combined org. layers were dried (MgSO$_4$), filtered off and evaporated in vacuo. The residue was purified by CC (Biotage, SNAP 25 g cartridge, solvent A: Hept; solvent B: EA; gradient in % B: 50 for 6CV, 50 to 70 over 3CV, 70 for 2CV) to afford 714 mg of colourless oil. LC-MS (B): $t_R$=0.82 min; [M+H]$^+$: 350.94.

227.5. (S)-2-Formyl-piperazine-1,4-dicarboxylic acid 4-benzyl ester 1-tert-butyl ester To a solution of intermediate 227.4 (697 mg) and DIPEA (1.02 mL) in DCM (35 mL) under argon was added dropwise a solution of sulphur trioxide pyridine complex (711 mg) in DMSO (2.82 mL). The resulting mixture was stirred at RT for 67 h, diluted with DCM and washed with water. The aq. layers were extracted with DCM. The combined org. layers were dried (MgSO$_4$), filtered off and evaporated in vacuo to afford 772 mg of yellow oil, used without further purification. LC-MS (B): $t_R$=0.90 min; [M+H]$^+$: 349.13.

227.6. (R)-2-Dimethylaminomethyl-piperazine-1,4-dicarboxylic acid 4-benzyl ester 1-tert-butyl ester A solution of intermediate 227.5 (761 mg), dimethylamine (2M in THF, 2.19 mL) and AcOH (0.125 mL) in DCM (16 mL) was stirred overnight at RT. NaBH(OAc)$_3$ (653 mg) was added, the resulting mixture was stirred at RT for 20 h, diluted with DCM and washed with water. The aq. layers were extracted with DCM. The combined org. layers were dried (MgSO$_4$), filtered off and evaporated in vacuo. The residue was purified by CC (Biotage, SNAP 25 g cartridge, solvent A: DCM; solvent B: DCM/MeOH 8/2+0.1% TEA; gradient in % B: 5 for 7CV, 5 to 25 over 2CV, 25 for 3CV) to afford 607 mg of yellow oil. LC-MS (B): $t_R$=0.68 min; [M+H]$^+$: 378.56.

227.7. (S)-2-Dimethylaminomethyl-piperazine-1-carboxylic acid tert-butyl ester To a flask containing intermediate 227.6 (592 mg) under argon was added Pd/C (10%, 332 mg) followed by DIPEA (0.268 mL) and EtOH (7 mL). The flask was evacuated and backfilled with argon three times, then evacuated and backfilled with hydrogen twice. The reaction mixture was stirred at RT under hydrogen for 5 h, filtrated over celite and the celite was washed with MeOH. The filtrate was evaporated and dried in vacuo to afford 333 mg of colourless oil that was used without purification. LC-MS (B): $t_R$=0.27 min; [M+H]$^+$: 244.22.

227.8. (R)-4-[4-(2-Amino-phenylcarbamoyl)-2-trifluoromethyl-thiazol-5-yl]-2-dimethylaminomethyl-piperazine-1-carboxylic acid tert-butyl ester A solution of intermediate 227.3 (489 mg), intermediate 227.7 (325 mg) and DIPEA (0.343 mL) in MeCN (10 mL) was heated at 80° C. for 5 days. After cooling down, the reaction mixture was diluted with EA and washed with water and brine. The aq. phases were extracted with EA. The combined org. layers were dried over MgSO$_4$, filtrated off and evaporated in vacuo. The crude was purified by CC (Biotage, SNAP 25 g cartridge, solvent A: DCM; solvent B: DCM/MeOH 8/2; gradient in % B: 5 for 3CV, 5 to 15 over 1CV, 15 for 5CV, 15 to 25 over 2CV, 25 for 5CV, 25 to 50 over 3CV, 50 for 2CV) to afford 382 mg of dark yellow foam. LC-MS (B): $t_R$=0.75 min; [M+H]$^+$: 528.84.

227.9. (R)-4-[4-(1H-Benzoimidazol-2-yl)-2-trifluoromethyl-thiazol-5-yl]-2-dimethylaminomethyl-piperazine-1-carboxylic acid tert-butyl ester A solution of intermediate 227.8 (362 mg) in AcOH (4 mL) was stirred at 90° C. for 2.5 h. The mixture was evaporated to dryness and the residue was purified by CC (Biotage, SNAP 10 g cartridge, solvent A: DCM; solvent B: DCM/MeOH 8/2; gradient in % B: 25 for 8CV, 25 to 50 over 3CV, 50 for 3CV) to afford 270 mg of yellow solid. LC-MS (B): $t_R$=0.74 min; [M+H]$^+$: 510.96.

227.10. {(R)-4-[4-(1H-Benzoimidazol-2-yl)-2-trifluoromethyl-thiazol-5-yl]-piperazin-2-ylmethyl}-dimethyl-amine This compound was prepared using a method analogous to that of Example 16 step 16.4, intermediate 227.9 replacing intermediate 16.3. LC-MS (B): $t_R$=0.52 min; [M+H]$^+$: 411.01.

227.11. 1-{(R)-4-[4-(1H-Benzoimidazol-2-yl)-2-trifluoromethyl-thiazol-5-yl]-2-dimethylaminomethyl-piperazin-1-yl}-2-(3,5-dimethyl-[1,2,4]triazol-1-yl)-ethanone This compound was prepared using a method analogous to that of Example 1 step 1.5, intermediate 227.10 replacing intermediate 1.4 and (3,5-dimethyl-[1,2,4]triazol-1-yl)-acetic acid replacing benzoimidazol-1-yl-acetic acid. LC-MS (G): $t_R$=0.64 min; [M+H]$^+$: 548.4.

EXAMPLE 228

1-{(R)-4-[4-(1H-Benzoimidazol-2-yl)-2-trifluoromethyl-thiazol-5-yl]-2-dimethylaminomethyl-piperazin-1-yl}-2-imidazo[4,5-b]pyridin-3-yl-ethanone This compound was prepared using a method analogous to that of Example 227 step 227.10, intermediate 14.2 replacing (3,5-dimethyl-[1,2,4]triazol-1-yl)-acetic acid. LC-MS (G): $t_R$=0.67 min; [M+H]$^+$: 570.3.

EXAMPLE 229

1-{(R)-4-[4-(1H-Benzoimidazol-2-yl)-thiazol-5-yl]-2-dimethylaminomethyl-piperazin-1-yl}-2-imidazo[4,5-b]pyridin-3-yl-ethanone

229.1. (S)-2-Hydroxymethyl-4-(4-methoxycarbonyl-thiazol-5-yl)-piperazine-1-carboxylic acid tert-butyl ester This compound was prepared using a method analogous to that of Example 1 step 1.1, (S)-1-Boc-2-hydroxymethyl-piperazine replacing 1-Boc-piperazine. LC-MS (B): $t_R$=0.71 min; [M+H]$^+$: 358.16.

229.2. (S)-2-Formyl-4-(4-methoxycarbonyl-thiazol-5-yl)-piperazine-1-carboxylic acid tert-butyl ester This compound was prepared using a method analogous to that of Example 227 step 227.5, intermediate 229.1 replacing intermediate 227.4. LC-MS (B): $t_R$=0.78 min; [M+H]$^+$: 356.09.

229.3. (R)-2-Dimethylaminomethyl-4-(4-methoxycarbonyl-thiazol-5-yl)-piperazine-1-carboxylic acid tert-butyl ester This compound was prepared using a method analogous to that of Example 227 step 227.6, intermediate 229.2 replacing intermediate 227.5. LC-MS (B): $t_R$=0.59 min; [M+H]$^+$: 385.04.

229.4. {(R)-4-[4-(1H-Benzoimidazol-2-yl)-thiazol-5-yl]-piperazin-2-ylmethyl}-dimethyl-amine This compound was prepared in three steps following the method described in Example 16 step 16.2 to 16.4, intermediate 229.3 replacing intermediate 16.1 and using MeOH instead of EtOH in step 16.2. LC-MS (B): $t_R$=0.68 min; [M+H]$^+$: 378.56.

229.5. 1-{(R)-4-[4-(1H-Benzoimidazol-2-yl)-thiazol-5-yl]-2-dimethylaminomethyl-piperazin-1-yl}-2-imidazo[4,5-b]pyridin-3-yl-ethanone This compound was prepared using a method analogous to that of Example 1 step 1.5, intermediate 229.4 replacing intermediate 1.4, intermediate 14.2 replacing benzoimidazol-1-yl-acetic acid and using DMF instead of DCM. LC-MS (G): $t_R$=0.45 min; [M+H]$^+$: 502.4.

EXAMPLE 230

2-(3,5-Dimethyl-[1,2,4]triazol-1-yl)-1-{(R)-4-[4-(4-fluoro-1H-benzoimidazol-2-yl)-2-trifluoromethyl-thiazol-5-yl]-2-methyl-piperazin-1-yl}-ethanone

230.1. 5-Bromo-2-trifluoromethyl-thiazole-4-carboxylic acid methyl ester

This compound was prepared using a method analogous to that of Precursor for Example 211 step 211.1, intermediate 227.2 replacing (3-methyl-1H-pyrazol-1-yl)acetic acid, using MeOH instead of EtOH and heating at 70° C. LC-MS (B): $t_R$=0.83 min. F-NMR (CD$_3$OD): –63.59 ppm (s).

230.2. (R)-4-(4-Methoxycarbonyl-2-trifluoromethyl-thiazol-5-yl)-2-methyl-piperazine-1-carboxylic acid tert-butyl ester This compound was prepared using a method analogous to that of Example 227 step 227.8, intermediate 230.1 replacing intermediate 227.3 and (R)-1-N-Boc-2-methylpiperazine replacing intermediate 227.7. LC-MS (B): $t_R$=0.97 min; [M+H]$^+$: 409.90.

230.3. 5-((R)-3-Methyl-piperazin-1-yl)-2-trifluoromethyl-thiazole-4-carboxylic acid methyl ester This compound was prepared using a method analogous to that of Example 16 step 16.4, intermediate 230.2 replacing intermediate 16.3. LC-MS (B): $t_R$=0.52 min; [M+H]$^+$: 309.97.

230.4. 5-{(R)-4-[2-(3,5-Dimethyl-[1,2,4]triazol-1-yl)-acetyl]-3-methyl-piperazin-1-yl}-2-trifluoromethyl-thiazole-4-carboxylic acid methyl ester This compound was prepared using a method analogous to that of Example 1 step 1.5, intermediate 230.3 replacing intermediate 1.4 and (3,5-dimethyl-[1,2,4]triazol-1-yl)-acetic acid replacing benzoimidazol-1-yl-acetic acid. LC-MS (B): $t_R$=0.68 min; [M+H]$^+$: 446.92.

230.5. 5-{(R)-4-[2-(3,5-Dimethyl-[1,2,4]triazol-1-yl)-acetyl]-3-methyl-piperazin-1-yl}-2-trifluoromethyl-thiazole-4-carboxylic acid This compound was prepared using a method analogous to that of Example 1 step 1.2, intermediate 230.4 replacing

230.6. 5-{(R)-4-[2-(3,5-Dimethyl-[1,2,4]triazol-1-yl)-acetyl]-3-methyl-piperazin-1-yl}-2-trifluoromethyl-thiazole-4-carboxylic acid (2-amino-3-fluoro-phenyl)-amide To a mixture of intermediate 230.5 (50 mg) and 3-fluorobenzene-1,2-diamine (15 mg) in DMF (0.65 mL) was added HATU (52.8 mg) and DIPEA (0.061 mL). The reaction mixture was stirred at RT for 4 h, diluted with DCM and washed with NaHCO$_3$. The org. phase was evaporated in vacuo. The residue was purified by preparative LC-MS (VI) to afford 30 mg of beige solid as a mixture of two regioisomers. LC-MS (B): $t_R$=0.75 min and 0.77 min; [M+H]$^+$: 541.07.

230.7. 2-(3,5-Dimethyl-[1,2,4]triazol-1-yl)-1-{(R)-4-[4-(4-fluoro-1H-benzoimidazol-2-yl)-2-trifluoromethyl-thiazol-5-yl]-2-methyl-piperazin-1-yl}-ethanone A solution of intermediate 230.6 (30 mg) in HCl (2M, 1.5 mL) was stirred at 95° C. for 2 h and evaporated in vacuo. The residue was purified by preparative LC-MS (V) to afford 25 mg of beige solid. LC-MS (G): $t_R$=0.88 min; [M+H]$^+$: 523.3.

EXAMPLE 231

1-{(R)-4-[4-(4,5-Difluoro-1H-benzoimidazol-2-yl)-2-trifluoromethyl-thiazol-5-yl]-2-methyl-piperazin-1-yl}-2-(3,5-dimethyl-[1,2,4]triazol-1-yl)-ethanone This compound was prepared in two steps following the method described in Example 230 steps 230.6 and 230.7, 1,2-diamino-3,4-difluorobenzene replacing 3-fluorobenzene-1,2-diamine in step 230.6. LC-MS (G): $t_R$=0.93 min; [M+H]$^+$: 541.3.

EXAMPLE 232

2-(3,5-Dimethyl-[1,2,4]triazol-1-yl)-1-{(R)-2-methyl-4-[2-trifluoromethyl-4-(4-trifluoromethyl-1H-benzoimidazol-2-yl)-thiazol-5-yl]-piperazin-1-yl}-ethanone This compound was prepared in two steps following the method described in Example 230 steps 230.6 and 230.7, 2,3-diaminobenzotrifluoride replacing 3-fluorobenzene-1,2-diamine in step 230.6. LC-MS (G): $t_R$=1.00 min; [M+H]$^+$: 573.3.

EXAMPLE 233

2-(3,5-Dimethyl-[1,2,4]triazol-1-yl)-1-{(R)-2-methyl-4-[4-(6-morpholin-4-yl-1H-benzoimidazol-2-yl)-2-trifluoromethyl-thiazol-5-yl]-piperazin-1-yl}-ethanone

233.1. 5-Morpholin-4-yl-2-nitro-phenylamine

To a solution of morpholine (0.88 mL) and 5-chloro-2-nitroaniline (1.76 g) in DMF (50 mL) was added TEA (2.78 mL). The mixture was stirred at 120° C. overnight, cooled down and the solvent was removed in vacuo. The residue was purified by CC (Biotage, SNAP 50 g cartridge, solvent A: Hept; solvent B: EA; gradient in % B: 10 for 3CV, 10 to 30 over 6CV, 30 for 2CV, 30 to 50 over 4CV, 50 for 6CV) to afford 380 mg of yellow powder. LC-MS (B): $t_R$=0.69 min; [M+H]$^+$: 224.15.

233.2. 4-Morpholin-4-yl-benzene-1,2-diamine

This compound was prepared using a method analogous to that of Example 14 step 14.2, intermediate 233.1 replacing intermediate 14.2 and using EtOH instead of MeOH/AcOH. LC-MS (B): $t_R$=0.68 min. $^1$H-NMR (CDCl$_3$): 6.67 (d, 1H, 8.3 Hz); 6.38 (d, 1H, 2.5 Hz); 6.33 (dd, 1H, 2.2 Hz and 8.3 Hz); 3.86 (m, 4H); 3.04 (m, 4H).

233.3. 2-(3,5-Dimethyl-[1,2,4]triazol-1-yl)-1-{(R)-2-methyl-4-[4-(6-morpholin-4-yl-1H-benzoimidazol-2-yl)-2-trifluoromethyl-thiazol-5-yl]piperazin-1-yl}-ethanone This compound was prepared using a method analogous to that of Example 181 step 181.5, intermediate 233.2 replacing intermediate 181.4, intermediate 230.5 replacing intermediate 179.2. LC-MS (G): $t_R$=0.65 min; [M+H]$^+$: 590.4.

EXAMPLE 234

2-(3,5-Dimethyl-[1,2,4]triazol-1-yl)-1-{(R)-2-methyl-4-[4-(6-[1,2,4]triazol-1-yl-1H-benzoimidazol-2-yl)-2-trifluoromethyl-thiazol-5-yl]-piperazin-1-yl}-ethanone

234.1. N-(2-Nitro-4-[1,2,4]triazol-1-yl-phenyl)-acetamide 1-(4'-Aminophenyl)-1,2,4-triazole (500 mg) was added to acetic anhydride (2.3 mL) over 10 min and the mixture was cooled down to 10° C. HNO$_3$ (65% in water, 0.65 mL) was added slowly to keep the temperature of the reaction mixture below 15° C. After the end of the addition, the reaction mixture was allowed to warm to RT over 1 h, was quenched with ice-cold water and stirred for 10 min. The resulting mixture was basified with aq. NH$_4$OH (25%) to pH=12 and extracted with DCM. The phases were separated and the org. phase was evaporated in vacuo. The residue was taken up in H$_2$SO$_4$ (2 mL), the resulting solution was cooled down to 0° C. and HNO$_3$ ((65% in water, 0.3 mL) was added. The mixture was stirred at 0° C. for 30 min and poured onto ice. After 10 min stirring, aq. NH$_4$OH (25%) was added until pH=2 and the mixture was extracted with DCM. The org. layer was evaporated in vacuo to afford 130 mg of orange solid. LC-MS (B): $t_R$=0.61 min; [M+H]$^+$: 248.09.

234.2. 2-Nitro-4-[1,2,4]triazol-1-yl-phenylamine

This compound was prepared using a method analogous to that of Example 181 step 181.3, intermediate 234.1 replacing intermediate 181.2. LC-MS (B): $t_R$=0.62 min; [M+H]$^+$: 206.07.

234.3. 4-[1,2,4]Triazol-1-yl-benzene-1,2-diamine

This compound was prepared using a method analogous to that of Example 165 step 165.2, intermediate 234.2 replacing 234.4. 2-(3,5-Dimethyl-[1,2,4]triazol-1-yl)-1-{(R)-2-methyl-4-[4-(6-[1,2,4]triazol-1-yl-1H-benzoimidazol-2-yl)-2-trifluoromethyl-thiazol-5-yl]-piperazin-1-yl}-ethanone This compound was prepared using a method analogous to that of Example 181 step 181.5, intermediate 234.3 replacing intermediate 181.4, intermediate 230.5 replacing intermediate 179.2 and using DMF instead of DCM. LC-MS (G): $t_R$=0.73 min; [M+H]$^+$: 572.3.

EXAMPLE 235

1-[2-(5-{(R)-4-[2-(3,5-Dimethyl-[1,2,4]triazol-1-yl)-acetyl]-3-methyl-piperazin-1-yl}-2-trifluoromethyl-thiazol-4-yl)-3H-benzoimidazol-5-yl]-pyrrolidin-2-one

235.1. 1-(4-Amino-3-nitro-phenyl)-pyrrolidin-2-one

This compound was prepared using a method analogous to that of Example 102 step 102.1, 1-(4-aminophenyl)-2-pyrrolidone replacing 4-(2-methoxyethoxy)aniline. LC-MS (B): $t_R$=0.56 min; [M+H]$^+$: 222.13.

235.2. 1-(3,4-Diamino-phenyl)-pyrrolidin-2-one

This compound was prepared using a method analogous to that of Example 165 step 165.2, intermediate 235.1 replacing intermediate 165.1 and using EtOH instead of EtOH/water. LC-MS (B): $t_R$=0.25 min; [M+H]$^+$: 192.17.

235.3. 1-[2-(5-{(R)-4-[2-(3,5-Dimethyl-[1,2,4]triazol-1-yl)-acetyl]-3-methyl-piperazin-1-yl}-2-trifluoromethyl-thiazol-4-yl)-3H-benzoimidazol-5-yl]-pyrrolidin-2-one This compound was prepared using a method analogous to that of Example 181 step 181.5, intermediate 235.2 replacing intermediate 181.4, intermediate 230.5 replacing intermediate 179.2 and using DMF instead of DCM. LC-MS (G): $t_R$=0.68 min; [M+H]$^+$: 588.4.

EXAMPLE 236

2-(3,5-Dimethyl-[1,2,4]triazol-1-yl)-1-((R)-2-methyl-4-{4-[6-(5-methyl-[1,2,4]oxadiazol-3-yl)-1H-benzoimidazol-2-yl]-2-trifluoromethyl-thiazol-5-yl}-piperazin-1-yl)-ethanone

236.1. N-[4-(5-Methyl-[1,2,4]oxadiazol-3-yl)-2-nitro-phenyl]-acetamide 4-(5-Methyl-1,2,4-oxadiazol-3-yl)aniline (500 mg) was added to acetic anhydride (2.1 mL) over 10 min and the mixture was cooled down to 10° C. HNO$_3$ (65% in water, 0.59 mL) was added slowly to keep the temperature of the reaction mixture below 15° C. After the end of the addition, the reaction mixture was allowed to warm to RT over 1 h, was quenched with ice-cold water and stirred for 10 min. The resulting mixture was basified with aq. NH$_4$OH (25%) to pH=12 and extracted with DCM. The phases were separated and the org. phase was evaporated in vacuo. LC-MS (B): $t_R$=0.75 min; [M]$^+$: 262.05.

236.2. 4-(5-Methyl-[1,2,4]oxadiazol-3-yl)-2-nitro-phenylamine

This compound was prepared using a method analogous to that of Example 181 step 181.3, intermediate 236.1 replacing intermediate 181.2. LC-MS (B): $t_R$=0.75 min; [M+H]$^+$: 220.03.

236.3. 4-(5-Methyl-[1,2,4]oxadiazol-3-yl)-benzene-1,2-diamine

This compound was prepared using a method analogous to that of Example 165 step 165.2, intermediate 236.2 replacing intermediate 165.1 and using EtOH instead of EtOH/water. LC-MS (B): $t_R$=0.44 min; [M+H]$^+$: 191.15.

236.4. 2-(3,5-Dimethyl-[1,2,4]triazol-1-yl)-1-((R)-2-methyl-4-{4-[6-(5-methyl-[1,2,4]oxadiazol-3-yl)-1H-benzoimidazol-2-yl]-2-trifluoromethyl-thiazol-5-yl}-piperazin-1-yl)-ethanone This compound was prepared using a method analogous to that of Example 181 step 181.5, intermediate 236.3 replacing intermediate 181.4, intermediate 230.5 replacing intermediate 179.2 and using DMF instead of DCM. LC-MS (G): $t_R$=0.84 min; [M+H]$^+$: 587.3.

EXAMPLE 237

2-(3,5-Dimethyl-[1,2,4]triazol-1-yl)-1-((R)-2-methyl-4-{4-[6-(1-methyl-piperidin-4-yl)-1H-benzoimidazol-2-yl]-2-trifluoromethyl-thiazol-5-yl}-piperazin-1-yl)-ethanone

237.1. 4-(1-Methyl-piperidin-4-yl)-benzene-1,2-diamine

This compound was prepared in three steps following the method described in Example 236 steps 236.1 to 236.3, 4-(1-methylpiperidin-4-yl)aniline replacing 4-(5-methyl-1,2,4-oxadiazol-3-yl)aniline in step 236.1. LC-MS (B): $t_R$=0.17 min; [M+H]$^+$: 206.10.

237.2. 2-(3,5-Dimethyl-[1,2,4]triazol-1-yl)-1-((R)-2-methyl-4-{4-[6-(1-methyl-piperidin-4-yl)-1H-benzoimidazol-2-yl]-2-trifluoromethyl-thiazol-5-yl}-piperazin-1-yl)-ethanone This compound was prepared using a method analogous to that of Example 181 step 181.5, intermediate 237.1 replacing intermediate 181.4, intermediate 230.5 replacing intermediate 179.2 and using DMF instead of DCM. LC-MS (G): $t_R$=0.58 min; [M+H]$^+$: 602.5.

EXAMPLE 238

2-(3,5-Dimethyl-[1,2,4]triazol-1-yl)-1-((R)-2-methyl-4-{4-[6-(tetrahydro-pyran-4-yl)-1H-benzoimidazol-2-yl]-2-trifluoromethyl-thiazol-5-yl}-piperazin-1-yl)-ethanone

238.1. 2-Nitro-4-(tetrahydro-pyran-4-yl)-phenylamine

This compound was prepared using a method analogous to that of Example 102 step 102.1, 4-(tetrahydropyran-4-yl)

phenylamine replacing 4-(2-methoxyethoxy)aniline. LC-MS (B): $t_R$=0.76 min; [M+H]$^+$: 223.06.

238.2.
4-(Tetrahydro-pyran-4-yl)-benzene-1,2-diamine

This compound was prepared using a method analogous to that of Example 101 step 101.1, intermediate 238.1 replacing 2-(4-amino-3-nitrophenoxy)ethan-1-ol. LC-MS (B): $t_R$=0.55 min; [M+H]$^+$: 193.19.

238.3. 2-(3,5-Dimethyl-[1,2,4]triazol-1-yl)-1-((R)-2-methyl-4-{4-[6-(tetrahydro-pyran-4-yl)-1H-benzoimidazol-2-yl]-2-trifluoromethyl-thiazol-5-yl}-piperazin-1-yl)-ethanone This compound was prepared using a method analogous to that of Example 163, intermediate 238.2 replacing intermediate 102.2, intermediate 230.5 replacing intermediate 147.3 and using DMF instead of DCM. LC-MS (G): $t_R$=0.72 min; [M+H]$^+$: 589.4.

EXAMPLE 239

1-((R)-4-{4-[5-(2-Amino-ethyl)-1H-benzoimidazol-2-yl]-2-trifluoromethyl-thiazol-5-yl}-2-methyl-piperazin-1-yl)-2-(3,5-dimethyl-[1,2,4]triazol-1-yl)-ethanone

239.1. [2-(4-Amino-3-nitro-phenyl)-ethyl]-carbamic acid benzyl ester

A flask was charged with 4-bromo-2-nitroaniline (505 mg), potassium (2-(((benzyloxy)carbonyl)amino)ethyl)trifluoroborate (745 mg), Pd(OAc)$_2$ (25.3 mg), 2-(dicyclohexylphosphino)-2',6'-dimethoxybiphenyl (94.6 mg) and Cs$_2$CO$_3$ (2.2 g) in dioxane/water (20 mL/2 mL). The reaction mixture was refluxed for 92 h, cooled down, diluted with EA and washed with water and brine. The aq. layers were extracted with EA, the combined org. layers were dried (MgSO$_4$), filtered off and evaporated to dryness. The residue was purified by CC (Biotage, SNAP 25 g cartridge, solvent A: Hept; solvent B: EA; gradient in % B: 10 for 3CV, 10 to 30 over 3CV, 30 for 4CV, 30 to 50 over 3CV, 50 for 5CV) to afford 143 mg of red oil. LC-MS (B): $t_R$=0.85 min; [M]$^+$: 316.07.

239.2. [2-(3,4-Diamino-phenyl)-ethyl]-carbamic acid benzyl ester

To a solution of intermediate 239.1 (94 mg) in DMF/MeOH (1 mL/1 mL) was added sodium dithionite (307 mg) followed by water (0.4 mL). The resulting orange suspension was stirred at RT for 73 h, was diluted with EA and washed with sat. Na$_2$CO$_3$, water and brine. The aq. layers were extracted with EA, the combined org. layers were dried (MgSO$_4$), filtered off and evaporated to dryness. The residue was purified by CC (Biotage, SNAP 10 g cartridge, solvent A: DCM; solvent B: DCM/MeOH 8/2; gradient in % B: 15 for 7CV, 15 to 25 over 3CV, 25 for 5CV) to afford 29 mg of brown resin. LC-MS (B): $t_R$=0.58 min; [M+H]$^+$: 286.18.

239.3. {2-[2-(5-{(R)-4-[2-(3,5-Dimethyl-[1,2,4]triazol-1-yl)-acetyl]-3-methyl-piperazin-1-yl}-2-trifluoromethyl-thiazol-4-yl)-1H-benzoimidazol-5-yl]-ethyl}-carbamic acid benzyl ester This compound was prepared using a method analogous to that of Example 163, intermediate 239.2 replacing intermediate 102.2, intermediate 230.5 replacing intermediate 147.3 and using DMF instead of DCM. LC-MS (B): $t_R$=0.74 min; [M+H]$^+$: 681.87.

239.4. 1-((R)-4-{4-[5-(2-Amino-ethyl)-1H-benzoimidazol-2-yl]-2-trifluoromethyl-thiazol-5-yl}-2-methyl-piperazin-1-yl)-2-(3,5-dimethyl-[1,2,4]triazol-1-yl)-ethanone This compound was prepared using a method analogous to that of Example 101 step 101.1, intermediate 239.3 replacing 2-(4-amino-3-nitrophenoxy)ethan-1-ol. LC-MS (G): $t_R$=0.56 min; [M+H]$^+$: 548.4.

EXAMPLE 240

2-(3,5-Dimethyl-[1,2,4]triazol-1-yl)-1-{(R)-2-methyl-4-[4-(6-piperidin-4-yl-1H-benzoimidazol-2-yl)-2-trifluoromethyl-thiazol-5-yl]-piperazin-1-yl}-ethanone

240.1. 4-Trifluoromethanesulfonyloxy-3,6-dihydro-2H-pyridine-1-carboxylic acid tert-butyl ester To a solution of 1-Boc-4-piperidone (3 g) in THF (40 mL) cooled down to −78° C. was added lithium bis(trimethylsilyl)amide (1M in THF, 15 mL). The reaction mixture was stirred at −78° C. for 30 min and a solution of 1,1,1-trifluoro-N-phenyl-N-((trifluoromethyl)sulfonyl)methanesulfonamide (5.3 g) in THF (10 mL) was added dropwise. The reaction mixture was allowed to warm to RT over 4 h and was further stirred at RT for 48 h. Water was added and the mixture was extracted with Et$_2$O. The org. layers were dried (Na$_2$SO$_4$), filtered off and evaporated in vacuo to afford 5.3 g of yellow oil that was used without purification and was not characterized.

240.2. 4-(3,4-Diamino-phenyl)-3,6-dihydro-2H-pyridine-1-carboxylic acid tert-butyl ester To a solution of intermediate 240.1 (840 mg) in DMF (18 mL) was added 3,4-diaminophenylboronic acid pinacol ester (594 mg), K$_3$PO$_4$ (1.08 g) and dichloro(1,1'-bis(diphenylphosphino)ferrocene) palladium (II) dichloromethane adduct (104 mg). The resulting mixture was degassed and heated under argon in the microwave oven at 85° C. for 3 h. Water/DCM were added. The phases were separated, the org. layer was dried (Na$_2$SO$_4$), filtered off and evaporated in vacuo. The residue was purified by preparative LC-MS (III) to afford 85 mg of brown solid. LC-MS (B): $t_R$=0.63 min; [M+H]$^+$: 290.01.

240.3. 4-(3,4-Diamino-phenyl)-piperidine-1-carboxylic acid tert-butyl ester

This compound was prepared using a method analogous to that of Example 14 step 14.2, intermediate 240.2 replacing intermediate 14.1 and using EtOH instead of MeOH/AcOH. LC-MS (B): $t_R$=0.63 min; [M+H-tBu]$^+$: 236.16.

240.4. 4-[2-(5-{(R)-4-[2-(3,5-Dimethyl-[1,2,4]triazol-1-yl)-acetyl]-3-methyl-piperazin-1-yl}-2-trifluoromethyl-thiazol-4-yl)-3H-benzoimidazol-5-yl]-piperidine-1-carboxylic acid tert-butyl ester This compound was prepared using a method analogous to that of Example 181 step 181.5, intermediate 240.3 replacing intermediate 181.4, intermediate 230.5 replacing intermediate 179.2 and using DMF instead of DCM. However no preparative LC-MS was performed after refluxing in AcOH. LC-MS (B): $t_R$=0.80 min; [M+H]$^+$: 688.09.

240.5. 2-(3,5-Dimethyl-[1,2,4]triazol-1-yl)-1-{(R)-2-methyl-4-[4-(6-piperidin-4-yl-1H-benzoimidazol-2-yl)-2-trifluoromethyl-thiazol-5-yl]-piperazin-1-yl}-ethanone This compound was prepared using a method analogous to that of Example 1 step 1.4, intermediate 240.4 replacing intermediate 1.3. However purification by preparative LC-MS (VII followed by XI) was performed. LC-MS (G): $t_R$=0.57 min; [M+H]$^+$: 588.4.

EXAMPLE 241

2-(3,5-Dimethyl-[1,2,4]triazol-1-yl)-1-{(R)-2-methyl-4-[4-(5-trifluoromethoxy-1H-benzoimidazol-2-yl)-2-trifluoromethyl-thiazol-5-yl]-piperazin-1-yl}-ethanone This compound was prepared using a method analogous to that of Example 147 step 147.4, intermediate 230.5 replacing intermediate 147.3 and 4-(trifluoromethoxy)benzene-1,2-diamine replacing 4-chloro-1,2-phenylenediamine. LC-MS (G): $t_R$=0.98 min; [M+H]$^+$: 589.3.

EXAMPLE 242

1-((R)-4-{4-[6-(Azetidin-3-yloxy)-1H-benzoimidazol-2-yl]-2-trifluoromethyl-thiazol-5-yl}-2-methyl-piperazin-1-yl)-2-(3,5-dimethyl-[1,2,4]triazol-1-yl)-ethanone 242.1. 3-(3-Amino-4-nitro-phenoxy)-azetidine-1-carboxylic acid tert-butyl ester A flask was charged with 5-fluoro-2-nitroaniline (329 mg), 1-Boc-3-hydroxyazetidine (346 mg) and NaH (65% in oil, 62.4 mg) in DMF (6 mL). The mixture was heated at 100° C. for 7 h, cooled down, and diluted water. The solvent was coevaporated with toluene. The residue was taken up in EA/water and the org. layer was evaporated in vacuo. The residue was purified by CC (Biotage, SNAP 25 g cartridge, solvent A: Hept; solvent B: EA; gradient in % B: 8 for 4CV, 8 to 66 over 10CV, 66 for 2CV) to afford 519 mg of orange foam. LC-MS (B): $t_R$=0.88 min. $^1$H-NMR (CDCl$_3$): 8.11 (d, 1H, 9.5 Hz); 6.22 (s, NH$_2$); 6.19 (dd, 1H, 2.6 Hz and 9.5 Hz); 5.97 (d, 1H, 2.5 Hz); 4.90 (m, 1H); 4.33 (m, 2H); 4.02 (m, 2H); 1.47 (s, 9H).

242.2. 3-(3,4-Diamino-phenoxy)-azetidine-1-carboxylic acid tert-butyl ester

This compound was prepared using a method analogous to that of Example 14 step 14.2, intermediate 242.1 replacing intermediate 14.1 and using EtOH instead of MeOH/AcOH. LC-MS (F): $t_R$=0.76 min; [M+H]$^+$: 280.23.

242.3. 3-[2-(5-{(R)-4-[2-(3,5-Dimethyl-[1,2,4]triazol-1-yl)-acetyl]-3-methyl-piperazin-1-yl}-2-trifluoromethyl-thiazol-4-yl)-3H-benzoimidazol-5-yloxy]-azetidine-1-carboxylic acid tert-butyl ester This compound was prepared using a method analogous to that of Example 147 step 147.4, intermediate 230.5 replacing intermediate 147.3 and intermediate 242.3 replacing 4-chloro-1,2-phenylenediamine. LC-MS (F): $t_R$=0.89 min; [M+H]$^+$: 676.22.

242.4. 1-((R)-4-{4-[6-(Azetidin-3-yloxy)-1H-benzoimidazol-2-yl]-2-trifluoromethyl-thiazol-5-yl}-2-methyl-piperazin-1-yl)-2-(3,5-dimethyl-[1,2,4]triazol-1-yl)-ethanone This compound was prepared using a method analogous to that of Example 16 step 16.4, intermediate 242.3 replacing intermediate 16.3. The compound was however purified by preparative LC-MS (VI, performed twice). LC-MS (G): $t_R$=0.57 min; [M+H]$^+$: 576.3.

EXAMPLE 243

1-{(S)-4-[4-(1H-Benzoimidazol-2-yl)-2-trifluoromethyl-thiazol-5-yl]-2-methyl-piperazin-1-yl}-2-(3,5-di methyl-[1,2,4]triazol-1-yl)-ethanone This compound was prepared in four steps following the method described in Example 227 steps 227.8 to 227.11, (S)-1-N-Boc-2-methylpiperazine replacing intermediate 227.7 in step 227.8. LC-MS (G): $t_R$=0.68 min; [M+H]$^+$: 505.3.

EXAMPLE 244

2-(3,5-Dimethyl-[1,2,4]triazol-1-yl)-1-((R)-2-methyl-4-{4-[6-(2-pyrrolidin-1-yl-ethyl)-1H-benzoimidazol-2-yl]-2-trifluoromethyl-thiazol-5-yl}-piperazin-1-yl)-ethanone 244.1. 1-(2-Chloro-ethyl)-4-nitro-benzene A solution of cyanuric chloride (1.83 g) in DMF (2 mL) was stirred at RT for 1 h. To the resulting white suspension was added DCM (25 mL) followed by 4-nitrophenethyl alcohol (1.59 g). The reaction mixture was stirred at RT for 4 h and diluted with 1M Na$_2$CO$_3$. The phases were separated, the org. layer was washed with 1M HCl and brine and evaporated in vacuo to afford 1.4 g of orange slurry. $^1$H-NMR (CDCl$_3$): 8.22 (m, 2H); 7.43 (m, 2H); 3.79 (t, 2H, 7.0 Hz); 3.20 (t, 2H, 6.8 Hz).

244.2. 1-[2-(4-Nitro-phenyl)-ethyl]-pyrrolidine

A solution of intermediate 244.1 (1 g), pyrrolidine (0.535 mL) and DIPEA (1.84 mL) in THF (8 mL) was stirred at 50° C. for 20 h and the solvent was removed in vacuo. The residue was taken up in water/DCM. The org. phase was evaporated to dryness to afford 940 mg of pale yellow oil. LC-MS (B): $t_R$=0.52 min; [M+H]$^+$: 221.08.

244.3. 4-(2-Pyrrolidin-1-yl-ethyl)-phenylamine

This compound was prepared using a method analogous to that of Example 101 step 101.1, intermediate 244.2 replacing 2-(4-amino-3-nitrophenoxy)ethan-1-ol. LC-MS (B): $t_R$=0.18 min; [M+H]$^+$: 191.22.

244.4. 2-Nitro-4-(2-pyrrolidin-1-yl-ethyl)-phenylamine

This compound was prepared using a method analogous to that of Example 236 steps 236.1 and 236.2, intermediate 244.3 replacing 4-(5-methyl-1,2,4-oxadiazol-3-yl)aniline in step 236.1. LC-MS (B): $t_R$=0.49 min; [M+H]$^+$: 236.14.

244.5.
4-(2-Pyrrolidin-1-yl-ethyl)-benzene-1,2-diamine

This compound was prepared using a method analogous to that of Example 101 step 101.1, intermediate 244.4 replacing 2-(4-amino-3-nitrophenoxy)ethan-1-ol. LC-MS (B): $t_R$=0.92 min.

244.6. 2-(3,5-Dimethyl-[1,2,4]triazol-1-yl)-1-((R)-2-methyl-4-{4-[6-(2-pyrrolidin-1-yl-ethyl)-1H-benzoimidazol-2-yl]-2-trifluoromethyl-thiazol-5-yl}-piperazin-1-yl)-ethanone This compound was prepared using a method analogous to that of Example 163, intermediate 244.5 replacing intermediate 102.2, intermediate 230.5 replacing intermediate 147.3 and using DMF instead of DCM. LC-MS (G): $t_R$=0.60 min; [M+H]$^+$: 602.4.

II. Biological Assays

A) FLIPR Assay:

The bioactivity of compounds is tested in a fluorometric imaging plate reader (FLIPR: Molecular Devices) using engineered CHO-K1 cells expressing the human CXCR3A coupled to a G protein (Galpha(16)). Cells are plated the day prior to bioassay in F12 medium supplemented with 10% FBS and G418 and hygromycin antibiotics to maintain recombinant selection. At the day of bioassay, cells are washed and dye loaded for one hour with Fluo-4-AM (Invitrogen) in Hanks Balanced Salt Solution (Invitrogen), buffered with 20 mM Hepes at pH 7.4 and sodium bicarbonate (0.015%), containing 5 mM probenecid. This buffer, but lacking the dye and containing probenecid at a concentration of 2.5 nM, is also is used for washing steps (wash buffer); or lacking both dye and probenecid but supplemented with 0.1% BSA for compound dilution steps (dilution buffer). Cells are washed free of excess dye and 60 microliter of wash buffer is added. Stock solutions of test compounds are made up at a concentration of 10 mM in DMSO, and serially diluted in dilution buffer to concentrations required for inhibition dose response curves. After a 10 minute incubation period at 37° C., 10 microliters of each compound dilution are transferred from a compound plate to the plate containing the recombinant cells in the FLIPR instrument according to the manufacturer's instructions. Following basal readings, 10 microliter CXCL10 agonist at a concentration of 20 nM (from Peprotech) is added, again using the FLIPR instrument. Changes in fluorescence are monitored before and after addition of the test compounds. Emission peak values above base level after CXCL10 addition are exported after base line subtraction. The program XLfit is used to fit the data to a single site dose response curve and to calculate IC$_{50}$ values.

B): Receptor Internalization Assay:

Stock solutions of test compounds are made up at a concentration of 10 mM in DMSO, and serially diluted in PBS containing 0.5% BSA to concentrations required for inhibition dose response curves. Diluted compounds are then mixed with an equal volume of CXCL10 (Peprotech) diluted in PBS. Anticoagulated venous human whole blood is added to the mixture, which is then incubated in a CO$_2$ incubator at 37° C. to allow for ligand mediated receptor internalization (final CXCL10 concentration is 9 nM). After 30', the blood is mixed with fluorescently labeled CXCR3 and CD3 specific antibodies (Becton Dickinson) and incubated on ice for 10 minutes. Samples are then mixed with BD FACS Lysing Solution (Becton Dickinson) in order to eliminate red blood cells. After washing the cells with PBS containing 0.5% BSA, the samples are then analyzed in a flow cytometer (FACS Canto II, Becton Dickinson). For data analysis using FACSDiva software (Becton Dickinson), the mean fluorescence corresponding to CXCR3 cell surface expression was determined on CD3 positive cells. The program GraphPad Prism is used to fit the data to a single site dose response curve and to calculate IC$_{50}$ values.

The calculated IC$_{50}$ values may fluctuate depending on the daily assay performance. Fluctuations of this kind are known to those skilled in the art. In the case where IC$_{50}$ values have been determined several times for the same compound, mean values are given. Data are shown in Table 1.

TABLE 1

| Example No | FLIPR IC$_{50}$ (nM) | Internalization IC$_{50}$ (nM) |
|---|---|---|
| 1 | 30 | 3080 |
| 2 | 198 | 3360 |
| 3 | 15 | 1200 |
| 4 | 15 | 2610 |
| 5 | 33 | nd |
| 6 | 130 | nd |
| 7 | 516 | nd |
| 8 | 392 | nd |
| 9 | 90 | nd |
| 10 | 1'070 | nd |
| 11 | 311 | nd |
| 12 | 314 | nd |
| 13 | 92 | nd |
| 14 | 11 | 1800 |
| 15 | 14 | 2420 |
| 16 | 2 | 524 |
| 17 | 6 | 447 |
| 18 | 1 | 2420 |
| 19 | 25 | 875 |
| 20 | 69 | nd |
| 21 | 2 | nd |
| 22 | 1 | 568 |
| 23 | 0.2 | 181 |
| 24 | 1 | 215 |
| 25 | 3 | 3140 |
| 26 | 1 | nd |
| 27 | 3 | 314 |
| 28 | 1 | nd |
| 29 | 4 | nd |
| 30 | 2 | 566 |
| 31 | 2 | 540 |
| 32 | 2 | 633 |
| 33 | 5 | nd |
| 34 | 10 | nd |
| 35 | 3 | 1510 |
| 36 | 17 | nd |
| 37 | 4 | 1490 |
| 38 | 3 | 1580 |
| 39 | 15 | 5880 |
| 40 | 20 | nd |
| 41 | 77 | nd |
| 42 | 547 | nd |
| 43 | 55 | 4090 |
| 44 | 3 | 3900 |
| 45 | 48 | nd |
| 46 | 3 | 1200 |
| 47 | 18 | nd |
| 48 | 448 | nd |
| 49 | 4 | 851 |
| 50 | 9 | 2230 |
| 51 | 1 | 66 |
| 52 | 136 | nd |
| 53 | 15 | nd |
| 54 | 112 | nd |
| 55 | 4 | 1660 |
| 56 | 4 | nd |
| 57 | 2 | 4130 |
| 58 | 34 | nd |

TABLE 1-continued

| Example No | FLIPR IC$_{50}$ (nM) | Internalization IC$_{50}$ (nM) |
|---|---|---|
| 59 | 4 | nd |
| 60 | 8 | 1400 |
| 61 | 2 | 458 |
| 62 | 6 | nd |
| 63 | 13 | nd |
| 64 | 111 | nd |
| 65 | 3 | 816 |
| 66 | 31 | nd |
| 67 | 9 | nd |
| 68 | 8 | 749 |
| 69 | 69 | nd |
| 70 | 13 | nd |
| 71 | 6 | 639 |
| 72 | 1 | 231 |
| 73 | 6 | 800 |
| 74 | 2 | 1040 |
| 75 | 15 | 721 |
| 76 | 10 | nd |
| 77 | 6 | 1440 |
| 78 | 11 | 3120 |
| 79 | 6 | 828 |
| 80 | 1 | 459 |
| 81 | 23 | nd |
| 82 | 96 | nd |
| 83 | 1 | 340 |
| 84 | 1 | 517 |
| 85 | 1 | 499 |
| 86 | 1 | nd |
| 87 | 1 | 205 |
| 88 | 1 | 126 |
| 89 | 1 | nd |
| 90 | 2 | nd |
| 91 | 0.4 | 895 |
| 92 | 1 | 317 |
| 93 | 1 | nd |
| 94 | 0.5 | nd |
| 95 | 4 | nd |
| 96 | 0.5 | 566 |
| 97 | 2 | nd |
| 98 | 9 | nd |
| 99 | 1 | 221 |
| 100 | 1 | 747 |
| 101 | 14 | nd |
| 102 | 14 | nd |
| 103 | 1 | 81 |
| 104 | 1 | 119 |
| 105 | 89 | nd |
| 106 | 99 | nd |
| 107 | 78 | nd |
| 108 | 4 | nd |
| 109 | 16 | 1970 |
| 110 | 487 | nd |
| 111 | 280 | nd |
| 112 | 10 | nd |
| 113 | 9 | 1510 |
| 115 | 1 | 809 |
| 116 | 3 | 306 |
| 117 | 75 | nd |
| 118 | 3 | 3780 |
| 119 | 2 | 2450 |
| 120 | 16 | nd |
| 121 | 42 | nd |
| 122 | 152 | nd |
| 123 | 69 | nd |
| Reference Example 114 | 2990 | nd |
| 124 | 10 | nd |
| 125 | 71 | nd |
| 126 | 68 | nd |
| 127 | 490 | nd |
| 128 | 47 | nd |
| 129 | 109 | nd |
| 130 | 3 | 2670 |
| 131 | 8 | nd |
| 132 | 3 | 6380 |
| 133 | 6 | nd |
| 134 | 115 | nd |
| 135 | 88 | nd |
| 136 | 26 | nd |
| 137 | 5 | 1140 |
| 138 | 4 | 1090 |
| 139 | 2 | 2930 |
| 140 | 6 | nd |
| 141 | 0.2 | 363 |
| 142 | 2 | 352 |
| 143 | 1 | 723 |
| 144 | 2 | 933 |
| 145 | 11 | nd |
| 146 | 1 | 492 |
| 147 | 1 | 39 |
| 148 | 24 | 4490 |
| 149 | 16 | 5070 |
| 150 | 45 | 5680 |
| 151 | 4 | 547 |
| 152 | 3 | 663 |
| 153 | 7 | 1030 |
| 154 | 14 | 3040 |
| 155 | 6 | 1100 |
| 156 | 64 | nd |
| 157 | 4 | nd |
| 158 | 5 | 3430 |
| 159 | 1 | 1540 |
| 160 | 2 | 92 |
| 161 | 2 | 146 |
| 162 | 1 | 181 |
| 163 | 5 | 47 |
| 164 | 1 | 93 |
| 165 | 1 | 98 |
| 166 | 1 | 111 |
| 167 | 1 | 140 |
| 168 | 3 | 435 |
| 169 | 0.3 | 685 |
| 170 | 6 | 1060 |
| 171 | 1 | 1080 |
| 172 | 1 | 73 |
| 173 | 0.5 | 395 |
| 174 | 0.2 | 53 |
| 175 | 0.1 | 227 |
| 176 | 0.1 | 111 |
| 177 | 3 | 7520 |
| 178 | 2 | 224 |
| 179 | 2 | 138 |
| 180 | 2 | 703 |
| 181 | 58 | 3090 |
| 182 | 27 | 2240 |
| 183 | 15 | 1440 |
| 184 | 53 | 3420 |
| 185 | 37 | 6620 |
| 186 | 4 | 1610 |
| 187 | 0.3 | 1110 |
| 188 | 4 | 3820 |
| 189 | 2 | 1760 |
| 190 | 1 | 514 |
| 191 | 1 | 470 |
| 192 | 1 | 116 |
| 193 | 1 | 210 |
| 194 | 8 | 1410 |
| 195 | 8 | 2710 |
| 196 | 6 | 6560 |
| 197 | 8 | 5310 |
| 198 | 2 | 6900 |
| 199 | 0.4 | 658 |
| 200 | 28 | 627 |
| 201 | 2 | 2860 |
| 202 | 1 | 44 |
| 203 | 5 | 2100 |
| 204 | 6 | 4180 |
| 205 | 2 | 111 |
| 206 | 2 | 260 |
| 207 | 1 | 332 |
| 208 | 1 | 310 |
| 209 | 3 | 101 |
| 210 | 1 | 121 |
| 211 | 1 | 227 |

TABLE 1-continued

| Example No | FLIPR IC$_{50}$ (nM) | Internalization IC$_{50}$ (nM) |
|---|---|---|
| 212 | 4 | 737 |
| 213 | 1 | 373 |
| 214 | 2 | 72 |
| 215 | 2 | 271 |
| 216 | 2 | 90 |
| 217 | 21 | 5010 |
| 218 | 8 | 540 |
| 219 | 4 | 1460 |
| 220 | 19 | 2620 |
| 221 | 6 | 1090 |
| 222 | 16 | 1500 |
| 223 | 27 | 1130 |
| 224 | 100 | nd |
| 225 | 54 | 3460 |
| 226 | 1 | 363 |
| 227 | 8 | 69 |
| 228 | 4 | 12 |
| 229 | 1 | 98 |
| 230 | 1 | 139 |
| 231 | 1 | 332 |
| 232 | 7 | 494 |
| 233 | 6 | 376 |
| 234 | 6 | 822 |
| 235 | 30 | nd |
| 236 | 3 | 265 |
| 237 | 2 | 84 |
| 238 | 1 | 103 |
| 239 | 0.1 | 324 |
| 240 | 2 | 222 |
| 241 | 2 | 169 |
| 242 | 4 | 438 |
| 243 | 3 | 1120 |
| 244 | 23 | 531 | nd: not tested

The invention claimed is:

1. A compound of Formula (I)

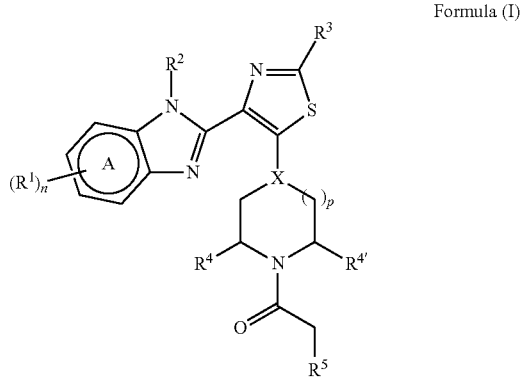

Formula (I)

wherein

X is CH or N;

ring A represents a benzene, pyridine, or pyrimidine ring;

$(R^1)_n$ represents one or two optional substituents each independently selected from $(C_{1-4})$alkyl; $(C_{1-4})$alkoxy; $(C_{1-3})$fluoroalkyl; $(C_{1-3})$fluoroalkoxy; halogen; cyano; $(C_{3-6})$cycloalkyl optionally mono-substituted with hydroxy; $(C_{1-3})$alkoxy-$(C_{1-4})$alkyl; $(C_{1-3})$alkoxy-$(C_{2-4})$alkoxy; hydroxy-$(C_{1-4})$alkyl; hydroxy-$(C_{2-4})$alkoxy; hydroxy; $(C_{1-4})$alkyl-sulfonyl; phenyl; 5-membered heteroaryl optionally substituted with $(C_{1-4})$alkyl; —CO—$(C_{1-4})$alkyl; —CO—$(C_{1-4})$alkoxy; —$(CH_2)_q$—$NR^6R^7$, wherein $R^6$ and $R^7$ are each independently hydrogen or $(C_{1-4})$alkyl and q is 0, 1, or 2; and -L-heterocyclyl, wherein -L- represents —O— or —$(CH_2)_r$—, r is 0, 1, or 2, and the heterocyclyl is a 4- to 7-membered mono-cyclic saturated ring containing one or two heteroatoms selected from nitrogen and oxygen and said heterocyclyl is optionally substituted with one substituent selected from $(C_{1-4})$alkyl, $(C_{1-4})$alkoxy, and oxo;

$R^2$ is hydrogen, $(C_{1-4})$alkyl, $(C_{1-3})$fluoroalkyl, $(C_{1-3})$alkoxy-$(C_{2-4})$alkyl, or hydroxy-$(C_{2-4})$alkyl;

$R^3$ is hydrogen; $(C_{1-4})$alkyl; $(C_{1-4})$alkoxy; $(C_{1-3})$fluoroalkyl; halogen; $(C_{3-6})$cycloalkyl, wherein optionally one ring carbon atom may be replaced by oxygen; $(C_{1-3})$alkoxy-$(C_{1-4})$alkyl; hydroxy-$(C_{1-4})$alkyl; —$(C_{1-3})$alkylene-COOH; —$(C_{1-3})$alkylene-$NR^8R^9$, wherein $R^8$ and $R^9$ are each independently $(C_{1-3})$alkyl; or 5- or 6-membered monocyclic heteroaryl or phenyl, wherein said 5- or 6-membered monocyclic heteroaryl or phenyl is unsubstituted, mono-substituted, or di-substituted wherein the substituents are each independently selected from $(C_{1-4})$alkyl, $(C_{1-4})$alkoxy, $(C_{1-3})$fluoroalkyl, $(C_{1-3})$fluoroalkoxy, halogen, and cyano;

$R^4$ and $R^{4'}$ are each independently hydrogen, $(C_{1-4})$alkyl, $(C_{1-3})$alkoxy-$(C_{1-4})$alkyl, or $R^{12}R^{13}N$—$(CH_2)$—wherein $R^{12}$ and $R^{13}$ are each independently $(C_{1-3})$alkyl; or $R^4$ and $R^{4'}$ together form a bridge —$(CH_2)_m$—, wherein m is 1 or 2;

p is 1 or 2; and $R^5$ is:

(I) aryl or 5- to 10-membered heteroaryl, wherein said aryl or heteroaryl independently is unsubstituted, mono-substituted, di-substituted, or tri-substituted, wherein the substituents are each independently selected from $(C_{1-4})$alkyl; $(C_{1-4})$alkoxy; $(C_{1-3})$fluoroalkyl; $(C_{1-3})$fluoroalkoxy; halogen; cyano; $(C_{1-3})$alkoxy-$(C_{1-4})$alkyl; $(C_{1-3})$alkoxy-$(C_{2-4})$alkoxy; hydroxy; —CO—$(C_{1-4})$alkoxy; hydroxy-$(C_{1-4})$alkyl; —$(C_{1-3})$alkylene-$NR^{10}R^{11}$, wherein $R^{10}$ and $R^{11}$ are each independently $(C_{1-3})$alkyl; phenyl; 5-membered heteroaryl; and heterocyclyl, wherein said heterocyclyl is a 5- to 7-membered mono-cyclic saturated ring containing one or two nitrogen atoms and is optionally substituted on a nitrogen having a free valency with $(C_{1-4})$alkyl; or (II) a 9- or 10-membered partially aromatic bicyclic heterocyclyl, wherein said heterocyclyl is a phenyl or 5- or 6-membered heteroaryl ring fused to a 5- or 6-membered saturated or partially unsaturated non-aromatic ring containing one or two heteroatoms independently selected from oxygen, sulphur and nitrogen, and said heterocyclyl is unsubstituted, mono-substituted, di-substituted or tri-substituted wherein the substituents are each independently selected from $(C_{1-4})$alkyl, $(C_{1-4})$alkoxy, halogen and oxo;

or a pharmaceutically-acceptable salt thereof.

2. A compound according to claim 1, wherein $R^3$ is hydrogen, $(C_{1-4})$alkyl, $(C_{1-3})$fluoroalkyl, halogen, or $(C_{3-6})$cycloalkyl wherein optionally one ring carbon atom may be replaced by oxygen, or a pharmaceutically-acceptable salt thereof.

3. A compound according to claim 1, wherein:

X is CH or N, p is 1 or 2, and $R^4$ and $R^{4'}$ are both hydrogen;

X is N, p is 1, and $R^4$ and $R^{4'}$ are both $(C_{1-4})$alkyl;

X is N; p is 1 or 2; $R^4$ is hydrogen; and $R^{4'}$ is $(C_{1-3})$alkoxy-$(C_{1-4})$alkyl, $R^{12}R^{13}N$—$(CH_2)$—wherein $R^{12}$ and $R^{13}$ are each independently $(C_{1-3})$alkyl, or $(C_{1-4})$alkyl; or X is N, p is 1, and $R^4$ and $R^{4'}$ together form an ethylene bridge;

or a pharmaceutically-acceptable salt thereof.

4. A compound according to claim 1, wherein said compound is a compound of Formula (II)

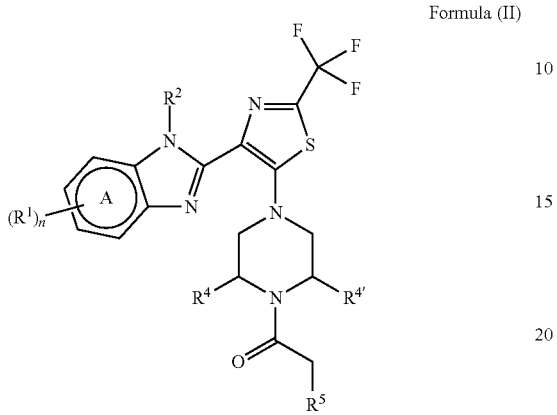

Formula (II)

wherein $R^2$ is hydrogen, $(C_{1-4})$alkyl, or $(C_{1-3})$alkoxy-$(C_{2-4})$alkyl;

$R^4$ is hydrogen and $R^{4'}$ is methyl and the carbon atom to which $R^{4'}$ is attached to is in absolute (R)-configuration, or $R^4$ and $R^{4'}$ are both hydrogen; and $R^5$ is:
- aryl, wherein said aryl is unsubstituted, mono-substituted, di-substituted, or tri-substituted, wherein the substituents are each independently selected from $(C_{1-4})$alkyl; $(C_{1-4})$alkoxy; $(C_{1-3})$fluoroalkyl; $(C_{1-3})$fluoroalkoxy; halogen; cyano; $(C_{1-3})$alkoxy-$(C_{1-4})$alkyl; $(C_{1-3})$alkoxy-$(C_{2-4})$alkoxy; hydroxy; hydroxy-$(C_{1-4})$alkyl; 5-membered heteroaryl; and heterocyclyl, wherein said heterocyclyl is a 5- to 7-membered mono-cyclic saturated ring containing one or two nitrogen atoms and is optionally substituted on a nitrogen having a free valency with $(C_{1-4})$alkyl;
- a 5- or 6-membered heteroaryl, wherein said heteroaryl is unsubstituted, mono-substituted, di-substituted, or tri-substituted, wherein the substituents are each independently selected from $(C_{1-4})$alkyl; $(C_{1-4})$alkoxy; $(C_{1-3})$fluoroalkyl; $(C_{1-3})$fluoroalkoxy; halogen; cyano; $(C_{1-3})$alkoxy-$(C_{1-4})$alkyl; $(C_{1-3})$alkoxy-$(C_{2-4})$alkoxy; hydroxy; —CO—$(C_{1-4})$alkoxy; hydroxy-$(C_{1-4})$alkyl; —$(C_{1-3})$alkylene-$NR^{10}R^{11}$, wherein $R^{10}$ and $R^{11}$ are each independently $(C_{1-3})$alkyl; phenyl; and heterocyclyl, wherein said heterocyclyl is a 5- to 7-membered mono-cyclic saturated ring containing one or two nitrogen atoms and is optionally substituted on a nitrogen having a free valency with $(C_{1-4})$alkyl;
- a 9- or 10-membered heteroaryl, wherein said heteroaryl is unsubstituted, mono-substituted, di-substituted, or tri-substituted, wherein the substituents are each independently selected from $(C_{1-4})$alkyl, $(C_{1-4})$alkoxy, fluoroalkyl, $(C_{1-3})$fluoroalkoxy; halogen, cyano, $(C_{1-3})$alkoxy-$(C_{1-4})$alkyl, $(C_{1-3})$alkoxy-$(C_{2-4})$alkoxy, hydroxy, and hydroxy-$(C_{1-4})$alkyl;
- a 9- or 10-membered partially aromatic bicyclic heterocyclyl, wherein said heterocyclyl consists of a phenyl or 6-membered heteroaryl ring fused to a 5- or 6-membered saturated or partially unsaturated non-aromatic ring containing one nitrogen atom and optionally one further heteroatom selected from oxygen and nitrogen; wherein said heterocyclyl is attached to the rest of the molecule through said non-aromatic nitrogen atom; and wherein said heterocyclyl group is unsubstituted, mono-substituted, di-substituted or tri-substituted wherein the substituents are each independently selected from $(C_{1-4})$alkyl, $(C_{1-4})$alkoxy, halogen and oxo;
- a 9-membered partially aromatic bicyclic heterocyclyl, wherein said heterocyclyl consists of a pyrazole or imidazole ring fused to a 6-membered saturated or partially unsaturated non-aromatic ring containing one or two heteroatoms independently selected from oxygen and nitrogen; wherein said heterocyclyl is attached to the rest of the molecule through an aromatic nitrogen atom of said pyrazole or imidazole ring; and wherein said heterocyclyl group is unsubstituted, mono-substituted, or di-substituted, wherein the substituents are each independently $(C_{1-4})$alkyl or oxo; or
- a 9- or 10-membered partially aromatic bicyclic heterocyclyl, wherein said heterocyclyl consists of a phenyl or 6-membered heteroaryl ring which is fused to a 5- or 6-membered saturated or partially unsaturated non-aromatic ring containing one or two heteroatoms independently selected from oxygen, sulphur and nitrogen, wherein said heterocyclyl is attached to the rest of the molecule through an aromatic carbon atom, and wherein said heterocyclyl group is unsubstituted, mono-substituted, or di-substituted wherein the substituents are each independently selected from $(C_{1-4})$alkyl, $(C_{1-4})$alkoxy, halogen and oxo;

or a pharmaceutically-acceptable salt thereof.

5. A compound according to claim 1, wherein the group

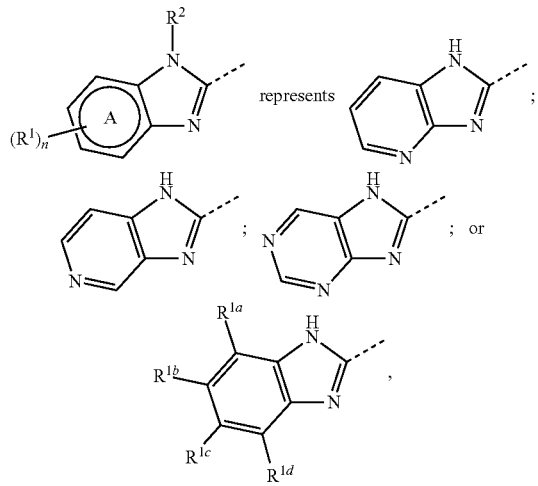

wherein:
(I) $R^{1a}$, $R^{1b}$, $R^{1c}$ and $R^{1d}$ are each hydrogen;
(II) $R^{1a}$ and $R^{1d}$ are each hydrogen;
one of $R^{1b}$ and $R^{1c}$ is selected from $(C_{1-4})$alkyl; $(C_{1-4})$alkoxy; $(C_{1-3})$fluoroalkyl; $(C_{1-3})$fluoroalkoxy; halogen; cyano; $(C_{3-6})$cycloalkyl optionally mono-substituted with hydroxy; $(C_{1-3})$alkoxy-$(C_{1-4})$alkyl; $(C_{1-3})$alkoxy-$(C_{2-4})$alkoxy; hydroxy-$(C_{1-4})$alkyl;

hydroxy-$(C_{2-4})$alkoxy; hydroxy; $(C_{1-4})$alkyl-sulfonyl; phenyl; 5-membered heteroaryl optionally substituted with $(C_{1-4})$alkyl; —CO—$(C_{1-4})$alkyl; —CO—$(C_{1-4})$alkoxy; —$(CH_2)_q$—$NR^6R^7$, wherein $R^6$ and $R^7$ independently represent hydrogen or $(C_{1-4})$alkyl and q is 0, 1, or 2; and -L-heterocyclyl, wherein -L- is —O— or —$(CH_2)_r$—, r is 0, 1, or 2, and the heterocyclyl is a 4- to 7-membered mono-cyclic saturated ring containing one or two heteroatoms independently selected from nitrogen and oxygen, and said heterocyclyl is optionally substituted with one substituent selected from $(C_{1-4})$alkyl, $(C_{1-4})$alkoxy, and oxo;

and the other of $R^{1b}$ and $R^{1c}$ is selected from hydrogen, $(C_{1-4})$alkyl, $(C_{1-4})$alkoxy, $(C_{1-3})$fluoroalkyl, and halogen; or (III) one of $R^{1a}$ and $R^{1d}$ is halogen and the remaining of $R^{1a}$, $R^{1b}$, $R^{1c}$ and $R^{1d}$ are each hydrogen;

or a pharmaceutically-acceptable salt thereof.

6. A compound according to claim 1, wherein the group

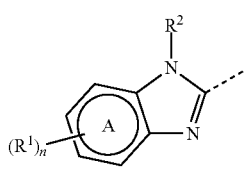

represents a group selected from:

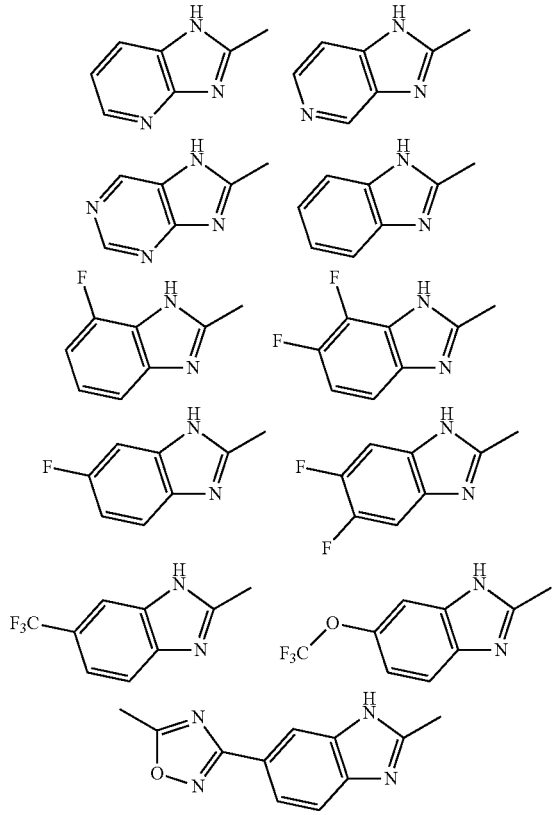

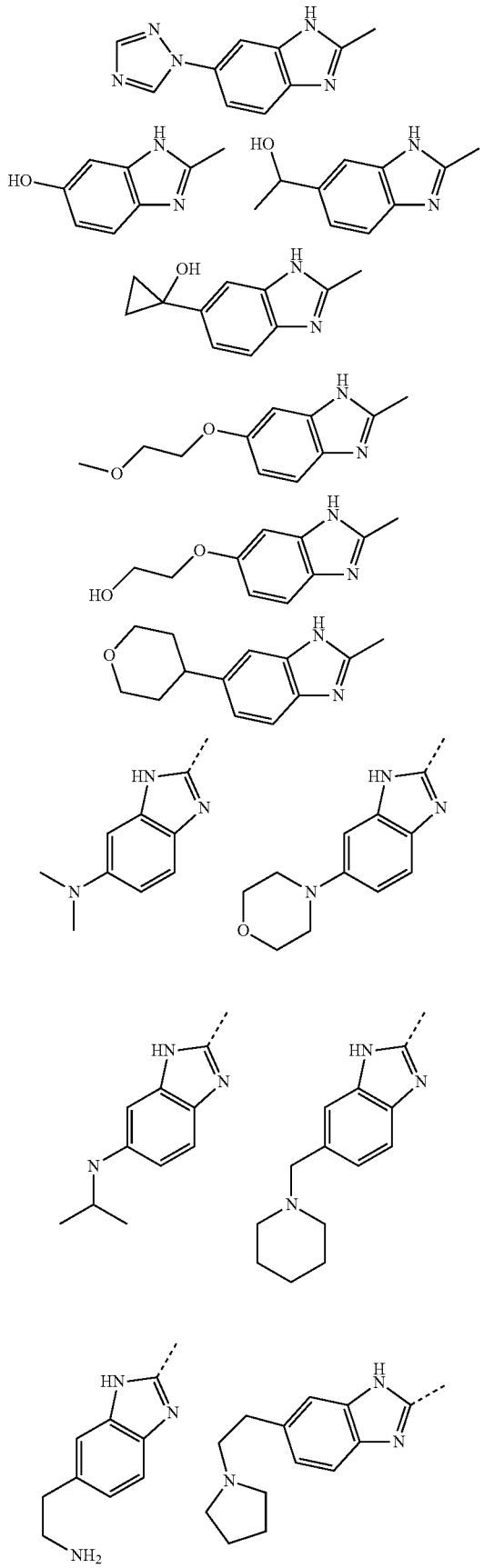

-continued

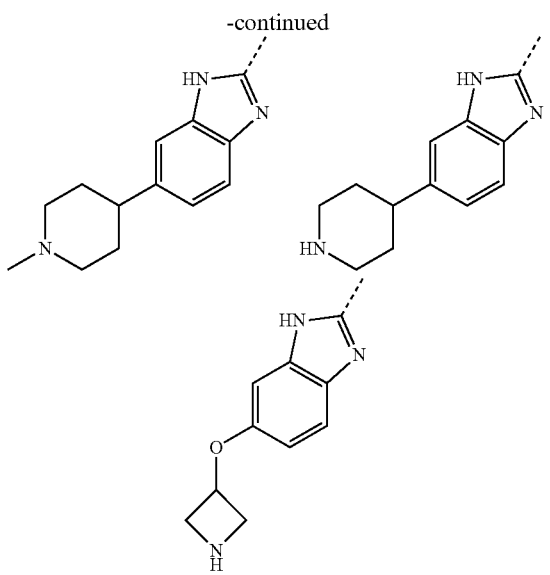

or a pharmaceutically-acceptable salt thereof.

7. A compound according to claim 1, wherein $R^5$ is:
- a 5-membered heteroaryl, wherein said heteroaryl contains one to three nitrogen atoms, is attached to the rest of the molecule at one of said nitrogen atoms, and is unsubstituted, mono-substituted, di-substituted, or tri-substituted, wherein the substituents are each independently selected from $(C_{1-4})$alkyl; $(C_{1-4})$alkoxy; $(C_{1-3})$fluoroalkyl; $(C_{1-3})$fluoroalkoxy; halogen; cyano; $(C_{1-3})$alkoxy-$(C_{1-4})$alkyl; $(C_{1-3})$alkoxy-$(C_{2-4})$alkoxy; hydroxy; —CO—$(C_{1-4})$alkoxy; hydroxy-$(C_{1-4})$alkyl; and —$(C_{1-3})$alkylene-$NR^{10}R^{11}$, wherein $R^{10}$ and $R^{11}$ are each independently $(C_{1-3})$alkyl, phenyl, or heterocyclyl wherein the heterocyclyl is a 5- to 7-membered monocyclic saturated ring containing one or two nitrogen atoms and is optionally substituted on a nitrogen having a free valency with $(C_{1-4})$alkyl;
- a 5- or 6-membered heteroaryl, wherein said heteroaryl contains one to three heteroatoms independently selected from oxygen, sulphur and nitrogen, is attached to the rest of the molecule at a ring carbon atom, and is unsubstituted, mono-substituted, or di-substituted, wherein the substituents are each independently selected from $(C_{1-4})$alkyl, $(C_{1-4})$alkoxy, $(C_{1-3})$fluoroalkyl, halogen, and phenyl;
- a 9- or 10-membered heteroaryl, wherein said heteroaryl contains one to three heteroatoms independently selected from oxygen, sulphur and nitrogen, is attached to the rest of the molecule at a ring carbon atom, and is unsubstituted, or mono-substituted or di-substituted, wherein the substituents are each independently selected from $(C_{1-4})$alkyl, $(C_{1-4})$alkoxy, $(C_{1-3})$fluoroalkyl, and halogen;
- a 9-membered heteroaryl, wherein said heteroaryl is a bicyclic aromatic ring containing one to three nitrogen atoms, is attached to the rest of the molecule at one of said nitrogen atoms, and is unsubstituted, mono-substituted, di-substituted, or tri-substituted, wherein the substituents are each independently selected from $(C_{1-4})$alkyl, $(C_{1-4})$alkoxy, $(C_{1-3})$fluoroalkyl, $(C_{1-3})$fluoroalkoxy, halogen, cyano, $(C_{1-3})$alkoxy-$(C_{1-4})$alkyl, $(C_{1-3})$alkoxy-$(C_{2-4})$alkoxy, hydroxy, and hydroxy-$(C_{1-4})$alkyl; or
- a 9- or 10-membered partially aromatic bicyclic heterocyclyl consisting of a phenyl or 6-membered heteroaryl ring fused to a 5- or 6-membered saturated or partially unsaturated non-aromatic ring containing one nitrogen atom and optionally one further heteroatom selected from oxygen and nitrogen, wherein said heterocyclyl is attached to the rest of the molecule through said non-aromatic nitrogen atom and said heterocyclyl group is unsubstituted, mono-substituted, di-substituted or tri-substituted, wherein the substituents are each independently selected from $(C_{1-4})$alkyl, $(C_{1-4})$alkoxy, halogen and oxo; or
- a 9-membered partially aromatic bicyclic heterocyclyl consisting of a pyrazole or imidazole ring which is fused to a 6-membered saturated or partially unsaturated non-aromatic ring containing one or two heteroatoms independently selected from oxygen and nitrogen, wherein said heterocyclyl is attached to the rest of the molecule through an aromatic nitrogen atom of said pyrazole or imidazole ring and is unsubstituted, mono-substituted, or di-substituted, wherein the substituents are each independently selected from $(C_{1-4})$alkyl and oxo;

or a pharmaceutically-acceptable salt thereof.

8. A compound according to claim 1, wherein $R^5$ is a 5- to 10-membered heteroaryl selected from: 3-methyl-pyrazol-1-yl, 3,5-dimethyl-pyrazol-1-yl, 3-trifluoromethyl-pyrazol-1-yl, 3,5-dimethyl-[1,2,4]triazol-1-yl, indazol-1-yl, pyrrolo[2,3-c]pyridin-1-yl, pyrrolo[2,3-b]pyridin-1-yl, 6-chloro-pyrrolo[2,3-b]pyridin-1-yl, 7-chloro-pyrrolo[2,3-c]pyridin-1-yl, 3-chloro-pyrrolo[2,3-b]pyridin-1-yl, 2-methyl-pyrrolo[2,3-b]pyridin-1-yl, 3-methyl-pyrrolo[2,3-b]pyridin-1-yl, 6-methyl-pyrrolo[2,3-b]pyridin-1-yl, 6-methoxy-pyrrolo[2,3-b]pyridin-1-yl, indol-1-yl, 5-fluoro-indol-1-yl, 6-fluoro-indol-1-yl, 7-fluoro-indol-1-yl, 4-chloro-indol-1-yl, 2-methyl-indol-1-yl, 7-methyl-indol-1-yl, 3-cyano-indol-1-yl, 7-cyano-indol-1-yl, 5-fluoro-3-methyl-indol-1-yl, 5,6-dichloro-indol-1-yl, 4-methoxy-indol-1-yl, 5-chloro-6-methoxy-indol-1-yl, 6-trifluoromethyl-indol-1-yl, imidazo[4,5-c]pyridin-1-yl, imidazo[4,5-c]pyridin-3-yl, imidazo[4,5-b]pyridin-3-yl, pyrazolo[3,4-b]pyridin-1-yl, pyrazolo[3,4-b]pyridin-2-yl, 3-chloro-pyrrolo[2,3-b]pyrazin-5-yl, benzoimidazol-1-yl, 2-methyl-benzoimidazol-1-yl, 2-trifluoromethyl-benzoimidazol-1-yl, pyrazol-1-yl, 4-chloro-pyrazol-1-yl, 5-methyl-pyrazol-1-yl, 4-methyl-pyrazol-1-yl, 3-methoxycarbonyl-pyrazol-1-yl, 4-dimethylaminomethyl-3-methyl-pyrazol-1-yl, 4-dimethylaminomethyl-3,5-dimethyl-pyrazol-1-yl, 3-phenyl-pyrazol-1-yl, 5-phenyl-pyrazol-1-yl, 4-piperidin-4-yl-pyrazol-1-yl, 4-(1-methyl-piperidin-4-yl)-pyrazol-1-yl, [1,2,4]triazol-1-yl, 3-bromo-[1,2,4]triazol-1-yl, 3-methyl-[1,2,4]triazol-1-yl, 5-methyl-[1,2,4]triazol-1-yl, 3-dimethylaminomethyl-5-methyl-[1,2,4]triazol-1-yl, [1,2,3]triazol-2-yl, 4-phenyl-[1,2,3]triazol-1-yl, 2-hydroxymethyl-pyrrolo[2,3-b]pyridin-1-yl, 5-methyl-[1,3,4]oxadiazol-3-yl, 5-phenyl-[1,3,4]oxadiazol-3-yl, 2-methyl-pyridin-5-yl, 2,6-dimethyl-pyridin-4-yl, 4,6-dimethyl-pyridin-2-yl, 2-methyl-thiazol-4-yl, 2,4-dimethyl-thiazol-5-yl, 1H-indazol-3-yl, indol-3-yl, indol-4-yl, 5-chloro-1H-indol-3-yl, 5-fluoro-1H-indol-3-yl, 1-methyl-1H-indol-3-yl, 5-methoxy-1H-indol-3-yl, 5-chloro-1H-benzoimidazol-2-yl, pyridin-3-yl, 6-methoxy-benzofuran-3-yl, benzo[b]thiophen-3-yl, 5-chloro-benzo[b]thiophen-3-yl, benzo[d]isoxazol-3-yl, 5-methoxy-benzo[d]isoxazol-3-yl, 5-methyl-benzo[d]isoxazol-3-yl, quinoxalin-6-yl, quinolin-7-yl, quinolin-8-yl, 2-methyl-imidazo[1,2-a]pyridin-3-yl, and 6-chloro-imidazo[1,2-b]pyridazin-2-yl;

or a pharmaceutically-acceptable salt thereof.

9. A compound according to claim 1, wherein $R^5$ is a 9- or 10-membered partially aromatic bicyclic heterocyclyl selected from: 3-1-benzooxazol-2-one-3-yl, 2,3-dihydro-pyrrolo[2,3-b]pyridin-1-yl, 1,3-dihydro-imidazo[4,5-b]pyridin-2-one-3-yl, 1,3-dihydro-benzoimidazol-2-one-1-yl, 3-methyl-1,3-dihydro-benzoimidazol-2-one-1-yl, 2,3-dihydro-indol-1-yl, 1,3-dihydro-indol-2-one-1-yl, 2,3-dihydro-benzo[1,4]oxazin-4-yl, 4H-benzo[1,4]oxazin-3-one-4-yl, 3,4-dihydro-2H-quinolin-1-yl, 3,4-dihydro-1H-quinolin-2-one-1-yl, 2,3-dihydro-1H-quinolin-4-one-1-yl, 2,3-dihydro-benzofuran-5-yl, 4H-benzo[1,4]oxazin-3-one-6-yl, 5-methyl-4,5,6,7-tetrahydro-pyrazolo[4,3-c]pyridin-1-yl, 5-methyl-4,5,6,7-tetrahydro-pyrazolo[4,3-c]pyridin-2-yl, 5-methyl-4,5,6,7-tetrahydro-imidazo[4,5-c]pyridin-3-yl, 5-methyl-4,5,6,7-tetrahydro-imidazo[4,5-c]pyridin-1-yl, 2-oxo-3H-oxazolo[4,5-b]pyridin-3-yl, 4-fluoro-2-oxo-3H-benzooxazol-3-yl, 2,3-dioxo-1H-indol-1-yl, 4-methyl-2-oxo-3H-benzooxazol-3-yl, 3,3-difluoro-2-oxo-1,3-dihydro-indol-1-yl, and 3,3-dimethyl-2-oxo-1,3-dihydro-indol-1-yl; or a pharmaceutically-acceptable salt thereof.

10. A compound according to claim 1, wherein $R^5$ is selected from:

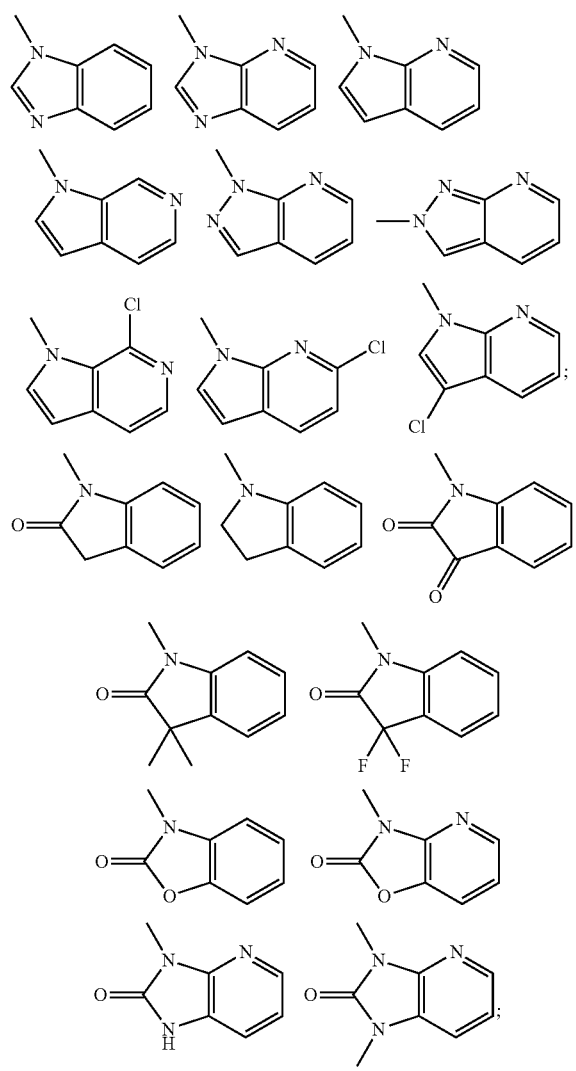

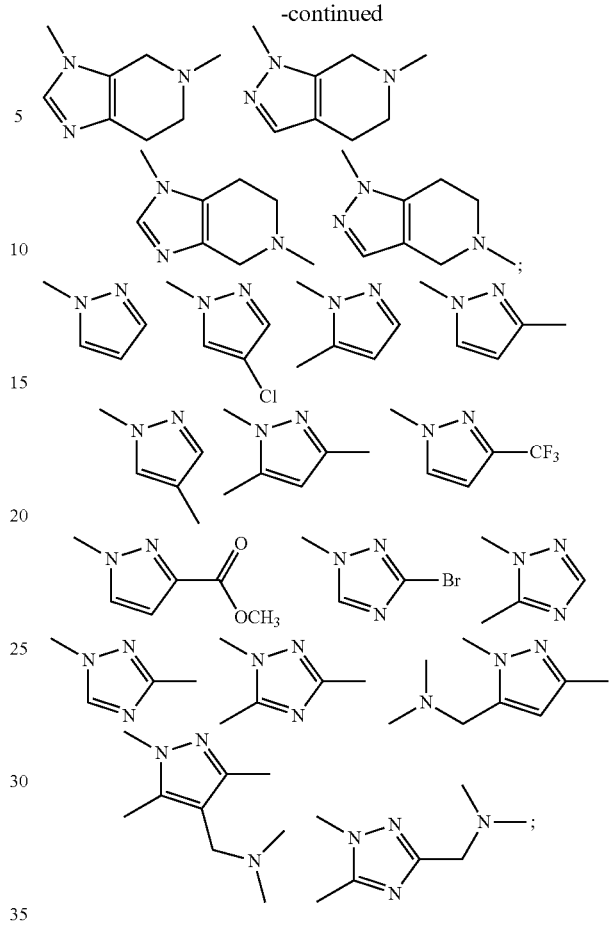

or a pharmaceutically-acceptable salt thereof.

11. A compound according to claim selected from:
2-Benzoimidazol-1-yl-1-{4-[4-(1H-benzoimidazol-2-yl)-thiazol-5-yl]-piperazin-1-yl}-ethanone;
1-{4-[4-(1H-Benzoimidazol-2-yl)-thiazol-5-yl]-piperazin-1-yl}-2-(2-methyl-benzoimidazol-1-yl)-ethanone;
1-(2-{4-[4-(1H-Benzoimidazol-2-yl)-thiazol-5-yl]-piperazin-1-yl}-2-oxo-ethyl)-3-methyl-1,3-dihydro-benzoimidazol-2-one;
1-{4-[4-(1H-Benzoimidazol-2-yl)-thiazol-5-yl]-piperazin-1-yl}-2-indol-1-yl-ethanone;
1-{4-[4-(1H-Benzoimidazol-2-yl)-thiazol-5-yl]-piperazin-1-yl}-2-(3-trifluoromethyl-pyrazol-1-yl)-ethanone;
1-{4-[4-(1H-Benzoimidazol-2-yl)-thiazol-5-yl]-piperazin-1-yl}-2-(3-methyl-pyrazol-1-yl)-ethanone;
1-{4-[4-(1H-Benzoimidazol-2-yl)-thiazol-5-yl]-piperazin-1-yl}-2-(2-methyl-thiazol-4-yl)-ethanone;
1-{4-[4-(1H-Benzoimidazol-2-yl)-thiazol-5-yl]-piperazin-1-yl}-2-(6-chloro-imidazo[1,2-b]pyridazin-2-yl)-ethanone;
1-{4-[4-(1H-Benzoimidazol-2-yl)-thiazol-5-yl]-piperazin-1-yl}-2-(2-methyl-imidazo[1,2-a]pyridin-3-yl)-ethanone;
1-{4-[4-(1H-Benzoimidazol-2-yl)-thiazol-5-yl]-piperazin-1-yl}-2-(3,5-dimethyl-[1,2,4]triazol-1-yl)-ethanone;
1-{4-[4-(1H-Benzoimidazol-2-yl)-thiazol-5-yl]-piperazin-1-yl}-2-(2,4-dimethyl-thiazol-5-yl)-ethanone;
1-{4-[4-(1H-Benzoimidazol-2-yl)-thiazol-5-yl]-piperazin-1-yl}-2-(5-methoxy-benzo[d]isoxazol-3-yl)-ethanone;

1-{4-[4-(1H-Benzoimidazol-2-yl)-thiazol-5-yl]-piperazin-1-yl}-2-(3,5-dimethyl-pyrazol-1-yl)-ethanone;
1-{4-[4-(1H-Benzoimidazol-2-yl)-thiazol-5-yl]-piperazin-1-yl}-2-imidazo[4,5-b]pyridin-3-yl-ethanone;
1-{4-[4-(1H-Benzoimidazol-2-yl)-thiazol-5-yl]-piperazin-1-yl}-2-pyrrolo[2,3-b]pyridin-1-yl-ethanone;
1-{(R)-4-[4-(1H-Benzoimidazol-2-yl)-thiazol-5-yl]-2-methyl-piperazin-1-yl}-2-pyrrolo[2,3-b]pyridin-1-yl-ethanone;
1-{(R)-4-[4-(1H-Benzoimidazol-2-yl)-thiazol-5-yl]-2-methyl-piperazin-1-yl}-2-imidazo[4,5-b]pyridin-3-yl-ethanone;
1-{(R)-4-[4-(1H-Benzoimidazol-2-yl)-thiazol-5-yl]-2-ethyl-piperazin-1-yl}-2-pyrrolo[2,3-b]pyridin-1-yl-ethanone;
1-{(R)-4-[4-(1H-Benzoimidazol-2-yl)-thiazol-5-yl]-2-methoxymethyl-piperazin-1-yl}-2-pyrrolo[2,3-b]pyridin-1-yl-ethanone;
1-{(R)-4-[4-(1H-Benzoimidazol-2-yl)-thiazol-5-yl]-2-methoxymethyl-piperazin-1-yl}-2-imidazo[4,5-b]pyridin-3-yl-ethanone;
1-{(R)-4-[4-(4-Fluoro-1H-benzoimidazol-2-yl)-thiazol-5-yl]-2-methyl-piperazin-1-yl}-2-pyrrolo[2,3-b]pyridin-1-yl-ethanone;
1-{(R)-2-Methyl-4-[4-(4-methyl-1H-benzoimidazol-2-yl)-thiazol-5-yl]-piperazin-1-yl}-2-pyrrolo[2,3-b]pyridin-1-yl-ethanone;
1-{(R)-4-[4-(6-Chloro-1H-benzoimidazol-2-yl)-thiazol-5-yl]-2-methyl-piperazin-1-yl}-2-pyrrolo[2,3-b]pyridin-1-yl-ethanone;
1-{(R)-4-[4-(6-tert-Butyl-1H-benzoimidazol-2-yl)-thiazol-5-yl]-2-methyl-piperazin-1-yl}-2-pyrrolo[2,3-b]pyridin-1-yl-ethanone;
1-{(R)-4-[4-(5-Methanesulfonyl-1H-benzoimidazol-2-yl)-thiazol-5-yl]-2-methyl-piperazin-1-yl}-2-pyrrolo[2,3-b]pyridin-1-yl-ethanone;
1-{(R)-4-[4-(5-Chloro-6-fluoro-1H-benzoimidazol-2-yl)-thiazol-5-yl]-2-methyl-piperazin-1-yl}-2-pyrrolo[2,3-b]pyridin-1-yl-ethanone;
1-{(R)-4-[4-(5-Chloro-6-methyl-1H-benzoimidazol-2-yl)-thiazol-5-yl]-2-methyl-piperazin-1-yl}-2-pyrrolo[2,3-b]pyridin-1-yl-ethanone;
1-{(R)-4-[4-(4,5-Difluoro-1H-benzoimidazol-2-yl)-thiazol-5-yl]-2-methyl-piperazin-1-yl}-2-pyrrolo[2,3-b]pyridin-1-yl-ethanone;
1-(2-{4-[4-(4-Chloro-1H-benzoimidazol-2-yl)-thiazol-5-yl]-piperazin-1-yl}-2-oxo-ethyl)-3-methyl-1,3-dihydro-benzoimidazol-2-one;
1-(2-{4-[4-(7-Methoxy-1H-benzoimidazol-2-yl)-thiazol-5-yl]-piperazin-1-yl}-2-oxo-ethyl)-3-methyl-1,3-dihydro-benzoimidazol-2-one;
1-Methyl-3-(2-{4-[4-(5-methyl-1H-benzoimidazol-2-yl)-thiazol-5-yl]-piperazin-1-yl}-2-oxo-ethyl)-1,3-dihydro-benzoimidazol-2-one;
1-Methyl-3-(2-oxo-2-{4-[4-(5-trifluoromethyl-1H-benzoimidazol-2-yl)-thiazol-5-yl]-piperazin-1-yl}-ethyl)-1,3-dihydro-benzoimidazol-2-one;
1-(2-{4-[4-(5-Methoxy-1H-benzoimidazol-2-yl)-thiazol-5-yl]-piperazin-1-yl}-2-oxo-ethyl)-3-methyl-1,3-dihydro-benzoimidazol-2-one;
1-(2-{4-[4-(6-Fluoro-1H-benzoimidazol-2-yl)-thiazol-5-yl]-piperazin-1-yl}-2-oxo-ethyl)-3-methyl-1,3-dihydro-benzoimidazol-2-one;
1-(2-{4-[4-(5,6-Dichloro-1H-benzoimidazol-2-yl)-thiazol-5-yl]-piperazin-1-yl}-2-oxo-ethyl)-3-methyl-1,3-dihydro-benzoimidazol-2-one;
1-(2-{4-[4-(5,6-Dimethoxy-1H-benzoimidazol-2-yl)-thiazol-5-yl]-piperazin-1-yl}-2-oxo-ethyl)-3-methyl-1,3-dihydro-benzoimidazol-2-one;
1-(2-{4-[4-(6-Chloro-7-methyl-1H-benzoimidazol-2-yl)-thiazol-5-yl]-piperazin-1-yl}-2-oxo-ethyl)-3-methyl-1,3-dihydro-benzoimidazol-2-one;
1-{4-[4-(1H-Benzoimidazol-2-yl)-2-bromo-thiazol-5-yl]-piperazin-1-yl}-2-pyrrolo[2,3-b]pyridin-1-yl-ethanone;
1-{4-[4-(1H-Benzoimidazol-2-yl)-2-ethyl-thiazol-5-yl]-piperazin-1-yl}-2-pyrrolo[2,3-b]pyridin-1-yl-ethanone;
1-{4-[4-(1H-Benzoimidazol-2-yl)-2-methyl-thiazol-5-yl]-piperazin-1-yl}-2-pyrrolo[2,3-b]pyridin-1-yl-ethanone;
1-{4-[4-(1H-Benzoimidazol-2-yl)-2-phenyl-thiazol-5-yl]-piperazin-1-yl}-2-pyrrolo[2,3-b]pyridin-1-yl-ethanone;
1-{4-[4-(1H-Benzoimidazol-2-yl)-2-chloro-thiazol-5-yl]-piperazin-1-yl}-2-pyrrolo[2,3-b]pyridin-1-yl-ethanone;
1-{4-[4-(1H-Benzoimidazol-2-yl)-2-(1-hydroxy-ethyl)-thiazol-5-yl]-piperazin-1-yl}-2-pyrrolo[2,3-b]pyridin-1-yl-ethanone;
1-{4-[4-(1H-Benzoimidazol-2-yl)-thiazol-5-yl]-[1,4]diazepan-1-yl}-2-pyrrolo[2,3-b]pyridin-1-yl-ethanone;
1-{4-[4-(1H-Benzoimidazol-2-yl)-thiazol-5-yl]-[1,4]diazepan-1-yl}-2-imidazo[4,5-b]pyridin-3-yl-ethanone;
1-{(S)-4-[4-(1H-Benzoimidazol-2-yl)-thiazol-5-yl]-2-methyl-piperazin-1-yl}-2-pyrrolo[2,3-b]pyridin-1-yl-ethanone;
1-{(S)-4-[4-(1H-Benzoimidazol-2-yl)-thiazol-5-yl]-2-methyl-piperazin-1-yl}-2-imidazo[4,5-b]pyridin-3-yl-ethanone;
1-{4-[4-(1H-Benzoimidazol-2-yl)-thiazol-5-yl]-piperidin-1-yl}-2-imidazo[4,5-b]pyridin-3-yl-ethanone;
1-{(R)-4-[4-(1H-Benzoimidazol-2-yl)-thiazol-5-yl]-2-ethyl-piperazin-1-yl}-2-imidazo[4,5-b]pyridin-3-yl-ethanone;
1-{(R)-4-[4-(1H-Benzoimidazol-2-yl)-2-isopropyl-thiazol-5-yl]-2-methyl-piperazin-1-yl}-2-imidazo[4,5-b]pyridin-3-yl-ethanone;
1-{(R)-4-[4-(1H-Benzoimidazol-2-yl)-2-trifluoromethyl-thiazol-5-yl]-2-methyl-piperazin-1-yl}-2-imidazo[4,5-b]pyridin-3-yl-ethanone;
1-{4-[4-(1H-Benzoimidazol-2-yl)-thiazol-5-yl]-piperazin-1-yl}-2-(4-methoxy-indol-1-yl)-ethanone;
1-{4-[4-(1H-Benzoimidazol-2-yl)-thiazol-5-yl]-piperazin-1-yl}-2-(5,6-dichloro-indol-1-yl)-ethanone;
1-{4-[4-(1H-Benzoimidazol-2-yl)-thiazol-5-yl]-piperazin-1-yl}-2-(5-fluoro-indol-1-yl)-ethanone;
1-{4-[4-(1H-Benzoimidazol-2-yl)-thiazol-5-yl]-piperazin-1-yl}-2-(6-fluoro-indol-1-yl)-ethanone;
1-{4-[4-(1H-Benzoimidazol-2-yl)-thiazol-5-yl]-piperazin-1-yl}-2-(7-methyl-indol-1-yl)-ethanone;
1-{4-[4-(1H-Benzoimidazol-2-yl)-thiazol-5-yl]-piperazin-1-yl}-2-(2-methyl-indol-1-yl)-ethanone;
1-(2-{4-[4-(1H-Benzoimidazol-2-yl)-thiazol-5-yl]-piperazin-1-yl}-2-oxo-ethyl)-1H-indole-3-carbonitrile;
1-{4-[4-(1H-Benzoimidazol-2-yl)-thiazol-5-yl]-piperazin-1-yl}-2-(4-chloro-indol-1-yl)-ethanone;
1-(2-{4-[4-(1H-Benzoimidazol-2-yl)-thiazol-5-yl]-piperazin-1-yl}-2-oxo-ethyl)-1H-indole-7-carbonitrile;
1-{4-[4-(1H-Benzoimidazol-2-yl)-thiazol-5-yl]-piperazin-1-yl}-2-(5-chloro-6-methoxy-indol-1-yl)-ethanone;

1-{4-[4-(1H-Benzoimidazol-2-yl)-thiazol-5-yl]-piperazin-1-yl}-2-(5-fluoro-3-methyl-indol-1-yl)-ethanone;
1-{4-[4-(1H-Benzoimidazol-2-yl)-thiazol-5-yl]-piperazin-1-yl}-2-(2-trifluoromethyl-benzoimidazol-1-yl)-ethanone;
1-{4-[4-(1H-Benzoimidazol-2-yl)-thiazol-5-yl]-piperazin-1-yl}-2-(6-chloro-pyrrolo[2,3-b]pyridin-1-yl)-ethanone;
1-{4-[4-(1H-Benzoimidazol-2-yl)-thiazol-5-yl]-piperazin-1-yl}-2-(2-methyl-pyrrolo[2,3-b]pyridin-1-yl)-ethanone;
1-{4-[4-(1H-Benzoimidazol-2-yl)-thiazol-5-yl]-piperazin-1-yl}-2-(3-methyl-pyrrolo[2,3-b]pyridin-1-yl)-ethanone;
1-(2-{4-[4-(1H-Benzoimidazol-2-yl)-thiazol-5-yl]-piperazin-1-yl}-2-oxo-ethyl)-1,3-dihydro-indol-2-one;
1-{4-[4-(1H-Benzoimidazol-2-yl)-thiazol-5-yl]-piperazin-1-yl}-2-(6-methoxy-pyrrolo[2,3-b]pyridin-1-yl)-ethanone;
1-{4-[4-(1H-Benzoimidazol-2-yl)-thiazol-5-yl]-piperazin-1-yl}-2-(6-methyl-pyrrolo[2,3-b]pyridin-1-yl)-ethanone;
3-(2-{4-[4-(1H-Benzoimidazol-2-yl)-thiazol-5-yl]-piperazin-1-yl}-2-oxo-ethyl)-1,3-dihydro-imidazo[4,5-b]pyridin-2-one;
1-{(2S,6R)-4-[4-(5-Chloro-1H-benzoimidazol-2-yl)-thiazol-5-yl]-2,6-dimethyl-piperazin-1-yl}-2-imidazo[4,5-b]pyridin-3-yl-ethanone;
1-{(R)-4-[4-(1H-Benzoimidazol-2-yl)-2-cyclopropyl-thiazol-5-yl]-2-methyl-piperazin-1-yl}-2-imidazo[4,5-b]pyridin-3-yl-ethanone;
1-Methyl-3-(2-oxo-2-{4-[4-(6-trifluoromethoxy-1H-benzoimidazol-2-yl)-thiazol-5-yl]-piperazin-1-yl}-ethyl)-1,3-dihydro-benzoimidazol-2-one;
2-(5-{4-[2-(3-Methyl-2-oxo-2,3-dihydro-benzoimidazol-1-yl)-acetyl]-piperazin-1-yl}-thiazol-4-yl)-1H-benzoimidazole-5-carbonitrile;
1-(2-{4-[4-(6-Hydroxymethyl-1H-benzoimidazol-2-yl)-thiazol-5-yl]-piperazin-1-yl}-2-oxo-ethyl)-3-methyl-1,3-dihydro-benzoimidazol-2-one;
1-(2-{4-[4-(1H-Benzoimidazol-2-yl)-thiazol-5-yl]-piperazin-1-yl}-2-oxo-ethyl)-3,4-dihydro-1H-quinolin-2-one;
4-(2-{4-[4-(1H-Benzoimidazol-2-yl)-thiazol-5-yl]-piperazin-1-yl}-2-oxo-ethyl)-4H-benzo[1,4]oxazin-3-one;
imidazo[4,5-b]pyridin-3-yl-ethanone;
1-{(R)-4-[4-(1H-Benzoimidazol-2-yl)-2-bromo-thiazol-5-yl]-2-methyl-piperazin-1-yl}-2-imidazo[4,5-b]pyridin-3-yl-ethanone;
1-{(R)-4-[4-(1H-Benzoimidazol-2-yl)-2-o-tolyl-thiazol-5-yl]-2-methyl-piperazin-1-yl}-2-imidazo[4,5-b]pyridin-3-yl-ethanone;
1-{(R)-4-[4-(1H-Benzoimidazol-2-yl)-2-(2-methoxy-phenyl)-thiazol-5-yl]-2-methyl-piperazin-1-yl}-2-imidazo[4,5-b]pyridin-3-yl-ethanone;
1-{(R)-4-[4-(6-Chloro-1H-benzoimidazol-2-yl)-thiazol-5-yl]-2-methyl-piperazin-1-yl}-2-imidazo[4,5-b]pyridin-3-yl-ethanone;
3-(2-{(R)-4-[4-(5-Chloro-1H-benzoimidazol-2-yl)-thiazol-5-yl]-2-methyl-piperazin-1-yl}-2-oxo-ethyl)-3H-benzooxazol-2-one;
2-Imidazo[4,5-b]pyridin-3-yl-1-{(R)-2-methyl-4-[4-(5-methyl-1H-benzoimidazol-2-yl)-thiazol-5-yl]-piperazin-1-yl}-ethanone;
1-{(R)-4-[4-(5-tert-Butyl-1H-benzoimidazol-2-yl)-thiazol-5-yl]-2-methyl-piperazin-1-yl}2 imidazo[4,5-b]pyridin-3-yl-ethanone;
1-{(R)-4-[4-(5-Chloro-6-methyl-1H-benzoimidazol-2-yl)-thiazol-5-yl]-2-methyl-piperazin-1-yl}-2-imidazo[4,5-b]pyridin-3-yl-ethanone;
2-Imidazo[4,5-b]pyridin-3-yl-1-{(R)-4-[4-(6-isopropyl-1H-benzoimidazol-2-yl)-thiazol-5-yl]-2-methyl-piperazin-1-yl}-ethanone;
1-{(R)-4-[4-(5-Chloro-6-fluoro-1H-benzoimidazol-2-yl)-thiazol-5-yl]-2-methyl-piperazin-1-yl}-2-imidazo[4,5-b]pyridin-3-yl-ethanone;
1-{(R)-4-[4-(4,5-Difluoro-1H-benzoimidazol-2-yl)-thiazol-5-yl]-2-methyl-piperazin-1-yl}-2-imidazo[4,5-b]pyridin-3-yl-ethanone;
1-{(R)-4-[4-(5,6-Difluoro-1H-benzoimidazol-2-yl)-thiazol-5-yl]-2-methyl-piperazin-1-yl}-2-imidazo[4,5-b]pyridin-3-yl-ethanone;
2-Imidazo[4,5-b]pyridin-3-yl-1-{(R)-2-methyl-4-[4-(5-trifluoromethyl-1H-benzoimidazol-2-yl)-thiazol-5-yl]-piperazin-1-yl}-ethanone;
1-{(R)-4-[4-(5-Chloro-6-trifluoromethyl-1H-benzoimidazol-2-yl)-thiazol-5-yl]-2-methyl-piperazin-1-yl}-2-imidazo[4,5-b]pyridin-3-yl-ethanone;
1-{(R)-4-[4-(5-Chloro-4-methyl-1H-benzoimidazol-2-yl)-thiazol-5-yl]-2-methyl-piperazin-1-yl}-2-imidazo[4,5-b]pyridin-3-yl-ethanone;
2-Imidazo[4,5-b]pyridin-3-yl-1-{(R)-2-methyl-4-[4-(4-trifluoromethyl-1H-benzoimidazol-2-yl)-thiazol-5-yl]-piperazin-1-yl}-ethanone;
1-{(R)-4-[4-(5-Fluoro-1H-benzoimidazol-2-yl)-thiazol-5-yl]-2-methyl-piperazin-1-yl)}-2-imidazo[4,5-b]pyridin-3-yl-ethanone;
1-{(R)-4-[4-(4-Fluoro-1H-benzoimidazol-2-yl)-thiazol-5-yl]-2-methyl-piperazin-1-yl}-2-imidazo[4,5-b]pyridin-3-yl-ethanone;
2-Imidazo[4,5-b]pyridin-3-yl-1-{(R)-2-methyl-4-[4-(1-methyl-1H-benzoimidazol-2-yl)-thiazol-5-yl]-piperazin-1-yl}-ethanone;
1-{(R)-4-[4-(6-Ethyl-1H-benzoimidazol-2-yl)-thiazol-5-yl]-2-methyl-piperazin-1-yl}-2-imidazo[4,5-b]pyridin-3-yl-ethanone;
2-Imidazo[4,5-b]pyridin-3-yl-1-{(R)-2-methyl-4-[4-(6-phenyl-1H-benzoimidazol-2-yl)-thiazol-5-yl]-piperazin-1-yl}-ethanone;
1-[2-(4-{4-[5-(2-Hydroxy-ethoxy)-1H-benzoimidazol-2-yl]-thiazol-5-yl}-piperazin-1-yl)-2-oxo-ethyl]-3-methyl-1,3-dihydro-benzoimidazol-2-one;
1-[2-(4-{4-[5-(2-Methoxy-ethoxy)-1H-benzoimidazol-2-yl]-thiazol-5-yl}-piperazin-1-yl)-2-oxo-ethyl]-3-methyl-1,3-dihydro-benzoimidazol-2-one;
1-(2-{(R)-4-[4-(1H-Benzoimidazol-2-yl)-2-trifluoromethyl-thiazol-5-yl]-2-methyl-piperazin-1-yl}-2-oxo-ethyl)-1,3-dihydro-indol-2-one;
3-(2-{(R)-4-[4-(1H-Benzoimidazol-2-yl)-2-trifluoromethyl-thiazol-5-yl]-2-methyl-piperazin-1-yl}-2-oxo-ethyl)-1,3-dihydro-imidazo[4,5-b]pyridin-2-one;
1-{4-[4-(1H-Benzoimidazol-2-yl)-thiazol-5-yl]-piperazin-1-yl}-2-(3,4-dihydro-2H-quinolin-1-yl)-ethanone;
1-{4-[4-(1H-Benzoimidazol-2-yl)-thiazol-5-yl]-piperazin-1-yl}-2-(2,3-dihydro-benzo[1,4]oxazin-4-yl)-ethanone;
1-(2-{4-[4-(1H-Benzoimidazol-2-yl)-thiazol-5-yl]-piperazin-1-yl}-2-oxo-ethyl)-2,3-dihydro-1H-quinolin-4-one;
1-{4-[4-(1H-Benzoimidazol-2-yl)-thiazol-5-yl]-piperazin-1-yl}-2-(7-fluoro-indol-1-yl)-ethanone;
1-{4-[4-(1H-Benzoimidazol-2-yl)-thiazol-5-yl]-piperazin-1-yl}-2-indazol-1-yl-ethanone;

1-{4-[4-(1H-Benzoimidazol-2-yl)-thiazol-5-yl]-piperazin-1-yl}-2-pyridin-3-yl-ethanone;
1-{4-[4-(1H-Benzoimidazol-2-yl)-thiazol-5-yl]-piperazin-1-yl}-2-(2-fluoro-4-methoxy-phenyl)-ethanone;
1-(2-{4-[4-(4-Hydroxy-1H-benzoimidazol-2-yl)-thiazol-5-yl]-piperazin-1-yl}-2-oxo-ethyl)-3-methyl-1,3-dihydro-benzoimidazol-2-one;
1-{(R)-4-[4-(1H-Benzoimidazol-2-yl)-2-oxetan-3-yl-thiazol-5-yl]-2-methyl-piperazin-1-yl}-2-imidazo[4,5-b]pyridin-3-yl-ethanone;
and a pharmaceutically-acceptable salt thereof.

12. A compound according to claim 1 selected from:
1-{(R)-4-[4-(1H-Benzoimidazol-2-yl)-2-ethyl-thiazol-5-yl]-2-methyl-piperazin-1-yl}-2-imidazo[4,5-b]pyridin-3-yl-ethanone;
1-{(R)-4-[4-(5-Chloro-1H-benzoimidazol-2-yl)-2-trifluoromethyl-thiazol-5-yl]-2-methyl-piperazin-1-yl}-2-imidazo[4,5-b]pyridin-3-yl-ethanone;
1-{(R)-4-[4-(1H-Benzoimidazol-2-yl)-2-(2-fluoro-phenyl)-thiazol-5-yl]-2-methyl-piperazin-1-yl}-2-imidazo[4,5-b]pyridin-3-yl-ethanone;
1-{(R)-4-[4-(1H-Benzoimidazol-2-yl)-2-m-tolyl-thiazol-5-yl]-2-methyl-piperazin-1-yl}-2-imidazo[4,5-b]pyridin-3-yl-ethanone;
1-1{(R)-4-[4-(1H-Benzoimidazol-2-yl)-2-p-tolyl-thiazol-5-yl]-2-methyl-piperazin-1-yl}-2-imidazo[4,5-b]pyridin-3-yl-ethanone;
1-(2-1{(R)-4-[4-(1H-Benzoimidazol-2-yl)-thiazol-5-yl]-2-methyl-piperazin-1-yl}-2-oxo-ethyl)-3,3-dimethyl-1,3-dihydro-indol-2-one;
3-(2-{(R)-4-[4-(1H-Benzoimidazol-2-yl)-thiazol-5-yl]-2-methyl-piperazin-1-yl}-2-oxo-ethyl)-4-methyl-3H-benzooxazol-2-one;
3-(2-{(R)-4-[4-(1H-Benzoimidazol-2-yl)-thiazol-5-yl]-2-methyl-piperazin-1-yl}-2-oxo-ethyl)-4-fluoro-3H-benzooxazol-2-one;
1-{(R)-4-[4-(5,6-Dimethoxy-1H-benzoimidazol-2-yl)-thiazol-5-yl]-2-methyl-piperazin-1-yl}-2-imidazo[4,5-b]pyridin-3-yl-ethanone;
1-{(R)-4-[4-(1H-Benzoimidazol-2-yl)-triazol-5-yl]-2-methyl-piperazin-1-yl}-2-(2-hydroxymethyl-pyrrolo[2,3-b]pyridin-1-yl)-ethanone;
1-{(R)-4-[4-(6-Hydroxymethyl-1H-benzoimidazol-2-yl)-2-trifluoromethyl-thiazol-5-yl]-2-methyl-piperazin-1-yl}-2-imidazo[4,5-b]pyridin-3-yl-ethanone;
1-{(R)-4-[4-(5,6-Dimethoxy-1H-benzoimidazol-2-yl)-2-trifluoromethyl-thiazol-5-yl]-2-methyl-piperazin-1-yl}-2-imidazo[4,5-b]pyridin-3-yl-ethanone;
1-{4-[4-(1H-Benzoimidazol-2-yl)-2-trifluoromethyl-thiazol-5-yl]-piperazin-1-yl}-2-imidazo[4,5-b]pyridin-3-yl-ethanone;
3-{4-(1H-Benzoimidazol-2-yl)-5-[(R)-3-methyl-4-(2-pyridin-[2,3-b]pyridin-1-yl-acetyl)-piperazin-1-yl]-thiazol-2-yl}-propionic acid;
3-(2-{(R)-4-[4-(1H-Benzoimidazol-2-yl)-thiazol-5-yl]-2-methyl-piperazin-1-yl}-2-oxo-ethyl)-3H-oxazolo[4,5-b]pyridin-2-one;
4-(2-{(R)-4-[4-(1H-Benzoimidazol-2-yl)-thiazol-5-yl]-2-methyl-piperazin-1-yl}-2-oxo-ethyl)-3H-oxazolo[4,5-b]pyridin-2-one;
1-{(R)-4-[4-(6-Cyclopropyl-1H-benzoimidazol-2-yl)-thiazol-5-yl]-2-methyl-piperazin-1-yl}-2-imidazo[4,5-b]pyridin-3-yl-ethanone;
1-{(R)-4-[4-(1H-Benzoimidazol-2-yl)-thiazol-5-yl]-2-methyl-piperazin-1-yl}-2-(4-phenyl-[1,2,3]triazol-1-yl)-ethanone;
1-{(R)-4-[4-(6-Hydroxymethyl-1H-benzoimidazol-2-yl)-thiazol-5-yl]-2-methyl-piperazin-1-yl}-2-imidazo[4,5-b]pyridin-3-yl-ethanone;
1-{(R)-4-[4-(1H-Benzoimidazol-2-yl)-thiazol-5-yl]-2-methyl-piperazin-1-yl}-2-(2-[1,2,3]triazol-2-yl-phenyl)-ethanone;
1-(2-{(R)-4-[4-(1H-Benzoimidazol-2-yl)-thiazol-5-yl]-2-methyl-piperazin-1-yl}-2-oxo-ethyl)-1H-indole-2,3-dione;
2-Benzoimidazol-1-yl-{(R)-4-[4-(1H-benzoimidazol-2-yl)-2-trifluoromethyl-thiazol-5-yl]-2-methyl-piperazin-1-yl}-ethanone;
1-{(R)-4-[4-(1H-Benzoimidazol-2-yl)-2-trifluoromethyl-thiazol-5-yl]-2-methyl-piperazin-1-yl}-pyrazol-1-yl-ethanone;
1-{(R)-4-[4-(1H-Benzoimidazol-2-yl)-2-trifluoromethyl-thiazol-5-yl]-2-methyl-piperazin-1-yl}-2-(3-methyl-pyrazol-1-yl)-ethanone;
1-{(R)-4-[4-(1H-Benzoimidazol-2-yl)-2-trifluoromethyl-thiazol-5-yl]-2-methyl-piperazin-1-yl}-2-(4-chloro-pyrazol-1-yl)-ethanone;
1-{(R)-4-[4-(1H-Benzoimidazol-2-yl)-2-trifluoromethyl-thiazol-5-yl]-2-methyl-piperazin-1-yl}-2-(5-methyl-pyrazol-1-yl)-ethanone;
1-{(R)-4-{4-(1H-Benzoimidazol-2-yl)-2-trifluoromethyl-thiazol-5-yl]-2-methyl-piperazin-1-yl}-2-(3-phenyl-pyrazol-1-yl)-ethanone;
1-{(R)-4-[4-(1H-Benzoimidazol-2-yl)-2-trifluoromethyl-thiazol-5-y]-2-methyl-piperazin-1-yl}-2-(3,5-dimethyl-[1,2,4]triazol-1-yl)-ethanone;
1-{(R)-4-[4-(1H-Benzoimidazol-2-yl)-2-trifluoromethyl-thiazol-5-yl]-2-methyl-piperazin-1-yl}-2-(2-[1,2,3]triazol-2-yl-phenyl)-ethanone;
1-{(R)-4-[4-(1H-Benzoimidazol-2-yl)-2-trifluoromethyl-thiazol-5-yl]-2-methyl-piperazin-1-yl}-2-(3-[1,2,3]triazol-2-yl-phenyl)-ethanone;
1-{(R)-4-[4-(1H-Benzoimidazol-2-yl)-2-hydroxymethyl-thiazol-5-yl]-2-methyl-piperazin-1-yl}-2-imidazo[4,5-b]pyridin-3-yl-ethanone;
1-{(R)-4-[4-(5-Acetyl-1H-benzoimidazol-2-yl)-2-trifluoromethyl-thiazol-5-yl]-2-methyl-piperazin-1-yl}-2-imidazo[4,5-b]pyridin-3-yl-ethanone;
1-{(R)-4-[4-(1-H-Benzoimidazol-2-yl)-2-trifluoromethyl-thiazol-5-yl]-2-methyl-piperazin-1-yl}-2-quinolin-8-yl-ethanone;
1-((R)-4-{4-[5-(1-Hydroxy-ethyl)-1H-benzoimidazol-2-yl]-2-trifluoromethyl-thiazol-5-yl}-2-methyl-piperazin-1-yl)-2-imidazo[4,5-b]pyridin-3-yl-ethanone;
1-{(R)-4-[4-(1H-Benzoimidazol-2-yl)-2-trifluoromethyl-thiazol-5-yl]-2-methyl-piperazin-1-yl}-2-(4-phenyl-[1,2,3]triazol-1-yl)-ethanone;
1-{(R)-4-[4-(1H-Benzoimidazol-2-yl)-2-dimethylaminomethyl-thiazol-5-yl]-2-methyl-piperazin-1-yl}-2-imidazo[4,5-b]pyridin-3-yl-ethanone;
1-{(R)-4-[4-(1H-Benzoimidazol-2-yl)-2-trifluoromethyl-thiazol-5-yl]-2-methyl-piperazin-1-yl}-2-pyrazolo[3,4-b]pyridin-2-yl-ethanone;
1-{(R)-4-[4-(1H-Benzoimidazol-2-yl)-2-trifluoromethyl-thiazol-5-yl]-2-methyl-piperazin-1-yl}-2-(2-pyrazol-1-yl-phenyl)-ethanone;
1-{(R)-4-[4-(1H-Benzoimidazol-2-yl)-2-trifluoromethyl-thiazol-5-yl]-2-methyl-piperazin-1-yl}-2-(5-phenyl-pyrazol-1-yl)-ethanone;
1-(2-{(R)-4-[4-(1H-Benzoimidazol-2-yl)-thiazol-5-yl]-2-methyl-piperazin-1-yl}-2-oxo-ethyl)-3,3-difluoro-1,3-dihydro-indol-2-one;

2-{5-[(R)-4-(2-Imidazo[4,5-b]pyridin-3-yl-acetyl)-3-methyl-piperazin-1-yl]-2-trifluoromethyl-thiazol-4-yl}-1H-benzoimidazole-5-carboxylic acid methyl ester;
1-{(R)-4-[4-(1H-Benzoimidazol-2-yl)-2-trifluoromethyl-thiazol-5-yl]-2-methyl-piperazin-1-yl}-2-imidazo[4,5-c]pyridin-1-yl-ethanone;
2-Imidazo[4,5-b]pyridin-3-yl-1-((R)-4-{4-[5-(2-methoxy-ethoxy)-1H-benzoimidazol-2-yl]-2-trifluoromethyl-thiazol-5-yl}-2-methyl-piperazin-1-yl)-ethanone;
1-((R)-4-{4-[5-(2-Hydroxy-ethoxy)-1H-benzoimidazol-2-yl]-2-trifluoromethyl-thiazol-5-yl}-2-methyl-piperazin-1-yl)-2-imidazo[4,5-b]pyridin-3-yl-ethanone;
1-((R)-4-{4-[5-(1-Hydroxy-cyclopropyl)-1H-benzoimidazol-2-yl]-2-trifluoromethyl-thiazol-5-yl}-2-methyl-piperazin-1-yl)-2-imidazo[4,5-b]pyridin-3-yl-ethanone;
1-(2-{(R)-4-[4-(1H-Benzoimidazol-2-yl)-2-trifluoromethyl-thiazol-5-yl]-2-methyl-piperazin-1-yl}-2-oxo-ethyl)-3,3-difluoro-1,3-dihydro-indol-2-one;
1-{(R)-4-[4-(1H-Benzoimidazol-2-yl)-2-trifluoromethyl-thiazol-5-yl]-2-methyl-piperazin-1-yl}-2-(3-bromo-[1,2,4]triazol-1-yl)-ethanone;
1-{(R)-4-[4-(1H-Benzoimidazol-2-yl)-2-trifluoromethyl-thiazol-5-yl]-2-methyl-piperazin-1-yl}-2-(4-methyl-pyrazol-1-yl)-ethanone;
1-{(R)-4-[4-(1H-Benzoimidazol-2-yl)-2-trifluoromethyl-thiazol-5-yl]-2-methyl-piperazin-1-yl}-2-(3,5-dimethyl-pyrazol-1-yl)-ethanone;
1-{(R)-4-[4-(1H-Benzoimidazol-2-yl)-2-trifluoromethyl-thiazol-5-yl]-2-methyl-piperazin-1-yl}-2-(3-trifluoromethyl-pyrazol-1-yl)-ethanone;
1-{(R)-4-[4-(1H-Benzoimidazol-2-yl)-2-trifluoromethyl-thiazol-5-yl]-2-methyl-piperazin-1-yl}-2-[1,2,4]triazol-1-yl-ethanone;
1-{(R)-4-[4-(1H-Benzoimidazol-2-yl)-2-trifluoromethyl-thiazol-5-yl]-2-methyl-piperazin-1-yl}-2-[2-(4-methyl-piperazin-1-yl)-phenyl]-ethanone;
1-{(R)-4-[4-(1H-Benzoimidazol-2-yl)-2-trifluoromethyl-thiazol-5-yl]-2-methyl-piperazin-1-yl}-2-(5-methyl-[1,3,4]oxadiazol-2-yl)-ethanone;
1-{(R)-4-[4-(1H-Benzoimidazol-2-yl)-2-trifluoromethyl-thiazol-5-yl]-2-methyl-piperazin-1-yl}-2-(5-phenyl-[1,3,4]oxadiazol-2-yl)-ethanone;
1-{(R)-4-[4-(1H-Benzoimidazol-2-yl)-2-trifluoromethyl-thiazol-5-yl]-2-methyl-piperazin-1-yl}-2-[1,2,3]triazol-2-yl-ethanone;
1-(2-{(R)-4-[4-(1H-Benzoimidazol-2-yl)-2-trifluoromethyl-thiazol-5-yl]-2-methyl-piperazin-1-yl}-2-oxo-ethyl)-1H-pyrazole-3-carboxylic acid methyl ester;
1-((R)-2-Methyl-4-{4-[6-(4-methyl-piperazin-1-yl)-1H-benzoimidazol-2-yl]-2-trifluoromethyl-thiazol-5-yl}-piperazin-1-yl)-2-pyrazol-1-yl-ethanone;
1-{(R)-4-[4-(6-Dimethylamino-1H-benzoimidazol-2-yl)-2-trifluoromethyl-thiazol-5-yl]-2-methyl-piperazin-1-yl}-2-pyrazol-1-yl-ethanone;
2-Imidazo[4,5-b]pyridin-3-yl-1-{(R)-4-[4-(3H-imidazo[4,5-b]pyridin-2-yl)-2trifluoromethyl-thiazol-5-yl]-2-methyl-piperazin-1-yl}-ethanone;
1-{(R)-2-Methyl-4-[4-(1-methyl-1H-benzoimidazol-2-yl)-trifluoromethyl-thiazol-5-yl]-piperazin-1-yl}-2-pyrazol-1-yl-ethanone;
1-((R)-4-{1-(2-Methoxy-ethyl)-1H-benzoimidazol-2-yl]-2-trifluoromethyl-thiazol-5-yl}-2-methyl-piperazin-1-yl)-2-pyrazol-1-yl-ethanone;
2-Imidazo[4,5-b]pyridin-3-yl-1-{(R)-4-[4-(3H-imidazo[4,5-c]pyridin-2-yl)-2-trifluoromethyl-thiazol-5-yl]-2-methyl-piperazin-1-yl}-ethanone;
2-Imidazo[4,5-b]pyridin-3-yl-1-{(R)-2-methyl-4-[4-(9H-purin-8-yl)-2-trifluoromethyl-thiazol-5-yl]-piperazin-1-yl}-ethanone;
1-{(R)-4-[4-(1H-Benzoimidazol-2-yl)-2-trifluoromethyl-thiazol-5-yl]-2-methyl-piperazin-1-yl}-2-(6-methyl-pyridin-3-yl)-ethanone;
1-{(R)-4-[4-(1H-Benzoimidazol-2-yl)-2-trifluoromethyl-thiazol-5-yl]-2-methyl-piperazin-1-yl}-2-(2,6-dimethyl-pyridin-4-yl)-ethanone;
1-{(R)-4-[4-(1H-Benzoimidazol-2-yl)-2-trifluoromethyl-thiazol-5-yl]-2-methyl-piperazin-1-yl}-2-(5-methyl-4,5,6,7-tetrahydro-imidazo[4,5-c]pyridin-1-yl)-ethanone;
1-{(R)-4-[4-(1H-Benzoimidazol-2-yl)-2-trifluoromethyl-thiazol-5-yl]-2-methyl-piperazin-1-yl}-2-(4-dimethylaminomethyl-3-methyl-pyrazol-1-yl)-ethanone;
1-{(R)-2-Methyl-4-[4-(6-piperidin-1-ylmethyl-1H-benzoimidazol-2-yl)-2-trifluoromethyl-thiazol-5-yl]-piperazin-1-yl}-2-pyrazol-1-yl-ethanone;
1-{(R)-4-[4-(1H-Benzoimidazol-2-yl)-2-trifluoromethyl-thiazol-5-yl]-2-methyl-piperazin-1-yl}-2-(5-methyl-[1,2,4]triazol-1-yl)-ethanone;
1-{(R)-4-[4-(1H-Benzoimidazol-2-yl)-2-trifluoromethyl-thiazol-5-yl]-2-methyl-piperazin-1-yl}-2-(3-methyl-[1,2,4]triazol-1-yl)-ethanone;
1-{(R)-4-[4-(6-Dimethylaminomethyl-1H-benzoimidazol-2-yl)-2-trifluoromethyl-thiazol-5-yl]-2-methyl-piperazin-1-yl}-2-pyrazol-1-yl-ethanone;
1-((R)-4-{4-[6-(3-Methoxy-pyrrolidin-1-ylmethyl)-1H-benzoimidazol-2-yl]-2-trifluoromethyl-thiazol-5-yl}-2-methyl-piperazin-1-yl)-2-pyrazol-1-yl-ethanone;
1-{(R)-4-[4-(1H-Benzoimidazol-2-yl)-2-trifluoromethyl-thiazol-5-yl]-2-methyl-piperazin-1-yl}-2-(4,6-dimethyl-pyridin-2-yl)-ethanone;
1-{(R)-4-[4-(1H-Benzoimidazol-2-yl)-thiazol-5-yl]-2-dimethylaminomethyl-piperazin-1-yl}-2-imidazo[4,5-b]pyridin-3-yl-ethanone;
2-(3,5-Dimethyl-[1,2,4]triazol-1-yl)-1-((R)-2-methyl-4-{4-[6-(1-methyl-piperidin-4-yl)-1H-benzoimidazol-2-yl]-2-trifluoromethyl-thiazol-5-yl}-piperazin-1-yl)-ethanone;
2-(3,5-Dimethyl-[1,2,4]triazol-1-yl)-1-((R)-2-methyl-4-{4-[6-(tetrahydro-pyran-4-yl)-1-benzoimidazol-2-yl]-2-trifluoromethyl-thiazol-5-yl}-piperazin-1-yl)-ethanone;
1-((R)-4-{4-[5-(2-Amino-ethyl)-1H-benzoimidazol-2-yl]-2-trifluoromethyl-thiazol-5yl]-2-methyl-piperazin-1-yl)-2-(3,5-dimethyl-[1,2,4]triazol-1-yl)-ethanone;
1-{(R)-4-[4-(1H-Benzoimidazol-2-yl)-2-trifluoromethyl-thiazol-5-yl]-2-methyl-piperazin-1-yl}-2-(4-piperidin-4-yl-pyrazol-1-yl)-ethanone;
1-{(R)-4-[4-(1H-Benzoimidazol-2-yl)-2-trifluoromethyl-thiazol-5-yl]-2-methyl-piperazin-1-yl}-2-[4-(1-methyl-piperidin-4-yl)-pyrazol-1-yl]-ethanone;
1-{(R)-4-[4-(1H-Benzoimidazol-2-yl)-2-trifluoromethyl-thiazol-5-yl]-2-methyl-piperazin-1-yl}-2-(5-methyl-4,5,6,7-tetrahydro-imidazo[4,5-c]pyridin-3-yl)-ethanone;
2-(3,5-Dimethyl-[1,2,4]triazol-1-yl)-1-((R)-2-methyl-4-{4-[6-(2-pyrrolidin-1-yl-ethyl)-1H-benzoimidazol-2-yl]-2-trifluoromethyl-thiazol-5-yl}-piperazin-yl)-ethanone;
1-{(R)-4-[4-(1H-Benzoimidazol-2-yl)-2-trifluoromethyl-thiazol-5-yl]-2-methyl-piperazin-1-yl}-2-(5-methyl-4,5,6,7-tetrahydro-pyrazolo[4,3-c]pyridin-2-yl)-ethanone;

1-{(R)-4-[4-(1H-Benzoimidazol-2-yl)-2-trifluoromethyl-thiazol-5-yl]-2-methyl-piperazin-1-yl}-2-(5-methyl-4,5,6,7-tetrahydro-pyrazolo[4,3-c]pyridin-1-yl)-ethanone;

1-{(R)-4-[4-(1H-Benzoimidazol-2-yl)-2-trifluoromethyl-thiazol-5-yl]-2-methyl-piperazin-1-yl}-2-(1,4,6,7-tetrahydro-pyrazolo[4,3-c]pyridin-5-yl)-ethanone;

1-{(R)-4-[4-(1H-Benzoimidazol-2-yl)-2-trifluoromethyl-thiazol-5-yl]-2-dimethylaminomethyl-piperazin-1-yl}-2-(3,5-dimethyl-[1,2,4]triazol-1-yl)-ethanone;

1-{(R)-4-[4-(1H-Benzoimidazol-2-yl)-2-trifluoromethyl-thiazol-5-yl]-2-methyl-piperazin-1-yl}-2-(4-dimethylaminomethyl-3,5-dimethyl-pyrazol-1-yl)-ethanone;

1-{(R)-4-[4-(1H-Benzoimidazol-2-yl)-2-trifluoromethyl-thiazol-5-yl]-2-dimethylaminomethyl-piperazin-1-yl}-2-imidazo[4,5-b]pyridin-3-yl-ethanone;

1-{(R)-4-[4-(1H-Benzoimidazol-2-yl)-2-trifluoromethyl-thiazol-5-yl]-2-methyl-piperazin-1-yl}-2-(3-dimethylaminomethyl-5-methyl-[1,2,4]triazol-1-yl)-ethanone;

2-(3,5-Dimethyl-[1,2,4]triazol-1-yl)-1-{(R)-2-methyl-4-[4-(5-trifluoromethoxy-1H-benzoimidazol-2-yl)-2-trifluoromethyl-thiazol-5-yl]-piperazin-1-yl}-ethanone;

2-(3,5-Dimethyl-[1,2,4]triazol-1-yl)-1-{(R)-2-methyl-4-[4-(6-morpholin-4-yl-1H-benzoimidazol-2-yl)-2-trifluoromethyl-thiazol-5-yl]-piperazin-1-yl}-ethanone;

1-((R)-4-{4-[6-(Azetidin-3-yloxy)-1H-benzoimidazol-2-yl]-2-trifluoromethyl-thiazol-5-yl}-2-methyl-piperazin-1-yl)-2-(3,5-dimethyl-[1,2,4]triazol-1-yl)-ethanone;

2-(3,5-Dimethyl-[1,2,4]triazol-1-yl)-1-{(R)-2-methyl-4-[4-(6-piperidin-4-yl-1H-benzoimidazol-2-yl)-2-trifluoromethyl-thiazol-5-yl]-piperazin-1-yl}-ethanone;

2-(3,5-Dimethyl-[1,2,4]triazol-1-yl)-1-{(R)-2-methyl-4-[4-(6-[1,2,4]triazol-1-yl-1H-benzoimidazol-2-yl)-2-trifluoromethyl-thiazol-5-yl]-piperazin-1-yl}-ethanone;

1-[2-(5-{(R)-4-[2-(3,5-Dimethyl-[1,2,4]triazol-1-yl)-acetyl]-3-methyl-piperazin-1-yl}-2-trifluoromethyl-thiazol-4-yl)-3H-benzoimidazol-5-yl]-pyrrolidin-2-one;

1-{(S)-4-[4-(1H-Benzoimidazol-2-yl)-2-trifluoromethyl-thiazol-5-yl]-2-methyl-piperazin-1-yl}-2-(3,5-dimethyl-[1,2,4]triazol-1-yl)-ethanone;

2-(3,5-Dimethyl-[1,2,4]triazol-1-yl)-1-((R)-2-methyl-4-{4-[6-(5-methyl-[1,2,4]oxadiazol-3-yl)-1H-benzoimidazol-2-yl]-2-trifluoromethyl-thiazol-5-yl}-piperazin-1-yl)-ethanone;

2-(3,5-Dimethyl-[1,2,4]triazol-1-yl)-1-{(R)-4-[4-(4-fluoro-1H-benzoimidazol-2-yl)-2-trifluoromethyl-thiazol-5-yl]-2-methyl-piperazin-1-yl}-ethanone;

1-{(R)-4-[4-(4,5-Difluoro-1H-benzoimidazol-2-yl)-2-trifluoromethyl-thiazol-5-yl]-2-methyl-piperazin-1-yl}-2-(3,5-dimethyl-[1,2,4]triazol-1-yl)-ethanone;

2-(3,5-Dimethyl-[1,2,4]triazol-1-yl)-1-{(R)-2-methyl-4-[2-trifluoromethyl-4-(4-trifluoromethyl-1-benzoimidazol-2-yl)-thiazol-5-yl]-piperazin-1-yl}-ethanone;

and a pharmaceutically-acceptable salt thereof.

13. A pharmaceutical composition comprising, as an active principle, a compound of Formula (I) according to claim 1, or a pharmaceutically acceptable salt thereof; and at least one therapeutically inert excipient.

14. A medicament comprising the compound according to claim 1, or a pharmaceutically acceptable salt thereof.

15. A method of treating a disease comprising administering an effective amount of the compound according to claim 1, or a pharmaceutically acceptable salt thereof, to a subject in need thereof, wherein the disease is selected from rheumatoid arthritis, multiple sclerosis, neuromyelitis optica, inflammatory bowel disease, Crohn's disease, ulcerative colitis, systemic lupus erythematosus, psoriasis, psoriatic arthritis, lupus nephritis, interstitial cystitis, celiac disease, myasthenia gravis, type I diabetes, uveitis, asthma, chronic obstructive pulmonary disorder, atherosclerosis, myocarditis, inflammatory myopathies, dry eye disease, sarcoidosis, influenza, cerebral malaria, transplant rejection, liver cirrhosis, systemic sclerosis, pulmonary arterial hypertension, neurodegeneration, Alzheimer's disease, HIV associated dementia, Huntington's chorea, Guillain-Barré syndrome, chronic inflammatory demyelinating polyneuropathy, brain tumor, colon cancer, breast cancer, and metastatic spread of cancer.

16. A method of treating a disease comprising administering an effective amount of the compound according to claim 12, or a pharmaceutically acceptable salt thereof, to a subject in need thereof, wherein the disease is selected from rheumatoid arthritis, multiple sclerosis, neuromyelitis optica, inflammatory bowel disease, Crohn's disease, ulcerative colitis, systemic lupus erythematosus, psoriasis, psoriatic arthritis, lupus nephritis, interstitial cystitis, celiac disease, myasthenia gravis, type I diabetes, uveitis, asthma, chronic obstructive pulmonary disorder, atherosclerosis, myocarditis, inflammatory myopathies, dry eye disease, sarcoidosis, influenza, cerebral malaria, transplant rejection, liver cirrhosis, systemic sclerosis, pulmonary arterial hypertension, neurodegeneration, Alzheimer's disease, HIV associated dementia, Huntington's chorea, Guillain-Barré syndrome, chronic inflammatory demyelinating polyneuropathy, brain tumor, colon cancer, breast cancer, and metastatic spread of cancer.

17. A pharmaceutical composition comprising, as an active principle, a compound of Formula (I) according to claim 12, or a pharmaceutically acceptable salt thereof; and at least one therapeutically inert excipient.

18. A compound according to claim 1, wherein $R^3$ is trifluoromethyl, or a pharmaceutically acceptable salt thereof.

19. A compound according to claim 4, wherein $R^2$ is hydrogen, or a pharmaceutically acceptable salt thereof.

20. A compound according to claim 4, wherein the group

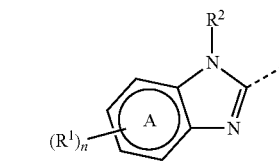

represents a group selected from:

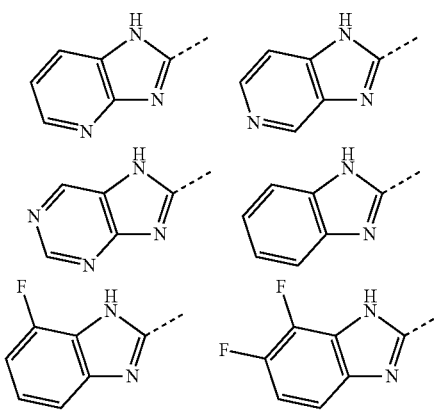

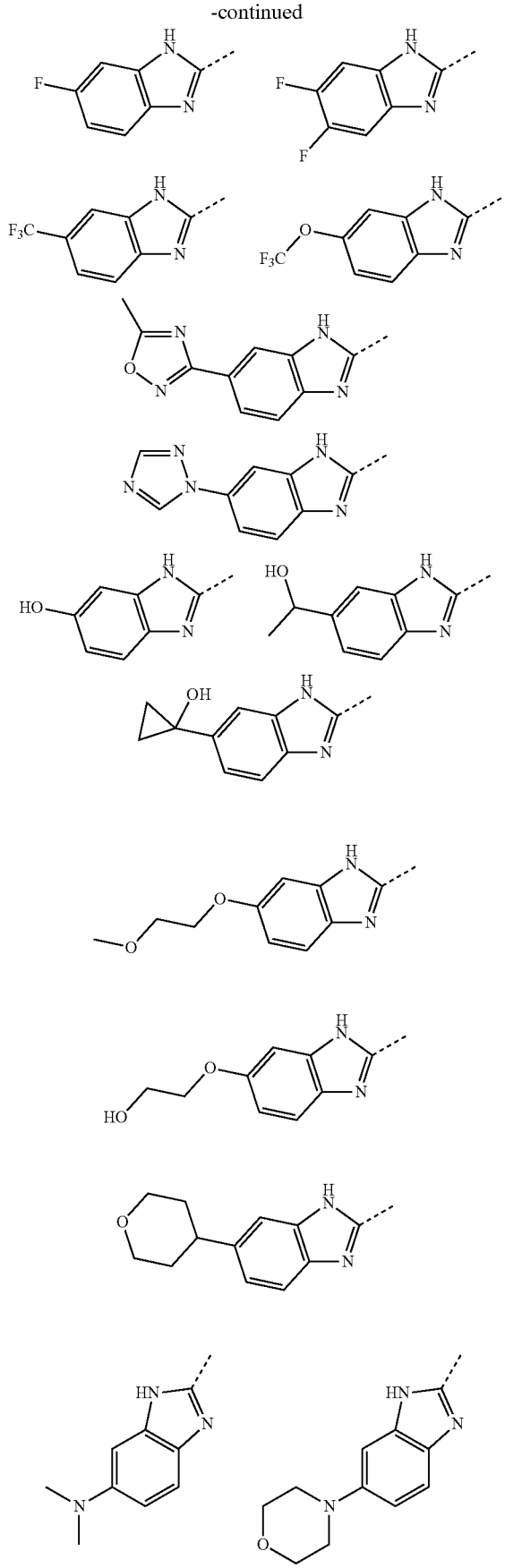

and tautomeric forms thereof;
or a pharmaceutically acceptable salt of said compound.

21. A compound according to claim 4, wherein $R^4$ is hydrogen and $R^{4'}$ is methyl and the carbon atom to which $R^{4'}$ is attached to is in absolute (R)-configuration;
or a pharmaceutically acceptable salt thereof.

22. A compound according to claim 20, wherein $R^4$ is hydrogen and $R^{4'}$ is methyl and the carbon atom to which $R^{4'}$ is attached to is in absolute (R)-configuration;
or a pharmaceutically acceptable salt thereof.

23. A compound according to claim 4, wherein:
$R^5$ is a 5-membered monocyclic or a 9-membered bicyclic aromatic ring containing one to three heteroatoms, wherein:
one of said heteroatoms is nitrogen, and the remaining heteroatoms, if present, are each independently selected from oxygen, nitrogen and sulfur;
said ring is attached to the rest of the molecule at said nitrogen atom; and
said ring is unsubstituted, mono-substituted, or di-substituted, wherein the substituents are each independently selected from $(C_{1-4})$alkyl, $(C_{1-4})$alkoxy, $(C_{1-3})$fluoroalkyl, halogen, and cyano;

or a pharmaceutically acceptable salt of thereof.

24. A compound according to claim 20, wherein
$R^5$ is a 5-membered monocyclic or a 9-membered bicyclic aromatic ring containing one to three heteroatoms, wherein:
one of said heteroatoms is nitrogen, and the remaining heteroatoms, if present, are each independently selected from oxygen, nitrogen and sulfur;
said ring is attached to the rest of the molecule at said nitrogen atom; and
said ring is unsubstituted, mono-substituted, or di-substituted, wherein the substituents are each independently selected from $(C_{1-4})$alkyl, $(C_{1-4})$alkoxy, $(C_{1-3})$fluoroalkyl, halogen, and cyano;
or a pharmaceutically acceptable salt thereof.

25. A compound according to claim 21, wherein
$R^5$ is a 5-membered monocyclic or a 9-membered bicyclic aromatic ring containing one to three heteroatoms, wherein:
one of said heteroatoms is nitrogen, and the remaining heteroatoms, if present, are independently selected from oxygen, nitrogen and sulfur;
said ring is attached to the rest of the molecule at said nitrogen atom; and
said ring is unsubstituted, mono-substituted, or di-substituted, wherein the substituents are independently selected from $(C_{1-4})$alkyl, $(C_{1-4})$alkoxy, $(C_{1-3})$fluoroalkyl, halogen, and cyano;
or a pharmaceutically acceptable salt thereof.

26. A compound according to claim 1, wherein the compound is 2-Imidazo[4,5-b]pyridin-3-yl-1-((R)-4-{4-[5-(2-methoxy-ethoxy)-1H-benzoimidazol-2-yl]-2-trifluoromethyl-thiazol-5-yl}-2-methyl-piperazin-1-yl)-ethanone
or a pharmaceutically acceptable salt thereof.

27. A compound according to claim 1, wherein the compound is 1-((R)-4-{4-[5-(2-Hydroxy-ethoxy)-1H-benzoimidazol-2-yl]-2-trifluoromethyl-thiazol-5-yl}-2-methyl-piperazin-1-yl)-2-imidazo[4,5-b]pyridin-3-yl-ethanone
or a pharmaceutically acceptable salt thereof.

28. A compound according to claim 1, wherein the compound is 1-{(R)-4-[4-(1H-Benzoimidazol-2-yl)-2-trifluoromethyl-thiazol-5-yl]-2-methyl-piperazin-1-yl}-2-(3-methyl-[1,2,4]triazol-1-yl)-ethanone
or a pharmaceutically acceptable salt thereof.

29. A compound according to claim 1, wherein the compound is 2-(3,5-Dimethyl-[1,2,4]triazol-1-yl)-1-{(R)-2-methyl-4-[4-(6-morpholin-4-yl-1H-benzoimidazol-2-yl)-2-trifluoromethyl-thiazol-5-yl]-piperazin-1-yl}-ethanone
or a pharmaceutically acceptable salt thereof.

30. A compound according to claim 1, wherein the compound is 2-(3,5-Dimethyl-[1,2,4]triazol-1-yl)-1-((R)-2-methyl-4-{4-[6-(5-methyl-[1,2,4]oxadiazol-3-yl)-1H-benzoimidazol-2-yl]-2-trifluoromethyl-thiazol-5-yl}-piperazin-1-yl)-ethanone
or a pharmaceutically acceptable salt thereof.

31. A compound according to claim 1, wherein the compound is 2-(3,5-Dimethyl-[1,2,4]triazol-1-yl)-1-((R)-2-methyl-4-{4-[6-(tetrahydro-pyran-4-yl)-1H-benzoimidazol-2-yl]-2-trifluoromethyl-thiazol-5-yl}-piperazin-1-yl)-ethanone
or a pharmaceutically acceptable salt thereof.

32. A method according to claim 15, wherein the transplant rejection is lung transplant rejection, kidney transplant rejection, or Graft-versus-Host disease.

33. A method according to claim 15, wherein the disease is rheumatoid arthritis, multiple sclerosis, neuromyelitis optica, inflammatory bowel disease, Crohn's disease, ulcerative colitis, systemic lupus erythematosus, psoriasis, psoriatic arthritis, lupus nephritis, interstitial cystitis, celiac disease, myasthenia gravis, type I diabetes, or uveitis.

34. A method according to claim 15, wherein the disease is rheumatoid arthritis, multiple sclerosis, inflammatory bowel disease, Crohn's disease, ulcerative colitis, systemic lupus erythematosus, psoriasis, lupus nephritis, interstitial cystitis, or myasthenia gravis.

35. A method according to claim 15, wherein the disease is asthma, chronic obstructive pulmonary disorder, atherosclerosis, myocarditis, inflammatory myopathies, dry eye disease, or sarcoidosis.

36. A method according to claim 15, wherein the disease is asthma, chronic obstructive pulmonary disorder, atherosclerosis, or myocarditis.

37. A method according to claim 15, wherein the disease is influenza or cerebral malaria.

38. A method according to claim 15, wherein the disease is lung transplant rejection, kidney transplant rejection, or Graft-versus-Host disease.

39. A method according to claim 15, wherein the disease is liver cirrhosis, systemic sclerosis, or pulmonary arterial hypertension.

40. A method according to claim 15, wherein the disease is neurodegeneration, Alzheimer's disease, HIV associated dementia, Huntington's chorea, Guillain-Barré syndrome, or chronic inflammatory demyelinating polyneuropathy.

41. A method according to claim 15, wherein the disease is brain tumor, colon cancer, breast cancer, or metastatic spread of cancer.

* * * * *